(12) United States Patent
Zhang et al.

(10) Patent No.: US 11,344,549 B2
(45) Date of Patent: May 31, 2022

(54) 2-SUBSTITUTED PYRAZOLE AMINO-4-SUBSTITUTED AMINO-5-PYRIMIDINE FORMAMIDE COMPOUND, COMPOSITION, AND APPLICATION THEREOF

(71) Applicant: BEIJING SCITECH-MQ PHARMACEUTICALS LIMITED, Beijing (CN)

(72) Inventors: Qiang Zhang, Beijing (CN); Yansheng Liu, Beijing (CN); Lantao Li, Beijing (CN); Xingfu Li, Beijing (CN); Chenming Hu, Beijing (CN)

( * ) Notice: Subject to any disclaimer, the term of this patent is extended or adjusted under 35 U.S.C. 154(b) by 14 days.

(21) Appl. No.: 16/642,552

(22) PCT Filed: Sep. 20, 2018

(86) PCT No.: PCT/CN2018/106694
§ 371 (c)(1),
(2) Date: Feb. 27, 2020

(87) PCT Pub. No.: WO2019/057112
PCT Pub. Date: Mar. 28, 2019

(65) Prior Publication Data
US 2021/0077489 A1     Mar. 18, 2021

(30) Foreign Application Priority Data

Sep. 21, 2017  (CN) .......................... 201710856218.0
Jul. 20, 2018   (CN) .......................... 201810801424.6

(51) Int. Cl.
| | |
|---|---|
| C07D 403/14 | (2006.01) |
| A61K 31/506 | (2006.01) |
| A61P 37/02 | (2006.01) |
| A61P 35/02 | (2006.01) |
| A61K 31/5377 | (2006.01) |
| C07D 401/14 | (2006.01) |
| C07D 403/12 | (2006.01) |
| C07D 405/14 | (2006.01) |
| C07D 417/14 | (2006.01) |

(52) U.S. Cl.
CPC ........ *A61K 31/506* (2013.01); *A61K 31/5377* (2013.01); *A61P 35/02* (2018.01); *A61P 37/02* (2018.01); *C07D 401/14* (2013.01); *C07D 403/12* (2013.01); *C07D 403/14* (2013.01); *C07D 405/14* (2013.01); *C07D 417/14* (2013.01)

(58) Field of Classification Search
CPC ..... C07D 403/14; C07D 417/14; A61P 35/02; A61P 37/02; A61K 31/5377

USPC ....................................................... 514/236.5
See application file for complete search history.

(56) References Cited

U.S. PATENT DOCUMENTS

| | | |
|---|---|---|
| 9,034,311 B2 | 5/2015 | Eastwood et al. |
| 2014/0179664 A1 | 6/2014 | Freeman et al. |
| 2015/0005281 A1 | 1/2015 | Hobson et al. |
| 2017/0137406 A1* | 5/2017 | Haq ..................... C07F 9/65583 |

FOREIGN PATENT DOCUMENTS

| | | |
|---|---|---|
| CN | 101218229 A | 7/2008 |
| CN | 103781780 A | 5/2014 |
| CN | 104169272 | * 11/2014 |
| CN | 104169272 A | 11/2014 |
| CN | 104262328 A | 1/2015 |
| CN | 105418616 A | 3/2016 |
| JP | 2011-518158 A | 6/2011 |
| JP | 2014-521623 A | 8/2014 |
| JP | 2014-521673 A | 8/2014 |
| JP | 2015-500862 A | 1/2015 |
| WO | 2013/014162 A1 | 1/2013 |
| WO | 2013/092854 A1 | 6/2013 |
| WO | 2015/123453 A1 | 8/2015 |
| WO | 2017/045615 A1 | 3/2017 |

OTHER PUBLICATIONS

International Search Report and Written Opinion for Application No. PCT/CN2018/106694, dated Dec. 25, 2018, 9 pages.

* cited by examiner

*Primary Examiner* — Kahsay Habte
(74) *Attorney, Agent, or Firm* — McCarter & English, LLP; Xin Zhang

(57) ABSTRACT

The present disclosure relates to a novel compound as a JAK inhibitor, a composition, and an application thereof. Specifically, the present disclosure provides a compound having high JAK inhibitory activity (as represented by formula (I)) or its isomer, solvate, hydrate, pharmaceutically-acceptable salt, and prodrug, and a pharmaceutical composition containing the compound. Also disclosed is a use of the present compound or pharmaceutical composition in preparation of a medicament for treating autoimmune diseases or cancers.

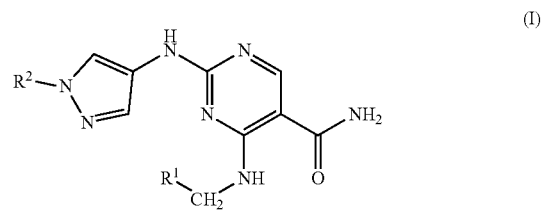

(I)

26 Claims, No Drawings

2-SUBSTITUTED PYRAZOLE AMINO-4-SUBSTITUTED AMINO-5-PYRIMIDINE FORMAMIDE COMPOUND, COMPOSITION, AND APPLICATION THEREOF

CROSS REFERENCE TO RELATED APPLICATIONS

The present application is a national application of PCT/CN2018/106694 filed on Sep. 20, 2018, which claims the priority of the Chinese Patent Application No. 201710856218.0 filed on Sep. 21, 2017 and the Chinese Patent Application No. 201810801424.6 filed on Jul. 20, 2018. The Chinese Patent Application No. 201710765745.0 and Chinese Patent Application No. 201810801424.6 are incorporated herein by reference as part of the disclosure of the present application.

TECHNICAL FIELD

The present disclosure belongs to the field of chemical medicine, and in particular, relates to a class of compounds having JAK kinase inhibitory activity or a pharmaceutically acceptable salt, an isomer, a solvate, a crystal or a prodrug thereof, and pharmaceutical compositions containing these compounds and use of these compounds or compositions in the manufacture of a medicament.

BACKGROUND OF THE INVENTION

JAK kinase (Janus kinase) and its downstream effectors, signal transduction and transcription activating proteins form an important cytokine signaling pathway, the JAK-STAT pathway. Studies have found that the JAK-STAT pathway can be activated by a variety of cytokines, growth factors and receptors, and is involved in cell proliferation, differentiation, apoptosis, angiogenesis, and immune regulation. The JAK kinase is a key kinase in the JAK-STAT signaling pathway. It was not until more than two decades after the kinase was discovered that the first JAK kinase inhibitor (tofacitinib) was approved for the treatment of rheumatoid arthritis in 2012 [Norman P., Selective JAK inhibitors in development for rheumatoid arthritis, Expert Opin Investig Drugs, 2014, 23: 1067-1077].

In mammals, three members of the JAK kinase family: JAK1, JAK2, and JAK3, as well as TYK2 are composed of more than 1,100 amino acids with a relative molecular mass of 120,000 to 140,000 and homology of 40% to 70%. These JAK kinase family members can be divided into 7 homologous domains (JH) in sequence from the C-terminus to the N-terminus: JH1 is a kinase region and is highly conserved in the JAK family. JH2 is a kinase-like region or a "pseudo" kinase region, which is a unique property of JAK protein that distinguishes it from other tyrosine proteins. Although this kinase region does not have catalytic activity, it regulates the activity of JH1. Mutations in this domain may often lead to an increase or decrease in JAK kinase activity, which in turn leads to the occurrence of certain diseases. JH3-JH4 is a SH2 domain (Src homology 2 domain) containing about 100 amino acid residues, which can specifically recognize and bind to the phosphorylated tyrosine residues on ligands. JH5-JH7 is a FERM domain, which is conserved and mainly regulates the binding of JAK to a receptor. As a member of the JAK kinase family, JAK3 also structurally contains the above-mentioned kinase regions, and mutations in specific amino acids in different domains will also cause changes in its kinase activity.

The JAK-STAT signaling pathway is an important intracellular signal transduction pathway in growth, activation, differentiation, apoptosis and function of various cells. STAT is a class of cytoplasmic proteins that can bind to DNA in the regulatory region of target genes. It is the downstream substrate of JAK. The STAT family includes 7 members: STAT1, STAT2, STAT3, STAT4, STAT5A, STAT5B, and STAT6. The interaction between JAKs and STATs plays an important role in the cytokine receptor signaling pathway [O'Sullivan L A et al., Cytokine receptor signaling through the JAK-STAT-Socs pathway in disease, Mol Immunol, 2007, 44: 2497-2506]. The binding of cytokine receptors on the cell surface to their respective cytokine ligands causes dimerization of receptor molecules, allowing the receptor-coupled JAK kinases to approach each other and be activated by interactive tyrosine phosphorylation. The JAK-STAT signaling pathway is a signal transduction pathway stimulated by multiple cytokine receptors. The JAK kinase mediates the signaling of most cytokines in cells, such as interleukins (IL), interferons (IFN), erythropoietin (EPO), granulocyte and macrophage colony stimulating factor (GMCSF), growth hormone (GH), prolactin (PRL), thrombopoietin (TPO), platelet derived growth factor (PDGF), and epidermal growth factor (EGF), etc. Moreover, different receptors can activate different subtypes of JAK kinases, thereby displaying differentiated biological functions [Pesu M. et al., Therapeutic targeting of Janus kinases, Immunol Rev, 2008, 223: 132-142].

JAK1 and JAK2 are expressed in all tissue cells of a human body. JAK3 is mainly expressed in various hematopoietic tissue cells, and is mainly present in bone marrow cells, thymocytes, NK cells, and activated B lymphocytes and T lymphocytes. The absence of JAK1 and JAK2 can cause fatal injury to a human body, and the absence of JAK3 can avoid toxic adverse reactions that damage other tissue cells [Yamaoka K., et al., JAK3 negatively regulates dendritic-cell cytokine production and survival, Blood, 2005, 106: 3227-3233]. Based on the functional characteristics and special tissue distributions of each subtype in the JAK kinase family, JAK3 has become a popular target for the treatment of autoimmune diseases, and more and more clinical studies have also focused on the treatment of rheumatoid arthritis by blocking the JAK3 signal transduction pathway. In 2012, a selective JAK3 inhibitor Tofacitinib passed clinical trials and was approved for the treatment of rheumatoid arthritis.

Tofacitinib (CP690550) is a pyrrolopyrimidine-type selective JAK3 kinase inhibitor developed by Pfizer, and its inhibitory activity against JAK3 ($IC_{50}$=1 nmol/L) is 20 times that of JAK2 ($IC_{50}$=20 nmol/L) and 100 times that of JAK1 ($IC_{50}$=112 nmol/L). By studying the stereochemical structure of Tofacitinib, it was found that its chiral structure determines that it can specifically bind to the JAK3 molecule, thereby inhibiting the phosphorylation of JAK3, further leading to the inhibition of STAT phosphorylation and the inhibition of downstream inflammatory cytokine synthesis. Tofacitinib has shown good clinical efficacy in clinical studies. In clinical trials of rheumatoid arthritis, the group given 5 or 10 mg of Tofacitinib showed significant statistical differences compared to the group given an equivalent amount of placebo. However, clinical trials have found that the use of Tofacitinib is associated with an increased risk of severe infection, and thus its long-term safety needs to be further studied.

The JAK-STAT signaling pathway plays an important role in the process of cell differentiation and proliferation, and changes in JAK activity will also lead to changes in the signaling of this pathway, which in turn affect cell functions. The key role of JAK kinase in JAK-STAT signaling and the specific tissue and cell distribution of JAK3 kinase make JAK3 a good target for treating diseases such as rheumatoid arthritis.

At present, JAK3 inhibitors are mainly used for the treatment of patients with moderate to severe rheumatoid arthritis. This class of drugs has shown very good therapeutic effects and good safety in the treatment, but the long-term safety needs to be further improved. During the clinical research of Tofacitinib, it was found that the use of this drug will cause certain adverse reactions, including infection, tuberculosis, tumors and liver damage. Hence, improving the efficacy of JAK3 inhibitors and reducing their toxic and side effects are the key issues to be solved urgently in this research field.

The ATP binding sites of several subtypes of the JAK kinase have higher homology and less structural difference, which are important reasons for the lack of selectivity of JAK inhibitors. There is still room for improving the efficacy, selectivity, and safety of a series of JAK kinase inhibitors that have been disclosed so far. There is still a need to develop JAK inhibitors with better efficacy and safety. Although highly selective JAK inhibitors are currently the focus of research in the field, in view of the fact that each member of the JAK kinase family is closely related to JAK-STAT signaling, pan-JAK inhibitors will significantly improve the efficacy and greatly reduce the dosage, thereby achieving the purpose of controlling toxic and side effects. In addition, the significant improvement in drug efficacy will help develop anti-inflammatory drugs through transdermal administration. The development of such drugs will provide a new way for the treatment of autoimmune diseases such as psoriasis, vitiligo, dermatitis, alopecia areata, rheumatoid arthritis, colitis, multiple sclerosis, systemic lupus erythematosus and Crohn's disease and cancers such as leukemia, lymphoma and multiple myeloma. The compounds disclosed herein show excellent biological activity as JAK kinase inhibitors.

SUMMARY OF THE INVENTION

The present disclosure provides a 2-(1-substituted pyrazol-4-amino)-4-substituted amino-5-pyrimidine carboxamide compound, and its use in the manufacture of a medicament for treating or preventing diseases caused by tyrosine kinases (e.g., JAK1, JAK2, JAK3, and TYK2) or variants thereof.

The present disclosure provides a compound, or an isomer, a solvate or a pharmaceutically acceptable salt thereof, or a pharmaceutical composition containing an effective polymorph, wherein the compound has a structural formula (I):

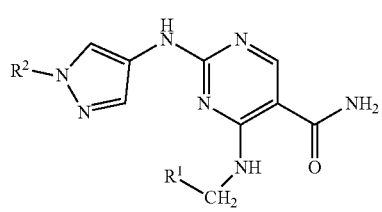

Formula (I)

wherein,
R$^1$ is

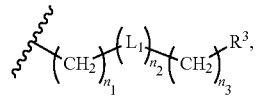

$n_1$ is 0 to 1, $n_2$ is 0 to 1, and $n_3$ is 0 to 5,
L$_1$ is

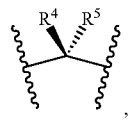

R$^4$ and/or R$^5$ are H, or linear C$_1$-C$_3$ alkyl;
R$^2$ is

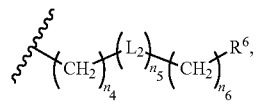

$n_4$ is 0 to 3, $n_5$ is 0 to 1, and $n_6$ is 0 to 5,
L$_2$ is

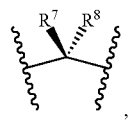

R$^7$ and/or R$^8$ are H, or linear C$_1$-C$_3$ alkyl;
the substituent R$^3$ in the compound of formula (I) is:
a) H, hydroxyl, or cyano,
b) linear or branched C$_1$-C$_5$ alkyl,
c) C$_3$-C$_8$ cycloalkyl, more preferably C$_3$-C$_7$ cycloalkyl,
d) linear or branched C$_1$-C$_5$ alkoxy,
e) linear or branched C$_1$-C$_5$ alkylthio,
f) a 5- to 7-membered heterocyclic ring, preferably, the 5- to 7-membered heterocyclic ring contains 1 to 2 heteroatoms selected from O and/or N and/or S, and when the heteroatom is N, N is attached to H, C$_1$-C$_4$ alkyl, or C$_1$-C$_3$ acyl, preferably acetyl, trifluoroacetyl, propanoyl, or N,N-diformyl, and when the heteroatom is S, S is attached to 0 to 2 oxygen atoms,
g) a substituted or unsubstituted 5-membered heteroaryl group, preferably, the substituted or unsubstituted 5-membered heteroaryl group has a structural formula of

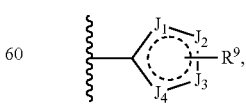

wherein J$_1$ and/or J$_2$ and/or J$_3$ and/or J$_4$ are C, N, S, or O; R$^9$ is linear or branched C$_1$-C$_3$ alkyl, alternatively, the substituted or unsubstituted 5-membered heteroaryl group has a structural formula of

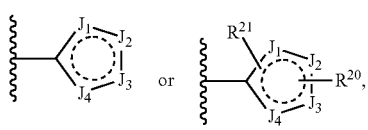

wherein:
$J_1$, $J_2$, $J_3$, and $J_4$ are each independently C, N, S, or O,
$R^{20}$ and $R^{21}$ are each independently a linear or branched $C_1$-$C_3$ alkyl group,
h) substituted or unsubstituted 6-membered aryl or heteroaryl,
preferably, the substituted or unsubstituted 6-membered aryl or heteroaryl group has a structural formula of

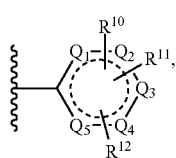

wherein:
$Q_1$, $Q_2$, $Q_3$, $Q_4$, and $Q_5$ are N or C;
$R^{10}$ and/or $R^{11}$ and/or $R^{12}$ are:
1) —F, —Cl, —Br, —CF$_3$, —OCF$_3$, or cyano;
2) —NR'R", wherein R' and R" are H or $C_1$-$C_3$ alkyl;
3) $C_1$-$C_3$ alkyl, $C_2$-$C_5$ alkynyl, or $C_3$-$C_5$ cycloalkyl;
4) SO$_2$R$^{13}$, wherein R$^{13}$ is H or $C_1$-$C_3$ alkyl;
5)

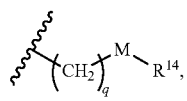

wherein q is 0 to 2, M is O or S, $R^{14}$ is H, or linear or branched $C_1$-$C_5$ alkyl;
6)

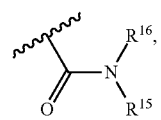

wherein $R^{15}$ and $R^{16}$ are linear alkyl,
alternatively, the substituted or unsubstituted 6-membered aryl or heteroaryl group has a structural formula of

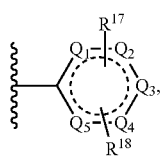

wherein:
$Q_1$, $Q_2$, $Q_3$, $Q_4$, and $Q_5$ are N or C;
$R^{17}$ and $R^{18}$ are each independently:
a) —H,
b) —F, —Cl, —Br, —CF$_3$, —OCF$_3$, or cyano,
c) —NR'R", wherein R' and R" are H or $C_1$-$C_3$ alkyl,
d) $C_1$-$C_3$ alkyl, $C_2$-$C_5$ alkynyl, $C_2$-$C_5$ alkenyl, or $C_3$-$C_5$ cycloalkyl,
e) SO$_2$R$^{13}$, wherein $R^{13}$ is H, or $C_1$-$C_3$ alkyl,
f)

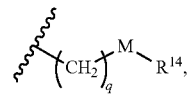

wherein q is 0 to 2, M is O or S, $R^{14}$ is H, or linear or branched $C_1$-$C_5$ alkyl,
g)

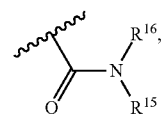

wherein $R^{15}$ and $R^{16}$ are linear $C_1$-$C_3$ alkyl,
h) —(CH$_2$)$_t$—R$^{19}$, wherein t is 1 to 2, and $R^{19}$ is $C_3$-$C_5$ cycloalkyl;
i) a ring containing 0 to 3 heteroatoms formed by a 6-membered aryl ring fused with a 5- or 6-membered ring, or a ring containing 1 to 3 heteroatoms formed by a 5-membered heteroaryl ring fused with a 5- or 6-membered ring, preferably, selected from:

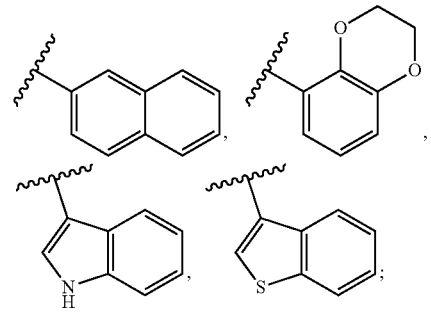

the substituent $R^6$ in the formula (I) is:
a) H, or hydroxyl,
b) —NR'R", wherein R' and R" are H, or $C_1$-$C_3$ alkyl,
c) linear or branched $C_1$-$C_5$ alkyl,
d) $C_3$-$C_8$ cycloalkyl,
e) linear or branched $C_1$-$C_5$ alkoxy,
f) linear or branched $C_1$-$C_5$ alkylthio,
g) heterocyclyl, preferably, the heterocyclyl is a 5- or 6-membered heterocyclyl containing oxygen and/or nitrogen, such as

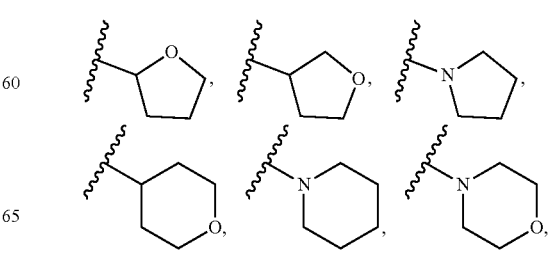

-continued

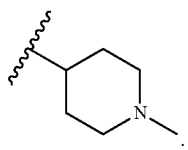

The present disclosure also provides a compound, or an isomer, a solvate or a pharmaceutically acceptable salt thereof, wherein the compound has a structural formula (I):

Formula (I)

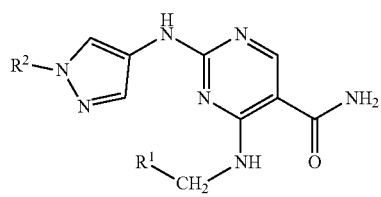

wherein,
R¹ is

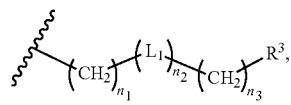

$n_1$ is 0 to 2, $n_2$ is 0 to 1, $n_3$ is 0 to 5,
$L_1$ is

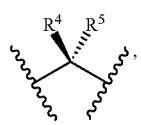

$R^4$ and/or $R^5$ are H, or linear $C_1$-$C_3$ alkyl;
$R^2$ is

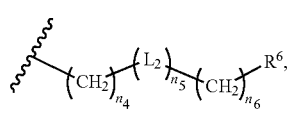

$n_4$ is 0 to 3, $n_5$ is 0 to 1, $n_6$ is 0 to 5,
$L_2$ is

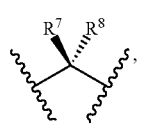

$R^7$ and/or $R^8$ are H, or linear $C_1$-$C_3$ alkyl;
$R^3$ is $C_1$-$C_3$ alkoxy substituted by $R^{22}$ or $C_1$-$C_3$ alkylthio substituted by $R^{22}$, and $R^{22}$ is hydroxyl, $C_1$-$C_3$ alkoxy, $C_1$-$C_3$ alkylthio, —NR'R", $C_1$-$C_3$ alkoxy substituted by hydroxyl, $C_1$-$C_3$ alkoxy substituted by amino, $C_1$-$C_3$ alkylthio substituted by hydroxyl, or $C_1$-$C_3$ alkylthio substituted by amino, wherein R' and R" is H or $C_1$-$C_3$ alkyl;

$R^6$ is:
a) H, or hydroxyl,
b) —NR'R", wherein R' and R" are H or $C_1$-$C_3$ alkyl,
c) linear or branched $C_1$-$C_5$ alkyl,
d) $C_3$-$C_8$ cycloalkyl,
e) linear or branched $C_1$-$C_5$ alkoxy,
f) linear or branched $C_1$-$C_5$ alkylthio, or
g)

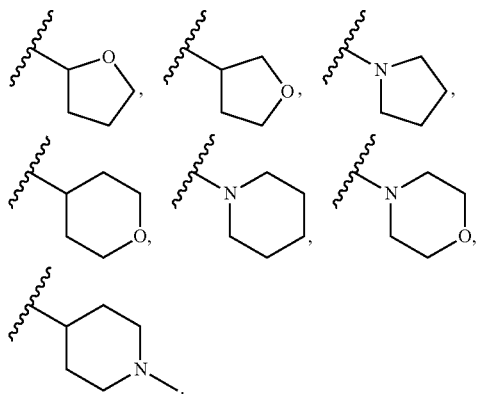

One aspect of the present disclosure provides an alkenyl-containing pyrimidine carboxamide compound, or an isomer, a hydrate, a solvate, a pharmaceutically acceptable salt, or a prodrug thereof, wherein the compound has a structural formula (I):

Formula (I)

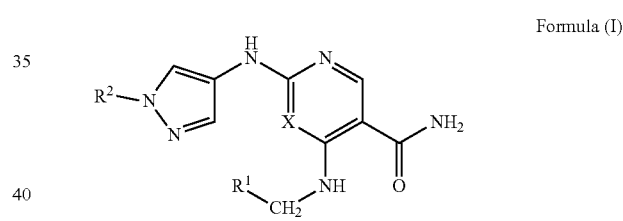

wherein X is N;
R¹ is

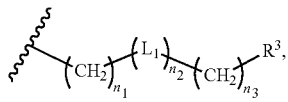

$n_1$ is an integer of 0 to 8, $n_2$ is an integer of 0 to 1, $n_3$ is an integer of 0 to 8, and the sum of $n_1$, $n_2$, and $n_3$ is 10 or less;
$L_1$ is

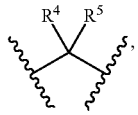

$R^4$ and $R^5$ are each independently H, or $C_1$-$C_3$ alkyl, and $R^4$ and $R^5$ are the same or different, $R^3$ is $C_2$-$C_8$ alkenyl which is unsubstituted or substituted with $C_1$-$C_3$ alkyl, or $C_4$-$C_8$ cycloalkenyl which is unsubstituted or substituted with $C_1$-$C_3$ alkyl;

$R^2$ is

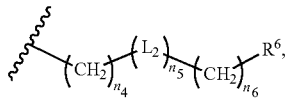

$n_4$ is an integer of 0 to 8, $n_5$ is an integer of 0 to 1, $n_6$ is an integer of 0 to 8, and the sum of $n_4$, $n_5$, and $n_6$ is 10 or less;
$L_2$ is

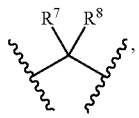

$R^7$ and $R^8$ are each independently H, or $C_1$-$C_3$ alkyl, and $R^7$ and $R^8$ are the same or different, $R^6$ is —H, hydroxyalkyl, $C_1$-$C_5$ alkyl, $C_3$-$C_8$ cycloalkyl, $C_1$-$C_5$ alkoxyalkyl, $C_1$-$C_5$ alkylthioalkyl, 5- to 6-membered heterocyclyl, or —NR'R", wherein R' and R" are each independently H, or $C_1$-$C_3$ alkyl.

Preferably, in the compound of formula (I), $R^3$ is

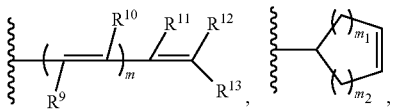

$R^9$, $R^{10}$, $R^{11}$, $R^{12}$, and $R^{13}$ are each independently H, or $C_1$-$C_3$ alkyl, and m is an integer of 0 to 2,
$m_1$ is an integer of 0 to 5, $m_2$ is an integer of 0 to 5, and the sum of $m_1$ and $m_2$ is less than or equal to 5.

Preferably, in the compound of formula (I), $n_1$ is an integer of 0 to 2, $n_2$ is an integer of 0 to 1, $n_3$ is an integer of 0 to 3, $R^4$ and $R^5$ are each independently H, or methyl, and $R^4$ and $R^5$ are the same or different;
$R^9$, $R^{10}$, $R^{11}$, $R^{12}$, and $R^{13}$ are each independently H, methyl or ethyl, and m is 0 or 1. More preferably, the sum of $n_1$, $n_2$ and $n_3$ is less than or equal to 5.

More preferably, in the compound of formula (I), $R^3$ is

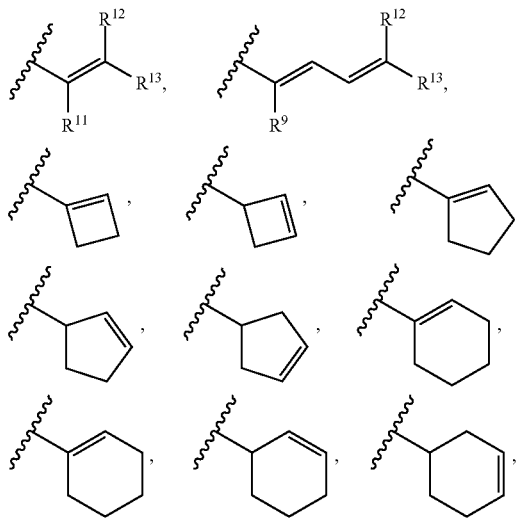

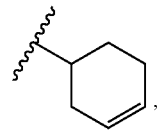

$R^9$, $R^{11}$, $R^{12}$, and $R^{13}$ are each independently H, methyl, or ethyl.

Preferably, $R^3$ is

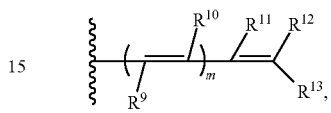

$R^9$ and $R^{10}$ are each independently H, or $C_1$-$C_3$ alkyl, and any one of $R^{11}$, $R^{12}$, and $R^{13}$ is $C_4$-$C_6$ alkyl, and the rest are each independently H, or $C_1$-$C_3$ alkyl, m is an integer of 0 to 2.

Preferably, in the compound of formula (I), $n_4$ is an integer of 0 to 3, $n_5$ is an integer of 0 to 1, $n_6$ is an integer of 0 to 5, $R^7$ and $R^8$ are each independently H, or methyl, and $R^7$ and $R^8$ are the same or different;
$R^6$ is —H, hydroxyethyl, hydroxypropyl, $C_1$-$C_5$ alkyl, $C_3$-$C_8$ cycloalkyl, $C_1$-$C_5$ alkoxyethyl, $C_1$-$C_5$ alkoxypropyl, $C_1$-$C_5$ alkylthioethyl, 5- to 6-membered heterocyclyl, or —NR'R", wherein R' and R" are each independently H, or $C_1$-$C_3$ alkyl.
More preferably, the sum of $n_4$, $n_5$, and $n_6$ is less than or equal to 5.

More preferably, in the compound of formula (I), $R^6$ is H, hydroxyethyl, hydroxypropyl, methyl, ethyl, propyl, isopropyl, tert-butyl, cyclopropyl, cyclobutyl, cyclopentyl, cyclohexyl, methoxyethyl, ethoxyethyl, propoxyethyl, isopropoxyethyl, methoxypropyl, ethoxypropyl, propoxypropyl, isopropoxypropyl, methylthioethyl, ethylthioethyl, propylthioethyl, isopropylthioethyl, 5- to 6-membered heterocyclyl, or —NR'R" wherein R' and R" are each independently H, methyl, or ethyl;
wherein the 5- to 6-membered heterocyclyl is a heterocyclyl containing 1 to 2 heteroatoms selected from N, O, and S, which is unsubstituted or substituted with 1 to 2 substituents selected from hydroxy, $C_1$-$C_3$ alkyl, and $C_1$-$C_3$ acyl.

More specifically, the heterocyclyl containing 1 to 2 heteroatoms selected from N, O, and S is selected from any one of the following groups:

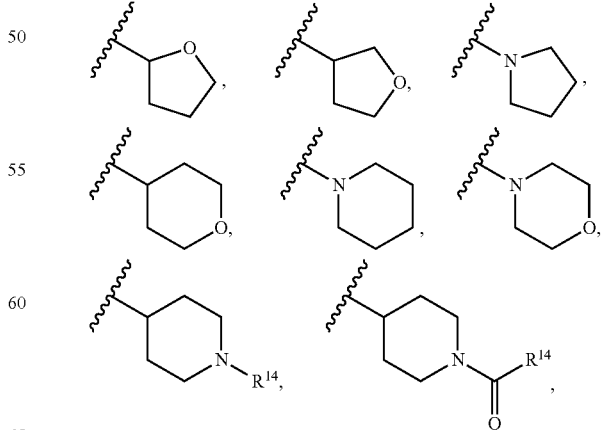

wherein $R^{14}$ is H, methyl, ethyl, propyl, or isopropyl.

According to some embodiments of the present disclosure, the pharmaceutically acceptable salt of the pyrimidine carboxamide compound is selected from one or more salts of the compound as follows: hydrochloride, hydrobromide, hydriodate, perchlorate, sulfate, nitrate, phosphate, formate, acetate, propionate, glycolate, lactate, succinate, maleate, tartrate, malate, citrate, fumarate, gluconate, benzoate, mandelate, mesylate, isethionate, benzenesulfonate, oxalate, palmitate, 2-naphthalenesulfonate, p-toluenesulfonate, cyclohexylaminosulfonate, salicylate, hexonate, trifluoroacetate, aluminum, calcium, chloroprocaine, choline, diethanolamine, ethylenediamine, lithium, magnesium, potassium, sodium, and zinc.

Another aspect of the present disclosure relates to use of the pyrimidine carboxamide compound, or an isomer, a hydrate, a solvate, a pharmaceutically acceptable salt, or a prodrug thereof in the manufacture of a medicament for the treatment of autoimmune diseases and cancers associated with tyrosine kinases JAK1, JAK2, JAK3, or TYK2, wherein the autoimmune diseases and cancers associated with tyrosine kinases JAK1, JAK2, JAK3, or TYK2 include fundus oculi disease, xerophthalmia, psoriasis, vitiligo, dermatitis, alopecia areata, rheumatoid arthritis, colitis, multiple sclerosis, systemic lupus erythematosus, Crohn's disease, atherosclerosis, pulmonary fibrosis, liver fibrosis, bone marrow fibrosis, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myelocytic leukemia, non-Hodgkin's lymphoma, nasopharyngeal cancer, esophageal cancer, brain tumor, B-cell and T-cell lymphoma, lymphoma, multiple myeloma, biliary tract cancerous sarcoma, and bile duct cancer.

Yet another aspect of the present disclosure provides a pharmaceutical composition comprising the pyrimidine carboxamide compound, or an isomer, a hydrate, a solvate, a pharmaceutically acceptable salt, or a prodrug thereof, and one or more pharmaceutically acceptable carriers or excipients.

According to some embodiments of the present disclosure, the pharmaceutical composition may further comprise one or more other therapeutic agents.

Unless otherwise stated, the following terms used in this disclosure (including the description and claims) have the definitions given below. In this disclosure, unless otherwise stated, the use of "or" or "and" means "and/or". Furthermore, the term "comprising" and other forms such as "including", "containing", and "having" are not limiting. The section headings used herein are for organizational purposes only and should not be construed as restrictions on the topics described.

"Alkyl" refers to an aliphatic hydrocarbon group. An alkyl group is saturated or unsaturated. An alkyl moiety, whether saturated or unsaturated, can be branched or linear. "Alkyl" can have 1 to 5 carbon atoms, preferably 1 to 3 carbon atoms. In one aspect, the alkyl group is selected from methyl, ethyl, propyl, isopropyl, n-butyl, isobutyl, sec-butyl and tert-butyl. Typical alkyl groups include, but are not limited to, methyl, ethyl, propyl, isopropyl, butyl, isobutyl, sec-butyl, tert-butyl, pentyl, neopentyl, hexyl, allyl, vinyl, ethynyl, but-2-enyl, but-3-enyl, etc.

The term "cycloalkyl" refers to a monocyclic or polycyclic aliphatic non-aromatic group in which each atom that makes up the ring (i.e., the backbone atom) is a carbon atom.

A cycloalkyl group can be saturated or partially unsaturated. A cycloalkyl group can be fused with an aromatic ring and the point of attachment is on a carbon that is not an carbon atom in the aromatic ring. A cycloalkyl group includes a group having 3-10 ring atoms. In some embodiments, a cycloalkyl group is selected from cyclopropyl, cyclobutyl, cyclopentyl, cyclopentenyl, cyclohexyl, cyclohexenyl, cycloheptyl, and cyclooctyl. A cycloalkyl group can be substituted or unsubstituted. Depending on the structure, a cycloalkyl group can be a monovalent group or a divalent group (i.e., a cycloalkylene group, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, etc.). In one aspect, a cycloalkyl group is $C_3$-$C_6$ cycloalkyl.

"Alkenyl" or "cycloalkenyl" refers to a straight-chain or cyclic hydrocarbon group consisting only of carbon and hydrogen atoms, which contains at least one double bond.

"Alkoxyalkyl" refers to a (alkyl)O(alkyl)-group, and "alkylthioalkyl" refers to a (alkyl)S(alkyl)-group, wherein the alkyl group is as defined herein. Preferably, the alkoxyalkyl group is $C_1$-$C_5$ alkoxyalkyl, more preferably $C_1$-$C_5$ alkoxy-$C_1$-$C_3$ alkyl, more preferably $C_1$-$C_5$ alkoxyethyl or $C_1$-$C_5$ alkoxypropyl. Preferably, the alkylthioalkyl group is $C_1$-$C_5$ alkylthioalkyl, more preferably $C_1$-$C_5$ alkylthio-$C_1$-$C_3$ alkyl, more preferably $C_1$-$C_5$ alkylthioethyl.

"Heterocyclyl" in the term "5- to 6-membered heterocyclyl" refers to an aromatic heterocyclic ring (also referred to as heteroaryl) and a heterocycloalkyl ring (also referred to as an aliphatic heterocyclic group) containing one or more heteroatoms in the ring, wherein each heteroatom in the ring is selected from O, S, and N, wherein each heterocyclyl group contains 5-6 atoms in its ring system. Moreover, the 5- to 6-membered heterocyclyl may be a heterocyclyl containing 1 to 2 heteroatoms selected from N, O, and S, which is unsubstituted or substituted with 1 to 2 substituents selected from hydroxy, $C_1$-$C_3$ alkyl, and $C_1$-$C_3$ acyl.

More specifically, the heterocyclyl containing 1 to 2 heteroatoms selected from N, O, and S is selected from any one of the following groups:

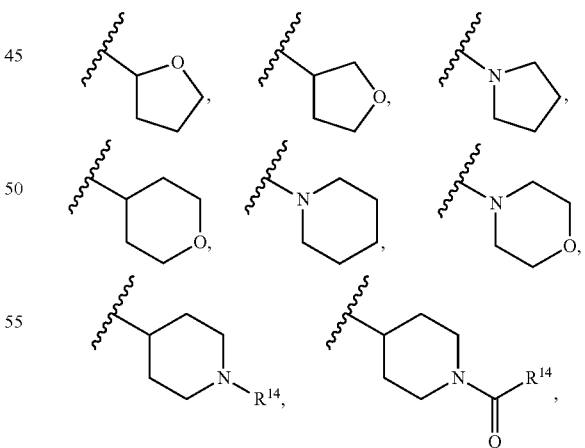

wherein $R^{14}$ is H, methyl, ethyl, propyl, or isopropyl.

In this disclosure, the term "isomer" refers to different compounds having the same molecular formula, and may include various isomeric forms such as stereoisomers and tautomers. "Stereoisomers" are isomers that differ only in the arrangement of their atoms in space. Certain compounds described herein contain one or more asymmetric centers and thus can give rise to enantiomers, diastereomers, and other stereoisomeric forms which can be defined as (R)- or (S)-based on absolute stereochemistry. The chemical entities, pharmaceutical compositions, and methods disclosed herein are intended to include all of these possible isomers, including racemic mixtures, optically pure forms, and intermediate mixtures. Optically active (R)- and (S)-isomers can be prepared using chiral synthons or chiral reagents or resolved using conventional techniques. The optical activity of a compound can be analyzed by any suitable method, including but not limited to chiral chromatography and polarimetry, and the degree of dominance of one stereoisomer over other isomers can be determined.

Specifically, for example, for the compound of formula (I) of the present disclosure, when $n_2$ or $n_5$ is not 0, and $R^4$ and $R^5$ are different, or $R^7$ and $R^8$ are different, the structure of $L_1$

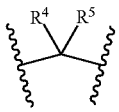

or $L_2$

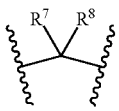

contains a chiral carbon atom; at this time, the structure of $L_1$

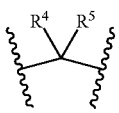

or $L_2$

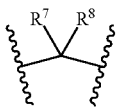

is meant to include all possible isomers, including racemic mixtures, optically pure forms of optically active (R)- and (S)-isomers, etc., that is, when $R^4$ and $R^5$ are different, $L_1$ is

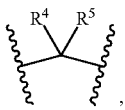

including

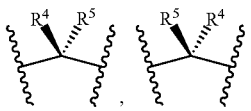

and racemates; when $R^7$ and $R^8$ are different, $L_2$ is

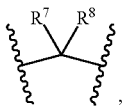

including

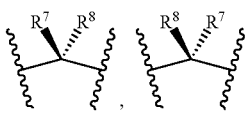

and racemates.

When a compound described herein contains an olefinic double bond, it means that the compound includes various cis- or trans-isomers, unless otherwise stated.

"Tautomers" are structurally different isomers that can be converted to each other through tautomerization. "Tautomerization" is a form of isomerization and includes a proton transfer tautomerization, which can be considered as a subset of acid-base chemistry. "Proton transfer tautomerization" involves the migration of a proton accompanied by a bond-level transformation, which is often exchange of a single bond with an adjacent double bond. When tautomerization is possible (for example, in solution), a chemical equilibrium of tautomers can be reached. An example of tautomerization is keto-enol tautomerization.

In this disclosure, a compound of formula (I), or an isomer, a crystal, a prodrug or a pharmaceutically acceptable salt thereof may exist in solvated and unsolvated forms. For example, the solvated form may be a water-soluble form. The present disclosure includes all of these solvated and unsolvated forms.

One aspect of the present disclosure is a pharmaceutical composition comprising a compound of formula (I). This composition can be applied to autoimmune diseases such as psoriasis, vitiligo, dermatitis, alopecia areata, rheumatoid arthritis, colitis, multiple sclerosis, systemic lupus erythematosus and Crohn's disease and cancers such as leukemia, lymphoma and multiple myeloma, including autoimmune-like diseases and cancers that are resistant to treatment with Tofacitinib, Peficitinib, Decernotinib, or other kinase inhibitors.

It is a further object of the present disclosure to provide a method for treating autoimmune diseases and cancers, which comprises administering to a subject a therapeutically effective amount of a composition comprising a compound disclosed herein. Autoimmune diseases and cancers that can be treated in this way are noted elsewhere herein, including autoimmune diseases, cancer, etc. that are resistant to the treatment of Tofacitinib, Peficitinib, Roxolitinib, Decernotinib or other kinase inhibitors.

One or more other therapies can also be used in combination in cancer treatment, including surgery, radiation therapy (such as gamma-ray, neutron beam radiation therapy, electron beam radiation therapy, proton therapy, brachytherapy and whole body radioisotope, etc.), endocrine therapy, biological response modifiers (e.g., interferon, interleukin, and tumor necrosis factor (TNF)), hyperthermia, cryotherapy, attenuation of any adverse effects (e.g., antiemetics), and other therapeutic drugs.

The present disclosure also includes the use of a compound disclosed herein or a pharmaceutically acceptable derivative thereof in the manufacture of a medicament for treatment of diseases such as autoimmune diseases such as fundus oculi disease, xerophthalmia, psoriasis, rheumatoid arthritis, rash, eczema, alopecia areata, atherosclerosis, pulmonary fibrosis, liver fibrosis, myelofibrosis, enteritis, and tumors, including diseases that are resistant to one or more other therapeutic agents as indicated elsewhere herein. The compounds disclosed herein can also be used in medicine to reduce or prevent diseases by inhibiting one or more kinases (e.g., JAK1, JAK2, JAK3, or TYK2).

The present disclosure also provides a method for preparing the corresponding compounds, and specific examples can be prepared by the following exemplary methods. The synthetic route of the series (I) compounds is shown below:

Synthetic route of the compound of formula (I)

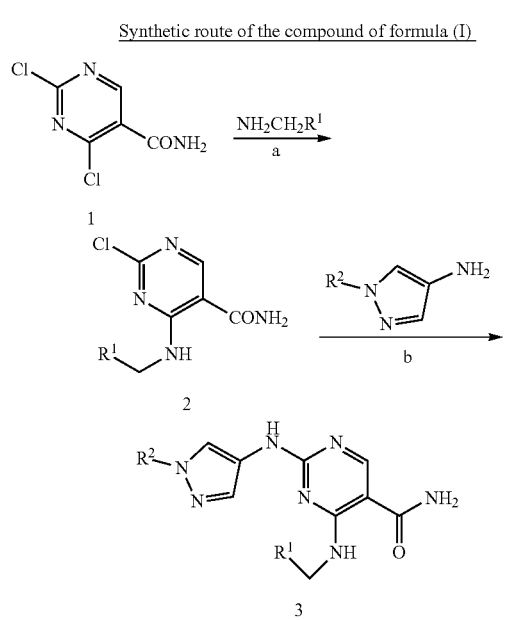

Reagents and reaction conditions: (a) DIEA, THF; (b) s-BuOH, TFA.

DETAILED DESCRIPTION OF THE EMBODIMENTS

In order to make the objectives, technical solutions, and advantages of the present disclosure more clear, the present disclosure is further described in detail below with reference to specific examples. It should be understood that the specific examples described here are only used to explain the present disclosure, and are not intended to limit the present disclosure. If specific technologies or conditions are not specified in examples, the technologies or conditions described in the literature of the field or the product instruction shall be used. If the manufacturers of reagents or instruments as used are not specified, the reagents or instruments are all conventional products that are commercially available. The term "and/or" as used herein includes any and all combinations of one or more listed items.

For the synthesis of some intermediates used in this disclosure, please see the Chinese Patent Application No. 2017108562180.

The intermediates are synthesized as follows:

Preparation of Intermediate 1
1-(2-methoxyethyl)-1H-pyrazol-4-amine

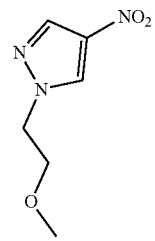

Step 1): Preparation of
1-(2-methoxyethyl)-4-nitro-1H-pyrazole

4-Nitro-1H-pyrazole (5 g, 44.21 mmol) was dissolved in DMF (20 mL). To the mixture were added $K_2CO_3$ (9.1 g, 65.85 mmol) and 1-bromo-2-methoxyethane (7.4 g, 53.24 mmol), and reacted at 50° C. for 16 hours. The reaction solution sodium sulfate, and filtered. The filtrate was evaporated to dryness and subjected to column chromatography (petroleum ether:ethyl acetate=3:1) to give 5 g of a brown oil with a yield of 66%. $^1$H NMR (400 MHz, DMSO-$d_6$) δ 8.85 (s, 1H), 8.27 (s, 1H), 4.35 (t, J=5.1 Hz, 2H), 3.73 (t, J=5.2 Hz, 2H), 3.24 (s, 3H). LCMS: m/z=172.1 (M+H)$^+$.

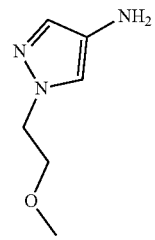

Step 2): Preparation of
1-(2-methoxyethyl)-1H-pyrazol-4-amine 1-(2-Methoxyethyl)-4-nitro-1H-pyrazole (5 g, 29.21 mmol) was dissolved in ethanol (25 mL) and ethyl acetate (25 mL). To the mixture was added Raney nickel (500 mg), and reacted under hydrogen atmosphere for 5 hours. The mixture was filtered through celite. The filtrate was evaporated to dryness to give 3.6 g of a brown solid with a yield of 87%. $^1$H NMR (400 MHz, DMSO-$d_6$) δ 7.01 (s, 1H), 6.90 (s, 1H), 4.04 (t, J=5.4 Hz, 2H), 3.89-3.63 (m, 2H), 3.58 (t, J=5.4 Hz, 2H), 3.20 (s, 3H). LCMS: m/z=142.1 (M+H)$^+$.

Preparation of Intermediate 2
1-(2-(methylthio)ethyl)-1H-pyrazol-4-amine

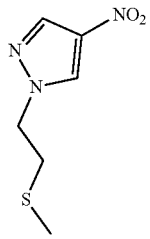

Step 1): Preparation of 1-(2-(methylthio)ethyl)-4-nitro-1H-pyrazole

4-Nitro-1H-pyrazole (400 mg, 3.54 mmol) was dissolved in anhydrous tetrahydrofuran (10 mL). To the mixture were added 2-(methylthio)-1-ethanol (424 mg, 4.60 mmol) and triphenylphosphine (1.4 g, 5.32 mmol). To the mixture was added DIAD (1.13 g, 5.60 mmol) dropwise at 0° C. under argon protection, and reacted at 25° C. for 4 hours. The reaction solution was quenched with saturated aqueous solution of ammonium chloride, extracted with ethyl acetate, dried over anhydrous sodium sulfate, and filtrated. The filtrate was evaporated to dryness and subjected to column chromatography (petroleum ether:ethyl acetate=4:1) to give 180 mg of a yellow oil with a yield of 54%. LCMS: m/z=188.0 (M+H)$^+$.

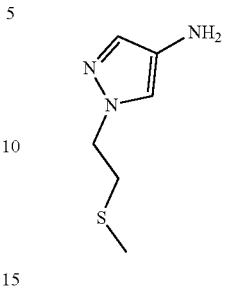

Step 2): Preparation of 1-(2-(methylthio)ethyl)-1H-pyrazol-4-amine 1-(2-(Methylthio)ethyl)-4-nitro-1H-pyrazole (300 mg, 1.60 mmol) was dissolved in a mixed solution of ethanol (2 mL) and ethyl acetate (2 mL). To the mixture was added Raney nickel (30 mg), and reacted for 5 hours under hydrogen atmosphere. The mixture was filtered through celite. The filtrate was evaporated to dryness to give 210 mg of a brown oil with a yield of 83%. $^1$H NMR (400 MHz, DMSO-d$_6$) δ 7.06 (s, 1H), 6.91 (s, 1H), 4.09 (t, J=6.9 Hz, 2H), 3.81 (s, 2H), 2.79 (t, J=6.9 Hz, 2H), 1.99 (s, 3H). LCMS: m/z=158.1 (M+H)$^+$.

TABLE 1

Synthesis of intermediates 3-22 (referring to the synthetic method of intermediate 1 or 2)

| Intermediate No. | R | Intermediate name | LCMS m/z = (M + H)$^+$ | Referring to the synthetic method of intermediate 1 or 2 |
|---|---|---|---|---|
| 3 | ethyl | 1-ethyl-1H-pyrazol-4-amine | 112.1 | 1 |
| 4 | isopropyl | 1-isopropyl-1H-pyrazol-4-amine | 126.1 | 1 |
| 5 | HO-CH$_2$CH$_2$- | 2-(4-amino-1H-pyrazol-1-yl)-1-ethanol | 128.1 | 1 |
| 6 | (CH$_3$)$_2$N-CH$_2$CH$_2$- | 1-[2-(dimethylamino)ethyl]-1H-pyrazol-4-amine | 155.1 | 2 |

TABLE 1-continued

Synthesis of intermediates 3-22 (referring to the synthetic method of intermediate 1 or 2)

| Intermediate No. | R | Intermediate name | LCMS m/z = (M + H)+ | Referring to the synthetic method of intermediate 1 or 2 |
|---|---|---|---|---|
| 7 | pyrrolidin-1-yl-ethyl | 1-[2-(pyrrolidin-1-yl)ethyl]-1H-pyrazol-4-amine | 181.1 | 2 |
| 8 | piperidin-1-yl-ethyl | 1-[2-(piperidin-1-yl)ethyl]-1H-pyrazol-4-amine | 195.2 | 1 |
| 9 | morpholinoethyl | 1-(2-morpholinoethyl)-1H-pyrazol-4-amine | 197.1 | 1 |
| 10 | cyclobutyl | 1-cyclobutyl-1H-pyrazol-4-amine | 138.1 | 2 |
| 11 | cyclopentyl | 1-cyclopentyl-1H-pyrazol-4-amine | 152.1 | 2 |
| 12 | cyclohexyl | 1-cyclohexyl-1H-pyrazol-4-amine | 166.1 | 1 |
| 13 | tetrahydro-2H-pyran-4-yl | 1-(tetrahydro-2H-pyran-4-yl)-1H-pyrazol-4-amine | 168.1 | 2 |
| 14 | octyl | 1-octyl-1H-pyrazol-4-amine | 196.2 | 1 |
| 15 | 6-(dimethylamino)hexyl | 1-[6-(dimethylamino)hexyl]-1H-pyrazol-4-amine | 211.2 | 1 |
| 16 | 2-hydroxy-2-methylpropyl | 1-(4-amino-1H-pyrazol-1-yl)-2-methyl-2-propanol | 156.1 | 1 |

TABLE 1-continued

Synthesis of intermediates 3-22 (referring to the synthetic method of intermediate 1 or 2)

| Intermediate No. | R | Intermediate name | LCMS m/z = (M + H)+ | Referring to the synthetic method of intermediate 1 or 2 |
|---|---|---|---|---|
| 17 | tetrahydrofuran-3-yl | 1-(tetrahydrofuran-3-yl)-1H-pyrazol-4-amine | 154.1 | 2 |
| 18 | (tetrahydrofuran-2-yl)methyl | 1-[(tetrahydrofuran-2-yl)methyl]-1H-pyrazol-4-amine | 168.1 | 1 |
| 19 | (tetrahydrofuran-3-yl)methyl | 1-[(tetrahydrofuran-3-yl)methyl]-1H-pyrazol-4-amine | 168.1 | 2 |
| 20 | (tetrahydro-2H-pyran-4-yl)methyl | 1-[(tetrahydro-2H-pyran-4-yl)methyl]-1H-pyrazol-4-amine | 182.1 | 1 |
| 21 | cycloheptyl | 1-cycloheptyl-1H-pyrazol-4-amine | 180.1 | 2 |
| 22 | 1-methylpiperidin-4-yl | 1-(1-methylpiperidin-4-yl)-1H-pyrazol-4-amine | 181.1 | 2 |

Preparation of Intermediate 23
1-cyclopropyl-1H-pyrazol-4-amine

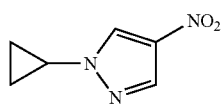 [SMILES: O=[N+]([O-])c1cnn(C2CC2)c1]

Step 1): Preparation of 1-cyclopropyl-4-nitro-1H-pyrazole

4-Nitro-1H-pyrazole (200 mg, 1.77 mmol) was dissolved in anhydrous dichloromethane (15 mL). To the mixture were added cyclopropylboronic acid (320 mg, 3.72 mmol), copper acetate (326 mg, 1.79 mmol), pyridine (144 mg, 1.82 mmol), and sodium carbonate (432 mg, 4.08 mmol), and reacted at 70° C. under argon protection for 4 hours. The reaction solution was concentrated and subjected to column chromatography (petroleum ether:ethyl acetate=4:1) to give 110 mg of a yellow oil with a yield of 41%. LCMS: m/z=154.1 (M+H)+.

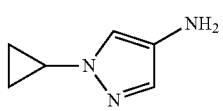

Step 2): Preparation of 1-cyclopropyl-1H-pyrazol-4-amine

1-Cyclopropyl-4-nitro-1H-pyrazole (110 mg, 0.72 mmol) was dissolved in a mixed solution of ethanol (2 mL) and ethyl acetate (2 mL). To the mixture was added Raney nickel (15 mg), and reacted for 3 hours under hydrogen atmosphere. The mixture was filtered through celite, and the filtrate was evaporated to dryness to give 90 mg of a brown oil with a yield of 90%. $^1$H NMR (400 MHz, DMSO-d$_6$) δ 7.02 (s, 1H), 6.86 (s, 1H), 3.89-3.61 (m, 2H), 3.50-3.45 (m, 1H), 0.91-0.73 (m, 4H). LCMS: m/z=124.1 (M+H)$^+$.

Preparation of Intermediate 24
1-(6-methoxyhexyl)-1H-pyrazol-4-amine

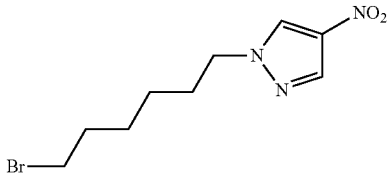 [SMILES: O=[N+]([O-])c1cnn(CCCCCCBr)c1]

Step 1): Preparation of
1-(6-bromohexyl)-4-nitro-1H-pyrazole

4-Nitro-1H-pyrazole (200 mg, 1.77 mmol) was dissolved in DMF (8 mL). To the mixture were added K$_2$CO$_3$ (732 mg, 5.30 mmol) and 1,6-dibromohexane (864 mg, 3.54 mmol), and reacted at 80° C. for 3 hours. The reaction solution was poured into ice water, extracted with ethyl acetate, dried over anhydrous sodium sulfate, and filtered. The filtrate was evaporated to dryness and subjected to column chromatography (petroleum ether:ethyl acetate=5:1) to give 300 mg of a colorless oil with a yield of 61%. LCMS: m/z=276.0 (M+H)$^+$.

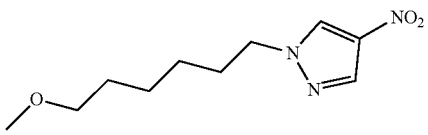 [SMILES: COCCCCCCn1cc([N+](=O)[O-])cn1]

Step 2): Preparation of
1-(6-methoxyhexyl)-4-nitro-1H-pyrazole 1-(6-Bromohexyl)-4-nitro-1H-pyrazole (300 mg, 1.09 mmol) was dissolved in a solution of sodium methoxide in methanol (33%, 7 mL), and reacted at 25° C. for 16 hours. The reaction solution was quenched with saturated brine, extracted with ethyl acetate, dried over anhydrous sodium sulfate, and filtered. The filtrate was evaporated to dryness and subjected to reversed-phase column chromatography (petroleum ether:ethyl acetate=5:1) to give 230 mg of a colorless oil with a yield of 93%. LCMS: m/z=228.1 (M+H)$^+$.

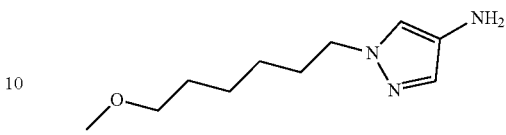

Step 3): Preparation of
1-(6-methoxyhexyl)-1H-pyrazol-4-amine 1-(6-Methoxyhexyl)-4-nitro-1H-pyrazole (230 mg, 1.01 mmol) was dissolved in a mixed solution of ethanol (2 mL) and ethyl acetate (2 mL). To the mixture was added Raney nickel (25 mg), and reacted for 3 hours under hydrogen atmosphere. The mixture was filtered through celite. The filtrate was evaporated to dryness to give 190 mg of a brown oil with a yield of 95%. LCMS: m/z=198.2 (M+H)$^+$.

Preparation of Intermediate 25
4-methyl-1-pentylamine

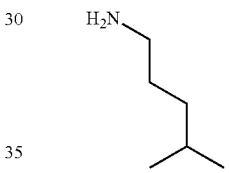

3-Methyl valeronitrile (400 mg, 4.11 mmol) was dissolved in anhydrous tetrahydrofuran (5 mL). To the mixture was added lithium aluminum hydride warmed to 25° C. and stirred for 16 hours. The mixture was cooled to 0° C., and to the mixture were added 0.4 mL of water, 0.4 mL of 15% solution of sodium hydroxide, and 1.2 mL of water in sequence. After stirring for 15 minutes, the mixture was filtered. The filtrate was evaporated to dryness at low temperature to give 300 mg of a yellow oil with a crude yield of 72%. $^1$H NMR (400 MHz, CDCl$_3$) δ 2.85 (t, J=7.6 Hz, 2H), 1.60-1.46 (m, 3H), 1.14-1.08 (m, 2H), 0.95 (d, 6H). LCMS: m/z=102.1 (M+H)$^+$.

TABLE 2

Synthesis of intermediates 26-28 (referring to the synthesis of intermediate 29)

| Intermediate No. | Intermediate structure | Intermediate name | LCMS m/z = (M + H)$^+$ |
|---|---|---|---|
| 26 | H$_2$N-CH$_2$-(2-ethylphenyl) | (2-ethylphenyl)methylamine | 136.1 |

TABLE 2-continued

Synthesis of intermediates 26-28 (referring to the synthesis of intermediate 29)

| Intermediate No. | Intermediate structure | Intermediate name | LCMS m/z = (M + H)+ |
|---|---|---|---|
| 27 | H2N—CH2—(2-methoxy-5-chlorophenyl with OMe and Cl) | (2-methoxy-5-chlorophenyl)methylamine | 172.0 |
| 28 | H2N—CH2—(2,6-dimethoxyphenyl) | (2,6-dimethoxyphenyl)methylamine | 168.1 |

Preparation of Intermediate 29
(2-(methoxymethyl)phenyl)methylamine

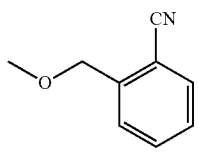

Step 1): Preparation of 2-(methoxymethyl)benzonitrile 2-(Chloromethyl)benzonitrile (500 mg, 3.30 mmol) was dissolved in a solution of sodium methoxide in methanol (33%, 5 mL), and reacted at 25° C. for 4 hours. The reaction solution was quenched with a saturated aqueous solution of ammonium chloride, extracted with ethyl acetate, dried over anhydrous sodium sulfate, and filtered. The filtrate was evaporated to dryness to give 450 mg of a pale yellow oil with a crude yield of 93%. LCMS: m/z=148.1 (M+H)+.

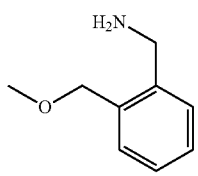

Step 2): Preparation of (2-(methoxymethyl)phenyl)methylamine 2-(Methoxymethyl)benzonitrile (450 mg, 3.06 mmol) was dissolved in anhydrous tetrahydrofuran (15 mL). To the mixture was added lithium aluminum hydride (354 mg, 9.32 mmol) at 0° C. under argon protection. After 10 minutes, the temperature was warmed to 25° C. and the mixture was reacted for 16 hours. At 0° C., to the mixture were added 0.4 mL of water, 0.4 mL of 15% solution of sodium hydroxide, and 1.2 mL of water in sequence. After stirring for 10 minutes, the mixture was filtered. The filtrate was evaporated to dryness to give 360 mg of a brown oil with a crude yield of 78%. LCMS: m/z=152.1 (M+H)+.

Preparation of Intermediate 30
(2-methylpyridin-3-yl)methylamine

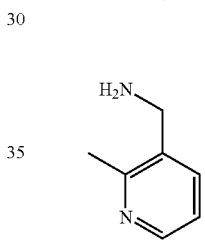

2-Methylnicotinamide (200 mg, 1.47 mmol) was dissolved in anhydrous tetrahydrofuran (5 mL). To the mixture was added a solution of borane in tetrahydrofuran (1M, 7.4 mL, 7.4 mmol) dropwise at 0° C. under argon. After 30 minutes of reaction, the temperature was heated to 60° C. and the mixture was reacted for 8 hours. The reaction was quenched with saturated aqueous solution of ammonium chloride, extracted with ethyl acetate, dried over anhydrous sodium sulfate, and filtered. The filtrate was evaporated to dryness to give 200 mg of a colorless oil. The crude product was used directly in the next reaction. LCMS: m/z=123.1 (M+H)+.

Preparation of Intermediate 31
[3-(dimethylcarbamoyl)benzyl]amine hydrochloride

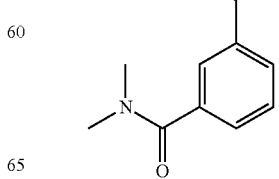

3-(((Tert-butoxycarbonyl)amino)methyl)benzoic acid (400 mg, 1.59 mmol) was dissolved in tetrahydrofuran (5 mL). To the mixture was added carbonyldiimidazole (337 mg, 2.39 mmol). After stirring for 3 hours, to the mixture was added a solution of dimethylamine in tetrahydrofuran (2 M, 3.2 mL, 6.4 mmol) dropwise. The tube was sealed and the mixture was reacted at 60° C. for 16 hours. The reaction solution was concentrated and subjected to column chromatography (petroleum ether:ethyl acetate=1:1). To the obtained white solid, a solution of hydrogen chloride in dioxane (4 M, 4 mL) was added. After stirring at 25° C. for 2 hours, the reaction solution was evaporated to dryness to give 263 mg of a white solid with a yield of 77%. LCMS: m/z=179.1 (M+H)$^+$.

EXAMPLES

Example 1 Preparation of 4-benzylamino-2-((1-methyl-1H-pyrazol-4-yl)amino)pyrimidin-5-carboxamide

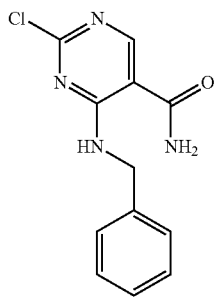 [SMILES: NC(=O)c1cnc(Cl)nc1NCc1ccccc1]

Step 1): Preparation of 2-chloro-4-(benzylamino)pyrimidin-5-carboxamide 2,4-Dichloropyrimidin-5-carboxamide (2 g, 10.42 mmol) was dissolved in tetrahydrofuran (20 mL). To the mixture were added benzylamine (1.12 g, 10.45 mmol) and diisopropylethylamine (4 g, 31.01 mmol), and reacted at 25° C. for 2 hours. To the mixture was added saturated brine (200 mL), stirred for 15 minutes, and then filtered. The filter cake was washed with petroleum ether to give 2.1 g of a white solid with a yield of 77%. $^1$H NMR (400 MHz, DMSO-d$_6$+ DCl/D$_2$O) δ 8.84 (s, 1H), 7.48-7.33 (m, 5H), 4.82 (s, 2H). LCMS: m/z=263.1 (M+H)$^+$.

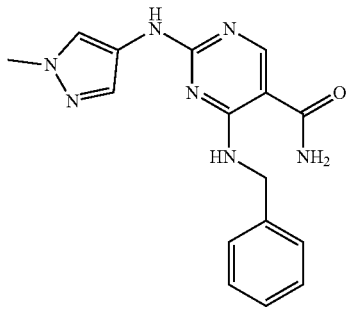 [SMILES: Cn1cc(Nc2ncc(C(N)=O)c(NCc3ccccc3)n2)cn1]

Step 2): Preparation of 4-benzylamino-2-((1-methyl-1H-pyrazol-4-yl)amino)pyrimidin-5-carboxamide 2-Chloro-4-(benzylamino)pyrimidin-5-carboxamide (100 mg, 0.38 mmol) was dissolved in sec-butanol (3 mL). To the mixture were added 1-methyl-1H-pyrazol-4-amine (40 mg, 0.41 mmol) and trifluoroacetic acid (0.1 mL). The tube was sealed and the mixture was reacted at 100° C. for 2 hours. The reaction solution was concentrated, and filtered. The solid was washed with acetonitrile to give 50 mg of a white solid with a yield of 41%. $^1$H NMR (300 MHz, DMSO-d$_6$+ DCl/D$_2$O) δ 8.75 (s, 1H), 7.73 (s, 1H), 7.55 (s, 1H), 7.42-7.36 (m, 5H), 4.79 (s, 2H), 3.79 (s, 3H). LCMS: m/z=324.1 (M+H)$^+$.

Example 2 Preparation of 4-((2-methoxybenzyl)amino)-2-((1-methyl-1H-pyrazol-4-yl)amino)pyrimidin-5-carboxamide

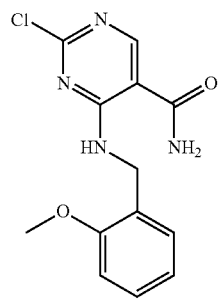 [SMILES: COc1ccccc1CNc1nc(Cl)ncc1C(N)=O]

Step 1): Preparation of 2-chloro-4-((2-methoxybenzyl)amino)pyrimidin-5-carboxamide 2,4-Dichloropyrimidin-5-carboxamide (80 mg, 0.42 mmol) was dissolved in tetrahydrofuran (3 mL). To the mixture were added 2-methoxybenzylamine (57 mg, 0.42 mmol) and diisopropylethylamine (161 mg, 1.25 mmol), respectively, and reacted at 25° C. for 2 hours. To the mixture was added saturated brine (30 mL), stirred for 15 minutes and then filtered. The filter cake was washed with petroleum ether to give 116 mg of a white solid with a yield of 95%. $^1$H NMR (400 MHz, DMSO-d$_6$+DCl/D$_2$O) δ 8.84 (s, 1H), 7.42-7.35 (m, 2H), 7.11 (d, J=8.2 Hz, 1H), 7.04-6.96 (m, 1H), 4.79 (s, 2H), 3.86 (s, 3H); $^{13}$C NMR (101 MHz, DMSO-d$_6$+DCl/D$_2$O) δ 166.77, 157.63, 156.84, 148.52, 147.71, 130.55, 129.68, 122.97, 121.08, 111.64, 96.61, 56.12, 42.39. LCMS: m/z=293.1 (M+H)$^+$.

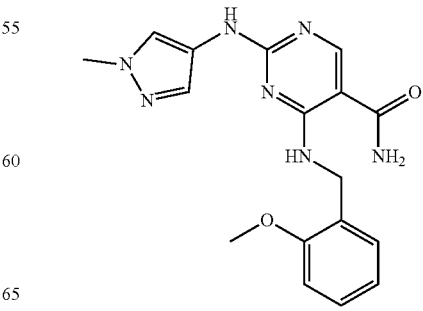

Step 2): Preparation of 4-((2-methoxybenzyl)amino)-2-((1-methyl-1H-pyrazol-4-yl)amino)pyrimidin-5-carboxamide 2-Chloro-4-((2-methoxybenzyl)amino)pyrimidin-5-carboxamide (116 mg, 0.40 mmol) was dissolved in sec-butanol (3 mL). To the mixture were added 1-methyl-1H-pyrazol-4-amine (39 mg, 0.40 mmol) and trifluoroacetic acid (0.1 mL). The tube was sealed and the mixture was reacted at 100° C. for 2 hours. The reaction solution was concentrated and subjected to column chromatography (dichloromethane: methanol=95:5). The crude product was washed with acetonitrile to give 15 mg of a white solid with a yield of 11%. $^1$H NMR (400 MHz, DMSO-d$_6$+DCl/D$_2$O) δ 8.68 (s, 1H), 7.68 (s, 1H), 7.50 (s, 1H), 7.32-7.22 (m, 1H), 7.11 (d, J=7.4 Hz, 1H), 7.05 (d, J=8.2 Hz, 1H), 6.95-6.82 (m, 1H), 4.66 (s, 2H), 3.83 (s, 3H), 3.75 (s, 3H). $^{13}$C NMR (101 MHz, DMSO-d$_6$+DCl/D$_2$O) δ 166.86, 161.02, 157.36, 149.69, 144.70, 131.25, 129.45, 128.42, 124.82, 123.12, 120.85, 119.52, 111.38, 100.76, 56.01, 40.98, 39.31. LCMS: m/z=354.2 (M+H)$^+$.

Example 3 Preparation of 4-((2-fluoro-6-methoxybenzyl)amino)-2-((1-methyl-1H-pyrazol-4-yl)amino)pyrimidin-5-carboxamide

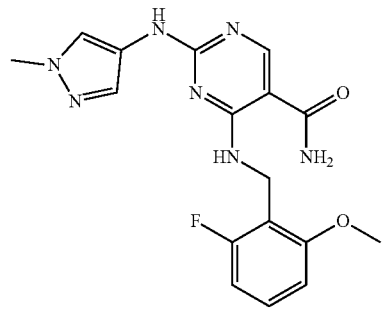

Step 2): Preparation of 4-((2-fluoro-6-methoxybenzyl)amino)-2-((1-methyl-1H-pyrazol-4-yl)amino)pyrimidin-5-carboxamide 2-Chloro-4-((2-fluoro-6-methoxybenzyl)amino)pyrimidin-5-carboxamide (75 mg, 0.24 mmol) was dissolved in sec-butanol (3 mL). To the mixture were added 1-methyl-1H-pyrazol-4-amine (27 mg, 0.28 mmol) and trifluoroacetic acid (0.1 mL). The tube was sealed and the mixture was reacted at 100° C. for 2 hours. The reaction solution was concentrated and filtered. The filter cake was washed with acetonitrile to give 65 mg of a white solid with a yield of 73%. $^1$H NMR (400 MHz, DMSO-d$_6$+DCl/D$_2$O) δ 8.72 (s, 1H), 8.03 (s, 1H), 7.75 (s, 1H), 7.45-7.34 (m, 1H), 7.03-6.93 (m, 1H), 6.93-6.83 (m, 1H), 4.83 (s, 2H), 3.89 (s, 3H), 3.88 (s, 3H). LCMS: m/z=372.2 (M+H)$^+$.

Example 4 Preparation of 4-((2,6-dimethylbenzyl)amino)-2-((1-methyl-1H-pyrazol-4-yl)amino)pyrimidin-5-carboxamide

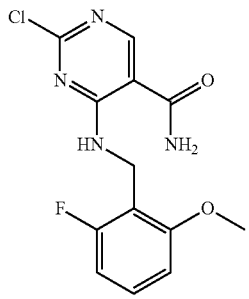 [SMILES: COc1cccc(F)c1CNc1nc(Cl)ncc1C(N)=O]

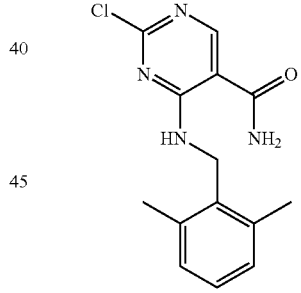

Step 1): Preparation of 2-chloro-4-((2-fluoro-6-methoxybenzyl)amino)pyrimidin-5-carboxamide 2,4-Dichloropyrimidin-5-carboxamide (210 mg, 1.09 mmol) was dissolved in tetrahydrofuran (8 mL). To the mixture were added (2-fluoro-6-methoxyphenyl)methylamine (170 mg, 1.09 mmol) and diisopropylethylamine (423 mg, 3.27 mmol), respectively, and reacted at 25° C. for 2 hours. To the mixture was added saturated brine (60 mL), stirred for 15 minutes and then filtered. The filter cake was washed with petroleum ether to give 75 mg of a white solid with a yield of 66%. $^1$H NMR (400 MHz, DMSO-d$_6$+DCl/D$_2$O) δ 8.82 (s, 1H), 7.50-7.40 (m, 1H), 7.03-6.96 (m, 1H), 6.95-6.87 (m, 1H), 4.77 (s, 2H), 3.88 (s, 3H). LCMS: m/z=311.1 (M+H)$^+$.

Step 1): Preparation of 2-chloro-4-((2,6-dimethylbenzyl)amino)pyrimidin-5-carboxamide 2,4-Dichloropyrimidin-5-carboxamide (70 mg, 0.36 mmol) was dissolved in tetrahydrofuran (4 mL). To the mixture were added (2,6-dimethylphenyl)methylamine (50 mg, 0.37 mmol) and diisopropylethylamine (141 mg, 1.09 mmol), and reacted at 25° C. for 2 hours. To the mixture was added saturated brine (30 mL), stirred for 15 minutes and then filtered. The filter cake was washed with petroleum ether to give 73 mg of a white solid with a yield of 69%. $^1$H NMR (400 MHz, DMSO-d$_6$+DCl/D$_2$O) δ 8.88 (s, 1H), 7.31-7.18 (m, 1H), 7.18-7.06 (m, 2H), 4.73 (s, 2H) 2.34 (s, 6H); $^{13}$C NMR (101 MHz, DMSO-d$_6$+DCl/D$_2$O) δ 166.98, 157.34, 148.46, 147.77, 137.93, 131.33, 129.36, 129.10, 96.61, 41.68, 19.77. LCMS: m/z=291.1 (M+H)$^+$.

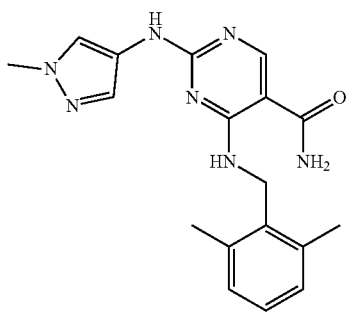

Step 2): Preparation of 4-((2,6-dimethylbenzyl)amino)-2-((1-methyl-1H-pyrazol-4-yl)amino)pyrimidin-5-carboxamide 2-Chloro-4-((2,6-dimethylbenzyl)amino)pyrimidin-5-carboxamide (73 mg, 0.25 mmol) was dissolved in sec-butanol (3 mL). To the mixture were added 1-methyl-1H-pyrazol-4-amine (30 mg, 0.31 mmol) and trifluoroacetic acid (0.1 mL). The tube was sealed and the mixture was reacted at 100° C. for 2 hours. The reaction solution was concentrated and filtered. The filter cake was washed with acetonitrile to give 50 mg of a white solid with a yield of 57%. $^1$H NMR (400 MHz, DMSO-$d_6$+DCl/$D_2$O) δ 8.76 (s, 1H), 8.08 (s, 1H), 7.75 (s, 1H), 7.18 (dd, J=8.6, 6.3 Hz, 1H), 7.14-7.08 (m, 2H), 4.74 (s, 2H), 3.90 (s, 3H), 2.32 (s, 6H). LCMS: m/z=352.2 (M+H)$^+$.

Example 5 Preparation of 4-((2,6-dichlorobenzyl)amino)-2-((1-methyl-1H-pyrazol-4-yl)amino)pyrimidin-5-carboxamide

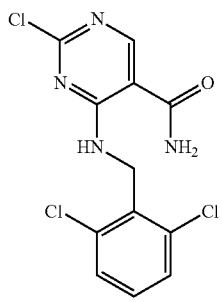 [SMILES: NC(=O)c1cnc(Cl)nc1NCc1c(Cl)cccc1Cl]

Step 1): 2-chloro-4-((2,6-dichlorobenzyl)amino)pyrimidin-5-carboxamide 2,4-Dichloropyrimidin-5-carboxamide (70 mg, 0.36 mmol) was dissolved in tetrahydrofuran (4 mL). To the mixture were added (2,6-dichlorophenyl)methylamine (64 mg, 0.36 mmol) and diisopropylethylamine (141 mg, 1.09 mmol), and reacted at 25° C. for 2 hours. To the mixture was added saturated brine (40 mL), stirred for 15 minutes and then filtered. The filter cake was washed with petroleum ether to give 110 mg of a white solid with a yield of 91%. $^1$H NMR (400 MHz, DMSO-$d_6$+DCl/$D_2$O) δ 8.93 (s, 1H), 7.67-7.60 (m, 2H), 7.60-7.50 (m, 1H), 5.03 (s, 2H). $^{13}$C NMR (101 MHz, DMSO-$d_6$+DCl/$D_2$O) δ 167.05, 157.86, 149.16, 147.94, 135.98, 132.68, 130.34, 129.74, 96.46, 42.77. LCMS: m/z=331.0 (M+H)$^+$.

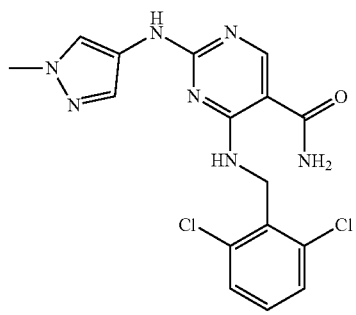 [SMILES: Cn1cc(Nc2ncc(C(N)=O)c(NCc3c(Cl)cccc3Cl)n2)cn1]

Step 2): Preparation of 4-((2,6-dichlorobenzyl)amino)-2-((1-methyl-1H-pyrazol-4-yl)amino)pyrimidin-5-carboxamide 2-Chloro-4-((2,6-dichlorobenzyl)amino)pyrimidin-5-carboxamide (112 mg, 0.34 mmol) was dissolved in sec-butanol (3 mL). To the mixture were added 1-methyl-1H-pyrazol-4-amine (40 mg, 0.41 mmol) and trifluoroacetic acid (0.1 mL). The tube was sealed and the mixture was reacted at 100° C. for 2 hours. The reaction solution was concentrated and then filtered. The filter cake was washed with acetonitrile to give 110 mg of a white solid with a yield of 83%. $^1$H NMR (400 MHz, DMSO-$d_6$+DCl/$D_2$O) δ 8.80 (s, 1H), 8.07 (s, 1H), 7.74 (s, 1H), 7.66-7.55 (m, 2H), 7.53-7.41 (m, 1H), 5.03 (s, 2H), 3.89 (s, 3H). LCMS: m/z=392.1 (M+H)$^+$.

Example 6 Preparation of 4-((2,6-difluorobenzyl)amino)-2-((1-(2-methoxyethyl)-1H-pyrazol-4-yl)amino)pyrimidin-5-carboxamide

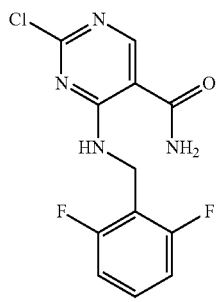 [SMILES: NC(=O)c1cnc(Cl)nc1NCc1c(F)cccc1F]

Step 1): Preparation of 2-chloro-4-((2,6-difluorobenzyl)amino)pyrimidin-5-carboxamide 2,4-Dichloropyrimidin-5-carboxamide (210 mg, 1.09 mmol) was dissolved in tetrahydrofuran (8 mL). To the mixture were added (2,6-difluorophenyl)methylamine (156 mg, 1.09 mmol) and diisopropylethylamine (423 mg, 3.27 mmol), respectively, and reacted at 25° C. for 2 hours. To the mixture was added saturated brine (80 mL), stirred for 15 minutes and then filtered. The filter cake was washed with petroleum ether to give 285 mg of a white solid with a yield of 87%. $^1$H NMR (400 MHz, DMSO-$d_6$+DCl/$D_2$O) δ 8.90 (s, 1H), 7.72-7.38 (m, 1H), 7.38-7.08 (m, 2H), 4.93 (s, 2H). LCMS: m/z=299.0 (M+H)$^+$.

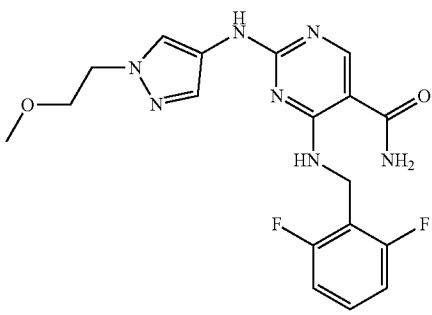 [SMILES: COCCn1cc(Nc2ncc(C(N)=O)c(NCc3c(F)cccc3F)n2)cn1]

Step 2): Preparation of 4-((2,6-difluorobenzyl)amino)-2-((1-(2-methoxyethyl)-1H-pyrazol-4-yl)amino)pyrimidin-5-carboxamide 2-Chloro-4-((2,6-difluorobenzyl)amino)pyrimidin-5-carboxamide (94 mg, 0.31) was dissolved in sec-butanol (3 mL). To the mixture were added 1-(2-methoxyethyl)-1H-pyrazol-4-amine (53 mg, 0.38 mmol) and trifluoroacetic acid (0.1 mL). The tube was sealed and the mixture was reacted at 100° C. for 2 hours. The reaction solution was concentrated and then filtered. The filter cake was washed with acetonitrile to give 80 mg of a white solid with a yield of 63%. $^1$H NMR (400 MHz, DMSO-d$_6$+DCl/D$_2$O) δ 8.78 (s, 1H), 8.09 (s, 1H), 7.75 (s, 1H), 7.58-7.39 (m, 1H), 7.19-7.14 (m, 2H), 4.90 (s, 2H), 4.32 (t, J=5.1 Hz, 2H), 3.70 (t, J=5.1 Hz, 2H), 3.21 (s, 3H). LCMS: m/z=404.2 (M+H)$^+$.

Example 7 Preparation of 4-((2-fluoro-6-methoxybenzyl)amino)-2-((1-(2-methoxyethyl)-1H-pyrazol-4-yl)amino)pyrimidin-5-carboxamide

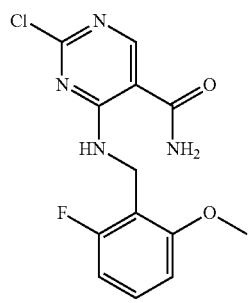 [SMILES: COc1cccc(F)c1CNc1nc(Cl)ncc1C(N)=O]

Step 1): Preparation of 2-chloro-4-((2-fluoro-6-methoxybenzyl)amino)pyrimidin-5-carboxamide 2,4-Dichloropyrimidin-5-carboxamide (210 mg, 1.09 mmol) was dissolved in tetrahydrofuran (8 mL). To the mixture were added (2-fluoro-6-methoxyphenyl)methylamine (170 mg, 1.09 mmol) and diisopropylethylamine (423 mg, 3.27 mmol), respectively, and reacted at 25° C. for 2 hours. To the mixture was added saturated brine (60 mL), stirred for 15 minutes and then filtered. The filter cake was washed with petroleum ether to give 75 mg of a white solid with a yield of 66%. $^1$H NMR (400 MHz, DMSO-d$_6$+DCl/D$_2$O) δ 8.82 (s, 1H), 7.50-7.40 (m, 1H), 7.03-6.96 (m, 1H), 6.95-6.87 (m, 1H), 4.77 (s, 2H), 3.88 (s, 3H). LCMS: m/z=311.1 (M+H)$^+$.

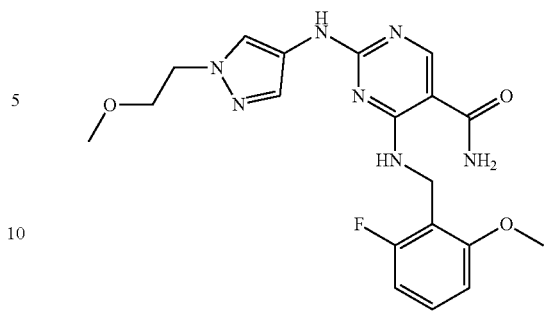

Step 2): Preparation of 4-((2-fluoro-6-methoxybenzyl)amino)-2-((1-(2-methoxyethyl)-1H-pyrazol-4-yl)amino)pyrimidin-5-carboxamide 2-Chloro-4-((2-fluoro-6-methoxybenzyl)amino)pyrimidin-5-carboxamide (118 mg, 0.38 mmol) was dissolved in sec-butanol (3 mL). To the mixture were added 1-(2-methoxyethyl)-1H-pyrazol-4-amine (64 mg, 0.45 mmol) and trifluoroacetic acid (0.1 mL). The tube was sealed and the mixture was reacted at 100° C. for 2 hours. The reaction solution was concentrated, filtered, and washed with acetonitrile to give 100 mg of a white solid with a yield of 63%. $^1$H NMR (400 MHz, DMSO-d$_6$+DCl/D$_2$O) δ 8.75 (s, 1H), 8.12 (s, 1H), 7.82 (s, 1H), 7.53-7.33 (m, 1H), 6.98 (d, J=8.4 Hz, 1H), 6.95-6.73 (m, 1H), 4.83 (s, 2H), 4.32 (t, J=5.1 Hz, 2H), 3.89 (s, 3H), 3.70 (t, J=5.1 Hz, 2H), 3.21 (s, 3H). LCMS: m/z=416.2 (M+H)$^+$.

Example 8 Preparation of 4-((5-hydroxypentyl)amino)-2-((1-methyl-1H-pyrazol-4-yl)amino)pyrimidin-5-carboxamide

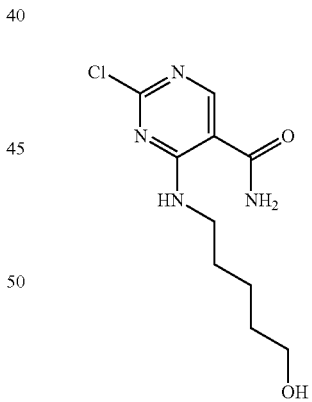

Step 1): Preparation of 2-chloro-4-((2-fluoro-6-methoxybenzyl)amino)pyrimidin-5-carboxamide 2,4-Dichloropyrimidin-5-carboxamide (100 mg, 0.52 mmol) was dissolved in tetrahydrofuran (4 mL). To the mixture were added 5-amino-1-pentanol (54 mg, 0.52 mmol) and disopropylethylamine (202 mg, 1.56 mmol), respectively, and reacted at 25° C. for 2 hours. To the mixture was added saturated brine (40 mL). After stirring for 15 minutes, the solid was filtered. The filter cake was washed with petroleum ether to five 80 mg of a white solid with a yield of 59%. LCMS: m/z=259.1 (M+H)$^+$.

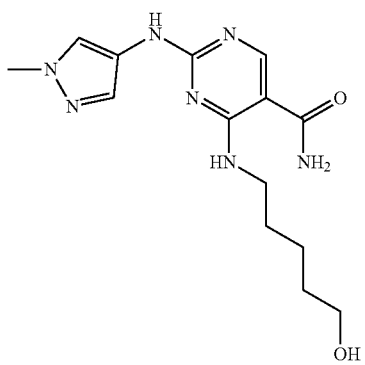 [SMILES: Cn1cc(Nc2ncc(C(N)=O)c(NCCCCCO)n2)cn1]

Step 2): Preparation of 4-((5-hydroxypentyl)amino)-2-((1-methyl-1H-pyrazol-4-yl)amino)pyrimidin-5-carboxamide 2-Chloro-4-((5-hydroxypentyl)amino)pyrimidin-5-carboxamide (80 mg, 0.31 mmol) was dissolved in sec-butanol (3 mL). To the mixture were added 1-methyl-1H-pyrazol-4-amine (37 mg, 0.38 mmol) and trifluoroacetic acid (0.1 mL). The tube was sealed and the mixture was reacted at 100° C. for 2 hours. The reaction solution was concentrated and filtered. The filter cake was washed with acetonitrile to give 70 mg of a white solid with a yield of 71%. $^1$H NMR (400 MHz, DMSO-d$_6$+DCl/D$_2$O) δ 8.68 (s, 1H), 7.96 (s, 1H), 7.68 (s, 1H), 3.87 (s, 3H), 3.60-3.47 (m, 2H), 3.39 (t, J=6.3 Hz, 2H), 1.69-1.54 (m, 2H), 1.51-1.40 (m, 2H), 1.40-1.29 (m, 2H). LCMS: m/z=320.2 (M+H)$^+$.

Example 9 Preparation of 4-((5-methoxypentyl)amino)-2-((1-methyl-1H-pyrazol-4-yl)amino)pyrimidin-5-carboxamide Step 1) and Step 2) are similar to those in Example 8

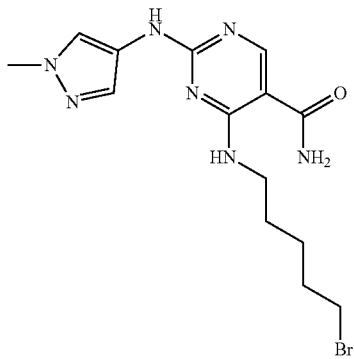 [SMILES: Cn1cc(Nc2ncc(C(N)=O)c(NCCCCCBr)n2)cn1]

Step 3): Preparation of 4-((5-bromopentyl)amino)-2-((1-methyl-1H-pyrazol-4-yl)amino)pyrimidin-5-carboxamide 4-((5-Hydroxypentyl)amino)-2-((1-methyl-1H-pyrazol-4-yl)amino)pyrimidin-5-carboxamide (60 mg, 0.19 mmol) was dissolved in anhydrous dichloromethane (4 mL). To the mixture were added carbon tetrabromide (187 mg, 0.56 mmol) and triphenylphosphine (148 mg, 0.56 mmol) in sequence at 0° C. under argon protection. The temperature was warmed to 25° C. and the mixture was reacted for 2 hours. The reaction solution was quenched with methanol, evaporated to dryness, and subjected to column chromatography (dichloromethane:methanol=10:1) to give 70 mg of a pale yellow solid with a yield of 95%. LCMS: m/z=382.1 (M+H)$^+$.

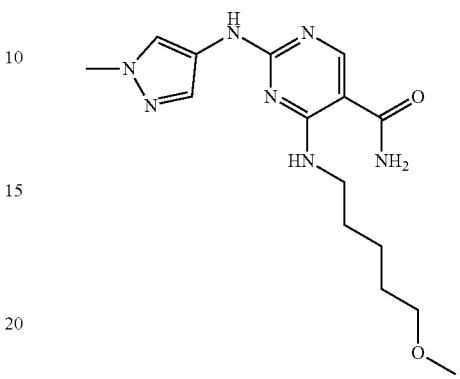

Step 4): Preparation of 4-((5-methoxypentyl)amino)-2-((1-methyl-1H-pyrazol-4-yl)amino)pyrimidin-5-carboxamide 4-((5-Bromopentyl)amino)-2-((1-methyl-1H-pyrazol-4-yl)amino)pyrimidin-5-carboxamide (70 mg, 0.18 mmol) was dissolved in a solution of sodium methoxide in methanol (33%, 7 mL), and reacted at 25° C. for 16 hours. The reaction solution was quenched with saturated brine, extracted with ethyl acetate, dried over anhydrous sodium sulfate, and filtered. The filtrate was evaporated to dryness and subjected to reversed-phase column chromatography (water:methanol=7:3). The crude product was washed with acetonitrile to give 35 mg of a white solid with a yield of 57%. $^1$H NMR (400 MHz, DMSO-d$_6$+DCl/D$_2$O) δ 8.69 (s, 1H), 8.02 (s, 1H), 7.76 (s, 1H), 3.90 (s, 3H), 3.53 (t, J=6.7 Hz, 2H), 3.31 (t, J=6.1 Hz, 2H), 3.20 (s, 3H), 1.69-1.57 (m, 2H), 1.57-1.44 (m, 2H), 1.44-1.30 (m, 2H). LCMS: m/z=334.2 (M+H)$^+$.

Example 10 Preparation of 4-((3-hydroxy-3-methylbutyl)amino)-2-((1-methyl-1H-pyrazol-4-yl)amino)pyrimidin-5-carboxamide

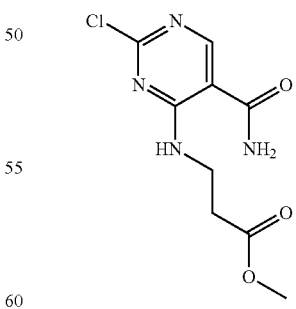

Step 1): Preparation of methyl 3-((5-carbamoyl-2-chloropyrimidin-4-yl)amino)propanoate 2,4-Dichloropyrimidine-5-carboxamide (100 mg, 0.52 mmol) was dissolved in tetrahydrofuran (4 mL). To the mixture were added methyl aminopropionate hydrochloride (73 mg, 0.52 mmol) and diisopropylethylamine (202 mg, 1.56 mmol), respectively, and reacted at 25° C. for 2 hours. To the mixture was added saturated brine (40 mL), stirred for 15 minutes, and then filtered. The filter cake was washed with petroleum ether to give 90 mg of a white solid with a yield of 67%. LCMS: m/z=259.1 (M+H)+.

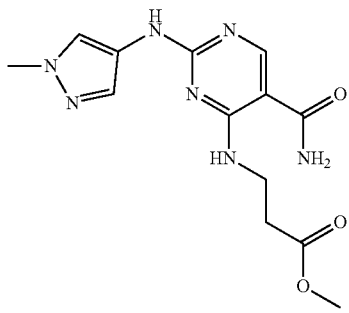 [SMILES: COC(=O)CCNc1nc(Nc2cnn(C)c2)ncc1C(N)=O]

Step 2): Preparation of methyl 3-((5-carbamoyl-2-((1-methyl-1H-pyrazol-4-yl)amino)pyrimidin-4-yl)amino)propanoate Methyl 3-((5-carbamoyl-2-chloropyrimidin-4-yl)amino)propanoate (90 mg, 0.35 mmol) was dissolved in sec-butanol (3 mL). To the mixture were added 1-methyl-1H-pyrazol-4-amine (41 mg, 0.42 mmol) and trifluoroacetic acid (0.1 mL). The tube was sealed and the mixture was reacted at 100° C. for 2 hours. The reaction solution was concentrated. The solid was filtered, and washed with acetonitrile to give 80 mg of a white solid with a yield of 72%. LCMS: m/z=320.1 (M+H)+.

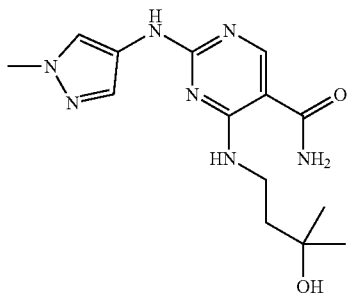 [SMILES: Cn1cc(Nc2ncc(C(N)=O)c(NCCC(C)(C)O)n2)cn1]

Step 3): Preparation of 4-((3-hydroxy-3-methylbutyl)amino)-2-((1-methyl-1H-pyrazol-4-yl)amino)pyrimidin-5-carboxamide Methyl 3-((5-carbamoyl-2-((1-methyl-1H-pyrazol-4-yl)amino)pyrimidin-4-yl)amino)propanoate (80 mg, 0.25 mmol) was dissolved in anhydrous tetrahydrofuran (2 mL). To the mixture was added methyl Grignard reagent (1 M, 0.75 mL, 0.75 mmol) dropwise at 0° C. under argon protection, and reacted at 25° C. for 16 hours. The reaction solution was quenched with saturated aqueous solution of ammonium chloride, extracted with ethyl acetate, washed with saturated brine, dried over anhydrous sodium sulfate, and filtered. The filtrate was evaporated to dryness and subjected to thin layer chromatography (dichloromethane:methanol=10:1). The crude product was washed with acetonitrile to give 15 mg of a white solid with a yield of 19%. 1H NMR (400 MHz, DMSO-d6+DCl/D2O) δ 8.57 (s, 1H), 8.01 (s, 1H), 7.62 (s, 1H), 3.78 (s, 3H), 3.63-3.47 (m, 2H), 1.71-1.56 (m, 2H), 1.08 (s, 6H). LCMS: m/z=320.2 (M+H)+.

Example 11 Preparation of 4-(((1-acetylpiperidin-4-yl)methyl)amino)-2-((1-methyl-1H-pyrazol-4-yl)amino)pyrimidin-5-carboxamide

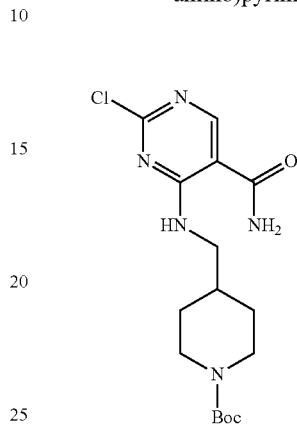

Step 1): Preparation of tert-butyl 4-(((5-carbamoyl-2-chloropyrimidin-4-yl)amino)methyl)piperidin-1-carboxylate 2,4-Dichloropyrimidin-5-carboxamide (100 mg, 0.52 mmol) was dissolved in tetrahydrofuran (4 mL). To the mixture were added tert-butyl 4-(aminomethyl)piperidin-1-carboxylate (112 mg, 0.52 mmol) and diisopropylethylamine (202 mg, 1.57 mmol), and reacted at 25° C. for 2 hours. To the mixture was added saturated brine (40 mL), stirred for 15 minutes and then filtered. The filter cake was washed with petroleum ether to give 150 mg of a white solid with a yield of 79%. LCMS: m/z=370.2 (M+H)+.

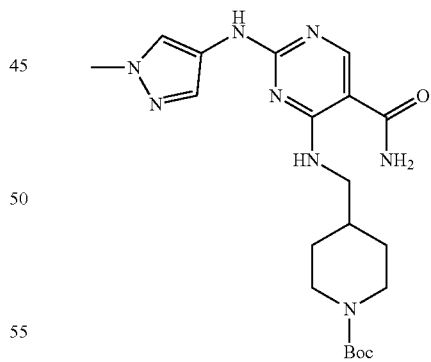

Step 2): Preparation of tert-butyl 4-(((5-carbamoyl-2-((1-methyl-1H-pyrazol-4-yl)amino)pyrimidin-4-yl)amino)methyl)piperidin-1-carboxylate Tert-butyl 4-(((5-carbamoyl-2-chloropyrimidin-4-yl)amino)methyl)piperidin-1-carboxylate (150 mg, 0.41 mmol) was dissolved in sec-butanol (3 mL). To the mixture were added 1-methyl-1H-pyrazol-4-amine (48 mg, 0.49 mmol) and trifluoroacetic acid (0.1 mL). The tube was sealed and the mixture was reacted at 100° C. for 2 hours. The reaction solution was concentrated and filtered. The filter cake was washed with petroleum ether to give 115 mg of a white solid with a yield of 66%. LCMS: m/z=431.2 (M+H)⁺.

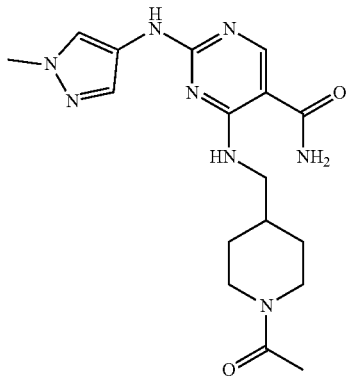 [SMILES: CC(=O)N1CCC(CNc2nc(Nc3cnn(C)c3)ncc2C(N)=O)CC1]

Step 3): Preparation of 4-(((1-acetylpiperidin-4-yl)methyl)amino)-2-((1-methyl-1H-pyrazol-4-yl)amino)pyrimidin-5-carboxamide Tert-butyl 4-(((5-carbamoyl-2-((1-methyl-1H-pyrazol-4-yl)amino)pyrimidin-4-yl)amino)methyl)piperidin-1-carboxylate (115 mg, 0.27 mmol) was dissolved in dichloromethane (3 mL). To the mixture was added slowly trifluoroacetic acid (1 mL) dropwise, and stirred at 25° C. for 2 hours. The reaction solution was evaporated to dryness. The crude product was dissolved in dichloromethane (4 mL). At 0° C. under argon protection, triethylamine (160 mg, 1.58 mmol) was added, and stirred for 2 minutes. Acetyl chloride (63 mg, 0.80 mmol) was then added dropwise, and reacted at 25° C. for 2 hours. The reaction solution was concentrated and subjected to thin layer chromatography (dichloromethane:methanol=10:1) to give 30 mg of a white solid with a two-step yield of 30%. ¹H NMR (400 MHz, DMSO-d₆+DCl/D₂O) δ 8.72 (s, 1H), 8.02 (s, 1H), 7.75 (s, 1H), 4.47-4.25 (m, 1H), 3.90 (s, 3H), 3.48 (d, J=6.7 Hz, 2H), 3.17-3.02 (m, 1H), 2.54 (s, 3H), 2.13-2.07 (m, 2H), 2.04-1.89 (m, 1H), 1.80-1.63 (m, 2H), 1.32-1.05 (m, 2H). LCMS: m/z=373.2 (M+H)⁺.

Example 12 Preparation of 4-((2-(1-acetylpiperidin-4-yl)ethyl)amino)-2-((1-methyl-1H-pyrazol-4-yl)amino)pyrimidin-5-carboxamide

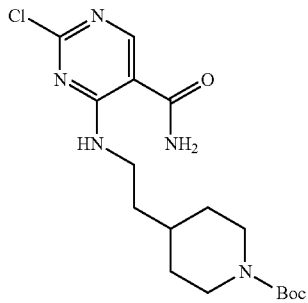 [SMILES: CC(C)(C)OC(=O)N1CCC(CCNc2nc(Cl)ncc2C(N)=O)CC1]

Step 1): Preparation of tert-butyl 4-(2-((5-carbamoyl-2-chloropyrimidin-4-yl)amino)ethyl)piperidin-1-carboxylate 2,4-Dichloropyrimidin-5-carboxamide (200 mg, 1.04 mmol) was dissolved in tetrahydrofuran (5 mL). To the mixture were added tert-butyl 4-(2-aminoethyl)piperidin-1-carboxylate (238 mg, 1.04 mmol) and diisopropylethylamine (404 mg, 3.13 mmol), respectively, and reacted at 25° C. for 2 hours. To the mixture was added saturated brine (50 mL), stirred for 15 minutes and then filtered. The filter cake was washed with petroleum ether to give 270 mg of a white solid with a yield of 68%. LCMS: m/z=384.2 (M+H)⁺.

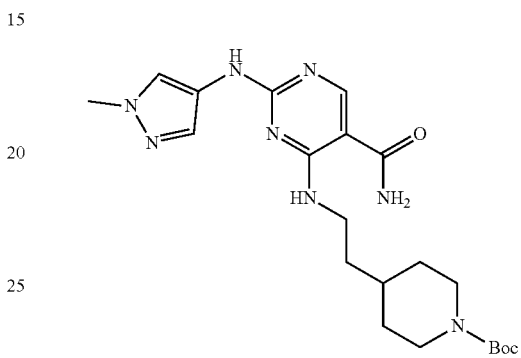

Step 2): Preparation of tert-butyl 4-(2-((5-carbamoyl-2-((1-methyl-1H-pyrazol-4-yl)amino)pyrimidin-4-yl)amino)ethyl)piperidin-1-carboxylate Tert-butyl 4-(2-((5-carbamoyl-2-chloropyrimidin-4-yl)amino)ethyl)piperidin-1-carboxylate (270 mg, 0.70 mmol) was dissolved in sec-butanol (3 mL). To the mixture were added 1-methyl-1H-pyrazol-4-amine (83 mg, 0.85 mmol) and trifluoroacetic acid (0.1 mL). The tube was sealed and the mixture was reacted at 100° C. for 2 hours. The reaction solution was concentrated. The solid was filtered and washed with acetonitrile to give 170 mg of a white solid with a yield of 54%. LCMS: m/z=445.3 (M+H)⁺.

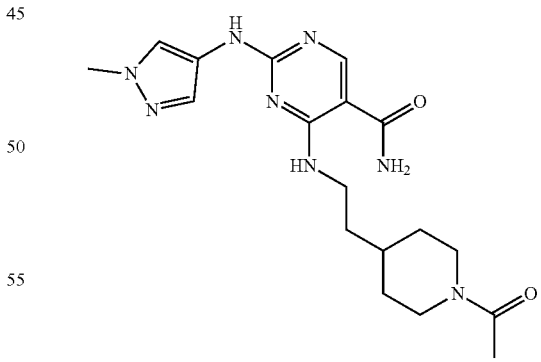

Step 3): Preparation of 4-((2-(1-acetylpiperidin-4-yl)ethyl)amino)-2-((1-methyl-1H-pyrazol-4-yl)amino)pyrimidin-5-carboxamide Tert-butyl 4-(2-((5-carbamoyl-2-((1-methyl-1H-pyrazol-4-yl)amino)pyrimidin-4-yl)amino)ethyl)piperidin-1-carboxylate (170 mg, 0.38 mmol) was dissolved in dichloromethane (6 mL). To the mixture was added slowly trifluoroacetic acid (2 mL) dropwise, and stirred at 25° C. for 2 hours. The reaction solution was evaporated to dryness. The crude product was dissolved in dichloromethane (6 mL). At 0° C. under argon protection, triethylamine (176 mg, 1.36 mmol) was added, and stirred for 2 minutes. Acetyl chloride (69 mg, 0.88 mmol) was then added, and reacted at 25° C. for 2 hours. The reaction solution was concentrated and subjected to thin layer chromatography (dichloromethane:methanol=10:1) to give 10 mg of a pale yellow solid with a two-step yield of 7%. $^1$H NMR (400 MHz, DMSO-$d_6$+DCl/$D_2O$) δ 8.58 (s, 1H), 7.90 (s, 1H), 7.63 (s, 1H), 4.34-4.08 (m, 1H), 3.79 (s, 3H), 3.77-3.64 (m, 1H), 3.53-3.37 (m, 2H), 3.04-2.83 (m, 1H), 2.45-2.38 (m, 1H), 1.98 (s, 3H), 1.69-1.55 (m, 2H), 1.52-1.37 (m, 3H), 1.11-0.79 (m, 2H). LCMS: m/z=387.2 (M+H)$^+$.

Example 13 Preparation of 4-((4-amino-2-fluorobenzyl)amino)-2-((1-methyl-1H-pyrazol-4-yl)amino)pyrimidin-5-carboxamide

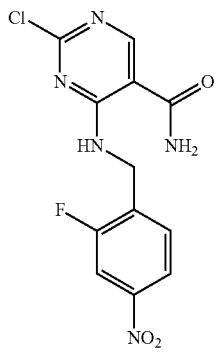 [SMILES: NC(=O)c1cnc(Cl)nc1NCc1ccc([N+](=O)[O-])cc1F]

Step 1): Preparation of 2-chloro-4-((2-fluoro-4-nitrobenzyl)amino)pyrimidin-5-carboxamide 2,4-Dichloropyrimidin-5-carboxamide (100 mg, 0.52 mmol) was dissolved in tetrahydrofuran (4 mL). To the mixture were added (2-fluoro-4-nitrophenyl)methylamine hydrochloride (108 mg, 0.52 mmol) and diisopropylethylamine hydrochloride (202 mg, 1.57 mmol), respectively, and reacted at 25° C. for 2 hours. To the mixture was added saturated brine (40 mL). After stirring for 15 minutes, the solid was filtered. The filter cake was washed with petroleum ether to give 120 mg of a yellow solid with a yield of 71%. LCMS: m/z=326.0 (M+H)$^+$.

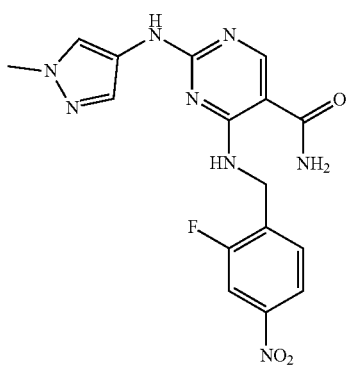 [SMILES: Cn1cc(Nc2ncc(C(N)=O)c(NCc3ccc([N+](=O)[O-])cc3F)n2)cn1]

Step 2): Preparation of 4-((2-fluoro-4-nitrobenzyl)amino)-2-((1-methyl-1H-pyrazol-4-yl)amino)pyrimidin-5-carboxamide 2-Chloro-4-((2-fluoro-4-nitrobenzyl)amino)pyrimidin-5-carboxamide (120 mg, 0.37 mmol) was dissolved in sec-butanol (3 mL). To the mixture were added 1-methyl-1H-pyrazol-4-amine (43 mg, 0.44 mmol) and trifluoroacetic acid (0.1 mL). The tube was sealed and the mixture was reacted at 100° C. for 2 hours. The reaction solution was concentrated. The solid was filtered, and washed with acetonitrile to give 80 mg of a brown solid with a yield of 56%. LCMS: m/z=387.1 (M+H)$^+$.

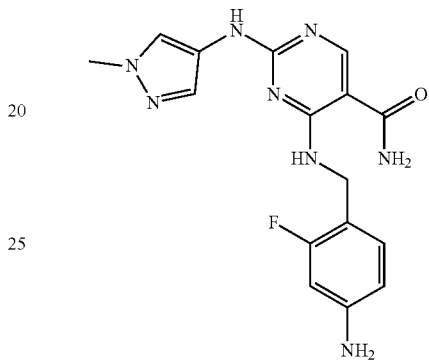

Step 3): Preparation of 4-((4-amino-2-fluorobenzyl)amino)-2-((1-methyl-1H-pyrazol-4-yl)amino)pyrimidin-5-carboxamide 4-((2-Fluoro-4-nitrobenzyl)amino)-2-((1-methyl-1H-pyrazol-4-yl)amino)pyrimidin-5-carboxamide (80 mg, 0.21 mmol) was dissolved in a mixed solution of ethanol (3 mL) and water (1 mL), and then a solid of ammonium chloride (112 mg, 2.10 mmol) and iron powder (117 mg, 2.10 mmol) were added. The mixture was heated to 70° C. and reacted for several hours. The reaction solution was cooled, filtered through celite, and subjected to thin layer chromatography (dichloromethane:methanol=10:1) to give 52 mg of a yellow solid with a yield of 70%. $^1$H NMR (400 MHz, DMSO-$d_6$+DCl/$D_2O$) δ 8.76 (s, 1H), 7.70 (s, 1H), 7.60-7.47 (m, 1H), 7.47-7.34 (m, 2H), 7.32-7.19 (m, 1H), 4.83 (s, 2H), 3.81 (s, 3H). LCMS: m/z=357.2 (M+H)$^+$.

Synthesis of Examples 14-227

The synthesis of subsequent specific examples follows the synthetic route shown below, using a method similar to that of Example 1 and using raw materials with different substituents, to synthesize the corresponding intermediate A and target compound B, as shown in Tables 3 and 4 below.

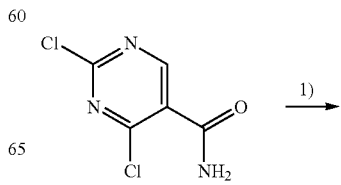

-continued

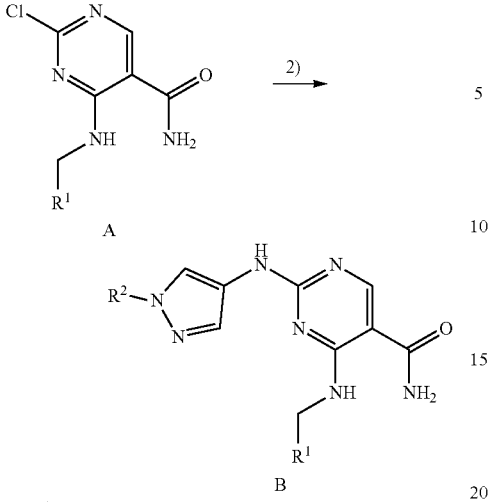

Reaction conditions: 1) R¹CH₂NH₂, DIEA, THF, 25° C., 2-16 h;

Reaction conditions: 1) R¹CH₂NH₂, DIEA, THF, 25° C., 2-16 h; 2)

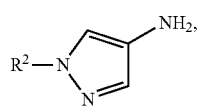

TFA, s-BuOH, 60-100° C., 2-16 h.

TABLE 3

Structures and characterization of intermediate compound A and target compound B of Examples 14-180

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 14 | *n-butyl* | *methyl* | 2-chloro-4-n butylamino pyrimidin-5-caboxamide | 229.1 | 4-n-butylamino-2-[(1-methyl-1-1H-pyrazol-4-yl)amino] pyrimidin-5-carboxamide | 290.2 | (400 MHz, DMSO-d₆ + DCl/D₂O) δ 8.63 (s, 1H), 7.90 (s, 1H), 7.63 (s, 1H), 3.82 (s, 3H), 3.50 (t, J = 7.1 Hz, 2H), 1.63-1.47 (m, 2H), 1.41-1.26 (m, 2H), 0.88 (t, J = 7.3 Hz, 3H). |
| 15 | *n-pentyl* | *methyl* | 2-chloro-4-(n-pentylamino) pyrimidin-5-carboxamide | 243.1 | 2[(1-methyl-1H-pyrazol-4-yl)amino]-4-(n-pentylamino) pyrimidin-5-carboxamide | 304.2 | (400 MHz, DMSO-d₆ + DCl/D₂O) δ 8.63 (s, 1H), 7.89 (s, 1H), 7.62 (s, 1H), 3.82 (s, 3H), 3.56-3.41 (m, 2H), 1.64-1.49 (m, 2H), 1.36-1.20 (m, 4H), 0.91-0.74 (m, 3H). |
| 16 | *isobutyl* | *methyl* | 2-chloro-4-isobutylamino-pyrimidin-5-carboxamide | 229.1 | 4-isobutylamino-2-[(1-methyl-1H-pyrazol-4-yl)amino] pyrimidin-5-carboxamide | 290.2 | (400 MHz, DMSO-d₆ + DCl/D₂O) δ 8.65 (s, 1H), 7.89 (s, 1H), 7.63 (s, 1H), 3.81 (s, 3H), 3.39-3.23 (m, 2H), 2.00-1.81 (m, 1H), 0.88 (d, J = 6.7 Hz, 6H). |

TABLE 3-continued

Structures and characterization of intermediate compound A and target compound B of Examples 14-180

| Ex. No. | R¹ | R² | Compound A Name | LC MS m/z = (M + H)⁺ | Compound B Name | LC MS m/z = (M + H)⁺ | ¹H NMR |
|---|---|---|---|---|---|---|---|
| 17 | | | 2-chloro-4-neopentylamino pyrimidin-5-carboxamide | 243.1 | 2-[(1-methyl-1H-pyrazol-4-yl)amino]-4-neopentylamino-pyrimidin-5-carboxamide | 304.2 | (400 MHz, DMSO-d₆ + DCl/D₂O) δ 8.59 (s, 1H), 7.91 (s, 1H), 7.86 (s, 1H), 3.77 (s, 3H), 3.23 (s, 2H), 0.79 (s, 9H). |
| 18 | | | 2-chloro-4-(isopentylamino) pyrimidin-5-carboxamide | 243.1 | 4-(isopentyl-amino)-2-[(1-methyl-1H-pyrazol-4-yl) amino]pyrimidin-5-carboxamide | 304.2 | (300 MHz, DMSO-d₆ + DCl/D₂O) δ 8.69 (s, 1H), 8.01 (s, 1H), 7.90 (s, 1H), 3.88 (s, 3H), 3.65-3.41 (m, 2H), 1.72-1.56 (m, 1H), 1.56-1.39 (m, 2H), 0.97-0.80 (m, 6H). |
| 19 | | | 2-chloro-4-[(3,3-dimethylbutyl) amino] pyrimidin-5-carboxamide | 257.1 | 4-[(3,3-dimethylbutyl)amino]-2-[(1-methy1-1H-pyrazol-4-yl)amino] pyrimidin-5-carboxamide | 318.2 | (400 MHz, DMSO-d₆ + DCl/D₂O) δ 8.62 (s, 1H), 7.91 (s, 1H), 7.63 (s, 1H), 3.80 (s, 3H), 3.53 (t, J = 8.1 Hz, 2H), 1.52-1.39 (m, 2H), 0.90 (s, 9H). |
| 20 | | | 2-chloro-4-[(4-methylpentyl) amino)pyrimidin-5-carboxamide | 257.1 | 2-[(1-methyl-1H-pyrazol-4-yl)amino]-4-[(4-methylpentyl) amino)pyrimidin-5-carboxamide | 318.2 | (400 MHz, DMSO-d₆ + DCl/D₂O) δ 8.67 (s, 1H), 7.95 (s, 1H), 7.68 (s, 1H), 3.87 (s, 3H), 3.55-3.45 (m, 2H), 1.71-1.45 (m, 3H), 1.27-1.16 (m, 2H), 0.91-0.74 (m, 6H). |
| 21 | | | 2-chloro-4-(heptylamino) pyrimidin-5-carboxamide | 271.1 | 2-[(1-methyl-1H-pyrazol-4-yl)amino]-4-(heptylamino) pyrimidin-5-carboxamide | 332.2 | (400 MHz, DMSO-d₆ + DCl/D₂O) δ 8.69 (s, 1H), 7.96 (s, 1H), 7.70 (s, 1H), 3.87 (s, 3H), 3.60-3.46 (m, 2H), 1.69-1.52 (m, 2H), 1.40-1.15 (m, 8H), 0.92-0.76 (m, 3H). |
| 22 | | | 2-chloro-4-[(cyanomethyl) amino]pyrimidin-5-carboxamide | 212.0 | 4-[(cyanomethyl)amino]-2-[(1-methyl-1H-pyrazol-4-yl) amino]pyrimidin-5-carboxamide | 273.1 | (400 MHz, DMSO-d₆ + DCl/D₂O) δ 8.83 (s, 1H), 8.14 (s, 1H), 7.81 (s, 1H), 4.66 (s, 2H), 3.91 (s, 3H). |
| 23 | | | 2-chloro-4-[(2-cyanoethyl) amino]pyrimidin-5-carboxamide | 226.0 | 4-[(2-cyanoethyl) amino]-2-[(1-methyl-1H-pyrazol-4-y1) amino]pyrimidin-5-carboxamide | 287.1 | (400 MHz, DMSO-d₆+ DCl/D₂O) δ 8.73 (s, 1H), 7.96 (s, 1H), 7.64 (s, 1H), 3.87 (s, 3H), 3.85-3.77 (m, 2H), 2.92 (t, J = 6.7 Hz, 2H). |
| 24 | | | 2-chloro-4-[(2 hydroxyethyl) amino]pyrimidin-5-carboxamide | 217.0 | 4-[(2-hydroxy-ethyl)amino]-2-[(1-methyl-1H-pyrazol-4-yl)amino] pyrimidin-5-carboxamide | 278.1 | (400 MHz, DMSO-d₆ + DCl/D₂O) δ 8.70 (s, 1H), 8.01 (s, 1H), 7.72 (s, 1H), 3.89 (s, 3H), 3.69-3.54 (m, 4H). |

TABLE 3-continued

Structures and characterization of intermediate compound A and target compound B of Examples 14-180

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 25 | (2-methoxyethyl) | | 2-chloro-4-[(2-methoxyethyl)amino]pyrimidin-5-carboxamide | 231.1 | 4-[(2-methoxyethyl)amino]-2-[(1-methyl-1H-pyrazol-4-yl)amino]pyrimidin-5-carboxamide | 292.1 | (300 MHz, DMSO-d₆ + DCl/D₂O) δ 8.72 (s, 1H), 8.05 (s, 1H), 7.96 (s, 1H), 3.90 (s, 3H), 3.77-3.67 (m, 2H), 3.63-3.51 (m, 2H), 3.31 (s, 3H). |
| 26 | (3-methoxypropyl) | | 2-chloro-4-[(3-methoxypropyl)amino]pyrimidin-5-carboxamide | 245.1 | 4-[(3-methoxypropyl)amino]-2-[(1-methyl-1H-pyrazol-4-yl)amino]pyrimidin-5-carboxamide | 306.2 | (400 MHz, DMSO-d₆ + DCl/D₂O) δ 8.68 (s, 1H), 7.98 (s, 1H), 7.70 (s, 1H), 3.87 (s, 3H), 3.78-3.51 (m, 2H), 3.42 (t, J = 6.0 Hz, 2H), 3.25 (s, 3H), 1.98-1.49 (m, 2H). |
| 27 | (cyclopropylmethyl) | | 2-chloro-4-[(cyclopropylmethyl)amino]pyrimidin-5-carboxamide | 227.1 | 4-[(cyclopropylmethyl)amino]-2-[(1-methyl-1H-pyrazol-4-yl)amino]pyrimidin-5-carboxamide | 288.1 | (300 MHz, DMSO-d₆ + DCl/D₂O) δ 8.71 (s, 1H), 7.98 (s, 1H), 7.71 (s, 1H), 3.88 (s, 3H), 3.47-3.37 (m, 2H), 1.22-1.05 (m, 1H), 0.58-0.42 (m, 2H), 0.37-0.21 (m, 2H). |
| 28 | (cyclobutylmethyl) | | 2-chloro-4-[(cyclobutylmethyl)amino]pyrimidin-5-carboxamide | 241.1 | 4-[(cyclobutylmethyl)amino]-2-[(1-methyl-1H-pyrazol-4-yl)amino]pyrimidin-5-carboxamide | 302.2 | (400 MHz, DMSO-d₆ + DCl/D₂O) δ 8.65 (s, 1H), 7.89 (s, 1H), 7.63 (s, 1H), 3.81 (s, 3H), 3.54 (d, J = 6.9 Hz, 2H), 2.69-2.55 (m, 1H), 2.05-1.90 (m, 2H), 1.89-1.77 (m, 2H), 1.75-1.58 (m, 2H). |
| 29 | (cyclopentylmethyl) | | 2-chloro-4-[(cyclopentylmethyl)amino]pyrimidin-5-carboxamide | 255.1 | 4-[(cyclopentylmethyl)amino]-2-[(1-methyl-1H-pyrazol-4-yl)amino]pyrimidin-5-carboxamide | 316.2 | (400 MHz, DMSO-d₆ + DCl/D₂O) δ 8.64 (s, 1H), 7.89 (s, 1H), 7.62 (s, 1H), 3.80 (s, 3H), 3.51-3.33 (m, 2H), 2.27-2.08 (m, 1H), 1.76-1.62 (m, 2H), 1.61-1.36 (m, 4H), 1.32-1.10 (m, 2H). |
| 30 | (cyclohexylmethyl) | | 2-chloro-4-[(cyclohexylmethyl)amino]pyrimidin-5-carboxamide | 269.1 | 4-[(cyclohexylmethyl)amino]-2-[(1-methyl-1H-pyrazol-4-yl)amino]pyrimidin-5-carboxamide | 330.2 | (400 MHz, DMSO-d₆ + DCl/D₂O) δ 8.54 (s, 1H), 8.25-8.21 (m, 2H), 3.77 (s, 3H), 3.27-3.20 (m, 2H), 1.62-1.25 (m, 6H), 1.11-0.86 (m, 3H), 0.86-0.68 (m, 2H). |
| 31 | (tetrahydro-2H-pyran-4-yl)methyl | | 2-chloro-4-[[(tetrahydro-2H-pyran-4-yl)methyl]amino]pyrimidin-5-carboxamide | 271.1 | 2-[(1-methyl-1H-pyrazol-4-yl)amino]-4-[[(tetrahydro-2H-pyran-4-yl)methyl]amino]pyrimidin-5-carboxamide | 332.2 | (400 MHz, DMSO-d₆ + DCl/D₂O) δ 8.62 (s, 1H), 7.89 (s, 1H), 7.63 (s, 1H), 3.86-3.68 (m, 5H), 3.43-3.31 (m, 2H), 3.25-3.09 (m, 2H), 1.91-1.76 (m, 1H), 1.55-1.39 (m, 2H), 1.23-1.11 (m, 2H). |
| 32 | (2-cyclopropylethyl) | | 2-chloro-4-[(2-cyclopropylethyl)amino]pyrimidin-5-carboxamide | 241.1 | 4-[(2-cyclopropylethyl)amino]-2-[(1-methyl-1H-pyrazol-4-yl)amino]pyrimidin-5-carboxamide | 302.2 | (400 MHz, DMSO-d₆ + DCl/D₂O) δ 8.64 (s, 1H), 7.91 (s, 1H), 7.64 (s, 1H), 3.82 (s, 3H), 3.56 (t, J = 6.9 Hz, 2H), 1.65-1.32 (m, 2H), 0.84-0.57 (m, 1H), 0.51-0.23 (m, 2H), 0.16-0.13 (m, 2H). |

TABLE 3-continued

Structures and characterization of intermediate compound A and target compound B of Examples 14-180

| Ex. No. | R¹ | R² | Compound A Name | Compound A LC MS m/z = (M + H)⁺ | Compound B Name | Compound B LC MS m/z = (M + H)⁺ | ¹H NMR |
|---|---|---|---|---|---|---|---|
| 33 | cyclopentylmethyl | | 2-chloro-4-[(2-cyclopentylethyl)amino]pyrimidin-5-carboxamide | 269.1 | 4-[(2-cyclopentylethyl)amino]-2-[(1-methyl-1H-pyrazol-4-yl)amino]pyrimidin-5-carboxamide | 330.2 | (400 MHz, DMSO-$d_6$ + DCl/$D_2O$) δ 8.62 (s, 1H), 7.89 (s, 1H), 7.62 (s, 1H), 3.80 (s, 3H), 3.48 (t, J = 7.6 Hz, 2H), 1.79-1.62 (m, 3H), 1.61-1.46 (m, 4H), 1.46 - 1.35 (m, 2H), 1.13 - 0.95 (m, 2H). |
| 34 | cyclohexylmethyl | | 2-chloro-4-[(2-cyclohexylethyl)amino]pyrimidin-5-carboxamide | 283.1 | 4-[(2-cyclohexylethyl)amino]-2-[(1-methyl-1H-pyrazol-4-yl)amino]pyrimidin-5-carboxamide | 344.2 | (400 MHz, DMSO-$d_6$ + DCl/$D_2O$) δ 8.63 (s, 1H), 7.90 (s, 1H), 7.61 (s, 1H), 3.82 (s, 3H), 3.52 (t, J = 7.6 Hz, 2H), 1.75-1.55 (m, 5H), 1.52-1.42 (m, 2H), 1.34-1.24 (m, 1H), 1.21-1.03 (m, 3H), 0.95-0.82 (m, 2H). |
| 35 | (tetrahydro-2H-pyran-4-yl)methyl | | 2-chloro-4-[[2-(tetrahydro-2H-pyran-4-yl)ethyl]amino]pyrimidin-5-carboxamide | 285.1 | 2-[(1-methyl-1H-pyrazol-4-yl)amino]-4-[[2-(tetrahydro-2H-pyran-yl)ethyl]amino]pyrimidin-5-carboxamide | 346.2 | (400 MHz, DMSO-$d_6$ + DCl/$D_2O$) δ 8.63 (s, 1H), 7.90 (s, 1H), 7.62 (s, 1H), 3.81 (s, 3H), 3.79-3.66 (m, 2H), 3.58-3.43 (m, 2H), 3.20 (t, J = 11.7 Hz, 2H), 1.62-1.40 (m, 5H), 1.22 - 1.00 (m, 2H). |
| 36 | 4-(dimethylamino)phenyl | | 2-chloro-4-{[4-(dimethylamino)benzyl]amino}pyrimidin-5-carboxamide | 306.1 | 4-{+4-(dimethylamino)benzyl]amino}-2-[(1-methyl-1H-pyrazol-4-yl)amino]pyrimidin-5-carboxamide | 367.2 | (400 MHz, DMSO-$d_6$ + DCl/$D_2O$) δ 8.74 (s, 1H), 7.96-7.79 (m, 2H), 7.74 (s, 1H), 7.68-7.43 (m, 3H), 4.82 (s, 2H), 3.82 (s, 3H), 3.14 (s, 6H). |
| 37 | 4-fluorophenyl | | 2-chloro-4-[(4-fluorobenzyl)amino[pyrimidin-5-carboxamide | 281.1 | 4-[(4-fluorobenzyl)amino]-2-[(1-methyl-1H-pyrazol-4-yl)amino]pyrimidin-5-carboxamide | 342.1 | (300 MHz, DMSO-$d_6$ + DCl/$D_2O$) δ 8.75 (s, 1H), 7.80 (s, 1H), 7.61 (s, 1H), 7.43-7.31 (m, 2H), 7.24-7.15 (m, 2H), 4.77 (s, 2H), 3.82 (s, 3H). |
| 38 | 4-methylphenyl | | 2-chloro-4-[(4-methylbenzyl)amino]pyrimidin-5-carboxamide | 277.1 | 4-[(4-methylbenzyl)amino]-2-[(1-methyl-1H-pyrazol-4-yl)amino]pyrimidin-5-carboxamide | 338.2 | (400 MHz, DMSO-$d_6$ + DCl/$D_2O$) δ 8.66 (s, 1H), 7.69 (s, 1H), 7.50 (s, 1H), 7.14 (d, J = 7.8 Hz, 2H), 7.09 (d, J = 7.8 Hz, 2H), 4.64 (s, 2H), 3.72 (s, 3H), 2.19 (s, 3H). |
| 39 | 4-chlorophenyl | | 2-chloro-4-[(4-chlorobenzyl)amino]pyrimidin-5-carboxamide | 297.0 | 4-[(4-chlorobenzyl)amino]-2-[(1-methyl-1H-pyrazol-4-yl)amino]pyrimidin-5-carboxamide | 358.1 | (400 MHz, DMSO-$d_6$ + DCl/$D_2O$) δ 8.69 (s, 1H), 7.67 (s, 1H), 7.46 (s, 1H), 7.42-7.36 (m, 2H), 7.35-7.28 (m, 2H), 4.73 (s, 2H), 3.76 (s, 3H). |

TABLE 3-continued

Structures and characterization of intermediate compound A and target compound B of Examples 14-180

| Ex. No. | R¹ | R² | Compound A Name | LC MS m/z = (M + H)⁺ | Compound B Name | LC MS m/z = (M + H)⁺ | ¹H NMR |
|---|---|---|---|---|---|---|---|
| 40 | 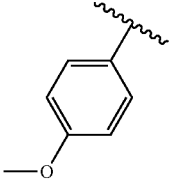 [SMILES: *c1ccc(OC)cc1] |  | 2-chloro-4-[(4-methoxybenzyl)amino]pyrimidin-5-carboxamide | 293.1 | 4-[(4-methoxybenzyl)amino-2-[(1-methyl-1H-pyrazol-4-yl)amino]pyrimidin-5-carboxamide | 354.2 | (300 MHz, DMSO-$d_6$ + DCl/$D_2O$) δ 8.73 (s, 1H), 7.81 (s, 1H), 7.59 (s, 1H), 7.33-7.22 (m, 2H), 6.94-6.89 (m, 2H), 4.70 (s, 2H), 3.82 (s, 3H), 3.74 (s, 3H). |
| 41 | 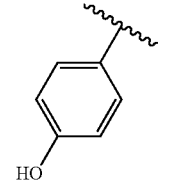 |  | 2-chloro-4-[(4-hydroxybenzyl)amino]pyrimidin-5-carboxamide | 279.1 | 4-[(4-hydroxybenzyl)amino-2-[(1-methyl-1H-pyrazol-4-yl)amino]pyrimidin-5-carboxamide | 340.1 | (400 MHz, DMSO-$d_6$ + DCl/$D_2O$) δ 8.73 (s, 1H), 7.85 (s, 1H), 7.64 (s, 1H), 7.15 (d, J = 8.1 Hz, 2H), 6.80 (d, J = 8.1 Hz, 2H), 4.65 (s, 2H), 3.84 (s, 3H). |
| 42 | 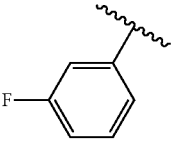 [SMILES: *c1cccc(F)c1] |  | 2-chloro-4-[(3-fluorobenzyl)amino]pyrimidin-5-carboxamide | 281.1 | 4-[(3-fluorobenzyl)amino]-2-[(1-methyl-1H-pyrazol-4-yl)amino]pyrimidin-5-carboxamide | 342.1 | (300 MHz, DMSO-$d_6$ + DCl/$D_2O$) δ 8.75 (s, 1H), 7.73 (s, 1H), 7.53 (s, 1H), 7.45-7.38 (m, 1H), 7.22-7.04 (m, 3H), 4.81 (s, 2H), 3.80 (s, 3H). |
| 43 | 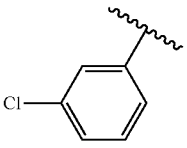 [SMILES: *c1cccc(Cl)c1] |  | 2-chloro-4-[(3-chlorobenzyl)amino]pyrimidin-5-carboxamide | 297.0 | 4-[(3-chlorobenzyl)amino]-2-[(1-methyl-1H-pyrazol-4-yl)amino]pyrimidin-5-carboxamide | 358.1 | (400 MHz, DMSO-$d_6$ + DCl/$D_2O$) δ 8.74 (s, 1H), 7.80 (s, 1H), 7.59 (s, 1H), 7.36-7.23 (m, 4H), 4.80 (s, 2H), 3.84 (s, 3H). |
| 44 | 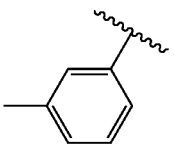 [SMILES: *c1cccc(C)c1] |  | 2-chloro-4-[(3-methylbenzyl)amino]pyrimidin-5-carboxamide | 277.1 | 4-[(3-methylbenzyl)amino]-2-[(1-methyl-1H-pyrazol-4-yl)amino]pyrimidin-5-carboxamide | 338.2 | (400 MHz, DMSO-$d_6$ + DCl/$D_2O$) δ 8.74 (s, 1H), 7.79 (s, 1H), 7.59 (s, 1H), 7.30-7.22 (m, 1H), 7.19-7.09 (m, 3H), 4.74 (s, 2H), 3.81 (s, 3H), 2.29 (s, 3H). |
| 45 | 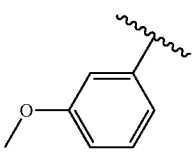 [SMILES: *c1cccc(OC)c1] |  | 2-chloro-4-[(3-methoxybenzyl)amino]pyrimidin-5-carboxamide | 293.1 | 4-[(3-methoxybenzyl)amino]-2-[(1-methyl-1H-pyrazol-4-yl)amino]pyrimidin-5-carboxamide | 354.2 | (400 MHz, DMSO-$d_6$ + DCl/$D_2O$) δ 8.68 (s, 1H), 7.69 (s 1H) 7.51 (s, 1H), 7.33-7.16 (m, 1H), 6.97-6.77 (m, 3H), 4.71 (s, 2H), 3.74 (s, 3H), 3.68 (s, 3H). |
| 46 | 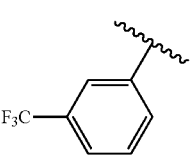 |  | 2-chloro-4-[(3-trifluoromethyl-benzyl)amino]pyrimidin-5-carboxamide | 331.0 | 4-[(3-trifluoromethylbenzyl)amino]-2-[(1-methyl-1H-pyrazol-4-yl)amino]pyrimidin-5-carboxamide | 392.1 | (400 MHz, DMSO-$d_6$ + DCl/$D_2O$) δ 8.73 (s, 1H), 8.05- 7.31 (m, 6H), 4.87 (s, 2H), 3.78 (s, 3H). |
| 47 | 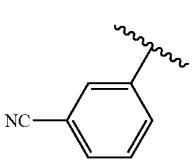 [SMILES: *c1cccc(C#N)c1] |  | 2-chloro-4-[(3-cyanobenzyl)amino]pyrimidin-5-carboxamide | 288.1 | 4-[(3-cyanobenzyl)amino]-2-[(1-methyl-1H-pyrazol-4-yl)amino]pyrimidin-5-carboxamide | 349.1 | (400 MHz, DMSO-$d_6$ + DCl/$D_2O$) δ 8.75 (s, 1H), 7.79-7.73 (m, 2H), 7.71-7.64 (m, 1H), 7.64-7.55 (m, 1H), 7.53 (s, 1H), 7.43-7.36 (m, 1H), 4.85 (s, 2H), 3.82 (s, 3H). |

TABLE 3-continued

Structures and characterization of intermediate compound A and target compound B of Examples 14-180

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 48 | 3-(N-methylcarbamoyl)phenyl | | 2-chloro-4-[[3-(dimethyl-carbamoyl)benzyl]amino]pyrimidin-5-carboxamide | 334.1 | 2-[(1-methyl-1H-pyrazol-4-yl)amino+-4-[[3-(dimethyl-carbamoyl)benzyl]amino]pyrimidin-5-carboxamide | 395.2 | (400 MHz, DMSO-d₆ + DCl/D₂O) δ 8.74 (s, 1H), 7.76 (s, 1H), 7.53 (s, 1H), 7.47-7.41 (m, 2H), 7.36-7.28 (m, 2H), 4.83 (s, 2H), 3.78 (s, 3H), 2.97 (s, 3H), 2.81 (s, 3H). |
| 49 | 2-fluorophenyl | | 2-chloro-4-[(2-fluorobenzyl)amino]pyrimidin-5-carboxamide | 281.1 | 4-[(2-fluorobenzyl)amino]-2-[(1-methyl-1H-pyrazol-4-yl)amino]pyrimidin-5-carboxamide | 342.1 | (400 MHz, DMSO-d₆ + DCl/D₂O) δ 8.76 (s, 1H), 7.71 (s, 1H), 7.49 (s, 1H), 7.43-7.14 (m, 4H), 4.82 (s, 2H), 3.79 (s, 3H). |
| 50 | 2-methylphenyl | | 2-chloro-4-[(2-methylbenzyl)amino]pyrimidin-5-carboxamide | 277.1 | 2-[(1-methyl-1H-pyrazol-4-yl)amino+-4-[(2-methylbenzyl)amino]pyrimidin-5-carboxamide | 338.2 | (400 MHz, DMSO-d₆ + DCl/D₂O) δ 8.76 (s, 1H), 7.63 (s, 1H), 7.53 (s, 1H), 7.32-7.26 (m, 4H), 4.73 (s, 2H), 3.76 (s, 3H), 2.32 (s, 3H). |
| 51 | 2-ethylphenyl | | 2-chloro-4-[(2-ethylbenzyl)amino]pyrimidin-5-carboxamide | 291.1 | 2-[(1-methyl-1H-pyrazol-4-yl)amino]-4-[(2-ethylbenzyl)amino]pyrimidin-5-carboxamide | 352.2 | (400 MHz, DMSO-d₆ + DCl/D₂O) δ 8.74 (s, 1H), 7.67 (s, 1H), 7.51 (s, 1H), 7.34-7.23 (m, 2H), 7.23-7.10 (m, 2H), 4.78 (s, 2H), 3.74 (s, 3H), 2.66 (q, J = 7.6 Hz, 2H), 1.17 (t, J = 7.5 Hz, 3H). |
| 52 | 2-cyclopropylphenyl | | 2-chloro-4-[(2-cyclopropyl-benzyl)amino]pyrimidin-5-carboxamide | 303.1 | 4-[(2-cyclopropyl-benzyl)amino]-2-[(1-methy1-1H-pyrazol-4-yl)amino]pyrimidin-5-carboxamide | 364.2 | (400 MHz, DMSO-d₆ + DCl/D₂O) δ 8.77 (s, 1H), 7.68 (s, 1H), 7.55 (s, 1H), 7.29-7.21 (m, 1H), 7.20-7.17 (m, 2H), 7.10-7.08 (m, 1H), 4.92 (s, 2H), 3.76 (s, 3H), 2.05-1.89 (m, 1H), 1.00-0.85 (m, 2H), 0.72-0.57 (m, 2H). |
| 53 | 2-chlorophenyl | | 2-chloro-4-[(2-chlorobenzyl)amino]pyrimidin-5-carboxamide | 297.0 | 4-[(2-chlorobenzyl)amino]-2-[(1-methyl-1H-pyrazol-4-yl)amino]pyrimidin-5-carboxamide | 358.1 | (400 MHz, DMSO-d₆ + DCl/D₂O) δ 8.77 (s, 1H), 7.60-7.48 (m, 2H), 7.44 (s, 1H), 7.39-7.31 (m, 2H), 7.30-7.24 (m, 1H), 4.82 (s, 2H), 3.76 (s, 3H). |
| 54 | 2-trifluoromethylphenyl | | 2-chloro-4-[(2-trifluoromethyl-benzyl)amino]pyrimidin-5-carboxamide | 331.0 | 2-[(1-methyl-1H-pyrazol-4-yl)amino]-4-[(2-trifluoromethyl-benzyl)amino]pyrimidin-5-carboxamide | 392.1 | (400 MHz, DMSO-d₆ + DCl/D₂O) δ 8.81 (s, 1H), 7.84 (s, 1H), 7.68 (s, 1H), 7.62-7.52 (m, 2H), 7.49-7.39 (m, 2H), 4.97 (s, 2H), 3.71 (s, 3H). |

TABLE 3-continued

Structures and characterization of intermediate compound A and target compound B of Examples 14-180

| Ex. No. | R¹ | R² | Compound A Name | Compound A LC MS m/z = (M + H)⁺ | Compound B Name | Compound B LC MS m/z = (M + H)⁺ | ¹H NMR |
|---|---|---|---|---|---|---|---|
| 55 | 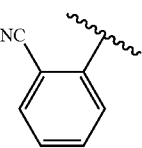 |  | 2-chloro-4-[(2-cyanobenzyl)amino]pyrimidin-5-carboxamide | 288.1 | 4-[(2-cyanobenzyl)amino]-2-[(1-methyl-1H-pyrazol-4-yl)amino]pyrimidin-5-carboxamide | 349.1 | (400 MHz, DMSO-$d_6$ + DCl/$D_2O$) δ 8.80 (s, 1H), 7.97-7.88 (m, 1H) 7.78-7.66 (m, 2H), 7.63 (s, 1H), 7.56-7.50 (m, 2H), 4.96 (s, 2H), 3.79 (s, 3H). |
| 56 | 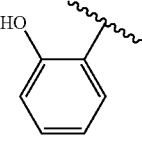 | | 2-chloro-4-[(2-hydroxybenzyl)amino]pyrimidin-5-carboxamide | 279.1 | 4-[(2-hydroxybenzyl)amino]-2-[(1-methyl-1H-pyrazol-4-yl)amino]pyrimidin-5-carboxamide | 340.1 | (400 MHz, DMSO-$d_6$ + DCl/$D_2O$) δ 8.72 (s, 1H), 7.79 (s, 1H), 7.63 (s, 1H), 7.18-7.11 (m, 1H), 7.11-7.03 (m, 2H), 6.81-6.74 (m, 1H), 4.68 (s, 2H), 3.83 (s, 3H). |
| 57 |  | | 2-chloro-4-[(2-ethoxybenzyl)amino]pyrimidin-5-carboxamide | 307.1 | 4-[(2-ethoxybenzyl)amino]-2-[(1-methyl-1H-pyrazol-4-yl)amino]pyrimidin-5-carboxamide | 368.2 | (400 MHz, DMSO-$d_6$ + DCl/$D_2O$) δ 8.71 (s, 1H), 7.80 (s, 1H), 7.60 (s, 1H), 7.36-7.24 (m, 1H) 7.24-7.12 (m, 1H), 7.05 (d, J = 8.2 Hz, 1H), 6.97-6.83 (m, 1H), 4.71 (s, 2H), 4.11 (q, J = 6.9 Hz, 2H), 3.82 (s, 3H), 1.37 (t, J = 6.9 Hz, 3H). |
| 58 | 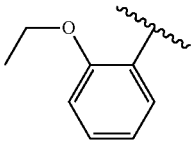 [SMILES: *c1ccccc1OCC] | | 2-chloro-4-[(2-isopropoxybenzyl)amino]pyrimidin-5-carboxamide | 321.1 | 4-[(2-isopropoxybenzyl)amino]-2-[(1-methyl-1H-pyrazol-4-yl)amino]pyrimidin-5-carboxamide | 382.2 | (400 MHz, DMSO-$d_6$ + DCl/$D_2O$) δ 8.72 (s, 1H), 7.86 (s, 1H), 7.64 (s, 1H), 7.32-7.25 (m, 1H) 7.20-7.12 (m, 1H) 7.07 (d, J = 8.2 Hz, 1H), 6.93-6.84 (m, 1H), 4.79-4.61 (m, 3H), 3.84 (s, 3H), 1.28 (d, J = 6.0 Hz, 6H). |
| 59 |  | | 2-chloro-4-[(2-trifluoromethoxybenzyl)amino]pyrimidin-5-carboxamide | 347.0 | 2-[(1-methyl-1H-pyrazol-4-yl)amino]-4-[(2-trifluoromethoxybenzyl)amino]pyrimidin-5-carboxamide | 408.1 | (300 MHz, DMSO-$d_6$ + DCl/$D_2O$) δ 8.77 (s, 1H), 7.68 (s, 1H), 7.54-7.33 (m, 5H) 4.84 (s, 2H), 3.76 (s, 3H). |
| 60 | 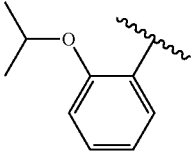 [SMILES: *c1ccccc1OC(C)C] | | 2-chloro-4-[[2-(methylsulfonyl)benzyl]amino]pyrimidin-5-carboxamide | 341.0 | 2-[(1-methyl-1H-pyrazol-4-yl)amino]-4-[[2-(methylsulfonyl)benzyl]amino]pyrimidin-5-carboxamide | 402.1 | (400 MHz, DMSO-$d_6$ + DCl/$D_2O$) δ 8.76 (s, 1H), 7.68-7.60 (m, 3H), 7.46-7.35 (m, 3H), 5.20 (s, 2H), 3.72 (s, 3H), 3.29 (s, 3H). |
| 61 |  | | 2-chloro-4-[[2-(methoxymethyl)benzyl]amino]pyrimidin-5-carboxamide | 307.1 | 4-[[2-(methoxymethyl)benzyl]amino]-2-[(1-methyl-1H-pyrazol-4-yl)amino]pyrimidin-5-carboxamide | 368.2 | (400 MHz, DMSO-$d_6$ + DCl/$D_2O$) δ 8.74 (s, 1H), 7.72 (s, 1H), 7.56 (s, 1H), 7.48-7.36 (m, 1H), 7.36-7.28 (m, 2H), 7.28-7.17 (m, 1H), 4.82 (s, 2H), 4.52 (s, 2H), 3.77 (s, 3H), 3.31 (s, 3H). |

TABLE 3-continued

Structures and characterization of intermediate compound A and target compound B
of Examples 14-180

| Ex. No. | R¹ | R² | Compound A | | Compound B | | |
|---|---|---|---|---|---|---|---|
| | | | Name | LC MS m/z = (M + H)⁺ | Name | LC MS m/z = (M + H)⁺ | ¹H NMR |
| 62 | 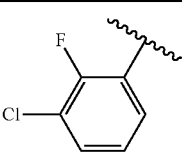 |  | 2-chloro-4-[(2,3-difluorobenzyl)amino]pyrimidin-5-carboxamide | 299.0 | 4-[(2,3-difluorobenzyl)amino]-2-[(1-methyl-1H-pyrazol-4-yl)amino]pyrimidin-5-carboxamide | 360.1 | (400 MHz, DMSO-d₆ + DCl/D₂O) δ 8.76 (s, 1H), 7.74 (s, 1H), 7.48 (s, 1H), 7.45-7.31 (m, 1H), 7.25-7.15 (m, 1H), 7.15-7.01 (m, 1H), 4.86 (s, 2H), 3.80 (s, 3H). |
| 63 | 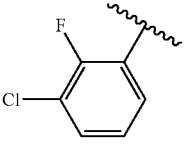 [SMILES: *c1cccc(Cl)c1F] | | 2-chloro-4-[(2-fluoro-3-chlorobenzyl)amino]pyrimidin-5-carboxamide | 315.0 | 4-[(2-fluoro-3-chlorobenzyl)amino]-2-[(1-methyl-1H-pyrazol-4-yl)amino]pyrimidin-5-carboxamide | 376.1 | (400 MHz, DMSO-d₆ + DCl/D₂O) δ 8.76 (s, 1H), 7.71 (s, 1H), 7.60-7.40 (m, 2H), 7.34-7.12 (m, 2H), 4.85 (s, 2H), 3.80 (s, 3H). |
| 64 |  | | 2-chloro-4-[(2,3-dichlorobenzyl)amino]pyrimidin-5-carboxamide | 331.0 | 4-[(2,3-dichlorobenzyl)amino]-2-[(1-methyl-1H-pyrazol-4-yl)amino]pyrimidin-5-carboxamide | 392.1 | (400 MHz, DMSO-d₆ + DCl/D₂O) δ 8.77 (s, 1H), 7.68-7.57 (m, 1H), 7.45 (s, 1H), 7.42-7.29 (m, 2H), 7.23 (d, J = 7.8 Hz, 1H), 4.84 (s, 2H), 3.73 (s, 3H). |
| 65 | 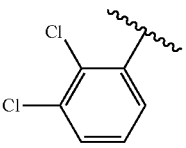 [SMILES: *c1cccc(Cl)c1Cl] | | 2-chloro-4-[(2-chloro-3-fluorobenzyl)amino]pyrimidin-5-carboxamide | 315.0 | 4-[(2-chloro-3-fluorobenzyl)amino]-2-[(1-methyl-1H-pyrazol-4-yl)amino]pyrimidin-5-carboxamide | 376.1 | (400 MHz, DMSO-d₆ + DCl/D₂O) δ 8.78 (s, 1H), 7.55 (s, 1H), 7.49-7.29 (m, 3H), 7.12 (s, 1H), 4.85 (s, 2H), 3.76 (s, 3H). |
| 66 |  | | 2-chloro-4-[(2-methyl-3-chlorobenzyl)amino]pyrimidin-5-carboxamide | 311.0 | 4-[(2-methyl-3-chlorobenzyl)amino]-2-[(1-methyl-1H-pyrazol-4-yl)amino]pyrimidin-5-carboxamide | 372.1 | (400 MHz, DMSO-d₆ + DCl/D₂O) δ 8.77 (s, 1H), 7.57 (s, 1H), 7.47 (s, 1H), 7.40 (d, J = 7.9 Hz, 1H), 7.29-7.04 (m, 2H), 4.78 (s, 2H), 3.74 (s, 3H), 2.36 (s, 3H). |
| 67 | 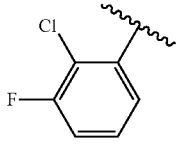 | | 2-chloro-4-[(2,3-dimethylbenzyl)amino]pyrimidin-5-carboxamide | 291.1 | 4-[(2,3-dimethylbenzyl)amino]-2-[(1-methyl-1H-pyrazol-4-yl)amino]pyrimidin-5-carboxamide | 352.2 | (400 MHz, DMSO-d₆ + DCl/D₂O) δ 8.76 (s, 1H), 7.74 (s, 1H), 7.61 (s, 1H), 7.18-6.98 (m, 3H), 4.75 (s, 2H), 3.79 (s, 3H), 2.29 (s, 3H), 2.21 (s, 3H). |
| 68 |  | | 2-chloro-4-[(2,3-dimethoxybenzyl)amino]pyrimidin-5-carboxamide | 323.1 | 4-[(2,3-dimethoxybenzyl)amino]-2-[(1-methyl-1H-pyrazol-4-yl)amino]pyrimidin-5-carboxamide | 384.2 | (400 MHz, DMSO-d₆ + DCl/D₂O) δ 8.74 (s, 1H), 7.75 (s, 1H) 7.58 (s, 1H), 7.14-6.97 (m, 2H), 6.78 (s, 1H), 4.76 (s, 2H), 3.83 (s, 3H), 3.80 (s, 3H), 3.78 (s, 3H). |
| 69 | 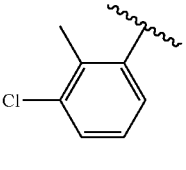 [SMILES: *c1cccc(Cl)c1C] | | 2-chloro-4-[(2,4-difluorobenzyl)amino]pyrimidin-5-carboxamide | 299.0 | 4-[(2,4-difluorobenzyl)amino]-2-[(1-methyl-1H-pyrazol-4-yl)amino]pyrimidin-5-carboxamide | 360.1 | (400 MHz, DMSO-d₆ + DCl/D₂O) δ 8.75 (s, 1H), 7.79 (s, 1H), 7.52 (s, 1H), 7.41-7.24 (m, 2H), 7.16-6.98 (m, 1H), 4.78 (s, 2H), 3.82 (s, 3H). |

TABLE 3-continued

Structures and characterization of intermediate compound A and target compound B of Examples 14-180

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 70 | 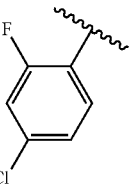 |  | 2-chloro-4-[(2-fluoro-4-chlorobenzyl)amino]pyrimidin-5-carboxamide | 315.0 | 4-[(2-fluoro-4-chlorobenzyl)amino]-2-[(1-methyl-1H-pyrazol-4-yl)amino]pyrimidin-5-carboxamide | 376.1 | (400 MHz, DMSO-d₆ + DCl/D₂O) δ 8.76 (s, 1H), 7.76 (s, 1H), 7.57-7.43 (m, 2H), 7.40-7.19 (m, 2H), 4.79 (s, 2H), 3.82 (s, 3H). |
| 71 | 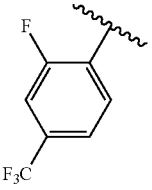 |  | 2-chloro-4-[(2-fluoro-4-(trifluoromethyl)benzyl)amino]pyrimidin-5-carboxamide | 349.0 | 4-[(2-fluoro-4-(trifluoromethyl)benzyl)amino]-2-[(1-methyl-1H-pyrazol-4-yl)amino]pyrimidin-5-carboxamide | 410.1 | (400 MHz, DMSO-d₆ + DCl/D₂O) δ 8.77 (s, 1H), 7.80-7.67 (m, 2H), 7.61-7.49 (m, 3H), 4.90 (s, 2H), 3.82 (s, 3H). |
| 72 | 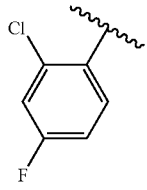 [SMILES: *c1ccc(F)cc1Cl] |  | 2-chloro-4-[(2-chloro-4-fluorobenzyl)amino]pyrimidin-5-carboxamide | 315.0 | 4-[(2-chloro-4-fluorobenzyl)amino]-2-[(1-methyl-1H-pyrazol-4-yl)amino]pyrimidin-5-carboxamide | 376.1 | (400 MHz, DMSO-d₆ + DCl/D₂O) δ 8.78 (s, 1H), 7.63 (s, 1H), 7.60-7.51 (m, 1H), 7.47 (s, 1H), 7.41-7.27 (m, 1H), 7.25-7.13 (m, 1H), 4.78 (s, 2H), 3.79 (s, 3H). |
| 73 | 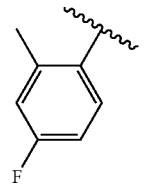 |  | 2-chloro-4-[(2-methyl-4-fluorobenzyl)amino]pyrimidin-5-carboxamide | 295.1 | 4-[(2-methyl-4-fluorobenzyl)amino]-2-[(1-methyl-1H-pyrazol-4-yl)amino]pyrimidin-5-carboxamide | 356.2 | (400 MHz, DMSO-d₆ + DCl/D₂O) δ 8.76 (s, 1H), 7.68 (s, 1H), 7.50 (s, 1H), 7.31-7.07 (m, 2H), 7.08-6.80 (m, 1H), 4.70 (s, 2H), 3.78 (s, 3H), 2.33 (s, 3H). |
| 74 | 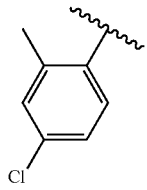 [SMILES: *c1ccc(Cl)cc1C] |  | 2-chloro-4-[(2-methyl-4-chlorobenzyl)amino]pyrimidin-5-carboxamide | 311.0 | 4-[(2-methyl-4-chlorobenzyl)amino]-2-[(1-methyl-1H-pyrazol-4-yl)amino]pyrimidin-5-carboxamide | 372.1 | (400 MHz, DMSO-d₆ + DCl/D₂O) δ 8.76 (s, 1H), 7.68-7.60 (m, 1H) 7.47 (s, 1H), 7.36 (s, 1H), 7.26-7.19 (m, 1H), 7.19-7.11 (m, 1H), 4.71 (s, 2H), 3.76 (s, 3H), 2.32 (s, 3H). |
| 75 | 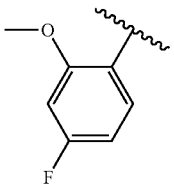 [SMILES: *c1ccc(F)cc1OC] |  | 2-chloro-4-[(2-methoxy-4-fluorobenzyl)amino]pyrimidin-5-carboxamide | 311.1 | 4-[(2-methoxy-4-fluorobenzyl)amino]-2-[(1-methyl-1H-pyrazol-4-yl)amino]pyrimidin-5-carboxamide | 372.2 | (400 MHz, DMSO-d₆ + DCl/D₂O) δ 8.73 (s, 1H), 7.79 (s, 1H), 7.56 (s, 1H), 7.28-7.07 (m, 1H), 7.07-6.92 (m, 1H), 6.82-6.68 (m, 1H), 4.66 (s, 2H), 3.88 (s, 3H), 3.82 (s, 3H). |
| 76 | 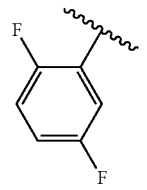 |  | 2-chloro-4-[(2,5-difluorobenzyl)amino]pyrimidin-5-carboxamide | 299.0 | 4-[(2,5-difluorobenzyl)amino]-2-[(1-methyl-1H-pyrazol-4-yl)amino]pyrimidin-5-carboxamide | 360.1 | (400 MHz, DMSO-d₆ + DCl/D₂O) δ 8.74 (s, 1H), 7.70 (s, 1H) 7.47 (s, 1H) 7.39-7.27 (m, 1H), 7.25-7.15 (m, 1H), 7.15-7.03 (m, 1H), 4.80 (s, 2H), 3.78 (s, 3H). |

TABLE 3-continued

Structures and characterization of intermediate compound A and target compound B of Examples 14-180

| Ex. No. | R¹ | R² | Compound A Name | Compound A LC MS m/z = (M + H)⁺ | Compound B Name | Compound B LC MS m/z = (M + H)⁺ | ¹H NMR |
|---|---|---|---|---|---|---|---|
| 77 | 2-F, 5-Cl phenyl | | 2-chloro-4-[(2-fluoro-5-chlorobenzyl)amino]pyrimidin-5-carboxamide | 315.0 | 4-[(2-fluoro-5-chlorobenzyl)amino]-2-[(1-methyl-1H-pyrazol-4-yl)amino]pyrimidin-5-carboxamide | 376.1 | (400 MHz, DMSO-$d_6$ + DCl/$D_2O$) δ 8.76 (s, 1H), 7.80 (s, 1H), 7.54 (s, 1H), 7.46-7.38 (m, 1H), 7.38-7.26 (m, 2H), 4.80 (s, 2H), 3.82 (s, 3H). |
| 78 | 2-F, 5-CF₃ phenyl | | 2-chloro-4-[(2-fluoro-5-(trifluoromethyl)benzyl)amino]pyrimidin-5-carboxamide | 349.0 | 4-[(2-fluoro-5-(trifluoromethyl)benzyl)amino]-2-[(1-methyl-1H-pyrazol-4-yl)amino]pyrimidin-5-carboxamide | 410.1 | (400 MHz, DMSO-$d_6$ + DCl/$D_2O$) δ 8.75 (s, 1H), 7.82 (s, 1H), 7.80-7.73 (m, 1H), 7.69 (s, 1H), 7.58-7.46 (m, 2H), 4.89 (s, 2H), 3.81 (s, 3H). |
| 79 | 2-Cl, 5-F phenyl | | 2-chloro-4-[(2-chloro-5-fluorobenzyl)amino]pyrimidin-5-carboxamide | 315.0 | 4-[(2-chloro-5-fluorobenzyl)amino]-2-[(1-methyl-1H-pyrazol-4-yl)amino]pyrimidin-5-carboxamide | 376.1 | (400 MHz, DMSO-$d_6$ + DCl/$D_2O$) δ 8.78 (s, 1H), 7.66-7.56 (m, 1H), 7.53 (s, 1H), 7.43 (s, 1H), 7.28-7.18 (m, 1H), 7.09 (d, J = 9.2 Hz, 1H), 4.79 (s, 2H), 3.76 (s, 3H). |
| 80 | 2-Me, 5-F phenyl | | 2-chloro-4-[(2-methyl-5-fluorobenzyl)amino]pyrimidin-5-carboxamide | 295.1 | 4-[(2-methyl-5-fluorobenzyl)amino]-2-[(1-methyl-1H-pyrazol-4-yl)amino]pyrimidin-5-carboxamide | 356.2 | (400 MHz, DMSO-$d_6$ + DCl/$D_2O$) δ 8.76 (s, 1H), 7.59 (s, 1H), 7.46 (s, 1H), 7.36-7.23 (m, 1H), 7.09-6.99 (m, 1H), 6.94 (d, J = 10.0 Hz, 1H), 4.72 (s, 2H), 3.74 (s, 3H), 2.29 (s, 3H). |
| 81 | 2-Me, 5-Cl phenyl | | 2-chloro-4-[(2-methyl-5-chlorobenzyl)amino]pyrimidin-5-carboxamide | 311.0 | 4-[(2-methyl-5-chlorobenzyl)amino]-2-[(1-methyl-1H-pyrazol-4-yl)amino]pyrimidin-5-carboxamide | 372.1 | (400 MHz, DMSO-$d_6$ + DCl/$D_2O$) δ 8.76 (s, 1H), 7.65 (s, 1H), 7.53 (s, 1H), 7.36-7.22 (m, 2H), 7.22-7.09 (m, 1H), 4.72 (s, 2H), 3.76 (s, 3H), 2.30 (s, 3H). |
| 82 | 2-CF₃, 5-F phenyl | | 2-chloro-4-[[2-(trifluoromethyl)-5-fluorobenzyl]amino]pyrimidin-5-carboxamide | 349.0 | 4-[[2-(trifluoromethyl)-5-fluorobenzyl]amino-2-[(1-methyl-1H-pyrazol-4-yl)amino]pyrimidin-5-carboxamide | 410.1 | (400 MHz, DMSO-$d_6$ + DCl/$D_2O$) δ 8.79 (s, 1H), 7.92 (dd, J = 8.8, 5.4 Hz, 1H), 7.52 (s, 1H), 7.44-7.32 (m, 2H), 7.25 (d, J = 9.7 Hz, 1H), 4.96 (s, 2H), 3.70 (s, 3H). |
| 83 | 2-OMe, 5-Cl phenyl | | 2-chloro-4-[(2-methoxy-5-chlorobenzyl)amino]pyrimidin-5-carboxamide | 327.0 | 4-[(2-methoxy-5-chlorobenzyl)amino]-2-[(1-methyl-1H-pyrazol-4-yl)amino]pyrimidin-5-carboxamide | 388.1 | (400 MHz, DMSO-$d_6$ + DCl/$D_2O$) δ 8.73 (s, 1H), 7.78 (s, 1H), 7.56 (s, 1H), 7.35 (dd, J = 8.7, 2.7 Hz, 1H), 7.20-7.06 (m, 2H), 4.69 (s, 2H), 3.87 (s, 3H), 3.81 (s, 3H). |

TABLE 3-continued

Structures and characterization of intermediate compound A and target compound B of Examples 14-180

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 84 | 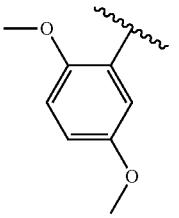 [SMILES: *c1cc(OC)ccc1OC] |  | 2-chloro-4-[(2,5-dimethoxybenzyl)amino]pyrimidin-5-carboxamide | 323.1 | 4-[(2,5-dimethoxy-benzyl)amino]-2-[(1-methyl-1H-pyrazol-4-yl)amino]pyrimidin-5-carboxamide | 384.2 | (400 MHz, DMSO-d₆ + DCl/D₂O) δ 8.73 (s, 1H), 7.81 (s, 1H), 7.62 (s, 1H), 7.01 (d, J = 9.0 Hz, 1H), 6.88-6.84 (m, 1H), 6.78-6.71 (m, 1H), 4.68 (s, 2H), 3.89-3.76 (m, 6H), 3.64 (s, 3H). |
| 85 | 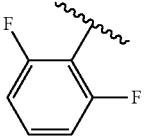 |  | 2-chloro-4-[(2,6-difluorobenzyl]amino]pyrimidin-5-carboxamide | 299.0 | 4-[(2,6-difluorobenzyl)amino]-2-[(1-methyl-1H-pyrazol-4-yl)amino]pyrimidin-5-carboxamide | 360.1 | (400 MHz, DMSO-d₆ + DCl/D₂O) δ 8.77 (s, 1H), 8.01 (s, 1H), 7.68 (s, 1H), 7.53-7.42 (m, 1H), 7.23-7.12 (m, 2H), 4.90 (s, 2H), 3.89 (s, 3H). |
| 86 | 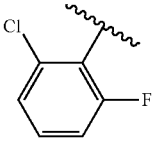 [SMILES: *c1c(F)cccc1Cl] |  | 2-chloro-4-[(2-fluoro-6-chlorobenzyl)amino]pyrimidin-5-carboxamide | 315.0 | 4-[(2-fluoro-6-chlorobenzyl)amino]-2-[(1-methyl-1H-pyrazol-4-yl)amino]pyrimidin-5-carboxamide | 376.1 | (400 MHz, DMSO-d₆ + DCl/D₂O) δ 8.78 (s, 1H), 8.03 (s, 1H), 7.70 (s, 1H), 7.55-7.38 (m, 2H), 7.37-7.23 (m, 1H), 4.94 (s, 2H), 3.88 (s, 3H). |
| 87 | 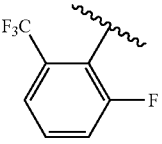 |  | 2-chloro-4-[[2-fluoro-6-(trifluoromethyl)benzyl]amino]pyrimidin-5-carboxamide | 349.0 | 4-[(2-fluoro-6-(trifluoromethyl)benzyl)amino]-2-[(1-methyl-1H-pyrazol-4-yl)amino]pyrimidin-5-carboxamide | 410.1 | (400 MHz, DMSO-d₆ + DCl/D₂O) δ 8.81 (s, 1H), 8.04 (s, 1H), 7.80-7.61 (m, 4H), 4.98 (s, 2H), 3.88 (s, 3H). |
| 88 | 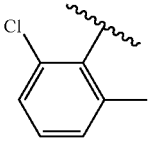 [SMILES: *c1c(C)cccc1Cl] |  | 2-chloro-4-[(2-methyl-6-chlorobenzyl)amino]pyrimidin-5-carboxamide | 311.0 | 4-[(2-methyl-6-chlorobenzyl)amino]-2-[(1-methyl-1H-pyrazol-4-yl)amino]pyrimidin-5-carboxamide | 372.1 | (400 MHz, DMSO-d₆ + DCl/D₂O) δ 8.76 (s, 1H), 8.06 (s, 1H), 7.71 (s, 1H), 7.46-7.36 (m, 1H), 7.36-7.20 (m, 2H), 4.88 (s, 2H), 3.89 (s, 3H), 2.35 (s, 3H). |
| 89 | 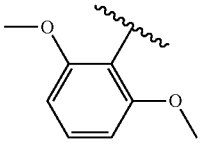 |  | 2-chloro-4-[(2,6-dimethoxybenzyl)amino]pyrimidin-5-carboxamide | 323.1 | 4-[(2,6-dimethoxybenzyl)amino]-2-[(1-methyl-1H-pyrazol-4-yl)amino]pyrimidin-5-carboxamide | 384.2 | (400 MHz, DMSO-d₆ + DCl/D₂O) δ 8.69 (s, 1H), 8.04 (s, 1H), 7.94 (s, 1H), 7.38-7.26 (m, 1H), 6.75-6.72 (m, 2H), 4.82 (s, 2H), 3.90 (s, 3H), 3.86-3.76 (m, 6H). |
| 90 | 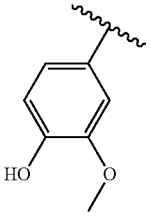 |  | 2-chloro-4-[(4-hydroxy-3-methoxybenzyl)amino]pyrimidin-5-carboxamide | 309.1 | 4-[(4-hydroxy-3-methoxybenzyl)amino]-2-[(1-methyl-1H-pyrazol-4-yl)amino]pyrimidin-5-carboxamide | 370.2 | (400 MHz, DMSO-d₆ + DCl/D₂O) δ 8.71 (s, 1H), 7.85 (s, 1H), 7.64 (s, 1H), 6.97-6.94 (m, 1H), 6.81-6.78 (m, 1H), 6.76-6.73 (m, 1H), 4.65 (s, 2H), 3.81 (s, 3H), 3.69 (s, 3H). |
| 91 | 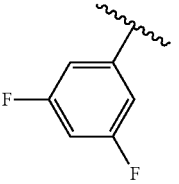 [SMILES: *c1cc(F)cc(F)c1] |  | 2-chloro-4-[(3,5-difluorobenzyl)amino]pyrimidin-5-carboxamide | 299.0 | 4-[(3,5-difluorobenzyl)amino]-2-[(1-methyl-1H-pyrazol-4-yl)amino]pyrimidin-5-carboxamide | 360.1 | (400 MHz, DMSO-d₆ + DCl/D₂O) δ 8.75 (s, 1H), 7.72 (s, 1H), 7.50 (s, 1H), 7.20-6.97 (m, 3H), 4.80 (s, 2H), 3.80 (s, 3H). |

TABLE 3-continued

Structures and characterization of intermediate compound A and target compound B of Examples 14-180

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 92 |  |  | 2-chloro-4-[[3-fluoro-5-(trifluoromethyl)benzyl]amino]pyrimidin-5-carboxamide | 349.0 | 4-[(3-fluoro-5-(trifluoromethyl)benzyl)amino]-2-[(1-methyl-1H-pyrazol-4-yl)amino]pyrimidin-5-carboxamide | 410.1 | (400 MHz, DMSO-$d_6$ + DCl/$D_2$O) δ 8.75 (s, 1H), 7.87 (s, 1H), 7.63-7.56 (m, 4H), 4.90 (s, 2H), 3.84 (s, 3H). |
| 93 | 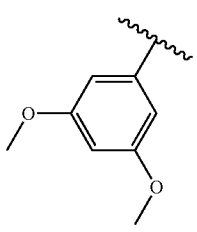 [SMILES: *c1cc(OC)cc(OC)c1] | | 2-chloro-4-[(3,5-dimethoxybenzyl)amino]pyrimidin-5-carboxamide | 323.1 | 4-[(3,5-dimethoxybenzyl)amino]-2-[(1-methyl-1H-pyrazol-4-yl)amino]pyrimidin-5-carboxamide | 384.2 | (400 MHz, DMSO-$d_6$ + DCl/$D_2$O) δ 8.73 (s, 1H), 7.80 (s, 1H), 7.63 (s, 1H), 6.60-6.45 (m, 2H), 6.42 (s, 1H), 4.71 (s, 2H), 3.81 (s, 3H), 3.71 (s, 6H). |
| 94 |  | 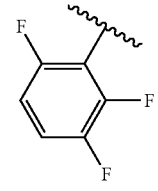 | 2-chloro-4-[(2,3,6-trifluorobenzyl)amino]pyrimidin-5-carboxamide | 317.0 | 4-[(2,3,6-trifluorobenzyl)amino]-2-[(1-methyl-1H-pyrazol-4-yl)amino]pyrimidin-5-carboxamide | 378.1 | (400 MHz, DMSO-$d_6$ + DCl/$D_2$O) δ 8.77 (s, 1H), 8.00 (s, 1H), 7.66 (s, 1H), 7.59-7.43 (m, 1H), 7.32-7.12 (m, 1H), 4.93 (s, 2H), 3.88 (s, 3H). |
| 95 |  | 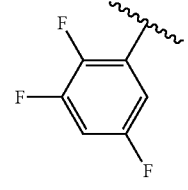 | 2-chloro-4-[(2,3,5-trifluorobenzyl)amino]pyrimidin-5-carboxamide | 317.0 | 4-[(2,3,5-trifluorobenzyl)amino]-2-[(1-methyl-1H-pyrazol-4-yl)amino]pyrimidin-5-carboxamide | 378.1 | (300 MHz, DMSO-$d_6$ + DCl/$D_2$O) δ 8.76 (s, 1H), 7.77 (s, 1H), 7.54-7.37 (m, 2H), 7.06-6.91 (m, 1H), 4.85 (s, 2H), 3.81 (s, 3H). |
| 96 |  | 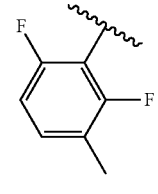 | 2-chloro-4-[(2,6-difluoro-3-methylbenzyl)amino]pyrimidin-5-carboxamide | 313.1 | 4-[(2,6-difluoro-3-methylbenzyl)amino]-2-[(1-methyl-1H-pyrazol-4-yl)amino]pyrimidin-5-carboxamide | 374.1 | (400 MHz, DMSO-$d_6$ + DCl/$D_2$O) δ 8.75 (s, 1H), 8.02 (s, 1H), 7.67 (s, 1H), 7.44-7.23 (m, 1H), 7.15-6.97 (m, 1H), 4.88 (s, 2H), 3.88 (s, 3H), 2.22 (s, 3H). |
| 97 |  | 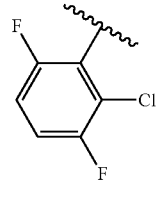 [SMILES: *c1c(F)ccc(F)c1Cl] | 2-chloro-4-[(2-chloro-3,6-difluorobenzyl)amino]pyrimidin-5-carboxamide | 333.0 | 4-[(2-chloro-3,6-difluorobenzyl)amino]-2-[(1-methyl-1H-pyrazol-4-yl)amino]pyrimidin-5-carboxamide | 394.1 | (400 MHz, DMSO-$d_6$ + DCl/$D_2$O) δ 8.73 (s, 1H), 8.00 (s, 1H), 7.89-7.26 (m, 3H), 3.88 (s, 2H), 2.56 (s, 3H). |
| 98 |  | 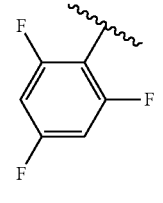 | 2-chloro-4-[(2,4,6-trifluorobenzyl)amino]pyrimidin-5-carboxamide | 317.0 | 4-[(2,4,6-trifluorobenzyl)amino]-2-[(1-methyl-1H-pyrazol-4-yl)amino]pyrimidin-5-carboxamide | 378.1 | (400 MHz, DMSO-$d_6$ + DCl/$D_2$O) δ 8.77 (s, 1H), 8.03 (s, 1H), 7.69 (s, 1H), 7.41-7.14 (m, 2H), 4.85 (s, 2H), 3.90 (s, 3H). |

TABLE 3-continued

Structures and characterization of intermediate compound A and target compound B of Examples 14-180

| Ex. No. | R¹ | R² | Compound A Name | Compound A LC MS m/z = (M + H)⁺ | Compound B Name | Compound B LC MS m/z = (M + H)⁺ | ¹H NMR |
|---|---|---|---|---|---|---|---|
| 99 | benzyl | ethyl | 2-chloro-4-(phenylethyl-amino)pyrimidin-5-carboxamide | 277.1 | 2-[(1-methyl-1H-pyrazol-4-yl)amino]-4-(phenylethyl-amino)pyrimidin-5-carboxamide | 338.2 | (400 MHz, DMSO-$d_6$ + DCl/$D_2O$) δ 8.65 (s, 1H), 7.91 (s, 1H), 7.64 (s, 1H), 7.33-7.25 (m, 2H), 7.25-7.16 (m, 3H), 3.80 (s, 3H), 3.74 (t, J = 7.5 Hz, 2H), 2.89 (t, J = 7.5 Hz, 2H). |
| 100 | 3-fluorobenzyl | ethyl | 2-chloro-4-[(3-fluorophenyl ethyl)amino]pyrimidin-5-carboxamide | 295.1 | 4-[(3-fluorophenyl-ethyl)amino]-2-[(1-methyl-1H-pyrazol-4-yl)amino]pyrimidin-5-carboxamide | 356.2 | (400 MHz, DMSO-$d_6$ + DCl/$D_2O$) δ 8.70 (s, 1H), 7.99 (s, 1H), 7.72 (s, 1H), 7.42-7.31 (m, 1H), 7.14-7.07 (m, 3H), 3.86 (s, 3H), 3.79 (t, J = 7.3 Hz, 2H), 2.95 (t, J = 7.3 Hz, 2H). |
| 101 | 3-methylbenzyl | ethyl | 2-chloro-4-[(3-methylphenyyl-ethyl)amino]pyrimidin-5-carboxamide | 291.1 | 2-[(1-methyl-1H-pyrazol-4-yl)amino]-4-[(3-methylphenyl-ethyl)amino]pyrimidin-5-carboxamide | 352.2 | (400 MHz, DMSO-$d_6$ + DCl/$D_2O$) δ 8.69 (s, 1H), 7.99 (s, 1H), 7.74 (s, 1H), 7.08-6.99 (m, 4H), 3.85 (s, 3H), 3.77 (t, J = 7.3 Hz, 2H), 2.87 (t, J = 7.3 Hz, 2H), 2.27 (s, 3H). |
| 102 | 3-chlorobenzyl | ethyl | 2-chloro-4-[(3-chlorophenyl ethyl)amino]pyrimidin-5-carboxamide | 311.0 | 2-[(1-methyl-1H-pyrazol-4-yl)amino]-4-[(3-chloro-phenylethyl)amino]pyrimidin-5-carboxamide | 372.1 | (400 MHz, DMSO-$d_6$ + DCl/$D_2O$) δ 8.69 (s, 1H), 7.97 (s, 1H), 7.69 (s, 1H), 7.36-7.28 (m, 3H), 7.24-7.18 (m, 1H), 3.86 (s, 3H), 3.83-3.72 (m, 2H), 2.94 (t, J = 7.1 Hz, 2H). |
| 103 | 3-(trifluoromethyl)benzyl | ethyl | 2-chloro-4-[[3-(trifluoromethyl)phenylethyl]amino]pyrimidin-5-carboxamide | 345.1 | 2-[(1-methy1-1H-pyrazol-4-yl)amino]-4-[[3-(trifluoro-methyl)phenyl-ethyl]amino]pyrimidin-5-carboxamide | 406.2 | (400 MHz, DMSO-$d_6$ + DCl/$D_2O$) δ 8.69 (s, 1H), 7.95 (s, 1H), 7.68 (s, 1H), 7.64-7.50 (m, 4H), 3.92-3.75 (m, 5H), 3.04 (t, J = 7.1 Hz, 2H). |
| 104 | 3-methoxybenzyl | ethyl | 2-chloro-4-[(3-methoxyphenyl-ethyl)amino]pyrimidin-5-carboxamide | 307.1 | 2-[(1-methyl-1H-pyrazol-4-yl)amino]-4-[(3-methoxy-phenylethyl)amino]pyrimidin-5-carboxamide | 368.2 | (400 MHz, DMSO-$d_6$ + DCl/$D_2O$) δ 8.69 (s, 1H), 7.98 (s, 1H), 7.73 (s, 1H), 7.22 (d, J = 7.8 Hz, 1H), 6.86-6.76 (m, 3H), 3.85 (s, 3H), 3.78 (t, J = 7.3 Hz, 2H), 3.73 (s, 3H), 2.89 (t, J = 7.3 Hz, 2H). |

TABLE 3-continued

Structures and characterization of intermediate compound A and target compound B of Examples 14-180

| Ex. No. | R¹ | R² | Compound A Name | Compound A LC MS m/z = (M + H)⁺ | Compound B Name | Compound B LC MS m/z = (M + H)⁺ | ¹H NMR |
|---|---|---|---|---|---|---|---|
| 105 | 2-fluorobenzyl | (1-methyl-1H-pyrazol-4-yl) | 2-chloro-4-[(2-fluorophenylethyl)amino]pyrimidin-5-carboxamide | 295.1 | 4-[(2-fluorophenylethyl)amino]-2-[(1-methyl-1H-pyrazol-4-yl)amino]pyrimidin-5-carboxamide. | 356.2 | (400 MHz, DMSO-$d_6$ + DCl/$D_2$O) δ 8.69 (s, 1H), 7.98 (s, 1H), 7.71 (s, 1H), 7.35-7.25 (m, 4H), 3.87 (s, 3H), 3.82 (t, J = 7.2 Hz, 2H), 2.97 (t, J = 7.1 Hz, 2H). |
| 106 | 2-methylbenzyl | (1-methyl-1H-pyrazol-4-yl) | 2-chloro-4-[(2-methylphenylethyl)amino]pyrimidin-5-carboxamide | 291.1 | 4-[(2-methylphenylethyl)amino]-2-[(1-methyl-1H-pyrazol-4-yl)amino]pyrimidin-5-carboxamide | 352.2 | (400 MHz, DMSO-$d_6$ + DCl/$D_2$O) δ 8.69 (s, 1H), 7.97 (s, 1H), 7.70 (s, 1H), 7.11-6.93 (m, 4H), 3.83 (s, 3H), 3.77 (t, J = 7.5 Hz, 2H), 2.89 (t, J = 7.4 Hz, 2H), 2.24 (s, 3H). |
| 107 | 2-methoxybenzyl | (1-methyl-1H-pyrazol-4-yl) | 2-chloro-4-[(2-methoxyphenylethyl)amino]pyrimidin-5-carboxamide | 307.1 | 4-[(2-methoxyphenylethyl)amino]-2-[(1-methyl-1H-pyrazol-4-yl)amino]pyrimidin-5-carboxamide | 368.2 | (400 MHz, DMSO-$d_6$ + DCl/$D_2$O) δ 8.67 (s, 1H), 7.94 (s, 1H), 7.70 (s, 1H), 7.26-7.19 (m, 1H), 7.19-7.11 (m, 1H), 6.99-6.95 (m, 1H), 6.90-6.88 (m, 1H), 3.83 (s, 3H), 3.80-3.67 (m, 5H), 2.91 (t, J = 7.0 Hz, 2H). |
| 108 | 2-fluoro-6-chlorobenzyl | (1-methyl-1H-pyrazol-4-yl) | 2-chloro-4-[(2-fluoro-6-chlorophenylethyl)amino]pyrimidin-5-carboxamide | 329.0 | 4-[(2-fluoro-6-chlorophenylethyl)amino]-2-[(1-methyl-1H-pyrazol-4-yl)amino]pyrimidin-5-carboxamide | 390.1 | (400 MHz, DMSO-$d_6$ + DCl/$D_2$O) δ 8.69 (s, 1H), 8.01 (s, 1H), 7.73 (s, 1H), 7.32-7.25 (m, 2H), 7.15-7.08 (m, 1H), 3.93 (s, 3H), 3.90-3.82 (m, 2H), 3.16-3.01 (m, 2H). |
| 109 | (1-methyl-1H-pyrazol-4-yl)methyl | pyridin-2-yl | 2-chloro-4-[[(1-methyl-1H-pyrazol-4-yl)methyl]amino]pyrimidin-5-carboxamide | 267.1 | 4-[[(1-methyl-1H-pyrazol-4-yl)methyl][amino]-2-[(1-methyl-1H-pyrazol-4-yl)amino]pyrimidin-5-carboxamide | 328.2 | (400 MHz, DMSO-$d_6$ + DCl/$D_2$O) δ 8.72 (s, 1H), 7.93 (s, 1H), 7.87 (s, 1H), 7.69 (s, 1H), 7.66 (s, 1H), 4.62 (s, 2H), 3.90 (s, 3H), 3.86 (s, 3H). |
| 110 | pyridin-2-ylmethyl | (1-methyl-1H-pyrazol-4-yl) | 2-chloro-4-[(pyridin-2-ylmethyl)amino]pyrimidin-5-carboxamide | 264.1 | 2-[(1-methyl-1H-pyrazol-4-yl)amino]-4-[(pyridin-2-ylmethyl)amino]pyrimidin-5-carboxamide | 325.1 | (400 MHz, DMSO-$d_6$ + DCl/$D_2$O) δ 8.93-8.78 (m, 2H), 8.66-8.46 (m, 1H), 8.08-7.89 (m, 2H), 7.67 (s, 1H), 7.31 (s, 1H), 5.25 (s, 2H), 3.84 (s, 3H). |
| 111 | pyridin-3-ylmethyl | (1-methyl-1H-pyrazol-4-yl) | 2-chloro-4-[(pyridin-3-ylmethyl)amino]pyrimidin-5-carboxamide | 264.1 | 2-[(1-methyl-1H-pyrazol-4-yl)amino]-4-[(pyridin-3-ylmethyl)amino]pyrimidin-5-carboxamide | 325.1 | (300 MHz, DMSO-$d_6$ + DCl/$D_2$O) δ 8.92-8.83 (m, 2H), 8.77 (s, 1H), 8.58-8.48 (m, 1H), 8.13-8.01 (m, 1H), 7.73 (s, 1H), 7.42 (s, 1H), 5.00 (s, 2H), 3.82 (s, 3H). |

TABLE 3-continued

Structures and characterization of intermediate compound A and target compound B of Examples 14-180

| | | | Compound A | | Compound B | |
|---|---|---|---|---|---|---|
| Ex. No. | R¹ | R² | Name | LC MS m/z = (M + H)⁺ | Name | LC MS m/z = (M + H)⁺ | ¹H NMR |
| 112 | 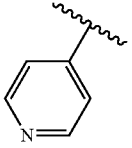 [SMILES: *c1ccncc1] |  | 2-chloro-4-[[(pyridin-4-ylmethyl)amino]pyrimidin-5-carboxamide | 264.1 | 2-[(1-methyl-1H-pyrazol-4-yl)amino]-4-[(pyridin-4-ylmethyl)amino]pyrimidin-5-carboxamide | 325.1 | (400 MHz, DMSO-$d_6$ + DCl/$D_2O$) δ 8.71 (s, 1H), 7.83 (s, 1H), 7.62 (s, 1H), 6.79 (d, J = 7.7 Hz, 4H), 4.64 (s, 2H), 3.82 (s, 3H). |
| 113 | 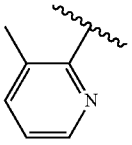 [SMILES: *c1ncccc1C] | | 2-chloro-4-[[(3-methylpyridin-2-yl)methyl]amino]pyrimidin-5-carboxamide | 278.1 | 2-[(1-methyl-1H-pyrazol-4-yl)amino]-4-[[(3-methyl-pyridin-2-yl)methyl]amino]pyrimidin-5-carboxamide | 339.2 | (400 MHz, DMSO-$d_6$ + DCl/$D_2O$) δ 8.82 (s, 1H), 8.57 (s, 1H), 8.50 (d, J = 7.8 Hz, 1H), 8.03-7.84 (m, 1H), 7.70-7.49 (m, 1H), 7.23 (s, 1H), 5.16 (s, 2H), 3.76 (s, 3H), 2.49 (s, 3H). |
| 114 |  | | 2-chloro-4-[[(2-fluoropyridin-3-yl)methyl]amino]pyrimidin-5-carboxamide | 282.0 | 4-[[(2-fluoro-pyridin-3-yl)methyl]amino]-2-[(1-methyl-1H-pyrazol-4-yl)amino]pyrimidin-5-carboxamide | 343.1 | (400 MHz, DMSO-$d_6$ + DCl/$D_2O$) δ 8.77 (s, 1H), 8.24-8.10 (m, 1H), 7.87-7.73 (m, 1H), 7.68 (s, 1H), 7.48 (s, 1H), 7.42-7.21 (m, 1H), 4.81 (s, 2H), 3.80 (s, 3H). |
| 115 | 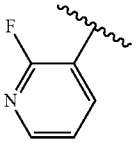 | | 2-chloro-4-[[(2-methylpyridin-3-yl)methyl]amino]pyrimidin-5-carboxamide | 278.1 | 4-[[(2-methyl pyridin-3-yl)methyl]amino]-2-[(1-methyl-1H-pyrazol-4-yl)amino]pyrimidin-5-carboxamide | 339.2 | (400 MHz, DMSO-$d_6$ + DCl/$D_2O$) δ 8.77 (s, 1H), 8.72-8.59 (m, 1H), 8.22 (s, 1H), 7.85-7.80 (m, 1H), 7.74 (s, 1H), 7.58-7.57 (m, 1H), 4.89 (s, 2H), 3.81 (s, 3H), 2.80 (s, 3H). |
| 116 |  | | 2-chloro-4-[[(2-methoxypyridin-3-yl)methyl]amino]pyrimidin-5-carboxamide | 294.1 | 4-[[(2-methoxy-pyridin-3-yl)methyl]amino]-2-[(1-methyl-1H-pyrazol-4-yl)amino]pyrimidin-5-carboxamide | 355.2 | (400 MHz, DMSO-$d_6$ + DCl/$D_2O$) δ 8.75 (s, 1H), 8.14 (dd, J = 5.1, 1.8 Hz, 1H), 7.65 (s, 1H), 7.62-7.53 (m, 1H), 7.49 (s, 1H), 7.10-6.97 (m, 1H), 4.69 (s, 2H), 4.01 (s, 3H), 3.78 (s, 3H). |
| 117 | 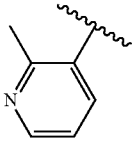 | | 2-chloro-4-[[(2-ethoxypyridin-3-yl)methyl]amino]pyrimidin-5-carboxamide | 308.1 | 4-[[(2-ethoxy pyridin-3-yl)methyl]amino]-2-[(1-methyl-1H-pyrazol-4-yl)amino]pyrimidin-5-carboxamide | 369.2 | (400 MHz, DMSO-$d_6$ + DCl/$D_2O$) δ 8.72 (s, 1H), 8.10 (dd, J = 5.1, 1.8 Hz, 1H), 7.69 (s, 1H), 7.63-7.52 (m, 1H), 7.51 (s, 1H), 7.09-6.88 (m, 1H), 4.68 (s, 2H), 4.41 (q, J = 7.0 Hz, 2H), 3.78 (s, 3H), 1.36 (t, J=7.0 Hz, 3H). |
| 118 |  | | 2-chloro-4-[[(2-2-isopropoxy pyridin-3-yl)methyl]amino]pyrimidin-5-carboxamide | 322.1 | 4-[[(2-iso-propoxypyridin-3-yl)methyl]amino]-2-[(1-methy1-1H-pyrazol-4-yl)amino]pyrimidin-5-carboxamide | 383.2 | (400 MHz, DMSO-$d_6$ + DCl/$D_2O$) δ 8.74 (s, 1H), 8.13 (dd, J = 5.3, 1.8 Hz, 1H), 7.81 (s, 1H), 7.72-7.59 (m, 1H), 7.56 (s, 1H), 7.15-6.93 (m, 1H), 5.47-5.26 (m, 1H), 4.68 (s, 2H), 3.83 (s, 3H), 1.32 (d, J = 6.1 Hz, 6H). |

TABLE 3-continued

Structures and characterization of intermediate compound A and target compound B of Examples 14-180

| | | | Compound A | | | Compound B | | |
|---|---|---|---|---|---|---|---|---|
| Ex. No. | R[1] | R[2] | Name | LC MS m/z = (M + H)+ | Name | LC MS m/z = (M + H)+ | $^1$H NMR |
| 119 | 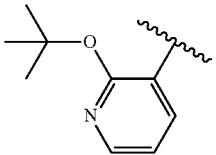 [SMILES: *c1cccnc1OC(C)(C)C] |  | 2-chloro-4-[[(2-tert-butoxypyridin-3-yl)methyl]amino]pyrimidin-5-carboxamide | 336.1 | 4-[[(2-tert-butoxypyridin-3-yl)methyl]amino]-2-[(1-methyl-1H-pyrazol-4-yl)amino]pyrimidin-5-carboxamide | 397.2 | (300 MHz, DMSO-$d_6$ + DCl/$D_2O$) δ 8.73 (s, 1H), 7.85 (s, 1H), 7.61 (s, 1H), 7.54-7.43 (m, 1H), 6.45-6.25 (m, 1H), 4.73-4.61 (m, 1H), 4.56 (s, 2H), 3.86 (s, 3H), 1.59 (s, 9H). |
| 120 | 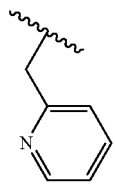 [SMILES: *Cc1ccccn1] | | 2-chloro-4-[[2-(pyridin-2-yl)ethyl]amino]pyrimidin-5-carboxamide | 278.1 | 2-[(1-methyl-1H-pyrazol-4-yl)amino]-4-[[2-(pyridin-2-yl)ethyl]amino]pyrimidin-5-carboxamide | 339.2 | (400 MHz, DMSO-$d_6$ + DCl/$D_2O$) δ 8.89-8.63 (m, 2H), 8.50 (s, 1H), 8.02-7.88 (m, 3H), 7.61 (s, 1H), 4.10-3.95 (m, 2H), 3.90 (s, 3H), 3.47 (t, J = 6.5 Hz, 2H). |
| 121 |  | | 2-chloro-4-[[2-(pyridin-3-yl)ethyl]amino]pyrimidin-5-carboxamide | 278.1 | 2-[(1-methyl-1H-pyrazol-4-yl)amino]-4-[[2-(pyridin-3-yl)ethyl]amino]pyrimidin-5-carboxamide | 339.2 | (400 MHz, DMSO-$d_6$ + DCl/$D_2O$) δ 8.89 (s, 1H), 8.86-8.81 (m, 1H), 8.71 (s, 1H), 8.57-8.49 (m, 1H), 8.11-8.02 (m, 1H), 7.98 (s, 1H), 7.74-7.65 (m, 1H), 4.02-3.72 (m, 5H), 3.20 (t, J = 6.8 Hz, 2H). |
| 122 | 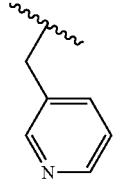 [SMILES: *Cc1cccnc1] | | 2-chloro-4-[[2-(6-methylpyridin-2-yl)ethyl]amino]pyrimidin-5-carboxamide | 292.1 | 2-[(1-methyl-1H-pyrazol-4-yl)amino]-4-[[2-(6-methylpyridin-2-yl)ethyl]amino]pyrimidin-5-carboxamide | 353.2 | (400 MHz, DMSO-$d_6$ + DCl/$D_2O$) δ 7.70 (s, 1H), 7.64-7.45 (m, 2), 7.45-7.23 (m, 1H), 7.08-6.87 (m, 2H), 3.42-3.19 (m, 5H), 2.67 (t, J = 6.4 Hz, 2H), 1.97 (s, 3H). |
| 123 |  | 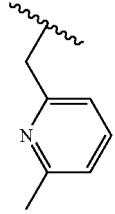 [SMILES: *Cc1cccc(C)n1] | 2-chloro-4-[(thiazol-2-ylmethyl)amino]pyrimidin-5-carboxamide | 270.0 | 2-[(1-methyl-1H-pyrazol-4-yl)amino]-4-[(thiazol-2-ylmethyl)amino]pyrimidin-5-carboxamide | 331.1 | (400 MHz, DMSO-$d_6$ + DCl/$D_2O$) δ 8.80 (s, 1H), 8.02 (d, J = 3.3 Hz, 1H), 7.96-7.83 (m, 2H), 7.54 (s, 1H), 5.22 (s, 2H), 3.87 (s, 3H). |
| 124 |  | 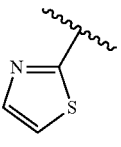 [SMILES: *c1nccs1] | 2-chloro-4-[(naphthalen-2-ylmethyl)amino]pyrimidin-5-carboxamide | 313.1 | 2-[(1-methyl-1H-pyrazol-4-yl)amino]-4-[(naphthalen-2-ylmethyl)amino]pyrimidin-5-carboxamide | 374.2 | (400 MHz, DMSO-$d_6$ + DCl/$D_2O$) δ 8.78 (s, 1H), 8.20-8.09 (m, 1H), 8.08-7.97 (m, 1H), 7.92 (d, J = 8.2 Hz, 1H), 7.71-7.56 (m, 2H), 7.56-7.44 (m, 2H), 7.43-7.31 (m, 2H), 5.25 (s, 2H), 3.27 (s, 3H). |
| 125 |  | 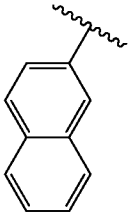 [SMILES: *c1ccc2ccccc2c1] | 2-chloro-4-[[(2,3-dihydrobenzo[b][1,4]dioxan-5-yl)methyl]amino]pyrimidin-5-carboxamide | 321.1 | 2-[(1-methyl-1H-pyrazol-4-yl)amino]-4-[[(2,3-dihydrobenzo[b][1,4]dioxan-5-yl)methyl]amino]pyrimidin-5-caboxamide | 382.2 | (400 MHz, DMSO-$d_6$ + DCl/$D_2O$) δ 8.74 (s, 1H), 7.78 (s, 1H), 7.56 (s, 1H), 6.90-6.76 (m, 2H), 6.76-6.67 (m, 1H), 4.69 (s, 2H), 4.37-4.31 (m, 2H), 4.31-4.26 (m, 2H), 3.82 (s, 3H). |

TABLE 3-continued

Structures and characterization of intermediate compound A and target compound B of Examples 14-180

| Ex. No. | R¹ | R² | Compound A Name | LC MS m/z = (M + H)⁺ | Compound B Name | LC MS m/z = (M + H)⁺ | ¹H NMR |
|---|---|---|---|---|---|---|---|
| 126 | (1H-indol-3-yl)methyl | methyl | 2-chloro-4-[[(1H-indol-3-yl)methyl]amino]pyrimidin-5-carboxamide | 302.1 | 2-[(1-methyl-1H-pyrazol-4-yl)amino]-4-[[(1H-indol-3-yl)methyl]amino]pyrimidin-5-carboxamide | 363.2 | (400 MHz, DMSO-d₆ + DCl/D₂O) δ 8.72 (s, 1H), 7.95 (s, 1H), 7.74 (s, 1H), 7.63-7.49 (m, 1H), 7.43 (d, J = 8.2 Hz, 1H), 7.35 (s, 1H), 7.21-7.08 (m, 1H), 7.08-6.96 (m, 1H), 4.90 (s, 2H), 3.75 (s, 3H). |
| 127 | (S)-2-phenylpropyl | methyl | (S)-2-chloro-4-[(2-phenylpropyl)amino]pyrimidin-5-carboxamide | 291.1 | (S)-2-[(1-methyl-1H-pyrazol-4-yl)amino]-4-[(2-phenylpropyl)amino]pyrimidin-5-carboxamide | 352.2 | (400 MHz, DMSO-d₆ + DCl/D₂O) δ 8.70 (s, 1H), 8.02 (s, 1H), 7.78 (s, 1H), 7.35-7.25 (m, 5H), 3.87 (s, 3H), 3.82-3.64 (m, 2H), 3.21-3.07 (m, 1H), 1.27 (d, J = 7.0 Hz, 3H). |
| 128 | (R)-2-phenylpropyl | methyl | (R)-2-chloro-4-[(2-phenylpropyl)amino]pyrimidin-5-carboxamide | 291.1 | (R)-2-[(1-methyl-1H-pyrazol-4-yl)amino]-4-[(2-phenylpropyl)amino]pyrimidin-5-carboxamide | 352.2 | (400 MHz, DMSO-d₆ + DCl/D₂O) δ 8.70 (s, 1H), 7.95 (s, 1H), 7.69 (s, 1H), 7.38-7.18 (m, 5H), 3.83 (s, 3H), 3.78-3.66 (m, 2H), 3.20-3.07 (m, 1H), 1.27 (d, J = 7.0 Hz, 3H). |
| 129 | benzyl | 2-methoxyethyl | 2-chloro-4-(benzylamino)pyrimidin-5-carboxamide | 263.1 | 4-benzylamino-2-[[1-(2-methyoxyethyl)-1H-pyrazol-4-yl]amino]pyrimidin-5-carbaoxaide | 368.2 | (400 MHz, DMSO-d₆ + DCl/D₂O) δ 8.67 (s, 1H), 7.77 (s, 1H), 7.51 (s, 1H), 7.35-7.19 (m, 5H), 4.71 (s, 2H), 4.13 (t, J = 5.3 Hz, 2H), 3.54 (t, J = 5.3 Hz, 2H), 3.08 (s, 3H). |
| 130 | benzyl | 2-(dimethylamino)ethyl | 2-chloro-4-(benzylamino)pyrimidin-5-carboxamide | 263.1 | 4-benzylamino-2-[[1-(2-dimethylamino)ethyl)-1H-pyrazol-4-yl]amino]pyrimidin-5-carbaoxaide | 381.2 | (400 MHz, DMSO-d₆ + DCl/D₂O) δ 8.76 (s, 1H), 7.96 (s, 1H), 7.65 (s, 1H), 7.44-7.34 (m, 4H), 7.34-7.25 (m, 1H), 4.82 (s, 2H), 4.65-4.50 (m, 2H), 3.67-3.40 (m, 2H), 2.73 (s, 6H). |
| 131 | 2,6-difluorobenzyl | H | 2-chloro-4-[(2,6-difluorobenzyl)amino]pyrimidin-5-carboxamide | 299.00 | 2-[(1H-pyrazol-4-yl)amino]-4-[(2,6-difluorobenzyl)amino]pyrimidin-5-carboxamide | 346.1 | (400 MHz, DMSO-d₆ + DCl/D₂O) δ 8.78 (s, 1H), 8.19 (s, 2H), 7.54-7.40 (m, 1H), 7.23-7.11 (m, 2H), 4.87 (s, 2H). |
| 132 | 2,6-difluorobenzyl | ethyl | 2-chloro-4-[(2,6-difluorobenzyl)amino]pyrimidin-5-carboxamide | 299.00 | 4-[(2,6-difluorobenzyl)amino]-2-[(1-ethyl-1H-pyrazol-4-yl)amino]pyrimidin-5-carboxamide | 374.1 | (400 MHz, DMSO-d₆ + DCl/D₂O) δ 8.76 (s, 1H), 8.05 (s, 1H), 7.70 (s, 1H), 7.51-7.40 (m, 1H), 7.22-7.07 (m, 2H), 4.90 (s, 2H), 4.18 (q, J = 7.3 Hz, 2H), 1.39 (t, J = 7.2 Hz, 3H). |

TABLE 3-continued

Structures and characterization of intermediate compound A and target compound B of Examples 14-180

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 133 | 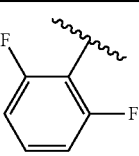 | 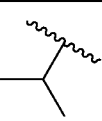 | 2-chloro-4-[(2,6-difluorobenzyl)amino]pyrimidin-5-carboxamide | 299.00 | 4-[(2,6-difluorobenzyl)amino]-2-[(1-isopropyl-1H-pyrazol-4-yl)amino]pyrimidin-5-carboxamide | 388.2 | (400 MHz, DMSO-d₆ + DCl/D₂O) δ 8.77 (s, 1H), 8.08 (s, 1H), 7.73 (s, 1H), 7.54-7.37 (m, 1H), 7.25-7.07 (m, 2H), 4.90 (s, 2H), 4.62-4.49 (m, 1H), 1.44 (d, J=6.7 Hz, 6H). |
| 134 | 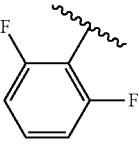 | 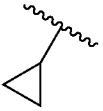 [SMILES: *C1CC1] | 2-chloro-4-[(2,6-difluorobenzyl)amino]pyrimidin-5-carboxamide | 299.00 | 4-[(2,6-difluorobenzyl)amino]-2-[(1-cyclopropyl-1H-pyrazol-4-yl)amino]pyrimidin-5-carboxamide | 386.1 | (400 MHz, DMSO-d₆ + DCl/D₂O) δ 8.76 (s, 1H), 8.04 (s, 1H), 7.65 (s, 1H), 7.51-7.43 (m, 1H), 7.22-7.13 (m, 2H), 4.90 (s, 2H), 3.81-3.69 (m, 1H), 1.05-0.95 (m, 4H). |
| 135 | 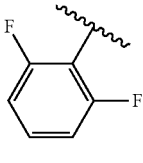 | 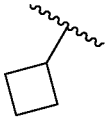 [SMILES: *C1CCC1] | 2-chloro-4-[(2,6-difluorobenzol-4-yl)amino]pyridin-5-carboxamide | 299.00 | 4-[(2,6-difluorobenzyl)amino]-2-[(1-cyclobutyl-1H-pyrazol-4-yl)amino]pyrimidin-5-carboxamide | 400.2 | (400 MHz, DMSO-d₆ + DCl/D₂O) δ 8.76 (s, 1H), 8.08 (s, 1H), 7.72 (s, 1H), 7.54-7.41 (m, 1H), 7.25-7.08 (m, 2H), 4.98-4.77 (m, 3H), 2.51-2.29 (m, 4H), 1.86-1.70 (m, 2H). |
| 136 | 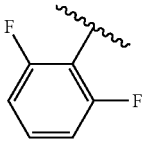 |  | 2-chloro-4-[(2,6-difluorobenzyl)amino]pyrimidin-5-carboxamide | 299.00 | 4-[(2,6-difluorobenzyl)amino]-2-[[1-(tetrahydrofuran-3-yl)-1H-pyrazol-4-yl)amino]pyrimidin-5-carboxamide | 416.2 | (400 MHz, DMSO-d₆ + DCl/D₂O) δ 8.76 (s, 1H), 8.08 (s, 1H), 7.71 (s, 1H), 7.56-7.38 (m, 1H), 7.19-7.12 (m, 2H), 5.12-4.96 (m, 1H), 4.89 (s, 2H), 4.04-3.70 (m, 4H), 2.44-2.33 (m, 1H), 2.31-2.09 (m, 1H). |
| 137 | 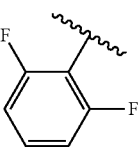 |  | 2-chloro-4-[(2,6-difluorobenzyl)amino]pyrimidin-5-carboxamide | 299.00 | 4-[(2,6-difluorobenzyl)amino]-2-[[1-(tetrahydro-2H-pyran-4-yl)-1H-pyrazol-4-yl)amino]pyrimidin-5-carboxamide | 430.2 | (400 MHz, DMSO-d₆ + DCl/D₂O) δ 8.77 (s, 1H), 8.07 (s, 1H), 7.72 (s, 1H), 7.51-7.37 (m, 1H), 7.27-7.10 (m, 2H), 4.90 (s, 2H), 4.51-4.38 (m, 1H), 4.00-3.88 (m, 2H), 3.56-3.38 (m, 2H), 2.03-1.85 (m, 4H). |
| 138 | 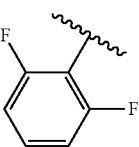 | 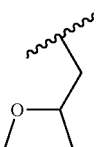 | 2-chloro-4-[(2,6-difluorobenzyl)amino]pyrimidin-5-carboxamide | 299.0 | 4-[(2,6-difluorobenzyl)amino]-2-[[1-((tetrahydrofuran-2-yl)methyl)-1H-pyrazol-4-yl]amino]pyrimidin-5-carboxamide | 430.2 | (400 MHz, DMSO-d₆ + DCl/D₂O) δ 8.75 (s, 1H), 8.06 (s, 1H), 7.68 (s, 1H), 7.58-7.40 (m, 1H), 7.23-7.07 (m, 2H), 4.90 (s, 2H), 4.24-4.08 (m, 3H), 3.72-3.49 (m, 2H), 1.97-1.48 (m, 4H). |
| 139 | 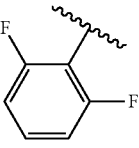 | 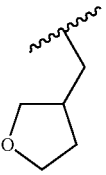 [SMILES: *CC1CCOC1] | 2-chloro-4-[(2,6-difluorobenzyl)amino]pyrimidin-5-carboxamide | 299.0 | 4-[(2,6-difluorobenzyl)amino]-2-[[1-tetrahydrofuran-3-yl)methyl)-1H-pyrazol-4-yl]amino]pyrimidin-5-carboxamide | 430.2 | (400 MHz, DMSO-d₆ + DCl/D₂O) δ 8.76 (s, 1H), 8.08 (s, 1H), 7.71 (s, 1H), 7.55-7.38 (m, 1H), 7.21-7.06 (m, 2H), 4.90 (s, 2H), 4.14 (d, J = 7.4 Hz, 2H), 3.81-3.38 (m, 4H), 2.78-2.64 (m, 1H), 1.99-1.84 (m, 1H), 1.69-1.52 (m, 1H). |

TABLE 3-continued

Structures and characterization of intermediate compound A and target compound B of Examples 14-180

| Ex. No. | R¹ | R² | Compound A Name | LC MS m/z = (M + H)⁺ | Compound B Name | LC MS m/z = (M + H)⁺ | ¹H NMR |
|---|---|---|---|---|---|---|---|
| 140 | 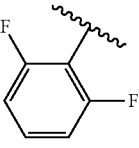 | 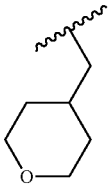 [SMILES: *CC1CCOCC1] | 2-chloro-4-[(2,6-difluorobenzyl)amino]pyrimidin-5-carboxamide | 299.0 | 4-[(2,6-difluorobenzyl)amino]-2-[[1-((tetrahydro-2H-pyran-4-yl)methyl)-1H-pyrazol-4-yl]amino]pyrimidin-5-carboxamide | 444.2 | (400 MHz, DMSO-d₆ + DCl/D₂O) δ 8.75 (s, 1H), 8.03 (s, 1H), 7.68 (s, 1H), 7.54-7.40 (m, 1H), 7.23-7.08 (m, 2H), 4.89 (s, 2H), 4.08-3.95 (m, 2H), 3.86-3.71 (m, 2H), 3.22 (t, J =11.1 Hz, 2H), 2.11-1.93 (m, 1H), 1.46-1.32 (m, 2H), 1.32-1.11 (m, 2H). |
| 141 | 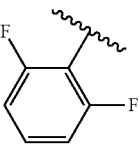 | 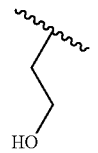 | 2-chloro-4-[(2,6-difluorobenzyl)amino]pyrimidin-5-carboxamide | 299.0 | 4-[(2,6-difluorobenzyl)amino]-2-[[1-(2-(hydroxyethyl)-1H-pyrazol-4-yl]amino]pyrimidin-5-carboxamide | 390.1 | (400 MHz, DMSO-d₆ + DCl/D₂O) δ 8.77 (s, 1H), 8.07 (s, 1H), 7.74 (s, 1H), 7.56-7.40 (m, 1H, 7.23-7.08 (m, 2H), 4.89 (s, 2H), 4.20 (t, J = 5.5 Hz, 2H), 3.74 (t, J = 5.5 Hz, 2H). |
| 142 | 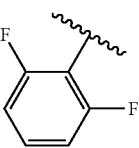 | 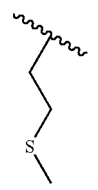 [SMILES: *CCSC] | 2-chloro-4-[(2,6-difluorobenzyl)amino]pyrimidin-5-carboxamide | 299.0 | 4-[(2,6-difluorobenzyl)amino]-2-[[1-(2-methylthioethyl)-1H-pyrazol-4-yl]amino]pyrimidin-5-carboxamide | 420.1 | (400 MHz, DMSO-d₆ + DCl/D₂O) δ 8.77 (s, 1H), 8.13 (s, 1H), 7.73 (s, 1H), 7.55-7.41 1H), 7.25-7.09 (m, 2H), 4.91 (s, 2H), 4.35 (t, J = 6.6 Hz, 2H), 2.90 (t, J = 6.6 Hz, 2H), 1.99 (s, 3H). |
| 143 | 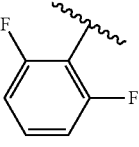 | 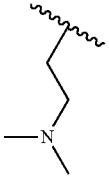 [SMILES: *CCN(C)C] | 2-chloro-4-[(2,6-difluorobenzyl)amino]pyrimidin-5-carboxamide | 299.0 | 4-[(2,6-difluorobenzyl)amino]-2-[[1-(2-(dimethylamino)ethylthioethyl)-1H-pyrazol-4-yl]amino]pyrimidin-5-carboxamide | 417.2 | (400 MHz, DMSO-d₆ + DCl/D₂O) δ 8.78 (s, 1H), 8.19 (s, 1H), 7.80 (s, 1H), 7.54-7.42 (m, 1H), 7.28-7.10 (m, 2H), 4.91 (s, 2H), 4.65 (t, J = 6.4 Hz, 2H), 3.59 (t, J = 8.4 Hz, 2H), 2.78 (s, 6H). |
| 144 | 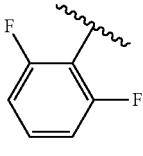 | 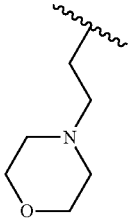 [SMILES: *CCN1CCOCC1] | 2-chloro-4-[(2,6-difluorobenzyl)amino]pyrimidin-5-carboxamide | 299.0 | 4-[(2,6-difluorobenzyl)amino]-2-[[1-(2-(morpholin-1-yl)ethyl)-1H-pyrazol-4-yl]amino]pyrimidin-5-carboxamide | 459.2 | (400 MHz, DMSO-d₆ + DCl/D₂O) δ 8.75 (s, 1H), 8.17 (s, 1H), 7.78 (s, 1H), 7.54-7.40 (m, 1H), 7.19-7.12 (m, 2H), 4.96-4.79 (m, 2H), 4.80-4.58 (m, 2H), 4.03-3.88 (m, 2H), 3.88-3.71 (m, 2H), 3.70-3.57 (m, 2H), 3.42-3.25 (m, 2H), 3.25-3.05 (m, 2H). |
| 145 | 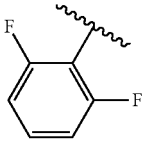 | 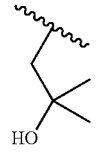 | 2-chloro-4-[(2,6-difluorobenzyl)amino]pyrimidin-5-carboxamide | 299.0 | 4-[(2,6-difluorobenzyl)amino]-2-[[1-(2-hydroxy-2-methylpropyl)-1H-pyrazol-4-yl]amino]pyrimidin-5-carboxamide | 418.2 | (400 MHz, DMSO-d₆ + DCl/D₂O) δ 8.78 (s, 1H), 8.10 (s, 1H), 7.76 (s, 1H), 7.54-7.40 (m, 1H), 7.27-7.08 (m, 2H), 4.88 (s, 2H), 4.09 (s, 2H), 1.08 (s, 6H). |
| 146 | 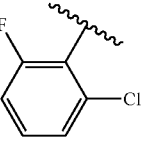 | 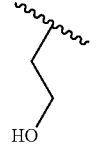 | 2-chloro-4-[(2-fluoro-6-chlorobenzyl)amino]pyrimidin-5-carboxamide | 315.0 | 4-[(2-fluoro-6-chlorobenzyl)amino]-2-[[1-(2-hydroxyethyl)-1H-pyrazol-4-yl]amino]pyrimidin-5-carboxamide | 406.1 | (400 MHz, DMSO-d₆ + DCl/D₂O) δ 8.76 (s, 1H), 8.08 (s, 1H), 7.73 (s, 1H), 7.55-7.37 (m, 2H), 7.37-7.21 (m, 1H), 4.94 (s, 2H), 4.18 (t, J = 5.4 Hz, 2H), 3.81-3.65 (m, 2H). |

TABLE 3-continued

Structures and characterization of intermediate compound A and target compound B of Examples 14-180

| Ex. No. | R¹ | R² | Compound A Name | Compound A LC MS m/z = (M + H)⁺ | Compound B Name | Compound B LC MS m/z = (M + H)⁺ | ¹H NMR |
|---|---|---|---|---|---|---|---|
| 147 | 2-F, 6-Cl phenyl | CH₂CH₂OCH₃ | 2-chloro-4-[(2-fluoro-6-chloro-benzyl)amino]pyrimidin-5-carboxamide | 315.0 | 4-[(2-fluoro-6-chlorobenzyl)amino]-2-[[1-(2-methoxyethyl)-1H-pyrazol-4-yl]amino]pyrimidin-5-carboxamide | 420.1 | (400 MHz, DMSO-$d_6$ + DCl/$D_2$O) δ 8.79 (s, 1H), 8.08 (s, 1H), 7.73 (s, 1H), 7.57-7.38 (m, 2H), 7.40-7.26 (m, 1H), 4.94 (s, 2H), 4.30 (t, J = 5.1 Hz, 2H), 3.68 (t, J = 5.1 Hz, 2H), 3.20 (s, 3H). |
| 148 | 2-F, 6-Cl phenyl | CH₂CH₂N(CH₃)₂ | 2-chloro-4-[(2-fluoro-6-chloro-benzyl)amino]pyrimidin-5-carboxamide | 315.0 | 4-[(2-fluoro-6-chlorobenzyl)amino]-2-[[1-(2-dimethylamino)ethyl)-1H-pyrazol-4-yl]amino]pyrimidin-5-carboxamide | 433.2 | (400 MHz, DMSO-$d_6$ + DCl/$D_2$O) δ 8.78 (s, 1H), 8.20 (s, 1H), 7.83 (s, 1H), 7.55-7.38 (m, 2H), 7.38-7.23 (m, 1H), 4.95 (s, 2H), 4.73-4.56 (m, 2H), 3.68-3.48 (m, 2H), 2.77 (s, 6H). |
| 149 | 2-F, 6-OMe phenyl | H | 2-chloro-4-[(2-fluoro-6-methoxybenzyl)amino]pyrimidin-5-carboxamide | 358.1 | 2-[(1H-pyrazol-4-yl)amino]-4-[(2-fluoro-6-methoxybenzyl)amino]pyrimidin-5-carboxamide | 358.1 | (400 MHz, DMSO-$d_6$ + DCl/$D_2$O) δ 8.74 (s, 1H), 8.11 (s, 2H), 7.45-7.33 (m, 1H), 6.97 (d, J = 8.4 Hz, 1H), 6.92-6.81 (m, 1H), 4.82 (s, 2H), 3.89 (s, 3H). |
| 150 | 2-F, 6-OMe phenyl | ethyl | 2-chloro-4-[(2-fluoro-6-methoxybenzyl)amino]pyrimidin-5-carboxamide | 311.1 | 4-[(2-fluoro-6-methoxybenzyl)amino]-2-[(1-ethyl-1H-pyrazol-4-yl)amino]pyrimidin-5-carboxamide | 386.1 | (400 MHz, DMSO-$d_6$ + DCl/$D_2$O) δ 8.73 (s, 1H), 8.09 (s, 1H), 7.77 (s, 1H), 7.47-7.32 (m, 1H), 6.97 (d, J = 8.4 Hz, 1H), 6.93-6.80 (m, 1H), 4.83 (s, 2H), 4.18 (q, J = 7.3 Hz, 2H), 3.89 (s, 3H), 1.40 (t, J = 7.3 Hz, 3H). |
| 151 | 2-F, 6-OMe phenyl | isopropyl | 2-chloro-4-[(2-fluoro-6-methoxybenzyl)amino]pyrimidin-5-carboxamide | 311.1 | 4-[(2-fluoro-6-methoxybenzyl)amino]-2-[(1-isopropyl-1H-pyrazol-4-yl)amino]pyrimidin-5-carboxamide | 400.2 | (400 MHz, DMSO-$d_6$ + DCl/$D_2$O) δ 8.73 (s, 1H), 8.10 (s, 1H), 7.77 (s, 1H), 7.45-7.31 (m, 1H), 6.99-6.97 (m, 2H), 4.83 (s, 2H), 4.62-4.45 (m, 1H), 3.89 (s, 3H), 1.44 (d, J = 6.5 Hz, 6H). |
| 152 | 2-F, 6-OMe phenyl | cyclopropyl | 2-chloro-4-[(2-fluoro-6-methoxybenzyl)amino]pyrimidin-5-carboxamide | 311.1 | 4-[(2-fluoro-6-methoxybenzyl)amino]-2-[(1-cyclopropyl-1H-pyrazol-4-yl)amino]pyrimidin-5-carboxamide | 398.2 | (400 MHz, DMSO-$d_6$ + DCl/$D_2$O) δ 8.72 (s, 1H), 8.08 (s, 1H), 7.73 (s, 1H), 7.46-7.34 (m, 1H), 6.97 (d, J = 8.4 Hz, 1H), 6.93-6.78 (m, 1H), 4.83 (s, 2H), 3.89 (s, 3H), 3.82-3.70 (m, 1H), 1.12-1.02 (m, 2H), 1.02-0.94 (m, 2H). |
| 153 | 2-F, 6-OMe phenyl | cyclobutyl | 2-chloro-4-[(2-fluoro-6-methoxybenzyl)amino]pyrimidin-5-carboxamide | 311.1 | 4-[(2-fluoro-6-methoxybenzyl)amino]-2-[(1-cyclobutyl-1H-pyrazol-4-yl)amino]pyrimidin-5-carboxamide | 412.2 | (400 MHz, DMSO-$d_6$ + DCl/$D_2$O) δ 8.72 (s, 1H), 8.11 (s, 1H), 7.79 (s, 1H), 7.47-7.32 (m, 1H), 6.97 (dd, J = 8.5, 3.6 Hz, 1H), 6.91-6.81 (m, 1H), 4.94-4.75 (m, 3H), 3.89 (s, 3H), 2.50-2.33 (m, 4H), 1.85-1.72 (m, 2H). |

TABLE 3-continued

Structures and characterization of intermediate compound A and target compound B of Examples 14-180

| Ex. No. | R¹ | R² | Compound A Name | LC MS m/z = (M + H)⁺ | Compound B Name | LC MS m/z = (M + H)⁺ | ¹H NMR |
|---|---|---|---|---|---|---|---|
| 154 | 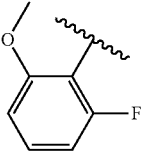 [SMILES: *c1c(F)cccc1OC] | 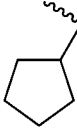 | 2-chloro-4-[(2-fluoro-6-methoxybenzyl)amino]pyrimidin-5-carboxamide | 311.1 | 4-[(2-fluoro-6-methoxybenzyl)amino]-2-[(1-cyclopentyl-1H-pyrazol-4-yl)amino]pyrimidin-5-carboxamide | 426.2 | (400 MHz, DMSO-$d_6$ + DCl/$D_2O$) δ 8.73 (s, 1H), 8.08 (s, 1H), 7.76 (s, 1H), 7.46-7.32 (m, 1H), 6.97 (d, J = 8.4 Hz, 1H), 6.91-6.82 (m, 1H), 4.83 (s, 2H), 4.78-4.67 (m, 1H), 3.88 (s, 3H), 2.17-2.04 (m, 2H), 1.96-1.86 (m, 2H), 1.84-1.70 (m, 2H), 1.69-1.58 (m, 2H), |
| 155 | 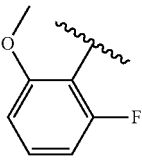 [SMILES: *c1c(F)cccc1OC] | 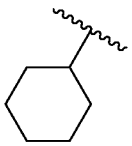 [SMILES: *C1CCCCC1] | 2-chloro-4-[(2-fluoro-6-methoxybenzyl)amino]pyrimidin-5-carboxamide | 311.1 | 4-[(2-fluoro-6-methoxybenzyl)amino]-2-[(1-cyclohexyl-1H-pyrazol-4-yl)amino]pyrimidin-5-carboxamide | 440.2 | (400 MHz, DMSO-$d_6$ + DCl/$D_2O$) δ 8.73 (s, 1H), 8.08 (s, 1H), 7.78 (s, 1H), 7.46-7.34 (m, 1H), 6.97 (d, J = 8.5 Hz, 1H), 6.92-6.82 (m, 1H), 4.83 (s, 2H), 4.26-4.09 (m, 1H), 3.89 (s, 3H), 2.12-1.94 (m, 2H), 1.86-1.76 (m, 2H), 1.74-1.62 (m, 3H), 1.49-1.29 (m, 2H), 1.29-1.07 (m, 1H). |
| 156 | 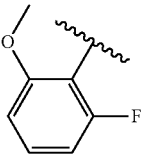 [SMILES: *c1c(F)cccc1OC] | 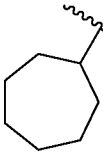 | 2-chloro-4-[(2-fluoro-6-methoxybenzyl)amino]pyrimidin-5-carboxamide | 311.1 | 4-[(2-fluoro-6-methoxybenzyl)amino]-2-[(1-cycloheptyl-1H-pyrazol-4-yl)amino]pyrimidin-5-carboxamide | 454.2 | (400 MHz, DMSO-$d_6$ + DCl/$D_2O$) δ 8.74 (s, 1H), 8.11 (s, 1H), 7.87-7.68 (m, 1H), 7.58 (s, 1H), 7.47-7.30 (m, 1H), 6.98-6.96 (m, 1H), 5.95 (s, 2H), 4.83 (s, 3H), 4.49-4.34 (m, 1H), 2.08-1.92 (m, 6H), 1.76-1.69 (m, 3H), 1.64-1.58 (m, 3H). |
| 157 | 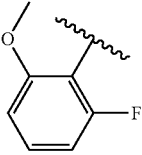 [SMILES: *c1c(F)cccc1OC] | 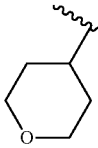 | 2-chloro-4-[(2-fluoro-6-methoxybenzyl)amino]pyrimidin-5-carboxamide | 311.1 | 4-[(2-fluoro-6-methoxybenzyl)amino]-2-[(1-(tetrahydro-2H-pyrazol-4-yl)amino]pyrimidin-5-carboxamide | 442.2 | (400 MHz, DMSO-$d_6$ + DCl/$D_2O$) δ 8.73 (s, 1H), 8.10 (s, 1H), 7.80 (s, 1H), 7.47-7.30 (m, 1H), 6.97 (d, J = 8.4 Hz, 1H), 6.91-6.81 (m, 1H), 4.83 (s, 2H), 4.53-4.34 (m, 1H), 3.99-3.91 (m, 2H), 3.89 (s, 3H), 3.54-3.43 (m, 2H), 2.05-1.87 (m, 4H). |
| 158 | 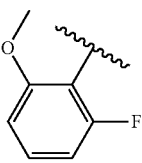 [SMILES: *c1c(F)cccc1OC] |  | 2-chloro-4-[(2-fluoro-6-methoxybenzyl)amino]pyrimidin-5-carboxamide | 311.1 | 4-[(2-fluoro-6-methoxybenzyl)amino]-2-[(1-(2-hydroxyethyl)-1H-pyrazol-4-yl)amino]pyrimidin-5-carboxamide | 402.2 | (400 MHz, DMSO-$d_6$ + DCl/$D_2O$) δ 8.74 (s, 1H), 8.12 (s, 1H), 7.86 (s, 1H), 7.51-7.33 (m, 1H), 7.01-6.96 (m, 2H), 4.83 (s, 2H), 4.22 (t, J = 5.5 Hz, 2H), 3.89 (s, 3H), 3.76 (t, J = 5.5 Hz, 2H). |
| 159 | 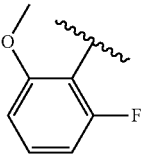 [SMILES: *c1c(F)cccc1OC] |  | 2-chloro-4-[(2-fluoro-6-methoxybenzyl)amino]pyrimidin-5-carboxamide | 311.1 | 4-[(2-fluoro-6-methoxybenzyl)amino]-2-[(1-(2-methylthioethyl)-1H-pyrazol-4-yl)amino]pyrimidin-5-carboxamide | 432.2 | (400 MHz, DMSO-$d_6$ + DCl/$D_2O$) δ 8.72 (s, 1H), 8.13 (s, 1H), 7.78 (s, 1H), 7.46-7.30 (m, 1H), 6.97 (d, J = 8.4 Hz, 1H), 6.92-6.78 (m, 1H), 4.83 (s, 2H), 4.33 (t, J = 6.7 Hz, 2H), 3.89 (s, 3H), 2.90 (t, J = 6.6 Hz, 2H), 2.00 (s, 3H). |

TABLE 3-continued

Structures and characterization of intermediate compound A and target compound B of Examples 14-180

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 160 | 2-methoxy-6-fluorophenyl | N-methyl-N-(2-aminoethyl) dimethylamino group | 2-chloro-4-[(2-fluoro-6-methoxybenzyl)amino]pyrimidin-5-carboxamide | 311.1 | 4-[(2-fluoro-6-methoxybenzyl)amino]-2-[(1-(2-dimethylamino)ethyl)-1H-pyrazol-4-yl)amino]pyrimidin-5-carboxamide | 429.2 | (400 MHz, DMSO-d₆ + DCl/D₂O) δ 8.76 (s, 1H), 8.21 (s, 1H), 7.91 (s, 1H), 7.50-7.32 (m, 1H), 6.97 (s, 1H), 6.92-6.85 (m, 1H), 4.84 (s, 2H), 4.66 (t, J = 6.4 Hz, 2H), 3.90 (s, 3H), 3.73-3.53 (m, 2H), 2.80 (s, 6H). |
| 161 | 2-methoxy-6-fluorophenyl | 1-methylpiperidin-4-yl | 2-chloro-4-[(2-fluoro-6-methoxybenzyl)amino]pyrimidin-5-carboxamide | 311.1 | 4-[(2-fluoro-6-methoxybenzyl)amino]-2-{[1-(1-methylpiperidin-4-yl)-1H-pyrazol-4-yl)amino]pyrimidin-5-carboxamide | 455.2 | (400 MHz, DMSO-d₆ + DCl/D₂O) δ 8.74 (s, 1H), 8.09 (s, 1H), 7.85 (s, 1H), 7.47-7.29 (m, 1H), 6.97 (d, J = 8.4 Hz, 1H), 6.93-6.77 (m, 1H), 4.83 (s, 2H), 4.63-4.45 (m, 1H), 3.89 (s, 3H), 3.61-3.46 (m, 2H), 3.29-3.18 (m, 2H), 2.78 (s, 3H), 2.38-2.29 (m, 2H), 2.29-2.15 (m, 2H). |
| 162 | 2-methoxy-6-fluorophenyl | 2-(pyrrolidin-1-yl)ethyl | 2-chloro-4-[(2-fluoro-6-methoxybenzyl)amino]pyrimidin-5-carboxamide | 311.1 | 4-[(2-fluoro-6-methoxybenzyl)amino]-2-[[1-(2-(pyrrolidin-1-yl)ethyl)-1H-pyrazol-4-yl)amino]pyrimidin-5-carboxamide | 455.2 | (400 MHz, DMSO-d₆ + DCl/D₂O) δ 8.72 (s, 1H), 8.17 (s, 1H), 7.89 (s, 1H), 7.48-7.28 (m, 1H), 7.03-6.93 (m, 1H), 6.93-6.81 (m, 1H), 4.83 (s, 2H), 4.67-4.55 (m, 2H), 3.89 (s, 3H), 3.75-3.60 (m, 2H), 3.54-3.32 (m, 2H), 3.07-2.82 (m, 2H), 2.09-1.88 (m, 2H), 1.88 - 1.71 (m, 2H). |
| 163 | 2-methoxy-6-fluorophenyl | 2-(piperidin-1-yl)ethyl | 2-chloro-4-[(2-fluoro-6-methoxybenzyl)amino]pyrimidin-5-carboxamide | 311.1 | 4-[(2-fluoro-6-methoxybenzyl)amino]-2-[[1-(2-piperidin-1-yl)ethyl)-1H-pyrazol-4-yl)amino]pyrimidin-5-carboxamide | 469.2 | (400 MHz, DMSO-d₆ + DCl/D₂O) δ 8.74 (s, 1H), 8.19 (s, 1H), 7.90 (s, 1H), 7.45-7.31 (m, 1H), 6.97 (d, J = 8.3 Hz, 1H), 6.92-6.84 (m, 1H), 4.84 (s, 2H), 4.69 (t, J = 6.9 Hz, 2H), 3.89 (s, 3H), 3.55 (t, J = 6.8 Hz, 2H), 3.44-3.31 (m, 2H), 3.03-2.89 (m, 2H), 1.90-1.74 (m, 4H), 1.72-1.62 (m, 1H), 1.47-1.28 (m, 1H). |
| 164 | 2-methoxy-6-fluorophenyl | 2-(morpholin-1-yl)ethyl | 2-chloro-4-[(2-fluoro-6-methoxybenzyl)amino]pyrimidin-5-carboxamide | 311.1 | 4-[(2-fluoro-6-methoxybenzyl)amino]-2-[[1-(2-morpholin-1-yl)ethyl)-1H-pyrazol-4-yl)amino]pyrimidin-5-carboxamide | 471.2 | (400 MHz, DMSO-d₆ + DCl/D₂O) δ 8.75 (s, 1H), 8.20 (s, 1H), 7.91 (s, 1H), 7.46-7.33 (m, 1H), 6.98 (d, J = 8.4 Hz, 1H), 6.90 (d, J = 8.9 Hz, 1H), 4.84 (s, 2H), 4.72 (t, J = 6.7 Hz, 2H), 3.99-3.93 (m, 2H), 3.90 (s, 3H), 3.86-3.77 (m, 2H), 3.72-3.62 (m, 2H), 3.45-3.31 (m, 2H), 3.23-3.13 (m, 2H). |

TABLE 3-continued

Structures and characterization of intermediate compound A and target compound B of Examples 14-180

| Ex. No. | R¹ | R² | Compound A Name | Compound A LC MS m/z = (M + H)⁺ | Compound B Name | Compound B LC MS m/z = (M + H)⁺ | ¹H NMR |
|---|---|---|---|---|---|---|---|
| 165 | 2-methoxy-6-fluorophenyl | n-octyl | 2-chloro-4-[(2-fluoro-6-methoxybenzyl)amino]pyrimidin-5-carboxamide | 311.1 | 4-[(2-fluoro-6-methoxybenzyl)amino]-2-[[1-octyl-1H-pyrazol-4-yl)amino]pyrimidin-5-carboxamide | 470.3 | (400 MHz, DMSO-$d_6$ + DCl/$D_2O$) δ 8.73 (s, 1H), 8.09 (s, 1H), 7.75 (s, 1H), 7.49-7.30 (m, 1H), 6.97 (d, J = 8.4 Hz, 1H), 6.91-6.80 (m, 1H), 4.81 (s, 2H), 4.13 (t, J = 6.8 Hz, 2H), 3.89 (s, 3H), 1.87-1.70 (m, 2H), 1.28-1.11 (m, 10H), 0.81 (t, J = 6.7 Hz, 3H). |
| 166 | 2-methoxy-6-fluorophenyl | 6-methoxyhexyl | 2-chloro-4-[(2-fluoro-6-methoxybenzyl)amino]pyrimidin-5-carboxamide | 311.1 | 4-[(2-fluoro-6-methoxybenzyl)amino]-2-[[1-(6-methoxyhexyl)-1H-pyrazol-4-yl)amino]pyrimidin-5-carboxamide | 472.2 | (400 MHz, DMSO-$d_6$ + DCl/$D_2O$) δ 8.74 (s, 1H), 8.13 (s, 1H), 7.82 (s, 1H), 7.43-7.42 (m, 2H), 6.92-6.78 (m, 1H), 4.82 (s, 2H), 4.16 (t, J = 6.8 Hz, 2H), 3.89 (s, 3H), 3.23 (t, J = 6.6 Hz, 2H), 3.17 (s, 3H), 1.87-1.72 (m, 2H), 1.48-1.34 (m, 2H), 1.33-1.15 (m, 4H). |
| 167 | 2-methoxy-6-fluorophenyl | 6-(dimethylamino)hexyl | 2-chloro-4-[(2-fluoro-6-methoxybenzyl)amino]pyrimidin-5-carboxamide | 311.1 | 4-[(2-fluoro-6-methoxybenzyl)amino]-2-[[1-(6-dimethylaminohexyl)-1H-pyrazol-4-yl)amino]pyrimidin-5-carboxamide | 485.3 | (400 MHz, DMSO-$d_6$ + DCl/$D_2O$) δ 8.73 (s, 1H), 8.09 (s, 1H), 7.79 (s, 1H), 7.46-7.35 (m, 1H), 6.99-6.96 (m, 1H), 6.90-6.88 (m, 1H), 4.83 (s, 2H), 4.15 (t, J = 6.9 Hz, 2H), 3.89 (s, 3H), 2.98 (t, J = 8.1 Hz, 2H), 2.71 (s, 6H), 1.87-1.71 (m, 2H), 1.68-1.51 (m, 2H), 1.39-1.15 (m, 4H). |
| 168 | 2-methoxy-6-fluorophenyl | 2-hydroxy-2-methylpropyl | 2-chloro-4-[(2-fluoro-6-methoxybenzyl)amino]pyrimidin-5-carboxamide | 311.1 | 4-[(2-fluoro-6-methoxybenzyl)amino]-2-[[1-(2-hydroxy-2-methylpropyl)-1H-pyrazol-4-yl)amino]pyrimidin-5-carboxamide | 430.2 | (400 MHz, DMSO-$d_6$ + DCl/$D_2O$) δ 8.74 (s, 1H), 8.09 (s, 1H), 7.82 (s, 1H), 7.44-7.33 (m, 1H), 6.97 (d, J = 8.4 Hz, 1H), 6.93-6.81 (m, 1H), 4.81 (s, 2H), 4.08 (s, 2H), 3.89 (s, 3H), 1.08 (s, 6H). |
| 169 | 2-fluoro-6-(trifluoromethyl)phenyl | 2-hydroxyethyl | 2-chloro-4-[(2-fluoro-6-(trifluoromethyl)benzyl]amino]pyrimidin-5-carboxamide | 349.0 | 4-[[2-fluoro-6-trifluoromethyl)benzyl]amino]-2-[[1-(2-hydroxyethyl)-1H-pyrazol-4-yl]amino]pyrimidin-5-carboxamide | 440.1 | (400 MHz, DMSO-$d_6$ + DCl/$D_2O$) δ 8.80 (s, 1H), 8.09 (s, 1H), 7.85-7.61 (m, 4H), 4.97 (s, 2H), 4.19 (t, J = 5.5 Hz, 2H), 3.72 (t, J = 5.6 Hz, 2H). |

TABLE 3-continued

Structures and characterization of intermediate compound A and target compound B of Examples 14-180

| | | | Compound A | | | Compound B | | |
|---|---|---|---|---|---|---|---|---|
| Ex. No. | R¹ | R² | Name | LC MS m/z = (M + H)⁺ | Name | LC MS m/z = (M + H)⁺ | ¹H NMR | |

| Ex. No. | R¹ | R² | Compound A Name | LC MS m/z = (M+H)⁺ | Compound B Name | LC MS m/z = (M+H)⁺ | ¹H NMR |
|---|---|---|---|---|---|---|---|
| 170 | 2-F, 6-CF₃ phenyl | -CH₂CH₂-O-CH₃ | 2-chloro-4-[(2-fluoro-6-(trifluoromethyl)benzyl]amino]pyrimidin-5-carboxamide | 349.0 | 4-[[2-fluoro-6-trifluoromethyl)benzyl]amino]-2-[[1-(2-methoxyethyl)-1H-pyrazol-4-yl]amino]pyrimidin-5-carboxamide | 454.2 | (400 MHz, DMSO-d₆ + DCl/D₂O) δ 8.82 (s, 1H), 8.11 (s, 1H), 7.84-7.63 (m, 4H), 4.98 (s, 2H), 4.32 (t, J = 5.1 Hz, 2H), 3.68 (d, J = 5.4 Hz, 2H), 3.18 (s, 3H). |
| 171 | 2-F, 6-CF₃ phenyl | -CH₂CH₂-N(CH₃)₂ | 2-chloro-4-[(2-fluoro-6-(trifluoromethyl)benzyl]amino]pyrimidin-5-carboxamide | 349.0 | 4-[[2-fluoro-6-trifluoromethyl)benzyl]amino]-2-[[1-(2-dimethylamino)ethyl)-1H-pyrazol-4-yl]amino]pyrimidin-5-carboxamide | 467.2 | (400 MHz, DMSO-d₆ + DCl/D₂O) δ 8.81 (s, 1H), 8.23 (s, 1H), 7.88-7.82 (m, 1H), 7.73-7.68 (m, 3H), 5.00 (s, 2H), 4.72-4.59 (m, 2H), 3.68-3.53 (m, 2H), 2.79 (s, 6H). |
| 172 | 2-methoxyphenyl | -CH₂CH₂-OH | 2-chloro-4-[(2-methoxybenzyl)amino]pyrimidin-5-carboxamide | 293.1 | 4-[(2-methoxybenzyl)amino]-2-[[1-(2-hydroxyethyl)-1H-pyrazol-4-yl]amino]pyrimidin-5-carboxamide | 384.2 | (400 MHz, DMSO-d₆ + DCl/D₂O) δ 8.72 (s, 1H), 7.88 (s, 1H), 7.60 (s, 1H), 7.37-7.27 (m, 1H), 7.24-7.15 (m, 1H), 7.14-7.04 (m, 1H), 7.00-6.81 (m, 1H), 4.71 (s, 2H), 4.12 (t, J = 5.6 Hz, 2H), 3.87 (s, 3H), 3.69 (t, J = 5.5 Hz, 2H). |
| 173 | 2-methoxy-5-chlorophenyl | -CH₂CH₂-OH | 2-chloro-4-[(2-methoxy-5-chlorobenzyl)amino]pyrimidin-5-carboxamide | 327.0 | 4-[(2-methoxy-5-chlorobenzyl)amino]-2-[[1-(2-hydroxyethyl)-1H-pyrazol-4-yl]amino]pyrimidin-5-carboxamide | 418.1 | (400 MHz, DMSO-d₆ + DCl/D₂O) δ 8.72 (s, 1H), 7.84 (s, 1H), 7.55 (s, 1H), 7.35 (dd, J = 9.0, 3.2 Hz, 1H), 7.18 (s, 1H), 7.10 (dd, J = 9.0, 2.9 Hz, 1H), 4.69 (s, 2H), 4.10 (t, J = 5.6 Hz, 2H), 3.87 (s, 3H), 3.69 (t, J = 5.4 Hz, 2H). |
| 174 | 2,6-dimethylphenyl | -CH₂CH₂-OH | 2-chloro-4-[(2,6-dimethylbenzyl)amino]pyrimidin-5-carboxamide | 291.1 | 4-[(2,6-dimethylbenzyl)amino]-2-[[1-(2-hydroxyethyl)-1H-pyrazol-4-yl]amino]pyrimidin-5-carboxamide | 382.2 | (400 MHz, DMSO-d₆ + DCl/D₂O) δ 8.77 (s, 1H), 8.20 (s, 1H), 7.80 (s, 1H), 7.25-7.04 (m, 3H), 4.74 (s, 2H), 4.24 (t, J = 5.4 Hz, 2H), 3.83-3.65 (m, 2H), 2.33 (s, 6H). |
| 175 | 2-chloro-6-methylphenyl | -CH₂CH₂-OH | 2-chloro-4-[(2-chloro-6-methylbenzyl)amino]pyrimidin-5-carboxamide | 311.0 | 4-[(2-chloro-6-methylbenzyl)amino]-2-[[1-(2-hydroxyethyl)-1H-pyrazol-4-yl]amino]pyrimidin-5-carboxamide | 402.1 | (400 MHz, DMSO-d₆ + DCl/D₂O) δ 8.77 (s, 1H), 8.15 (s, 1H), 7.75 (s, 1H), 7.40 (d, J = 7.9 Hz, 1H), 7.35-7.24 (m, 2H), 4.88 (s, 2H), 4.21 (t, J = 5.5 Hz, 2H), 3.73 (t, J = 5.5 Hz, 2H), 2.35 (s, 3H). |
| 176 | 2,6-dichlorophenyl | -CH₂CH₂-OH | 2-chloro-4-[(2,6-dichlorobenzyl)amino]pyrimidin-5-carboxamide | 331.0 | 4-[(2,6-dichlorobenzyl)amino]-2-[[1-(2-hydroxyethyl)-1H-pyrazol-4-yl]amino]pyrimidin-5-carboxamide | 422.1 | (400 MHz, DMSO-d₆ + DCl/D₂O) δ 8.79 (s, 1H), 8.13 (s, 1H), 7.76 (s, 1H), 7.65-7.52 m, 2H), 7.51-7.39 (m, 1H), 5.03 (s, 2H), 4.20 (t, J = 5.5 Hz, 2H), 3.73 (t, J = 5.6 Hz, 2H). |

TABLE 3-continued

Structures and characterization of intermediate compound A and target compound B of Examples 14-180

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 177 | 2,3,6-trifluorophenyl (F, F, F substituted) | 2-hydroxyethyl | 2-chloro-4-[(2,3,6-trifluorobenzyl)amino]pyrimidin-5-carboxamide | 317.0 | 4-[(2,3,6-trifluorobenzyl)amino]-2-[[1-(2-hydroxyethyl)-1H-pyrazol-4-yl]amino]pyrimidin-5-caboxamide | 408.1 | (400 MHz, DMSO-d₆ + DCl/D₂O) δ 8.74 (s, 1H), 8.02 (s, 1H), 7.67 (s, 1H), 7.61-7.45 (m, 1H), 7.27-7.10 (m, 1H), 4.92 (s, 2H), 4.25-4.11 (m, 2H), 3.80-3.64 (m, 2H). |
| 178 | 2,6-difluoro-3-methylphenyl | 2-hydroxyethyl | 2-chloro-4-[(2,6-difluoro-3-methylbenzyl)amino]pyrimidin-5-carboxamide | 313.1 | 4-[(2,6-difluoro-3-methylbenzyl)amino]-2-[[1-(2-hydroxyethyl)-1H-pyrazol-4-yl]amino]pyrimidin-5-carboxamide | 404.2 | (400 MHz, DMSO-d₆ + DCl/D₂O) δ 8.77 (s, 1H), 8.09 (s, 1H), 7.75 (s, 1H), 7.42-7.25 (m, 1H), 7.12-7.00 (m, 1H), 4.88 (s, 2H), 4.20 (t, J = 5.5 Hz, 2H), 3.79- 3.66 (m, 2H), 2.23 (s, 3H). |
| 179 | 2-chloro-3,6-difluorophenyl | 2-hydroxyethyl | 2-chloro-4-[(2-chloro-3,6-difluorobenzyl)amino]pyrimidin-5-carboxamide | 333.0 | 4-[(2-chloro-3,6-difluorobenzyl)amino]-2-[[1-(2-hydroxyethyl)-1H-pyrazol-4-yl]amino]pyrimidin-5-carboxamide | 424.1 | (400 MHz, DMSO-d₆ + DCl/D₂O) δ 8.76 (s, 1H), 8.06 (s, 1H), 7.70 (s, 1H), 7.58-7.46 (m, 1H), 7.43-7.27 (m, 1H), 4.96 (s, 2H), 4.17 (t, J = 5.5 Hz, 2H), 3.81-3.62 (m, 2H). |
| 180 | 2-fluoro-3-methoxyphenyl | 2-methoxyethyl | 2-chloro-4-[[2-fluoro-3-methyoxybenzyl]amino]pyrimidin-5-carboxamide | 311.1 | 4-[[2-fluoro-3-methoxybenzyl]amino]-2-[[1-(2-methoxyethyl)-1H-pyrazol-4-yl]amino]pyrimidin-5-carboxamide | 416.2 | (400 MHz, DMSO-d₆ + DCl/D₂O) δ 8.76 (s, 1H), 7.81 (s, 1H), 7.58 (s, 1H), 7.21-7.04 (m, 1H), 6.95-6.77 (m, 1H), 4.81 (s, 2H), 4.21 (t, J = 5.3 Hz, 2H), 3.85 (s, 3H), 3.63 (t, J = 5.2 Hz, 2H), 3.18 (s, 3H). |

TABLE 4

Structures and characterization of intermediate compound A and target compound B of Examples 181 to 227

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 181 | isopentyl | tert-butyl | 2-chloro-4-(isopentylamino)pyrimidin-5-carboxamide | 243 | 2-((1-tert-butyl-1H-pyrazol-4-yl)amino)-4-(isopentylamino)pyrimidin-5-carboxamide | 346 | ¹H NMR (400 MHz, DMSO-d₆) δ 10.50 (s, 1H), 10.02 (s, 1H), 8.53 (s, 1H), 8.46-8.10 (m, 1H), 8.02 (s, 1H), 7.88-7.32 (m, 2H), 3.77-3.35 (m, 2H), 1.73-1.37 (m, 12H), 0.90 (d, J = 6.5 Hz, 6H). |
| 182 | isopentyl | tetrahydro-2H-pyran-4-yl | 2-chloro-4-(isopentylamino)pyrimidin-5-carboxamide | 243 | 4-(isopentylamino)-2-((1-(tetrahydro-2H-pyran-4-yl)-1H-pyrazol-4-yl)amino)pyrimidin-5-carboxamide | 374 | ¹H NMR (400 MHz, DMSO-d₆) δ 10.34 (s, 1H), 9.87 (s, 1H), 8.51 (s, 1H), 8.29-8.05 (m, 1H), 7.97 (s, 1H), 7.65 (s, 1H), 7.61-7.24 (m, 1H), 4.51-4.25 (m, 1H), 4.03-3.86 (m, 2H), 3.63-3.34 (m, 4H), 2.06-1.75 (m, 4H), 1.72- |

TABLE 4-continued

Structures and characterization of intermediate compound A and target compound B of Examples 181 to 227

| | | | Compound A | | Compound B | | |
|---|---|---|---|---|---|---|---|
| Ex. No. | R[1] | R[2] | Name | LC MS m/z = (M + H)+ | Name | LC MS m/z = (M + H)+ | $^1$H NMR |
| | | | | | | | 1.57 (m, 1H), 1.57-1.40 (m, 2H), 0.91 (d, J = 6.6 Hz, 6H). |
| 183 | 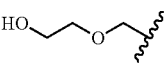 |  | 2-chloro-4-((2-(2-hydroxyethoxy)ethyl)amino)pyrimidin-5-carboxamide | 261 | 2-((1-tert-butyl-1H-pyrazol-4-yl)amino)-4-((2-(2-hydroxyethoxy)ethyl)amino)pyrimidin-5-carboxamide | 364 | $^1$H NMR (400 MHz, DMSO-$d_6$) δ 10.54 (s, 1H), 10.10 (s, 1H), 8.55 (s, 1H), 8.46-8.12 (m, 1H), 8.03 (s, 1H), 7.77-7.54 (m, 2H), 4.40 (s, 1H), 3.78-3.57 (m, 4H), 3.55-3.36 (m, 4H), 1.52 (s, 9H). |
| 184 | 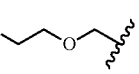 | 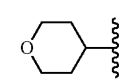 | 2-chloro-4-((2-(2-hydroxyethoxy)ethyl)amino)pyrimidin-5-carboxamide | 261 | 4-((2-(2-hydroxyethoxy)ethyl)amino)-2-((1-(tetrahydro-2H-pyran-4-yl)-1H-pyrazol-4-yl)amino)pyrimidin-5-carboxamide | 392 | $^1$H NMR (400 MHz, DMSO-$d_6$) δ 10.71-10.41 (m, 1H), 10.10 (s, 1H), 8.55 (s, 1H), 8.41-8.08 (m, 1H), 7.99 (s, 1H), 7.75-7.42 (m, 2H), 4.50 (s, 1H), 4.46-4.33 (m, 1H), 4.03-3.88 (m, 2H), 3.75-3.58 (m, 4H), 3.54-3.50 (m, 2H), 3.50-3.41 (m, 4H), 2.05-1.80 (m, 4H). |
| 185 | 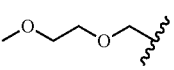 [SMILES: *COCCOC] |  | 2-chloro-4-((2-(2-methoxyethoxy)ethyl)amino)pyrimidin-5-carboxamide | 275 | 2-((1-tert-butyl-1H-pyrazol-4-yl)amino)-4-((2-(2-methoxyethoxy)ethyl)amino)pyrimidin-5-carboxamide | 378 | $^1$H NMR (400 MHz, DMSO-$d_6$) δ 9.42 (s, 1H), 9.26 (s, 1H), 8.45 (s, 1H), 7.97 (s, 1H), 7.83-7.56 (m, 1H), 7.50 (s, 1H), 7.29-6.79 (m, 1H), 3.70-3.57 (m, 4H), 3.57-3.51 (m, 2H), 3.48-3.41 (m, 2H), 3.24 (s, 3H), 1.50 (s, 9H). |
| 186 | 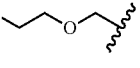 | 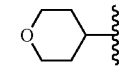 | 2-chloro-4-((2-(2-methoxyethoxy)ethyl)amino)pyrimidin-5-carboxamide | 275 | 4-((2-(2-methoxyethoxy)ethyl)amino)-2-((1-(tetrahydro-2H-pyran-4-yl)-1H-pyrazol-4-yl)amino)pyrimidin-5-carboxamide | 406 | $^1$H NMR (400 MHz, DMSO-$d_6$) δ 10.50 (s, 1H), 10.07 (s, 1H), 8.52 (s, 1H), 8.40-8.05 (m, 1H), 7.99 (s, 1H), 7.73-7.50 (m, 2H), 4.47-4.32 (m, 1H), 4.02-3.90 (m, 2H), 3.75-3.66 (m, 2H), 3.66-3.59 (m, 2H), 3.60-3.53 (m, 2H), 3.52-3.38 (m, 4H), 3.24 (s, 3H), 2.04-1.84 (m, 4H). |
| 187 | 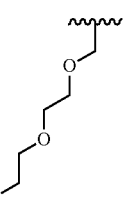 | 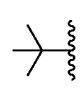 | 2-chloro-4-((2-(2-(2-hydroxyethoxy)ethoxy)ethyl)amino)pyrimidin-5-carboxamide | 305 | 2-((1-tert-butyl-1H-pyrazol-4-yl)amino)-4-((2-(2-(2-hydroxyethoxy)ethoxy)ethyl)amino)pyrimidin-5-carboxamide | 408 | $^1$H NMR (400 MHz, DMSO-$d_6$) δ 9.63 (s, 1H), 9.42 (s, 1H), 8.45 (s, 1H), 7.98 (s, 1H), 7.90-7.59 (m, 1H), 7.53 (s, 1H), 7.34-6.92 (m, 1H), 4.92-4.28 (m, 1H), 3.74-3.58 (m, 4H), 3.58-3.50 (m, 4H), 3.47 (t, J = 5.2 Hz, 2H), 3.41 (t, J = 5.2 Hz, 2H), 1.50 (s, 9H). |
| 188 |  |  | 2-chloro-4-((2-ethylbenzyl)amino)pyrimidin-5-carboxamide | 291 | 2-((1-ethyl-1H-pyrazol-4-yl)amino)-4-((2-ethylbenzyl)amino)pyrimidin-5-carboxamide | 366 | $^1$H NMR (400 MHz, DMSO-$d_6$ + DCl/$D_2O$) δ 8.68 (s, 1H), 7.65 (s, 1H), 7.48 (s, 1H), 7.27-7.18 (m, 2H), 7.17-7.06 (m, 2H), 4.72 (s, 2H), 3.94 (q, J = 7.3 Hz, 2H), 2.59 (q, J = 7.5 Hz, 2H), 1.19 (t, J = 7.3 Hz, 3H), 1.10 (t, J = 7.5 Hz, 3H). |
| 189 |  |  | 2-chloro-4-((2-ethylbenzyl)amino)pyrimidin-5-carboxamide | 291 | 4-((2-ethylbenzyl)amino)-2-((1-propyl-1H-pyrazol-4-yl)amino)pyrimidin-5-carboxamide | 380 | $^1$H NMR (400 MHz, DMSO-$d_6$ + DCl/$D_2O$) δ 7.65 (s, 1H), 7.51 (s, 1H), 7.47 (s, 1H), 7.17-7.15 (m, 2H), 7.06-7.02 (m, 2H), 4.64 (s, 2H), |

TABLE 4-continued

Structures and characterization of intermediate compound A and target compound B of Examples 181 to 227

| Ex. No. | R¹ | R² | Compound A Name | Compound A LC MS m/z = (M + H)⁺ | Compound B Name | Compound B LC MS m/z = (M + H)⁺ | ¹H NMR |
|---|---|---|---|---|---|---|---|
| | | | | | amino)pyrimidin-5-carboxamide | | 3.95-3.77 (m, 2H), 2.58-2.53 (m, 2H), 1.62-1.41 (m, 2H), 1.02 (t, J = 7.5 Hz, 3H), 0.72-0.46 (m, 3H). |
| 190 | 2-ethylphenyl | isopropyl | 2-chloro-4-((2-ethylbenzyl)amino)pyrimidin-5-carboxamide | 291 | 4-((2-ethylbenzyl)amino)-2-((1-isopropyl-1H-pyrazol-4-yl)amino)pyrimidin-5-carboxamide | 380 | ¹H NMR (400 MHz, DMSO-d₆ + DCl/D₂O) δ 8.67 (s, 1H), 7.70 (s, 1H), 7.49 (s, 1H), 7.29-7.14 (m, 2H), 7.14-7.04 (m, 2H), 4.69 (s, 2H), 4.41-4.12 (m, 1H), 2.63-2.52 (m, 2H), 1.21 (d, J = 6.7 Hz, 6H), 1.07 (t, J = 7.5 Hz, 3H). |
| 191 | 2-ethylphenyl | cyclopropyl | 2-chloro-4-((2-ethylbenzyl)amino)pyrimidin-5-carboxamide | 291 | 2-((1-cyclopropyl-1H-pyrazol-4-yl)amino)-4-((2-ethylbenzyl)amino)pyrimidin-5-carboxamide | 378 | ¹H NMR (400 MHz, DMSO-d₆ + DCl/D₂O) δ 8.66 (s, 1H), 7.67 (s, 1H), 7.43 (s, 1H), 7.23-7.14 (m, 2H), 7.14-7.02 (m, 2H), 4.69 (s, 2H), 3.63-3.37 (m, 1H), 2.57 (q, J = 7.5 Hz, 2H), 1.08 (t, J = 7.5 Hz, 3H), 0.95-0.72 (m, 4H). |
| 192 | 2-ethylphenyl | tert-butyl | 2-chloro-4-((2-ethylbenzyl)amino)pyrimidin-5-carboxamide | 291 | 2-((1-tert-butyl-1H-pyrazol-4-yl)amino)-4-((2-ethylbenzyl)amino)pyrimidin-5-carboxamide | 394 | ¹H NMR (400 MHz, DMSO-d₆) δ 10.49 (s, 1H), 10.25 (s, 1H), 8.59 (s, 1H), 8.44-8.05 (m, 1H), 7.90 (s, 1H), 7.81-7.58 (m, 1H), 7.56-7.46 (m, 1H), 7.30-7.23 (m, 2H), 7.23-7.11 (m, 2H), 4.77 (d, J = 5.6 Hz, 2H), 2.65 (q, J = 7.5 Hz, 2H), 1.38 (s, 9H), 1.17 (t, J = 7.5 Hz, 3H). |
| 193 | 2-ethylphenyl | tetrahydro-2H-pyran-4-yl | 2-chloro-4-((2-ethylbenzyl)amino)pyrimidin-5-carboxamide | 291 | 4-((2-ethylbenzyl)amino)-2-((1-(tetrahydro-2H-pyran-4-yl)amino)pyrimidin-5-carboxamide | 422 | ¹H NMR (400 MHz, DMSO-d₆ + DCl/D₂O) δ 8.67 (s, 1H), 7.66 (s, 1H), 7.48 (s, 1H), 7.22-7.16 (m, 2H), 7.12-7.06 (m, 2H), 4.71 (s, 2H), 4.22-4.05 (m, 1H), 3.91-3.70 (m, 2H), 3.33 (t, J = 11.2 Hz, 2H), 2.57 (q, J = 7.5 Hz, 2H), 1.82-1.50 (m, 4H), 1.08 (t, J = 7.5 Hz, 3H). |
| 194 | 2-propylphenyl | methyl | 2-chloro-4-((2-propylbenzyl)amino)pyrimidin-5-carboxamide | 305 | 2-((1-methyl-1H-pyrazol-4-yl)amino)-4-((2-propylbenzyl)amino)pyrimidin-5-carboxamide | 366 | ¹H NMR (400 MHz, DMSO-d₆) δ 10.53 (s, 1H), 10.25 (s, 1H), 8.58 (s, 1H), 8.35-8.14 (m, 1H), 7.72-7.55 (m, 2H), 7.49 (s, 1H), 7.30-7.23 (m, 2H), 7.23-7.10 (m, 2H), 4.77 (d, J = 5.5 Hz, 2H), 3.73 (s, 3H), 2.67-2.56 (m, 2H), 1.64-1.49 (m, 2H), 0.90 (t, J = 7.3 Hz, 3H). |
| 195 | 2-isopropylphenyl | methyl | 2-chloro-4-((2-isopropylbenzyl)amino)pyrimidin-5-carboxamide | 305 | 4-((2-isopropylbenzyl)amino)-2-((1-methyl-1H-pyrazol-4-yl)amino)pyrimidin-5-carboxamide | 366 | ¹H NMR (400 MHz, DMSO-d₆ + DCl/D₂O) δ 8.69 (s, 1H), 7.72 (s, 1H), 7.50 (s, 1H), 7.34 (d, J = 7.8 Hz, 1H), 7.31-7.23 (m, 1H), 7.19-7.07 (m, 2H), 4.75 (s, 2H), 3.71 (s, 3H), 3.07 (p, J = 6.8 Hz, 1H), 1.13 (d, J = 6.7 Hz, 6H). |

TABLE 4-continued

Structures and characterization of intermediate compound A and target compound B of Examples 181 to 227

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 196 | 2-cyclopropylmethyl phenyl | | 2-chloro-4-((2-(cyclopropylmethyl)benzyl)amino)pyrimidin-5-carboxamide | 317 | 4-((2-(cyclopropylmethyl)benzyl)amino)-2-((1-methyl-1H-pyrazol-4-yl)amino)pyrimidin-5-carboxamide | 378 | ¹H NMR (400 MHz, DMSO-d₆) δ 9.44 (s, 1H), 9.39-9.13 (m, 1H), 8.50 (s, 1H), 7.94-7.58 (m, 2H), 7.52 (s, 1H), 7.47-7.33 (m, 2H), 7.32-7.13 (m, 3H), 4.76-4.61 (m, 2H), 3.65 (s, 3H), 2.60 (d, J = 6.8 Hz, 2H), 1.08-0.95 (m, 1H), 0.53-0.44 (m, 2H), 0.23-0.13 (m, 2H). |
| 197 | 2-methoxyphenyl | tert-butyl | 2-chloro-4-((2-methoxybenzyl)amino)pyrimidin-5-carboxamide | 293 | 2-((1-tert-butyl-1H-pyrazol-4-yl)amino)-4-((2-methoxybenzyl)amino)pyrimidin-5-carboxamide | 396 | ¹H NMR (400 MHz, DMSO-d₆) δ 10.15 (s, 1H), 10.09 (s, 1H), 8.54 (s, 1H), 8.21-7.96 (m, 1H), 7.92 (s, 1H), 7.55-7.46 (m, 1H), 7.36-7.19 (m, 2H), 7.17-7.10 (m, 1H), 7.10-7.01 (m, 1H), 6.96-6.85 (m, 1H), 4.70 (d, J = 6.0 Hz, 2H), 3.84 (s, 3H), 1.42 (s, 9H). |
| 198 | 2,6-difluorophenyl | tert-butyl | 2-chloro-4-((2,6-difluorobenzyl)amino)pyrimidin-5-carboxamide | 299 | 2-((1-tert-butyl-1H-pyrazol-4-yl)amino)-4-((2,6-difluorobenzyl)amino)pyrimidin-5-carboxamide | 402 | ¹H NMR (400 MHz, DMSO-d₆) δ 10.23 (s, 1H), 10.16 (s, 1H), 8.56 (s, 1H), 8.23-8.04 (m, 1H), 7.85 (s, 1H), 7.62-7.44 (m, 2H), 7.35-7.23 (m, 1H), 7.23-7.12 (m, 1H), 7.12-6.99 (m, 1H), 4.80 (d, J = 6.0 Hz, 2H), 1.40 (s, 9H). |
| 199 | 2-chloro-6-fluorophenyl | ethyl | 2-chloro-4-((2-chloro-6-fluorobenzyl)amino)pyrimidin-5-carboxamide | 315 | 4-((2-chloro-6-fluorobenzyl)amino)-2-((1-ethyl-1H-pyrazol-4-yl)amino)pyrimidin-5-carboxamide | 390 | ¹H NMR (300 MHz, DMSO-d₆ + DCl/D₂O) δ 8.70 (s, 1H), 8.02 (s, 1H), 7.67 (s, 1H), 7.51-7.33 (m, 2H), 7.31-7.15 (m, 1H), 4.87 (s, 2H), 4.11 (q, J = 7.3 Hz, 2H), 1.31 (t, J = 7.3 Hz, 3H). |
| 200 | 2-chloro-6-fluorophenyl | propyl | 2-chloro-4-((2-chloro-6-fluorobenzyl)amino)pyrimidin-5-carboxamide | 315 | 4-((2-chloro-6-fluorobenzyl)amino)-2-((1-propyl-1H-pyrazol-4-yl)amino)pyrimidin-5-carboxamide | 404 | ¹H NMR (300 MHz, DMSO-d₆ + DCl/D₂O) δ 8.77 (s, 1H), 8.08 (s, 1H), 7.75 (s, 1H), 7.58-7.41 (m, 2H), 7.38-7.22 (m, 1H), 4.95 (s, 2H), 4.11 (t, J = 6.8 Hz, 2H), 2.00-1.64 (m, 2H), 0.82 (t, J = 7.3 Hz, 3H). |
| 201 | 2-chloro-6-fluorophenyl | isopropyl | 2-chloro-4-((2-chloro-6-fluorobenzyl)amino)pyrimidin-5-carboxamide | 315 | 4-((2-chloro-6-fluorobenzyl)amino)-2-((1-isopropyl-1H-pyrazol-4-yl)amino)pyrimidin-5-carboxamide | 404 | ¹H NMR (300 MHz, DMSO-d₆ + DCl/D₂O) δ 8.78 (s, 1H), 8.10 (s, 1H), 7.76 (s, 1H), 7.56-7.38 (m, 2H), 7.38-7.24 (m, 1H), 4.95 (s, 2H), 4.68-4.45 (m, 1H), 1.44 (d, J = 6.6 Hz, 6H). |
| 202 | 2-chloro-6-fluorophenyl | cyclopropyl | 2-chloro-4-((2-chloro-6-fluorobenzyl)amino)pyrimidin-5-carboxamide | 315 | 4-((2-chloro-6-fluorobenzyl)amino)-2-((1-cyclopropyl-1H-pyrazol-4-yl)amino)pyrimidin-5-carboxamide | 402 | ¹H NMR (400 MHz, DMSO-d₆ + DCl/D₂O) δ 8.67 (s, 1H), 7.99 (s, 1H), 7.62 (s, 1H), 7.44-7.31 (m, 2H), 7.27-7.18 (m, 1H), 4.85 (s, 2H), 3.75-3.61 (m, 1H), 1.06-0.81 (m, 4H). |
| 203 | 2-chloro-6-fluorophenyl | tert-butyl | 2-chloro-4-((2-chloro-6-fluorobenzyl)amino)pyrimidin-5-carboxamide | 315 | 2-((1-tert-butyl-1H-pyrazol-4-yl)amino)-4-((2-chloro-6-fluorobenzyl) | 418 | ¹H NMR (400 MHz, DMSO-d₆) δ 10.41 (s, 1H), 10.32 (s, 1H), 8.57 (s, 1H), 8.31-8.12 (m, 1H), 8.08 (s, 1H), 7.69 (s, 1H), 7.63-7.52 |

TABLE 4-continued

Structures and characterization of intermediate compound A and target compound B of Examples 181 to 227

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| | | | | | amino)pyrimidin-5-carboxamide | | (m, 1H), 7.53-7.38 (m, 2H), 7.37-7.26 (m, 1H), 4.99-4.82 (m, 2H), 1.52 (s, 9H). |
| 204 | 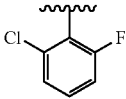 [SMILES: *c1c(F)cccc1Cl] |  | 2-chloro-4-((2-chloro-6-fluorobenzyl)amino)pyrimidin-5-carboxamide | 315 | 4-((2-chloro-6-fluorobenzyl)amino)-2-((1-cyclobutyl-1H-pyrazol-4-yl)amino)pyrimidin-5-carboxamide | 416 | ¹H NMR (300 MHz, DMSO-d₆ + DCl/D₂O) δ 8.68 (s, 1H), 8.03 (s, 1H), 7.68 (s, 1H), 7.48-7.30 (m, 2H), 7.29-7.12 (m, 1H), 4.97-4.69 (m, 3H), 2.44-2.20 (m, 4H), 1.79-1.49 (m, 2H). |
| 205 | 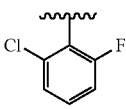 [SMILES: *c1c(F)cccc1Cl] |  | 2-chloro-4-((2-chloro-6-fluorobenzyl)amino)pyrimidin-5-carboxamide | 315 | 4-((2-chloro-6-fluorobenzyl)amino)-2-((1-cyclopentyl-1H-pyrazol-4-yl)amino)pyrimidin-5-carboxamide | 430 | ¹H NMR (400 MHz, DMSO-d₆ + DCl/D₂O) δ 8.77 (s, 1H), 8.07 (s, 1H), 7.73 (s, 1H), 7.53-7.39 (m, 2H), 7.39-7.27 (m, 1H), 4.95 (s, 2H), 4.82-4.63 (m, 1H), 2.20-2.01 (m, 2H), 2.00-1.84 (m, 2H), 1.84-1.70 (m, 2H), 1.71-1.51 (m, 2H). |
| 206 | 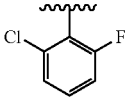 [SMILES: *c1c(F)cccc1Cl] |  | 2-chloro-4-((2-chloro-6-fluorobenzyl)amino)pyrimidin-5-carboxamide | 315 | 4-((2-chloro-6-fluorobenzyl)amino)-2-((1-cyclohexyl-1H-pyrazol-4-yl)amino)pyrimidin-5-carboxamide | 444 | ¹H NMR (400 MHz, DMSO-d₆ + DCl/D₂O) δ 8.66 (s, 1H), 8.00 (s, 1H), 7.69 (s, 1H), 7.44-7.28 (m, 2H), 7.27-7.13 (m, 1H), 4.84 (s, 2H), 4.21-3.93 (m, 1H), 2.02-1.79 (m, 2H), 1.78-1.65 (m, 2H), 1.65-1.45 (m, 3H), 1.39-1.15 (m, 2H), 1.18-0.96 (m, 1H). |
| 207 | 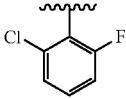 [SMILES: *c1c(F)cccc1Cl] |  | 2-chloro-4-((2-chloro-6-fluorobenzyl)amino)pyrimidin-5-carboxamide | 315 | 4-((2-chloro-6-fluorobenzyl)amino)-2-((1-(tetrahydro-2H-pyran-4-yl)-1H-pyrazol-4-yl)amino)pyrimidin-5-carboxamide | 446 | ¹H NMR (400 MHz, DMSO-d₆ + DCl/D₂O) δ 8.71 (s, 1H), 8.03 (s, 1H), 7.70 (s, 1H), 7.48-7.32 (m, 2H), 7.31 7.18 (m, 1H), 4.88 (s, 2H), 4.53-4.29 (m, 1H), 4.00-3.82 (m, 2H), 3.50-3.24 (m, 2H), 2.12-1.62 (m, 4H). |
| 208 | 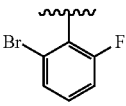 [SMILES: *c1c(F)cccc1Br] |  | 2-chloro-4-((2-bromo-6-fluorobenzyl)amino)pyrimidin-5-carboxamide | 359 | 4-((2-bromo-6-fluorobenzyl)amino)-2-((1-methyl-1H-pyrazol-4-yl)amino)pyrimidin-5-carboxamide | 420 | ¹H NMR (400 MHz, DMSO-d₆) δ 10.45 (s, 1H), 10.26 (s, 1H), 8.55 (s, 1H), 8.31-8.05 (m, 1H), 7.96 (s, 1H), 7.68-7.61 (m, 1H), 7.61-7.47 (m, 2H), 7.47-7.27 (m, 2H), 4.89 (d, J = 6.0 Hz, 2H), 3.85 (s, 3H). |
| 209 | 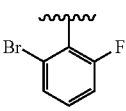 [SMILES: *c1c(F)cccc1Br] |  | 2-chloro-4-((2-bromo-6-fluorobenzyl)amino)pyrimidin-5-carboxamide | 359 | 4-((2-bromo-6-fluorobenzyl)amino)-2-((1-ethyl-1H-pyrazol-4-yl)amino)pyrimidin-5-carboxamide | 434 | ¹H NMR (400 MHz, DMSO-d₆) δ 10.46 (s, 1H), 10.35-9.85 (m, 1H), 8.56 (s, 1H), 8.33-8.08 (m, 1H), 8.00 (s, 1H), 7.80-7.48 (m, 3H), 7.46-7.25 (m, 2H), 4.90 (d, J = 6.0 Hz, 2H), 4.14 (q, J = 7.2 Hz, 2H), 1.36 (t, J = 7.3 Hz, 3H). |
| 210 | 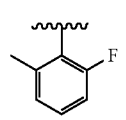 |  | 2-chloro-4-((2-fluoro-6-methylbenzyl)amino)pyrimidin-5-carboxamide | 295 | 4-((2-fluoro-6-methylbenzyl)amino)-2-((1-methyl-1H-pyrazol-4-yl)amino)pyrimidin-5-carboxamide | 356 | ¹H NMR (400 MHz, DMSO-d₆) δ 9.49 (s, 1H), 9.34-9.19 (m, 1H), 8.49 (s, 1H), 7.89 (s, 1H), 7.80-7.58 (m, 1H), 7.52 (s, 1H), 7.34-7.22 (m, 1H), 7.13-6.93 (m, 3H), 4.78-4.58 (m, 2H), 3.80 (s, 3H), 2.36 (s, 3H). |

TABLE 4-continued

Structures and characterization of intermediate compound A and target compound B of Examples 181 to 227

| Ex. No. | R¹ | R² | Compound A Name | LC MS m/z = (M + H)⁺ | Compound B Name | LC MS m/z = (M + H)⁺ | ¹H NMR |
|---|---|---|---|---|---|---|---|
| 211 | 2-fluoro-6-methylphenyl | CH₂CH₃ | 2-chloro-4-((2-fluoro-6-methylbenzyl)amino)pyrimidin-5-carboxamide | 295 | 4-((2-fluoro-6-methylbenzyl)amino)-2-((1-ethyl-1H-pyrazol-4-yl)amino)pyrimidin-5-carboxamide | 370 | ¹H NMR (400 MHz, DMSO-d₆) δ 10.27 (s, 1H), 10.03 (s, 1H), 8.51 (s, 1H), 8.25-8.05 (m, 1H), 7.99 (s, 1H), 7.63 (s, 1H), 7.57-7.37 (m, 1H), 7.37-7.23 (m, 1H), 7.18-7.02 (m, 2H), 4.86-4.64 (m, 2H), 4.14 (q, J = 7.2 Hz, 2H), 2.34 (s, 3H), 1.36 (t, J = 7.2 Hz, 3H). |
| 212 | 2-fluoro-6-(trifluoromethyl)phenyl | CH₂CH₃ | 2-chloro-4-((2-fluoro-6-(trifluoromethyl)benzyl)amino)pyrimidin-5-carboxamide | 349 | 2-((1-ethyl-1H-pyrazol-4-yl)amino)-4-((2-fluoro-6-(trifluoromethyl)benzyl)amino)pyrimidin-5-carboxamide | 424 | ¹H NMR (400 MHz, DMSO-d₆ + DCl/D₂O) δ 8.72 (s, 1H), 8.01 (s, 1H), 7.71-7.56 (m, 4H), 4.90 (s, 2H), 4.10 (q, J = 7.3 Hz, 2H), 1.30 (t, J = 7.3 Hz, 3H). |
| 213 | 2-fluoro-6-(trifluoromethyl)phenyl | C(CH₃)₃ | 2-chloro-4-((2-fluoro-6-(trifluoromethyl)benzyl)amino)pyrimidin-5-carboxamide | 349 | 2-((1-tert-butyl-1H-pyrazol-4-yl)amino)-4-((2-fluoro-6-(trifluoromethyl)benzyl)amino)pyrimidin-5-carboxamide | 452 | ¹H NMR (400 MHz, DMSO-d₆) δ 10.33 (s, 1H), 10.12 (s, 1H), 8.58 (s, 1H), 8.25-8.10 (m, 1H), 8.07 (s, 1H), 7.77-7.61 (m, 4H), 7.60-7.37 (m, 1H), 4.93 (d, J = 6.0 Hz, 2H), 1.51 (s, 9H). |
| 214 | 2-ethyl-6-fluorophenyl | CH₃ | 2-chloro-4-((2-ethyl-6-fluorobenzyl)amino)pyrimidin-5-carboxamide | 309 | 4-((2-ethyl-6-fluorobenzyl)amino)-2-((1-methyl-1H-pyrazol-4-yl)amino)pyrimidin-5-carboxamide | 370 | ¹H NMR (400 MHz, DMSO-d₆) δ 9.50 (s, 1H), 9.27 (s, 1H), 8.49 (s, 1H), 7.89 (s, 1H), 7.81-7.59 (m, 1H), 7.53 (s, 1H), 7.42-7.24 (m, 1H), 7.18-6.88 (m, 3H), 4.83-4.53 (m, 2H), 3.80 (s, 3H), 2.83-2.59 (m, 2H), 1.13 (t, J = 7.5 Hz, 3H). |
| 215 | 2-ethyl-6-fluorophenyl | CH₂CH₃ | 2-chloro-4-((2-ethyl-6-fluorobenzyl)amino)pyrimidin-5-carboxamide | 309 | 2-((1-ethyl-1H-pyrazol-4-yl)amino)-4-((2-ethyl-6-fluorobenzyl)amino)pyrimidin-5-carboxamide | 384 | ¹H NMR (400 MHz, DMSO-d₆) δ 9.50 (s, 1H), 9.26 (s, 1H), 8.49 (s, 1H), 7.93 (s, 1H), 7.83-7.59 (m, 1H), 7.55 (s, 1H), 7.40-7.27 (m, 1H), 7.16-6.86 (m, 3H), 4.79-4.59 (m, 2H), 4.09 (q, J = 7.3 Hz, 2H), 2.79-2.60 (m, 2H), 1.34 (t, J = 7.2 Hz, 3H), 1.13 (t, J = 7.5 Hz, 3H). |
| 216 | 2-ethyl-6-fluorophenyl | C(CH₃)₃ | 2-chloro-4-((2-ethyl-6-fluorobenzyl)amino)pyrimidin-5-carboxamide | 309 | 2-((1-tert-butyl-1H-pyrazol-4-yl)amino)-4-((2-ethyl-6-fluorobenzyl)amino)pyrimidin-5-carboxamide | 412 | ¹H NMR (400 MHz, DMSO-d₆) δ 9.49 (s, 1H), 9.31-8.99 (m, 1H), 8.50 (s, 1H), 8.15-7.88 (m, 1H), 7.71 (s, 1H), 7.60 (s, 1H), 7.41-7.25 (m, 1H), 7.19-6.81 (m, 3H), 4.85-4.52 (m, 2H), 2.92-2.59 (m, 2H), 1.50 (s, 9H), 1.14 (t, J = 7.7 Hz, 3H). |
| 217 | 2-fluoro-6-methoxyphenyl | C(CH₃)₃ | 2-chloro-4-((2-fluoro-6-methoxybenzyl)amino)pyrimidin-5-carboxamide | 311 | 2-((1-tert-butyl-1H-pyrazol-4-yl)amino)-4-((2-fluoro-6-methoxybenzyl)amino)pyrimidin-5-carboxamide | 414 | ¹H NMR (400 MHz, DMSO-d₆) δ 10.49 (s, 1H), 10.42 (s, 1H), 8.56 (s, 1H), 8.29-8.14 (m, 1H), 8.11 (s, 1H), 7.73 (s, 1H), 7.66-7.49 (m, 1H), 7.45-7.34 (m, 1H), 6.96 (d, J = 8.4 Hz, 1H), 6.92-6.82 (m, 1H), 4.90-4.68 (m, 2H), 3.88 (s, 3H), 1.53 (s, 9H). |

TABLE 4-continued

Structures and characterization of intermediate compound A and target compound B of Examples 181 to 227

| | | | Compound A | | Compound B | | |
|---|---|---|---|---|---|---|---|
| Ex. No. | R¹ | R² | Name | LC MS m/z = (M + H)⁺ | Name | LC MS m/z = (M + H)⁺ | ¹H NMR |
| 218 | 2,6-dimethylphenyl | ethyl | 2-chloro-4-((2,6-dimethylbenzyl)amino)pyrimidin-5-carboxamide | 291 | 4-((2,6-dimethylbenzyl)amino)-2-((1-ethyl-1H-pyrazol-4-yl)amino)pyrimidin-5-carboxamide | 366 | ¹H NMR (400 MHz, DMSO-d₆) δ 10.57 (s, 1H), 9.96 (s, 1H), 8.66-8.48 (m, 1H), 8.24 (s, 1H), 8.04 (s, 1H), 7.75-7.63 (m, 1H), 7.63-7.49 (m, 1H), 7.21-7.12 (m, 1H), 7.12-7.04 (m, 2H), 4.71 (d, J = 4.7 Hz, 2H), 4.15 (q, J = 7.2 Hz, 2H), 2.32 (s, 6H), 1.36 (t, J = 7.2 Hz, 3H). |
| 219 | 2,6-dimethylphenyl | isopropyl | 2-chloro-4-((2,6-dimethylbenzyl)amino)pyrimidin-5-carboxamide | 291 | 4-((2,6-dimethylbenzyl)amino)-2-((1-isopropyl-1H-pyrazol-4-yl)amino)pyrimidin-5-carboxamide | 380 | ¹H NMR (400 MHz, DMSO-d₆) δ 10.66 (s, 1H), 10.00 (s, 1H), 8.60 (s, 1H), 8.49-8.13 (m, 1H), 8.05 (s, 1H), 7.84-7.66 (m, 1H), 7.66-7.54 (m, 1H), 7.20-7.12 (m, 1H), 7.12-7.04 (m, 2H), 4.72 (d, J = 4.7 Hz, 2H), 4.53 (p, J = 6.7 Hz, 1H), 2.32 (s, 6H), 1.41 (d, J = 6.6 Hz, 6H). |
| 220 | 2,6-dimethylphenyl | tert-butyl | 2-chloro-4-((2,6-dimethylbenzyl)amino)pyrimidin-5-carboxamide | 291 | 2-((1-tert-butyl-1H-pyrazol-4-yl)amino)-4-((2,6-dimethylbenzyl)amino)pyrimidin-5-carboxamide | 394 | ¹H NMR (400 MHz, DMSO-d₆) δ 10.58 (s, 1H), 9.96 (s, 1H), 8.60 (s, 1H), 8.37-8.18 (m, 1H), 8.11 (s, 1H), 7.74 (s, 1H), 7.68-7.49 (m, 1H), 7.16 (dd, J = 8.6, 6.3 Hz, 1H), 7.13-7.04 (m, 2H), 4.72 (d, J = 4.8 Hz, 2H), 2.32 (s, 6H), 1.53 (s, 9H). |
| 221 | 2,6-dimethylphenyl | tetrahydropyran-4-yl | 2-chloro-4-((2,6-dimethylbenzyl)amino)pyrimidin-5-carboxamide | 291 | 4-((2,6-dimethylbenzyl)amino)-2-((1-(tetrahydro-2H-pyran-4-yl)-1H-pyrazol-4-yl)amino)pyrimidin-5-carboxamide | 422 | ¹H NMR (400 MHz, DMSO-d₆ + DCl/D₂O) δ 8.68 (s, 1H), 8.05 (s, 1H), 7.72 (s, 1H), 7.11 (dd, J = 8.6, 6.3 Hz, 1H), 7.07-7.01 (m, 2H), 4.67 (s, 2H), 4.49-4.33 (m, 1H), 3.95-3.78 (m, 2H), 3.48-3.28 (m, 2H), 2.25 (s, 6H), 1.97-1.77 (m, 4H). |
| 222 | 2-ethyl-6-methylphenyl | methyl | 2-chloro-4-((2-ethyl-6-methylbenzyl)amino)pyrimidin-5-carboxamide | 305 | 4-((2-ethyl-6-methylbenzyl)amino)-2-((1-methyl-1H-pyrazol-4-yl)amino)pyrimidin-5-carboxamide | 366 | ¹H NMR (400 MHz, DMSO-d₆) δ 9.52 (s, 1H), 9.06 (s, 1H), 8.48 (s, 1H), 7.91 (s, 1H), 7.80-7.63 (m, 1H), 7.55 (s, 1H), 7.23-7.14 (m, 1H), 7.14-7.05 (m, 2H), 7.01 (s, 1H), 4.75-4.48 (m, 2H), 3.80 (s, 3H), 2.67 (q, J = 7.5 Hz, 2H), 2.33 (s, 3H), 1.14 (t, J = 7.5 Hz, 3H). |
| 223 | 2-ethynylphenyl | methyl | 2-chloro-4-((2-ethynylbenzyl)amino)pyrimidin-5-carboxamide | 287 | 4-((2-ethynylbenzyl)amino)-2-((1-methyl-1H-pyrazol-4-yl)amino)pyrimidin-5-carboxamide | 348 | ¹H NMR (400 MHz, DMSO-d₆ + DCl/D₂O) δ 8.70 (s, 1H), 7.54 (d, J = 7.4 Hz, 1H), 7.49-7.45 (m, 1H), 7.45-7.40 (m, 1H), 7.39-7.33 (m, 1H), 7.33-7.27 (m, 1H), 7.20 (d, J = 7.7 Hz, 1H), 4.83 (s, 2H), 4.54 (s, 1H), 3.72 (s, 3H). |
| 224 | 3,5-dimethyl-1H-pyrazol-4-yl | methyl | 2-chloro-4-(((3,5-dimethyl-1H-pyrazol-4-yl)methyl)amino)pyrimidin-5-carboxamide | 281 | 4-(((3,5-dimethyl-1H-pyrazol-4-yl)methyl)amino)-2-((1-methyl-1H-pyrazol-4-yl)amino)pyrimidin-5-carboxamide | 342 | ¹H NMR (400 MHz, DMSO-d₆) δ 10.54 (s, 1H), 9.91 (s, 1H), 8.56 (s, 1H), 8.32-8.10 (m, 1H), 7.93 (s, 1H), 7.79-7.46 (m, 3H), 4.49 (d, J = 4.9 Hz, 2H), 3.84 (s, 3H), 2.15 (s, 6H). |

TABLE 4-continued

Structures and characterization of intermediate compound A and target compound B of Examples 181 to 227

| | | | Compound A | | Compound B | | |
|---|---|---|---|---|---|---|---|
| Ex. No. | $R^1$ | $R^2$ | Name | LC MS m/z = $(M + H)^+$ | Name | LC MS m/z = $(M + H)^+$ | $^1$H NMR |
| 225 | (2-vinylbenzyl) | | 2-chloro-4-((2-vinylbenzyl)amino)pyrimidin-5-carboxamide | 289 | 2-((1-methyl-1H-pyrazol-4-yl)amino)-4-((2-vinylbenzyl)amino)pyrimidin-5-carboxamide | 350 | $^1$H NMR (400 MHz, DMSO-d$_6$ + DCl/D$_2$O) δ 8.67 (s, 1H), 7.66-7.53 (m, 2H), 7.46 (s, 1H), 7.32-7.12 (m, 3H), 6.96 (dd, J = 17.3, 11.0 Hz, 1H), 5.74 (dd, J =17.3, 1.4 Hz, 1H), 5.32 (dd, J = 10.9, 1.4 Hz, 1H), 4.77 (s, 2H), 3.68 (s, 3H). |
| 226 | (2-(prop-1-en-1-yl)benzyl) | | 2-chloro-4-((2-(prop-1-en-1-yl)benzyl)amino)pyrimidin-5-carboxamide | 303 | 2-((1-methyl-1H-pyrazol-4-yl)amino)-4-((2-(prop-1-en-1-yl)benzyl)amino)pyrimidin-5-carboxamide | 364 | $^1$H NMR (400 MHz, DMSO-d$_6$) δ 10.38 (s, 1H), 10.16 (s, 1H), 8.54 (s, 1H), 8.18 (s, 1H), 7.66 (s, 1H), 7.62-7.50 (m, 2H), 7.46 (d, J = 7.1 Hz, 1H), 7.39-7.23 (m, 3H), 6.57 (d, J = 11.5 Hz, 1H), 6.04-5.78 (m, 1H), 4.68 (d, J = 5.7 Hz, 2H), 3.73 (s, 3H), 1.69 (dd, J = 6.9, 1.7 Hz, 3H). |
| 227 | (2-allylbenzyl) | | 4-((2-allylbenzyl)amino)-2-chloropyrimidin-5-carboxamide | 303 | 4-((2-allylbenzyl)amino)-2-((1-methyl-1H-pyrazol-4-yl)amino)pyrimidin-5-carboxamide | 364 | $^1$H NMR (400 MHz, DMSO-d$_6$ + DCl/D$_2$O) δ 8.67 (s, 1H), 7.60 (s, 1H), 7.46 (s, 1H), 7.26-7.10 (m, 4H), 5.95-5.80 (m, 1H), 5.04-4.85 (m, 2H), 4.74-4.62 (m, 2H), 3.68 (s, 3H), 3.37 (d, J = 6.4 Hz, 2H). |

Example 228 Preparation of 4-(but-3-en-1-ylamino)-2-((1-(tert-butyl)-1H-pyrazol-4-yl)amino)pyrimidin-5-carboxamide

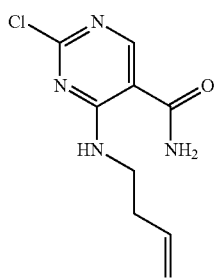

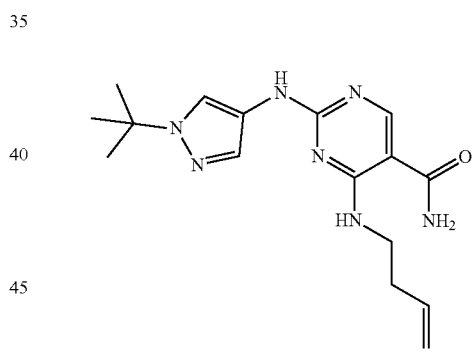

Step 1): Preparation of 2-chloro-4-(but-3-en-1-ylamino)pyrimidin-5-carboxamide 2,4-Dichloropyrimidin-5-carboxamide (400 mg, 2.08 mmol) and triethylamine (633 mg, 6.25 mmol) were dissolved in tetrahydrofuran (10 mL). To the mixture was added but-3-en-1-amine hydrochloride (225 mg, 2.1 mmol), and reacted at 25° C. for 3 hours. To the mixture was added saturated brine (200 mL), stirred for 15 minutes, and then filtered. The filter cake was washed with petroleum ether to give 380 mg of a white solid. MS: 227 [M+H]$^+$.

Step 2): Preparation of 4-(but-3-en-1-ylamino)-2-((1-tert-butyl)-1H-pyrazol-4-yl)amino)pyrimidin-5-carboxamide 2-Chloro-4-(but-3-en-1-ylamino)pyrimidin-5-carboxamide (70 mg, 0.29 mmol) was dissolved in sec-butanol (3 mL). To the mixture were added 1-tert-butyl-1H-pyrazol-4-amine (49 mg, 0.35 mmol) and trifluoroacetic acid (0.1 mL). The tube was sealed and the mixture was reacted at 100° C. for 2 hours. The reaction solution was concentrated, and filtered. The solid was washed with acetonitrile to give 50 mg of a white solid. $^1$H NMR (400 MHz, DMSO-d$_6$) δ 10.52 (s, 1H), 10.04 (s, 1H), 8.53 (s, 1H), 8.30-8.10 (m, 1H), 8.02 (s, 1H), 7.71-7.52 (m, 2H), 5.92-5.72 (m, 1H), 5.20-4.97 (m, 2H), 3.68-3.53 (m, 2H), 2.43-2.28 (m, 2H), 1.52 (s, 9H). Chemical formula: C$_{16}$H$_{23}$N$_7$O, MS: 330 (M+H)$^+$.

Example 229 Preparation of 2-((1-tert-butyl-1H-pyrazol-4-yl)amino)-4-((2-methylallyl)amino)pyrimidin-5-carboxamide

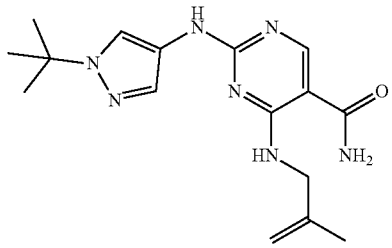 [SMILES: C=C(C)CNc1nc(Nc2cnn(C(C)(C)C)c2)ncc1C(N)=O]

The operation was the similar as in Example 228. 2-Methylprop-2-en-1-amine was used in place of but-3-en-1-amine hydrochloride in step 1) to give a white solid. $^1$H NMR (400 MHz, DMSO-d$_6$) δ 10.36 (s, 1H), 10.12 (s, 1H), 8.55 (s, 1H), 8.29-8.09 (m, 1H), 7.98 (s, 1H), 7.70-7.49 (m, 2H), 4.90-4.80 (m, 2H), 4.10 (d, J=5.7 Hz, 2H), 1.76 (s, 3H), 1.51 (s, 9H). Chemical formula: $C_{16}H_{23}N_7O$, MS: 330 (M+H)$^+$.

Example 230 Preparation of 2-((1-(tert-butyl)-1H-pyrazol-4-yl)amino)-4-((3-methylbut-2-en-1-yl)amino)pyrimidin-5-carboxamide

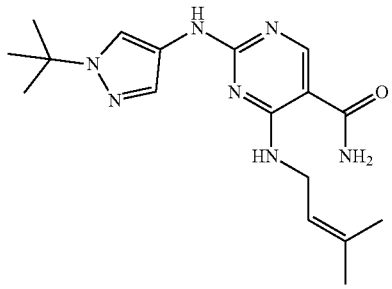 [SMILES: CC(C)=CCNc1nc(Nc2cnn(C(C)(C)C)c2)ncc1C(N)=O]

The operation was similar to that in Example 228. 3-Methylbut-2-en-1-amine was used in place of but-3-en-1-amine hydrochloride in step 1) to give a white solid. $^1$H NMR (400 MHz, DMSO-d$_6$) δ 10.48 (s, 1H), 9.94 (s, 1H), 8.51 (s, 1H), 8.36-8.10 (m, 1H), 8.06 (s, 1H), 7.81-7.40 (m, 2H), 5.41-5.22 (m, 1H), 4.24-3.92 (m, 2H), 1.71 (s, 3H), 1.67 (s, 3H), 1.50 (s, 9H). Chemical formula: $C_{17}H_{25}N_7O$, MS: 344 (M+H)$^+$.

Example 231 Preparation of 2-((1-(tert-butyl)-1H-pyrazol-4-yl)amino)-4-(pent-4-en-1-ylamino)pyrimidin-5-carboxamide

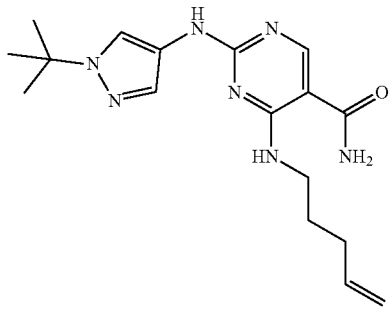 [SMILES: C=CCCCNc1nc(Nc2cnn(C(C)(C)C)c2)ncc1C(N)=O]

The operation was similar to that in Example 228. Pent-4-en-1-amine was used in place of but-3-en-1-amine hydrochloride in step 1) to give a white solid. $^1$H NMR (400 MHz, DMSO-d$_6$) δ 10.39 (s, 1H), 10.00 (s, 1H), 8.49 (s, 1H), 8.18 (s, 1H), 8.02 (s, 1H), 7.71-7.50 (m, 2H), 5.91-5.73 (m, 1H), 5.10-4.91 (m, 2H), 3.60-3.45 (m, 2H), 2.14-2.02 (m, 2H), 1.78-1.63 (m, 2H), 1.52 (s, 9H). Chemical formula: $C_{17}H_{25}N_7O$, MS: 344 (M+H)$^+$.

Example 232 Preparation of 4-((2-methylallyl)amino)-2-((1-(tetrahydro-2H-pyran-4-yl)-1H-pyrazol-4-yl)amino)pyrimidin-5-carboxamide

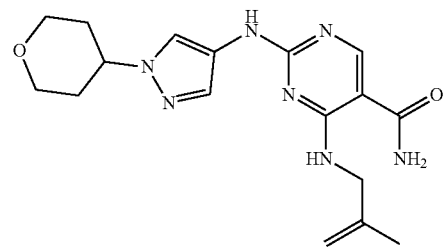 [SMILES: C=C(C)CNc1nc(Nc2cnn(C3CCOCC3)c2)ncc1C(N)=O]

The operation was similar to that in Example 228. 2-Methylprop-2-en-1-amine was used in place of but-3-en-1-amine hydrochloride in step 1), and 1-(tetrahydro-2H-pyran-4-yl)-1H-pyrazol-4-amine was used in place of 1-tert-butyl-1H-pyrazol-4-amine in step 2) to give a white solid. $^1$H NMR (400 MHz, DMSO-d$_6$) δ 10.55 (s, 1H), 10.16 (s, 1H), 8.59 (s, 1H), 8.37-8.16 (m, 1H), 7.95 (s, 1H), 7.72-7.53 (m, 2H), 4.92-4.76 (m, 2H), 4.45-4.31 (m, 1H), 4.09 (d, J=5.8 Hz, 2H), 4.01-3.88 (m, 2H), 3.48-3.41 (m, 2H), 2.02-1.82 (m, 4H), 1.76 (s, 3H). Chemical formula: $C_{17}H_{23}N_7O_2$, MS: 358 (M+H)$^+$.

Example 233 Preparation of 4-((3-methylbut-2-en-1-yl)amino)-2-((1-(tetrahydro-2H-pyran-4-yl)-1H-pyrazol-4-yl)amino)pyrimidin-5-carboxamide

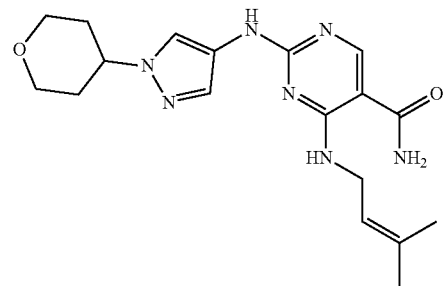 [SMILES: CC(C)=CCNc1nc(Nc2cnn(C3CCOCC3)c2)ncc1C(N)=O]

The operation was similar to that in Example 228. 3-Methylbut-2-en-1-amine was used in place of but-3-en-1-amine hydrochloride in step 1), and 1-(tetrahydro-2H-pyran-4-yl)-1H-pyrazol-4-amine was used in place of 1-tert-butyl-1H-pyrazol-4-amine in step 2) to give a white solid. $^1$H NMR (400 MHz, DMSO-d$_6$) δ 10.47 (s, 1H), 9.93 (s, 1H), 8.50 (s, 1H), 8.29-8.07 (m, 1H), 8.00 (s, 1H), 7.71-7.50 (m, 2H), 5.36-5.24 (m, 1H), 4.46-4.30 (m, 1H), 4.20-4.06 (m, 2H), 4.00-3.87 (m, 2H), 3.54-3.38 (m, 2H), 2.02-1.80 (m, 4H), 1.71 (s, 3H), 1.68 (s, 3H). Chemical formula: $C_{18}H_{25}N_7O_2$, MS: 372 (M+H)$^+$.

Example 234 Preparation of 4-(but-3-en-1-ylamino)-2-((1-(tetrahydro-2H-pyran-4-yl)-1H-pyrazol-4-yl)amino)pyrimidin-5-carboxamide

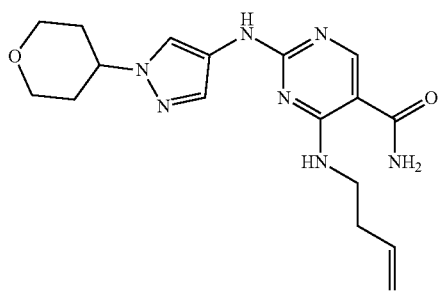 [SMILES: C=CCCNc1nc(Nc2cnn(C3CCOCC3)c2)ncc1C(N)=O]

The operation was similar to that in Example 228. 1-(Tetrahydro-2H-pyran-4-yl)-1H-pyrazol-4-amine was used in place of 1-tert-butyl-1H-pyrazol-4-amine in step 2) to give a white solid. $^1$H NMR (400 MHz, DMSO-d$_6$) δ 10.63 (s, 1H), 10.06 (s, 1H), 8.55 (s, 1H), 8.38-8.12 (m, 1H), 7.99 (s, 1H), 7.76-7.45 (m, 2H), 5.95-5.73 (m, 1H), 5.21-5.02 (m, 2H), 4.48-4.29 (m, 1H), 4.04-3.87 (m, 2H), 3.69-3.53 (m, 2H), 3.52-3.34 (m, 2H), 2.43-2.28 (m, 2H), 2.01-1.81 (m, 4H). Chemical formula: C$_{17}$H$_{23}$N$_7$O$_2$, MS: 358 (M+H)$^+$.

Example 235 Preparation of 2-((1-(tetrahydro-2H-pyran-4-yl)-1H-pyrazol-4-yl)amino)-4-(pent-4-en-1-ylamino)pyrimidin-5-carboxamide

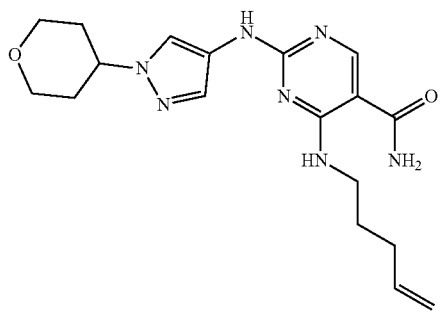 [SMILES: C=CCCCNc1nc(Nc2cnn(C3CCOCC3)c2)ncc1C(N)=O]

The operation was similar to that in Example 228. Pent-4-en-1-amine was used in place of but-3-en-1-amine hydrochloride in step 1), and 1-(tetrahydro-2H-pyran-4-yl)-1H-pyrazol-4-amine was used in place of 1-tert-butyl-1H-pyrazol-4-amine in step 2) to give a white solid. $^1$H NMR (400 MHz, DMSO-d$_6$) δ 10.41 (s, 1H), 10.00 (s, 1H), 8.48 (s, 1H), 8.28-8.07 (m, 1H), 7.97 (s, 1H), 7.70-7.52 (m, 2H), 5.91-5.75 (m, 1H), 5.10-4.92 (m, 2H), 4.46-4.33 (m, 1H), 4.01-3.91 (m, 2H), 3.57-3.41 (m, 4H), 2.15-2.05 (m, 2H), 2.02-1.86 (m, 4H), 1.77-1.64 (m, 2H). Chemical formula: C$_{18}$H$_{25}$N$_7$O$_2$, MS: 372 (M+H)$^+$.

Example 236 Preparation of 2-((1-(tert-butyl)-1H-pyrazol-4-yl)amino)-4-((cyclopent-3-en-1-ylmethyl)amino)pyrimidin-5-carboxamide Step 1): Preparation of 2-chloro-4-((cyclopent-3-en-1-ylmethyl)amino)pyrimidin-5-carboxamide

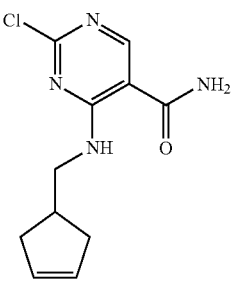 [SMILES: NC(=O)c1cnc(Cl)nc1NCC1CC=CC1]

2,4-Dichloropyrimidin-5-carboxamide (400 mg, 2.08 mmol) and triethylamine (633 mg, 6.25 mmol) were dissolved in tetrahydrofuran (10 mL). To the mixture was added cyclopent-3-en-1-ylmethylamine hydrochloride (281 mg, 2.1 mmol), and reacted at 25° C. for 3 hours. To the mixture was added saturated brine (200 mL), stirred for 15 minutes, and then filtered. The filter cake was washed with petroleum ether to give 380 mg of a white solid. MS: 253 [M+H]$^+$.

Step 2): Preparation of 2-((1-(tert-butyl)-1H-pyrazol-4-yl)amino)-4-((cyclopent-3-en-1-ylmethyl)amino)pyrimidin-5-carboxamide

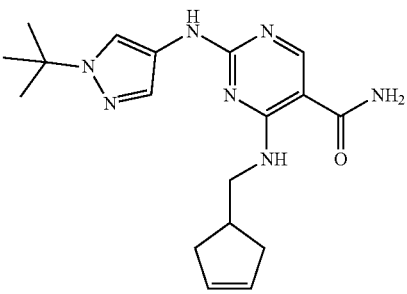 [SMILES: CC(C)(C)n1cc(Nc2ncc(C(N)=O)c(NCC3CC=CC3)n2)cn1]

2-Chloro-4-((cyclopent-3-en-1-ylmethyl)amino)pyrimidin-5-carboxamide (127 mg, 0.5 mmol) was dissolved in sec-butanol (3 mL). To the mixture were added 1-tert-butyl-1H-pyrazol-4-amine (84 mg, 0.6 mmol) and trifluoroacetic acid (0.1 mL). The tube was sealed and the mixture was reacted at 100° C. for 2 hours. The reaction solution was concentrated and purified by column chromatography to give 50 mg of a white solid. $^1$H NMR (400 MHz, DMSO-d$_6$) δ 10.58 (s, 1H), 10.16 (s, 1H), 8.55 (s, 1H), 8.37-8.14 (m, 1H), 8.02 (s, 1H), 7.71-7.52 (m, 2H), 5.75-5.63 (m, 2H), 3.57-3.44 (m, 2H), 2.72-2.56 (m, 1H), 2.49-2.39 (m, 2H), 2.15-2.01 (m, 2H), 1.52 (s, 9H). MS: 356 [M+H]$^+$.

Example 237: Preparation of 4-((cyclopent-3-en-1-ylmethyl)amino)-2-((1-(tetrahydro-2H-pyran-4-yl)-1H-pyrazol-4-yl)amino)pyrimidin-5-carboxamide Step 1: This Step is Similar to that in Step 1 of Example 236

Step 2: Preparation of 4-((cyclopent-3-en-1-ylmethyl)amino)-2-((1-(tetrahydro-2H-pyran-4-yl)-1H-pyrazol-4-yl)amino)pyrimidin-5-carboxamide

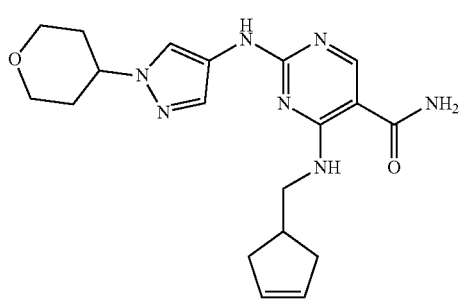 [SMILES: NC(=O)c1cnc(Nc2cnn(C3CCOCC3)c2)nc1NCC1CC=CC1]

The operation was similar to that in Step 2 of Example 236. 1-(Tetrahydro-2H-pyran-4-yl)-1H-pyrazol-4-amine is used in place of 1-tert-butyl-1H-pyrazol-4-amine to give a white solid. $^1$H NMR (400 MHz, DMSO-d$_6$) δ 10.62 (s, 1H), 10.16 (s, 1H), 8.56 (s, 1H), 8.26 (s, 1H), 7.98 (s, 1H), 7.71-7.53 (m, 2H), 5.75-5.65 (m, 2H), 4.46-4.31 (m, 1H), 4.01-3.90 (m, 2H), 3.57-3.39 (m, 4H), 2.70-2.55 (m, 1H), 2.48-2.36 (m, 2H), 2.17-2.04 (m, 2H), 2.03-1.82 (m, 4H). MS: 384 [M+H]$^+$.

Example 238: Preparation of 4-(allylamino)-2-((1-(tert-butyl)-1H-pyrazol-4-yl)amino)pyrimidin-5-carboxamide

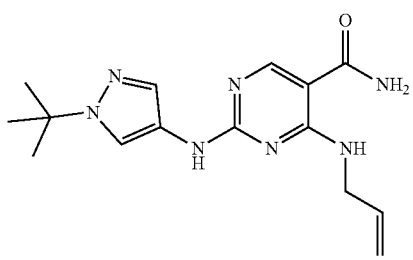 [SMILES: C=CCNc1nc(Nc2cnn(C(C)(C)C)c2)ncc1C(N)=O]

The operation was similar to that in Example 236. Allylamine hydrochloride was used in place of cyclopent-3-en-1-ylmethylamine hydrochloride to give an off-white solid. $^1$H NMR (400 MHz, DMSO-d$_6$) δ 10.71 (s, 1H), 10.16 (s, 1H), 8.62 (s, 1H), 8.31 (s, 1H), 8.00 (s, 1H), 7.77-7.54 (m, 2H), 6.07-5.89 (m, 1H), 5.27-5.11 (m, 2H), 4.25-4.12 (m, 2H), 1.51 (s, 9H). MS: 316 [M+H]$^+$.

Example 239: Preparation of (Z)-2-((1-tert-butyl-1H-pyrazol-4-yl)amino)-4-((pent-2-en-1-yl)amino)pyrimidin-5-carboxamide

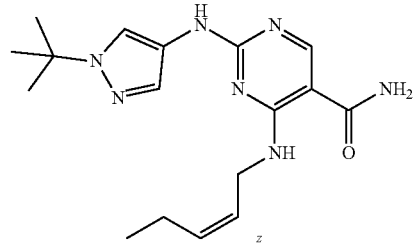 [SMILES: CC/C=C\CNc1nc(Nc2cnn(C(C)(C)C)c2)ncc1C(N)=O]

The operation was similar to that in Example 236. (Z)-pent-2-en-1-amine was used in place of cyclopent-3-en-1-ylmethylamine hydrochloride to give an off-white solid. $^1$H NMR (400 MHz, DMSO-d$_6$) δ 9.44 (s, 1H), 9.18 (d, J=28.1 Hz, 1H), 8.46 (s, 1H), 8.02 (d, J=9.3 Hz, 1H), 7.83-7.56 (m, 1H), 7.48 (s, 1H), 7.23-6.97 (m, 1H), 5.72-5.52 (m, 2H), 4.14-4.03 (m, 2H), 2.14-1.98 (m, 2H), 1.49 (s, 9H), 0.99-0.91 (m, 3H). MS: 344 [M+H]$^+$.

Example 240: Preparation of (E)-2-((1-tert-butyl-1H-pyrazol-4-yl)amino)-4-((4-methylpent-2-en-1-yl)amino)pyrimidin-5-carboxamide

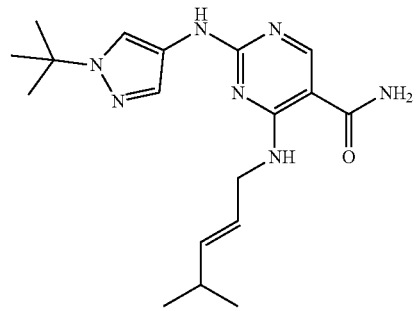 [SMILES: CC(C)/C=C/CNc1nc(Nc2cnn(C(C)(C)C)c2)ncc1C(N)=O]

The operation was similar to that in Example 236. (E)-4-methylpent-2-en-1-amine was used in place of cyclopent-3-en-1-ylmethylamine hydrochloride to give an off-white solid. $^1$H NMR (400 MHz, DMSO-d$_6$) δ 9.45 (s, 1H), 9.24 (s, 1H), 8.46 (s, 1H), 8.01 (s, 1H), 7.87-7.51 (m, 1H), 7.48 (s, 1H), 7.39-6.79 (m, 1H), 5.75-5.39 (m, 2H), 4.25-3.86 (m, 2H), 2.40-2.10 (m, 1H), 1.49 (s, 9H), 0.94 (d, J=6.7 Hz, 6H). MS: 358 [M+H]$^+$.

Example 241: Preparation of (E)-2-((1-tert-butyl-1H-pyrazol-4-yl)amino)-4-((pent-3-en-1-yl)amino)pyrimidin-5-carboxamide

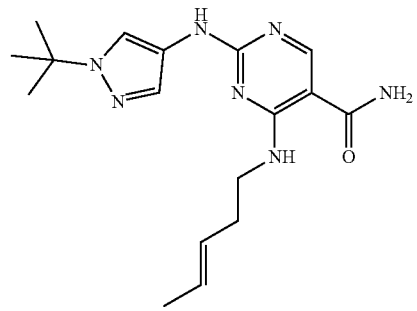 [SMILES: C/C=C/CCNc1nc(Nc2cnn(C(C)(C)C)c2)ncc1C(N)=O]

The operation was similar to that in Example 236. (E)-pent-3-en-1-amine was used in place of cyclopent-3-en-1-ylmethylamine hydrochloride to give an off-white solid. $^1$H NMR (400 MHz, DMSO-d$_6$) δ 9.41 (s, 1H), 9.19 (s, 1H), 8.44 (s, 1H), 8.00 (s, 1H), 7.67-7.53 (m, 1H), 7.50 (s, 1H), 7.21-6.93 (m, 1H), 5.58-5.36 (m, 2H), 3.52-3.47 (m, 2H), 2.37-2.20 (m, 2H), 1.63 (d, J=5.9 Hz, 3H), 1.49 (s, 9H). MS: 344 [M+H]$^+$.

Example 242: Preparation of 2-((1-tert-butyl-1H-pyrazol-4-yl)amino)-4-((3-methylbut-3-en-1-yl)amino)pyrimidin-5-carboxamide

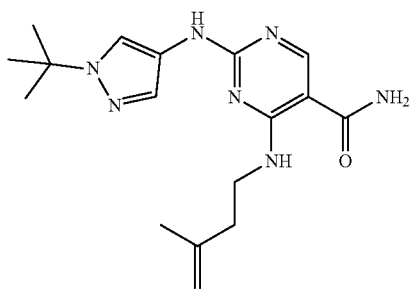 [SMILES: C=C(C)CCNc1nc(Nc2cnn(C(C)(C)C)c2)ncc1C(N)=O]

The operation was similar to that in Example 236. 3-Methylbut-3-en-1-amine was used in place of cyclopent-3-en-1-ylmethylamine hydrochloride to give an off-white solid. $^1$H NMR (400 MHz, DMSO-d$_6$) δ 9.40 (s, 1H), 9.17 (s, 1H), 8.44 (s, 1H), 7.97 (s, 1H), 7.82-7.59 (m, 1H), 7.52 (s, 1H), 7.18-6.87 (m, 1H), 4.84-4.77 (m, 1H), 4.77-4.72 (m, 1H), 3.67-3.50 (m, 2H), 2.39-2.22 (m, 2H), 1.73 (s, 3H), 1.49 (s, 9H). MS: 344 [M+H]$^+$.

Example 243: Preparation of 2-((1-tert-butyl-1H-pyrazol-4-yl)amino)-4-((4-methylpent-3-en-1-yl)amino)pyrimidin-5-carboxamide

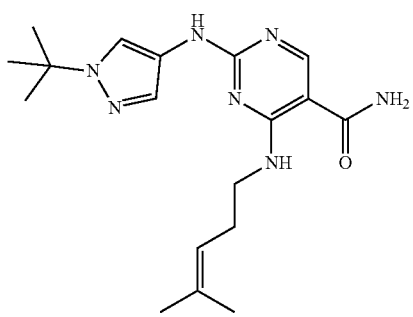 [SMILES: CC(C)=CCCNc1nc(Nc2cnn(C(C)(C)C)c2)ncc1C(N)=O]

The operation was similar to that in Example 236. 4-Methylpent-3-en-1-amine was used in place of cyclopent-3-en-1-ylmethylamine hydrochloride to give an off-white solid. $^1$H NMR (400 MHz, DMSO-d$_6$) δ 9.41 (s, 1H), 9.16 (s, 1H), 8.45 (s, 1H), 8.01 (s, 1H), 7.82-7.55 (m, 1H), 7.50 (s, 1H), 7.24-6.87 (m, 1H), 5.21-5.11 (m, 1H), 3.54-3.43 (m, 2H), 2.36-2.22 (m, 2H), 1.67 (s, 3H), 1.57 (s, 3H), 1.49 (s, 9H). MS: 358 [M+H]$^+$.

Example 244: Preparation of 2-((1-tert-butyl-1H-pyrazol-4-yl)amino)-4-((4-methylpent-4-en-1-yl)amino)pyrimidin-5-carboxamide

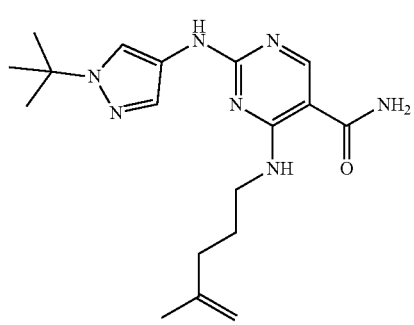 [SMILES: C=C(C)CCCNc1nc(Nc2cnn(C(C)(C)C)c2)ncc1C(N)=O]

The operation was similar to that in Example 236. 4-Methylpent-4-en-1-amine was used in place of cyclopent-3-en-1-ylmethylamine hydrochloride to give an off-white solid. $^1$H NMR (400 MHz, DMSO-d$_6$) δ 9.46 (s, 1H), 9.27 (s, 1H), 8.45 (s, 1H), 8.00 (s, 1H), 7.86-7.59 (m, 1H), 7.51 (s, 1H), 7.31-6.76 (m, 1H), 4.78-4.63 (m, 2H), 3.52-3.44 (m, 2H), 2.06 (t, J=7.7 Hz, 2H), 1.80-1.70 (m, 2H), 1.69 (s, 3H), 1.50 (s, 9H). MS: 358 [M+H]$^+$.

Example 245: Preparation of 2-((1-tert-butyl-1H-pyrazol-4-yl)amino)-4-((5-methylhex-4-en-1-yl)amino)pyrimidin-5-carboxamide

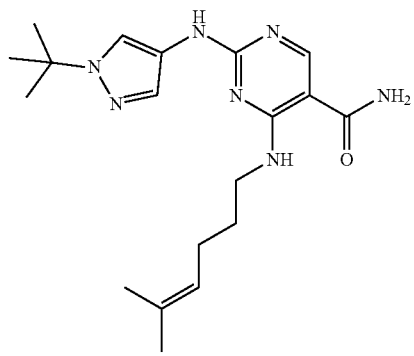 [SMILES: CC(C)=CCCCNc1nc(Nc2cnn(C(C)(C)C)c2)ncc1C(N)=O]

The operation was similar to that in Example 236. 5-Methylhex-4-en-1-amine was used in place of cyclopent-3-en-1-ylmethylamine hydrochloride to give an off-white solid. $^1$H NMR (400 MHz, DMSO-d$_6$) δ 9.40 (s, 1H), 9.21 (s, 1H), 8.44 (s, 1H), 7.98 (s, 1H), 7.82-7.54 (m, 1H), 7.52 (s, 1H), 7.26-6.84 (m, 1H), 5.21-5.01 (m, 1H), 2.07-1.99 (m, 2H), 1.64 (s, 6H), 1.57-1.53 (m, 4H), 1.49 (s, 9H). MS: 372 [M+H]$^+$.

Example 246: Preparation of (E)-2-((1-tert-butyl-1H-pyrazol-4-yl)amino)-4-((5-methylhex-2-en-1-yl)amino)pyrimidin-5-carboxamide

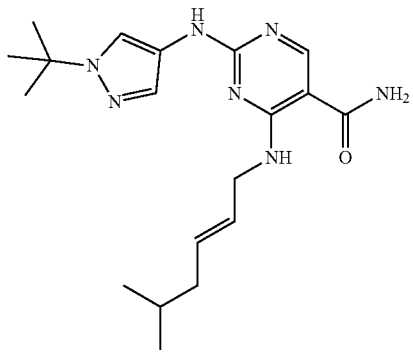 [SMILES: CC(C)C/C=C/CNc1nc(Nc2cnn(C(C)(C)C)c2)ncc1C(N)=O]

The operation was similar to that in Example 236. (E)-5-Methylhex-2-en-1-amine was used in place of cyclopent-3-en-1-ylmethylamine hydrochloride to give an off-white solid. $^1$H NMR (400 MHz, DMSO-d$_6$) δ 9.40 (s, 1H), 9.18 (s, 1H), 8.44 (s, 1H), 8.01 (s, 1H), 7.77-7.54 (m, 1H), 7.50 (s, 1H), 7.22-6.80 (m, 1H), 5.56-5.44 (m, 1H), 5.44-5.31 (m, 1H), 3.55-3.42 (m, 2H), 2.35-2.14 (m, 3H), 1.50 (s, 9H), 0.93 (d, J=6.7 Hz, 6H). MS: 372 [M+H]$^+$.

Example 247: Preparation of 2-((1-tert-butyl-1H-pyrazol-4-yl)amino)-4-(((2E,4E)-hex-2,4-dien-1-yl)amino)pyrimidin-5-carboxamide

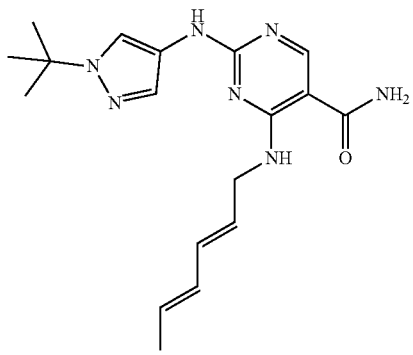 [SMILES: C/C=C/C=C/CNc1nc(Nc2cnn(C(C)(C)C)c2)ncc1C(N)=O]

The operation was similar to that in Example 236. (2E,4E)-Hex-2,4-dien-1-amine was used in place of cyclopent-3-en-1-ylmethylamine hydrochloride to give an off-white solid. $^1$H NMR (400 MHz, DMSO-d$_6$) δ 9.48 (s, 1H), 9.29 (s, 1H), 8.47 (s, 1H), 7.98 (s, 1H), 7.86-7.58 (m, 1H), 7.49 (s, 1H), 7.34-6.92 (m, 1H), 6.22-5.99 (m, 2H), 5.82-5.70 (m, 1H), 5.70-5.55 (m, 1H), 4.19-4.02 (m, 2H), 1.69 (d, J=6.7 Hz, 3H), 1.48 (s, 9H). MS: 356 [M+H]$^+$.

Example 248: Preparation of 2-((1-tert-butyl-1H-pyrazol-4-yl)amino)-4-(((2E,4E)-hept-2,4-dien-1-yl)amino)pyrimidin-5-carboxamide

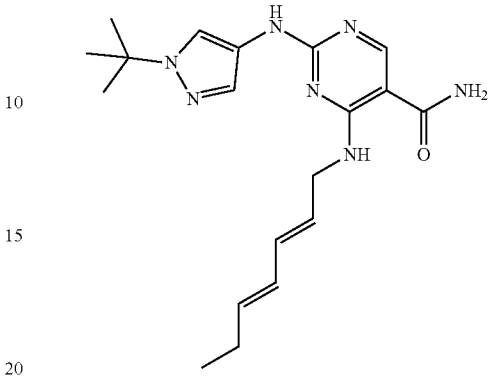

The operation was similar to that in Example 236. (2E,4E)-Hept-2,4-dien-1-amine was used in place of cyclopent-3-en-1-ylmethylamine hydrochloride to give an off-white solid. $^1$H NMR (400 MHz, DMSO-d$_6$) δ 9.44 (s, 1H), 9.25 (s, 1H), 8.47 (s, 1H), 7.98 (s, 1H), 7.88-7.58 (m, 1H), 7.48 (s, 1H), 7.32-6.86 (m, 1H), 6.16 (dd, J=15.1, 10.4 Hz, 1H), 6.04 (dd, J=15.1, 10.5 Hz, 1H), 5.86-5.60 (m, 2H), 4.21-4.05 (m, 2H), 2.12-1.96 (m, 2H), 1.48 (s, 9H), 0.94 (t, J=7.5 Hz, 3H). MS: 370 [M+H]$^+$.

Assay Example 1. Inhibitory Assay of Compounds Disclosed Herein on the Activities of JAK1, JAK2, JAK3, and TYK2 Kinases In an enzymatic reaction assembled in vitro, different concentrations of compounds were added to detect the inhibitory effect of the compounds on the specific enzymatic reaction. The particular assay method was as follows:

I. Instruments, Materials and Reagents Used for Assay

TABLE 5

Instruments, materials, and reagents used for assay

| Name | Brand | Model/Catalog No. |
|---|---|---|
| Multifunctional plate reader | Perkin Elmer | Envision |
| 384-well plate | Perkin Elmer | 607290 |
| ULight ™-labeled JAK-1 (Tyr1023) Peptide | Perkin Elmer | TRF-0121-M |
| Eu-W1024-labeled Anti-Phosphotyrosine Antibody (PT66) | Perkin Elmer | AD0068 |
| 10× Detection Buffer | Perkin Elmer | |
| JAK1 kinase | Carna Biosciences | 08-144 |
| JAK2 kinase | Carna Biosciences | 08-045 |
| JAK3 kinase | Carna Biosciences | 08-046 |
| HEPES | GIBCO | 15630-080 |
| EGTA | Sigma | 03777-10G |
| EDTA | Sigma | EDS-100G |
| MgCl$_2$ | Sigma | 63069-100ML |
| DTT | Sigma | 43816-10ML |
| Tween-20 | Sigma | P7949-100ML |
| DMSO | Life Science | 0231-500ML |
| Tofacitinib | Selleck | S5001 |
| Ruxolitinib | Selleck | S1378 |

II. Assay Method

The particular experimental conditions of JAK1, JAK2, JAK3, and TYK2 are described below, and JAK3 is used as an example.

1. Preparation of Reagents:

Preparation of EDTA solution (0.5 M, pH 8.0): 14.612 g of EDTA powder was accurately weighed, to which ultrapure water was added to make up to 100 mL (if insoluble solid present, the suspension was heated to 37° C.; the pH was adjusted to 8.0 with 1N NaOH solution.)

1×Kinase Assay Buffer: To a reagent bottle were added 25 mL of HEPES solution (1 M), 190.175 mg of EGTA, 5 mL of $MgCl_2$ solution (1 M), 1 mL of DTT, and 50 µL of Tween-20. To the mixture, ultrapure water was added to make up to 500 mL (the pH was adjusted to 7.5).

1×Detection Buffer: 1 mL of 10×Detection Buffer was taken, to which 9 mL of water was added, and the mixture was mixed well.

4×Stop Solution: 0.8 mL of the above EDTA solution (0.5 M, pH 8.0), 1 mL of 10×Detection Buffer and 8.2 mL of ultrapure water were mixed well.

4×JAK3 Kinase Solution: A stock solution of kinase was diluted to a concentration of 0.36 nM with 1×Kinase Assay Buffer, mixed well, and preserved on ice.

4×Substrate Solution: A stock solution of a substrate ULight™-labeled JAK-1 (Tyr1023) peptide was diluted to 200 nM with 1×Kinase Assay Buffer, and mixed well.

4×ATP Solution: A stock solution of ATP was diluted to a concentration of 40 µM with 1×Kinase Assay Buffer, and mixed well.

4×Detection Solution: A detection antibody Europium-anti-phospho-tyrosine antibody (PT66) was diluted with 1×Detection Buffer to a concentration of 8 nM, and mixed well.

2×Substrate/ATP Mixed Solution: A 4×substrate solution and 600 µl of 4×ATP solution were mixed well in an equal volume (prepared before use).

2. Experimental Steps

1) Dilution of the Compounds

In a 96-well plate, the compounds were diluted using a 3-fold dilution with DMSO to get 11 gradients, and another pure DMSO solution was used as positive control; in a new 96-well plate, the above solutions were diluted 25 times with ultrapure water (DMSO concentration was 4%).

2) Transfer of the Compounds to a 384-Well Plate

The compound solutions diluted with ultrapure water in the above 96-well plate were transferred to the corresponding wells of a 384-well plate in duplexes.

3) Addition of the 4×kinase solution: 2.5 µl of the above 4×kinase solution was taken with a pipetter, added to the corresponding reaction wells of the 384-well plate, mixed well, and pre-reacted at room temperature for 5 minutes.

4) Addition of the 2×substrate/ATP mixture: 5 µl of the above 2×substrate/ATP mixture was taken with a pipetter and added to the corresponding reaction wells of a 384-well plate.

5) Negative control: Negative control wells were set in the 384-well plate. To the negative control wells were added 2.5 µl/well of 4×substrate, 2.5 µl of 4×enzyme solution, 2.5 µl of 1×Kinase Assay Buffer, and 2.5 µl of ultrapure water containing 4% DMSO.

6) The mixture was mixed well by centrifugation, and reacted at room temperature for 60 min in dark.

7) Stop of the Enzymatic Reaction:

5 µl of the above 4×stop solution was pipetted into the corresponding wells of the 384-well plate, centrifuged and mixed well. The mixture was reacted at room temperature for 5 minutes.

8) Color Development:

5 µl of the above 4×detection solution was pipetted into the wells of the 384-well plate, centrifuged and mixed well. The mixture was reacted at room temperature for 60 min.

9) The 384-well plate was placed into a plate reader and the signal was detected by using corresponding program.

10) Calculation of Inhibition Ratio and $IC_{50}$:

Well reading value=10000*EU665 value/EU615 value

Inhibition ratio=[1−(experimental well reading value−negative control well reading value)/ (positive control well reading value−negative control well reading value)]*100%

The drug concentration and corresponding inhibition ratio were input into GraphPad Prism5 for processing to calculate the corresponding $IC_{50}$ values.

III. Assay Conditions:

JAK1 Kinase Activity Assay:

JAK1 (the final concentration was 10 nM); ATP (the final concentration was 10 µM); ULight™-labeled JAK-1 (Tyr1023) Peptide (the final concentration was 100 nM); the enzymatic reaction time was 2 hours. The maximum final concentration of compounds was 2.5 µM. After a 3-fold gradient dilution, 11 concentrations were obtained, with the minimum final concentration of 0.042 nM. The final DMSO concentration was 1%.

JAK2 Kinase Activity Assay:

JAK2 (the final concentration was 0.25 nM); ATP (the final concentration was 5 µM); ULight™-labeled JAK-1 (Tyr1023) Peptide (the final concentration was 50 nM); the enzymatic reaction time was 1 hour. The maximum final concentration of compounds was 2.5 µM. After a 3-fold gradient dilution, 11 concentrations were obtained, with the minimum final concentration of 0.042 nM. The final DMSO concentration was 1%.

JAK3 Kinase Activity Assay:

JAK3 (the final concentration was 0.36 nM); ATP (the final concentration was 10 µM); ULight™-labeled JAK-1 (Tyr1023) Peptide (the final concentration was 50 nM); the enzymatic reaction time was 1 hour. The maximum final concentration of compounds was 2.5 µM. After a 3-fold gradient dilution, 11 concentrations were obtained, with the minimum final concentration of 0.042 nM. The final DMSO concentration was 1%.

TYK2 Kinase Activity Assay:

TYK2 (the final concentration was 8 nM); ATP (the final concentration was 20 µM); ULight™-labeled JAK-1 (Tyr1023) Peptide (the final concentration was 100 nM); the enzymatic reaction time was 2 hours. The maximum final concentration of compounds was 2.5 µM. After a 3-fold gradient dilution, 11 concentrations were obtained, with the minimum final concentration of 0.042 nM. The final DMSO concentration was 1%.

Tables 6 and 7 show the assay results of inhibitory activities of a part of compounds disclosed herein against the tyrosine kinases JAK1, JAK2, JAK3, and TYK2. The $IC_{50}$ values in the following tables indicate the compound concentrations at which 50% of the maximum inhibition ratio of the enzyme is reached. NT indicates that the corresponding enzyme was not tested.

TABLE 6

Assay results of inhibitory activities of a part of compounds disclosed herein against JAK1, JAK2, JAK3 and TYK2 tyrosine kinases

| Example No. | JAK1 IC$_{50}$ (nM) | JAK2 IC$_{50}$ (nM) | JAK3 IC$_{50}$ (nM) | TYK2 IC$_{50}$ (nM) |
|---|---|---|---|---|
| 1 | 84.74 | 9.50 | 0.17 | NT |
| 2 | 2.53 | 2.19 | 0.68 | 1.66 |
| 3 | 2.81 | 0.57 | 0.30 | 0.64 |
| 4 | 22.17 | 4.49 | 3.63 | 4.19 |
| 5 | 23.42 | 1.67 | 0.25 | NT |
| 6 | 29.91 | 1.27 | 0.20 | NT |
| 7 | 9.18 | 1.01 | 0.32 | NT |
| 8 | 80.30 | 5.77 | 3.89 | NT |
| 9 | NT | NT | 9.28 | NT |
| 10 | NT | 11.17 | 3.92 | NT |
| 11 | NT | 33.32 | 30.67 | NT |
| 12 | 351.90 | NT | 12.17 | NT |
| 13 | NT | 3.62 | 1.40 | NT |
| 14 | 44.19 | 5.56 | 2.18 | NT |
| 15 | 20.06 | NT | 3.06 | NT |
| 16 | 50.55 | 4.58 | 2.53 | NT |
| 17 | 18.59 | 7.47 | 2.17 | NT |
| 18 | 13.91 | 3.00 | 0.59 | 13.84 |
| 19 | 23.22 | 1.65 | 0.62 | NT |
| 20 | 19.24 | 3.18 | 1.64 | NT |
| 21 | NT | NT | 13.91 | NT |
| 22 | NT | NT | 33.73 | NT |
| 23 | NT | 85.15 | 47.93 | NT |
| 24 | NT | NT | 37.07 | NT |
| 25 | NT | 3.08 | 7.58 | NT |
| 26 | NT | NT | 8.31 | NT |
| 27 | NT | 10.07 | 4.54 | NT |
| 28 | 35.16 | 4.10 | 1.75 | NT |
| 29 | 23.73 | 1.96 | 0.96 | NT |
| 30 | 50.84 | 3.39 | 0.56 | NT |
| 31 | NT | 8.92 | 8.37 | NT |
| 32 | 24.03 | 3.15 | 1.09 | NT |
| 33 | 69.50 | NT | 3.29 | NT |
| 34 | NT | 17.88 | 4.44 | NT |
| 35 | NT | NT | 9.55 | NT |
| 36 | NT | NT | 18.72 | NT |
| 37 | NT | NT | 15.66 | NT |
| 38 | NT | NT | 15.20 | NT |
| 39 | NT | NT | 46.34 | NT |
| 40 | NT | NT | 21.80 | NT |
| 41 | NT | NT | 39.78 | NT |
| 42 | 27.03 | 5.34 | 1.12 | NT |
| 43 | NT | NT | 0.90 | NT |
| 44 | NT | 10.55 | 0.96 | NT |
| 45 | 93.90 | NT | 3.56 | NT |
| 46 | NT | NT | 5.34 | NT |
| 47 | NT | 11.64 | 2.51 | NT |
| 48 | NT | NT | 10.62 | NT |
| 49 | 16.29 | 5.68 | 4.49 | NT |
| 50 | 15.69 | 2.74 | 0.72 | NT |
| 51 | 1.08 | 1.01 | 0.36 | 0.20 |
| 52 | 2.60 | 6.67 | 0.96 | NT |
| 53 | 47.84 | 3.82 | 0.58 | NT |
| 54 | 24.66 | 6.05 | 0.93 | NT |
| 55 | 57.00 | 8.87 | 2.64 | NT |
| 56 | NT | 9.20 | 2.47 | NT |
| 57 | NT | NT | 3.88 | NT |
| 58 | 102.00 | NT | 10.87 | NT |
| 59 | NT | NT | 10.23 | NT |
| 60 | 278.30 | NT | 8.39 | NT |
| 61 | NT | NT | 3.68 | NT |
| 62 | 17.84 | 3.36 | 0.65 | NT |
| 63 | NT | NT | 3.96 | NT |
| 64 | NT | NT | 3.23 | NT |
| 65 | NT | NT | 3.14 | NT |
| 66 | NT | NT | 15.79 | NT |
| 67 | NT | NT | 5.61 | NT |
| 68 | NT | NT | 5.46 | NT |
| 69 | NT | NT | 14.45 | NT |
| 70 | NT | NT | 36.17 | NT |
| 71 | NT | NT | 52.81 | NT |
| 72 | NT | NT | 4.90 | NT |
| 73 | NT | NT | 9.19 | NT |
| 74 | NT | NT | 12.35 | NT |
| 75 | NT | NT | 6.42 | NT |
| 76 | 23.00 | 2.24 | 0.29 | NT |
| 77 | 15.58 | 0.94 | 0.39 | NT |
| 78 | 88.86 | 7.73 | 4.24 | NT |
| 79 | 22.91 | 1.14 | 0.21 | NT |
| 80 | 37.14 | 4.78 | 0.34 | NT |
| 81 | 5.31 | 3.50 | 0.58 | NT |
| 82 | 26.96 | 1.53 | 0.43 | NT |
| 83 | 15.76 | 1.12 | 0.42 | NT |
| 84 | NT | 2.65 | 1.18 | NT |
| 85 | 13.42 | 0.58 | 0.20 | NT |
| 86 | 6.20 | 0.58 | 0.26 | 0.62 |
| 87 | 29.31 | 3.08 | 0.24 | 1.72 |
| 88 | NT | 3.29 | 1.30 | NT |
| 89 | NT | NT | 4.07 | NT |
| 90 | NT | NT | 2.55 | NT |
| 91 | 129.80 | 6.43 | 0.47 | NT |
| 92 | NT | 15.99 | 2.01 | NT |
| 93 | NT | NT | 14.08 | NT |
| 94 | 27.18 | 1.86 | 0.10 | NT |
| 95 | NT | 2.64 | 0.66 | NT |
| 96 | 37.43 | 2.96 | 0.50 | NT |
| 97 | 55.99 | 3.12 | 0.30 | NT |
| 98 | NT | 4.53 | 1.23 | NT |
| 99 | 121.60 | 1.80 | 2.89 | NT |
| 100 | NT | NT | 3.16 | NT |
| 101 | NT | NT | 15.44 | NT |
| 102 | NT | NT | 3.73 | NT |
| 103 | NT | NT | 6.85 | NT |
| 104 | NT | NT | 16.42 | NT |
| 105 | 42.43 | 2.75 | 2.46 | NT |
| 106 | 60.26 | 3.61 | 1.24 | NT |
| 107 | NT | NT | 4.20 | NT |
| 108 | 57.29 | 2.07 | 1.52 | NT |
| 109 | NT | NT | 53.19 | NT |
| 110 | NT | NT | 7.07 | NT |
| 111 | NT | 40.32 | 4.39 | NT |
| 112 | 2.93 | 4.28 | 1.10 | NT |
| 113 | NT | NT | 7.69 | NT |
| 114 | NT | NT | 5.41 | NT |
| 115 | NT | NT | 6.92 | NT |
| 116 | NT | 8.53 | 1.76 | NT |
| 117 | NT | NT | 7.78 | NT |
| 118 | NT | NT | 9.89 | NT |
| 119 | NT | NT | 17.36 | NT |
| 120 | NT | NT | 7.02 | NT |
| 121 | NT | NT | 19.21 | NT |
| 122 | NT | NT | 25.01 | NT |
| 123 | NT | NT | 18.53 | NT |
| 124 | NT | NT | 4.85 | NT |
| 125 | NT | 8.60 | 1.28 | NT |
| 126 | NT | 5.80 | 2.67 | NT |
| 127 | 15.33 | 2.53 | 1.24 | NT |
| 128 | NT | NT | 3.19 | NT |
| 129 | 43.06 | 9.21 | 1.44 | NT |
| 130 | 217.60 | 7.90 | 3.15 | NT |
| 131 | 4.34 | 0.83 | 0.27 | NT |
| 132 | 14.27 | 0.51 | 0.12 | NT |
| 133 | 22.76 | 0.47 | 0.19 | NT |
| 134 | NT | 1.19 | 0.82 | NT |
| 135 | 30.29 | 0.61 | 0.73 | NT |
| 136 | 17.82 | 0.57 | 0.16 | NT |
| 137 | 16.38 | 0.27 | 0.12 | 1.51 |
| 138 | 88.88 | 1.24 | 0.27 | NT |
| 139 | 32.44 | 0.70 | 0.45 | NT |
| 140 | 61.61 | 0.67 | 0.32 | NT |
| 141 | 7.69 | 0.43 | 0.13 | NT |
| 142 | 16.62 | 0.76 | 0.24 | NT |
| 143 | 54.95 | 3.20 | 0.30 | NT |
| 144 | 57.42 | 0.74 | 0.18 | NT |
| 145 | 20.32 | 2.08 | 0.32 | NT |
| 146 | 4.32 | 0.50 | 0.19 | NT |
| 147 | 12.37 | 0.97 | 0.31 | NT |
| 148 | 29.96 | 1.60 | 0.48 | NT |

TABLE 6-continued

Assay results of inhibitory activities of a part of compounds disclosed herein against JAK1, JAK2, JAK3 and TYK2 tyrosine kinases

| Example No. | JAK1 IC$_{50}$ (nM) | JAK2 IC$_{50}$ (nM) | JAK3 IC$_{50}$ (nM) | TYK2 IC$_{50}$ (nM) |
|---|---|---|---|---|
| 149 | 1.14 | 0.72 | 0.22 | NT |
| 150 | 3.22 | 0.42 | 0.41 | 0.58 |
| 151 | 2.77 | 0.61 | 0.42 | 0.89 |
| 152 | 10.03 | 0.58 | 0.52 | 0.62 |
| 153 | NT | 0.59 | 1.25 | NT |
| 154 | NT | NT | 4.08 | NT |
| 155 | NT | NT | 7.35 | NT |
| 156 | NT | NT | 2.88 | NT |
| 157 | 1.86 | 0.14 | 0.41 | NT |
| 158 | 0.52 | 0.03 | 0.20 | NT |
| 159 | 3.24 | 0.67 | 0.66 | NT |
| 160 | 18.01 | 0.95 | 0.56 | 0.82 |
| 161 | 6.00 | 0.30 | 0.24 | NT |
| 162 | 98.69 | 0.99 | 0.57 | NT |
| 163 | NT | 1.91 | 0.65 | NT |
| 164 | 13.11 | 0.81 | 0.35 | NT |
| 165 | NT | NT | 97.49 | NT |
| 166 | NT | 0.99 | 1.03 | NT |
| 167 | NT | 1.54 | 0.69 | NT |
| 168 | 4.66 | 0.79 | 0.27 | NT |
| 169 | 6.28 | 0.68 | 0.15 | NT |
| 170 | 18.49 | 0.99 | 0.16 | NT |
| 171 | NT | 1.66 | 1.36 | NT |
| 172 | 15.55 | 0.95 | 0.56 | NT |
| 173 | 3.52 | 0.56 | 0.28 | NT |
| 174 | 54.67 | 3.06 | 0.51 | NT |
| 175 | 45.02 | 1.35 | 0.39 | NT |
| 176 | 16.46 | 0.42 | 0.13 | NT |
| 177 | 31.05 | 0.85 | 0.13 | NT |
| 178 | NT | 0.78 | 1.12 | NT |
| 179 | NT | 0.77 | 0.81 | NT |
| 180 | NT | NT | 2.18 | NT |
| 181 | 9.49 | 2.40 | 4.40 | 33.41 |
| 182 | 26.77 | NT | 1.98 | NT |
| 183 | 78.97 | NT | 1.37 | NT |
| 184 | 137.00 | NT | 18.86 | NT |
| 185 | NT | NT | 66.35 | NT |
| 186 | 269.40 | NT | 44.22 | NT |
| 187 | NT | NT | 92.18 | NT |
| 188 | 0.99 | 0.18 | 1.29 | NT |
| 189 | 2.37 | 1.69 | 3.58 | NT |
| 190 | 1.17 | 0.56 | 2.54 | NT |
| 191 | 1.56 | NT | 0.68 | NT |
| 192 | 3.66 | 1.25 | 4.17 | 4.76 |
| 193 | 1.86 | 0.30 | 1.78 | 2.30 |
| 194 | 6.24 | NT | 4.31 | NT |
| 195 | 0.45 | NT | 3.99 | NT |
| 196 | 7.67 | NT | 1.36 | NT |
| 197 | 4.86 | 0.84 | 1.46 | 3.88 |
| 198 | 10.34 | 1.19 | 2.78 | 12.39 |
| 199 | 1.82 | 0.51 | 2.46 | 0.53 |
| 200 | 4.22 | 0.96 | 1.71 | NT |
| 201 | 2.92 | 0.58 | 1.67 | NT |
| 202 | 5.91 | 0.76 | 1.11 | NT |
| 203 | 4.79 | 0.80 | 4.07 | 2.63 |
| 204 | 6.07 | 0.73 | 2.68 | NT |
| 205 | 7.92 | 1.59 | 4.36 | NT |
| 206 | 26.14 | 3.26 | 9.47 | NT |
| 207 | 2.80 | 0.42 | 1.04 | 0.76 |
| 208 | 1.00 | NT | 0.52 | NT |
| 209 | 2.30 | NT | 0.77 | NT |
| 210 | 1.22 | NT | 1.11 | 0.92 |
| 211 | 1.27 | NT | 3.39 | 1.95 |
| 212 | 2.56 | NT | 0.59 | NT |
| 213 | 10.77 | 3.31 | 7.14 | NT |
| 214 | 0.45 | NT | 0.48 | 1.19 |
| 215 | 0.28 | NT | 0.58 | 1.08 |
| 216 | 1.26 | 0.97 | 18.33 | NT |
| 217 | 4.02 | 0.99 | 8.81 | 2.15 |
| 218 | 7.07 | NT | 4.28 | 7.42 |
| 219 | 34.86 | NT | 4.07 | 28.17 |
| 220 | 12.82 | 8.98 | 15.64 | 16.86 |
| 221 | 13.54 | 1.61 | 2.80 | 3.88 |
| 222 | NT | NT | 20.39 | NT |
| 223 | 18.42 | NT | 2.64 | 20.45 |
| 224 | 24.07 | 4.92 | 4.21 | NT |
| 225 | 1.64 | 1.27 | 3.75 | 2.34 |
| 226 | 3.23 | 2.09 | 1.95 | 9.02 |
| 227 | 3.32 | NT | 3.72 | 9.89 |

TABLE 7

Assay results of inhibitory activities of a part of compounds disclosed herein against JAK1, JAK2, JAK3, and TYK2 tyrosine kinases

| Examples No. | JAK1 IC$_{50}$ (nM) | JAK2 IC$_{50}$ (nM) | JAK3 IC$_{50}$ (nM) | TYK2 IC$_{50}$ (nM) |
|---|---|---|---|---|
| 228 | NT | 13.9 | 3.3 | 20.3 |
| 229 | NT | 2.8 | 27.2 | 24.3 |
| 230 | 28.1 | 1.7 | 4.2 | 26.3 |
| 231 | 50.1 | 2.5 | 3.0 | 59.3 |
| 232 | 34.4 | 2.0 | 3.6 | NT |
| 233 | 6.5 | 0.9 | 2.1 | NT |
| 234 | 31.0 | 1.2 | 2.3 | NT |
| 235 | 18.0 | 0.7 | 1.5 | NT |
| 236 | 7.6 | 2.6 | 33.5 | 22.8 |
| 237 | 8.6 | NT | 8.5 | NT |
| 238 | 11.5 | 3.6 | 50.2 | NT |
| 239 | 8.7 | 4.0 | 34.8 | NT |
| 240 | NT | NT | 158.2 | NT |
| 241 | 19.5 | 2.0 | 38.4 | NT |
| 242 | 8.0 | 1.5 | 15.5 | 20.1 |
| 243 | NT | NT | 61.1 | NT |
| 244 | 10.8 | 3.0 | 28.6 | NT |
| 245 | 40.8 | 16.9 | 0.0 | 200.6 |
| 246 | 345.3 | 42.5 | 6.1 | 965.3 |
| 247 | NT | NT | 155.7 | NT |
| 248 | NT | NT | 421.5 | NT |

Assay Example 2. Quantitative AlphaLISA Detection of Phosphorylation of STAT5 in HEL Cells by Compounds Disclosed Herein HEL cells were treated with Tofacitinib and compounds in section Si at different concentrations, stimulated with 100 ng/mL IL-4, and then quantitatively detected for pSTAT5 signal using AlphaLISA.

TABLE 8

| Assay reagents: | | |
|---|---|---|
| Name | Brand | Catalog Number |
| IL-4 | R&D | 204-IL-010 |
| Tofacitinib | Selleckchem | S5001 |
| pSTAT5(Tyr705) | PerkinElmer | ALSU-PST5-B500 |
| HEL | Cell Bank of the Chinese Academy of Sciences (Shanghai, China) | |

I. Dilution and Preparation of Related Solutions

1. Acceptor Mix: Prepared immediately before use. Reaction Buffer 1, Reaction Buffer 2, Activation Buffer, and Acceptor Beads were mixed at a ratio of 47:47:4:2 and placed on an ice box (to be used within 30 minutes)

Donor Mix: Prepared immediately before use. Dilution Buffer and Donor Beads were mixed at a ratio of 49:1 and placed on an ice box (operated in weak light, and to be used within 30 minutes).

2. Positive control lysate: Lyophilized powder+250 μL of water; it was aliquoted (10.5 μL per tube) and stored at −20° C. (to be used up within one month).

II. Experiment Procedure

1. HEL cells were collected and washed three times with PBS under centrifugation (1000 rpm, 4 min). The cells were seeded in a 96-well plate at 100,000 cells/well/45 μL DMEM (without phenol red). Two replicates were made at each concentration and cultured for 1 h;

2. 15 μL of Tofacitinib at different concentrations was added to each well, mixed well with a pipetter, and then cultured for 1 h;

3. 20 μL of 400 ng/mL TL-4 was added to each well, mixed well, and incubated for 15 min;

4. Subsequently, 20 μL of 5×Lysis buffer was added to each well, and mixed well on a smart mixer (350 rpm, 10 min); after lysing, the mixture was centrifuged at low speed, 800 rpm, for 1 min;

5. 10 μL of the above lysate was pipetted into a 384-well plate;

6. 5 μL of Acceptor Mix was added to each well; the mixture was sealed, wrapped with a tin foil to protect from light, mixed well for 1 to 2 min, and incubated at room temperature for 2 h (shaked at low speed on a smart mixer during incubation);

7. 5 μL of Donor Mix was added to each well; the mixture was sealed, wrapped with a tin foil, mixed well for 1 to 2 min, and incubated at room temperature for 2 h (operated in weak light, and shaked at low speed on a smart mixer during incubation);

8. The corresponding program was opened in a multi-functional plate reader Envision to read the plate readings;

9. Calculation of inhibition ratio and $IC_{50}$:

Inhibition ratio=[1−(experimental well reading value−negative control well reading value)/ (positive control well reading value−negative control well reading value)]*100%

The drug concentration and corresponding inhibition ratio were input into GraphPad Prism5 to calculate the corresponding $IC_{50}$ values.

Table 9 shows the results of a part of compounds disclosed herein for quantitative AlphaLISA detection of phosphorylation of STAT5 in HEL cells.

TABLE 9

The results of a part of compounds disclosed herein for quantitative detection of phosphorylation of STAT5 in HEL cells

| Example No. | Phosphorylation activity of STAT5 in HEL cells, $IC_{50}$ (nM) |
|---|---|
| 2 | 92.7 |
| 3 | 38.5 |
| 5 | 21.8 |
| 6 | 74.4 |
| 7 | 44.9 |
| 51 | 62.9 |
| 77 | 124.8 |
| 79 | 250.3 |
| 82 | 178.5 |
| 85 | 198.1 |
| 86 | 63.3 |
| 87 | 70.5 |
| 94 | 308.9 |
| 147 | 84.7 |
| 149 | 148.9 |
| 150 | 54.5 |
| 151 | 38.3 |
| 152 | 31.3 |

TABLE 9-continued

The results of a part of compounds disclosed herein for quantitative detection of phosphorylation of STAT5 in HEL cells

| Example No. | Phosphorylation activity of STAT5 in HEL cells, $IC_{50}$ (nM) |
|---|---|
| 157 | 33.2 |
| 158 | 189.9 |
| 159 | 144.2 |
| 160 | 33.8 |
| 170 | 142.2 |
| Tofacitinib | 145.7 |

Assay Example 3. Assay of Inhibitory Activities of Compounds Disclosed Herein on the Proliferation of Mouse Spleen Cells The particular experiment steps were as follows:

1) Dilution of compounds: using a 3-fold gradient dilution starting from the highest concentration of 5000 nM to give a total of 9 concentrations (the maximum final concentration of the drug used in this experiment was 5000 nM and the lowest final concentration was 0.76 nM).

2) A petri dish with a diameter of 6 cm was taken, in which a cell filter sieve with a hole diameter of 70 m was placed, and then 2 mL of HBSS solution was added to the sieve to infiltrate the bottom of the petri dish;

3) Adult Balb/c mice were euthanized with carbon dioxide, immersed in 75% alcohol for 1 minute, placed in a safety cabinet, and a small opening was made in the middle of the left ventral side of the mouse, so as to expose the abdominal wall for the spleen;

4) The spleen was removed, the surrounding adipose tissue of the spleen was removed, and then the spleen was placed on the cell filter sieve in the petri dish and cut appropriately;

5) The spleen was gently grounded with the flat part of the tip of a syringe piston to obtain a cell suspension;

6) The cell suspension was collected from the petri dish, and the collected cell suspension was slowly added to a 15 ml centrifuge tube containing 5 ml of Ficoll-Paque PLUS;

7) The mixture was centrifuged at 400 g for 30 minutes at room temperature;

8) After the centrifugation, the upper layer was slowly removed with a pipette, and then the middle layer, that is, the spleen cells, was slowly pipetted;

9) The collected spleen cell suspension was placed in another 15 ml centrifuge tube. To the tube was added 10 ml RPMI1640 complete medium, and centrifuged at 300 g at 4° C. for 4 minutes;

10) The supernatant was discarded. A complete medium was added to resuspend the cells, and then the cells were counted. The cell suspension was washed again according to the step 9);

11) The cells were transferred to a petri dish (containing 2.5 μg/mL concanavalin A) at a cell density of 2 million/mL to 5 million/mL and cultured overnight;

12) The next day, the cells were transferred to a 15 mL centrifuge tube and centrifuged at a speed of 300 g for 5 minutes;

13) The supernatant was discarded. 5 mL of RPMI 1640 complete culture medium was added, and pipetted uniformly. The cell suspension (10 μL) was taken out, mixed with 10 μL of trypan blue, and counted with a cell counter. Cell number and viability were recorded.

14) The cell suspension was seeded into a 96-well plate, and each well was seeded with 80 μl of the cell suspension with a density of 100,000 cells/well;

15) 20 μl of the corresponding 5×compound solution that was diluted with the culture medium as mentioned above was added to each well, and mixed well;

16) After 72 hours of incubation, 10 μL of CCK-8 reagent was added to each well, and incubated for 2 hours (the reaction time can be adjusted according to the color depth);

17) The OD value was read on a multifunctional plate reader at 450 nm.

18) Processing of data:

Cell survival ratio (%)=[(As−Ab)/(Ac−Ab)]*100%

As: OD value of experimental wells (cells-containing medium, CCK-8, compounds),

Ac: OD value of control wells (cells-containing medium, CCK-8),

Ab: OD value of blank wells (medium without cells and compounds, CCK-8),

Then, the values were input into Graphpad Prism5 software for curve fitting to calculate $IC_{50}$.

Table 10 and Table 11 show the assay results of inhibitory activities of the compounds disclosed herein on the proliferation of mouse spleen cells, wherein A means that $IC_{50}$ is less than or equal to 100 nM, B means that $IC_{50}$ is greater than 100 nM but less than or equal to 500 nM, C means that $IC_{50}$ is greater than 500 nM but less than or equal to 1000 nM, and D means that $IC_{50}$ is greater than 1000 nM.

TABLE 10

Assay results of inhibitory activities of the compounds disclosed herein on the proliferation of mouse spleen cells

| No. Example | $IC_{50}$ on Spleen Cell (nM) |
|---|---|
| 1 | B |
| 2 | A |
| 3 | A |
| 4 | B |
| 5 | A |
| 6 | A |
| 7 | A |
| 8 | D |
| 9 | C |
| 10 | D |
| 13 | B |
| 14 | B |
| 15 | B |
| 16 | B |
| 17 | B |
| 18 | B |
| 19 | A |
| 20 | B |
| 25 | D |
| 26 | D |
| 27 | B |
| 28 | B |
| 29 | A |
| 30 | A |
| 31 | D |
| 32 | B |
| 33 | B |
| 34 | C |
| 35 | D |
| 42 | B |
| 43 | B |
| 44 | B |
| 45 | C |
| 46 | D |
| 47 | D |
| 48 | D |
| 49 | B |
| 50 | A |
| 51 | A |
| 52 | A |
| 53 | A |
| 54 | B |
| 55 | B |
| 56 | D |
| 57 | A |
| 58 | B |
| 59 | A |
| 60 | C |
| 61 | B |
| 62 | B |
| 63 | B |
| 64 | B |
| 65 | A |
| 67 | B |
| 68 | C |
| 72 | B |
| 73 | B |
| 75 | B |
| 76 | A |
| 77 | A |
| 78 | C |
| 79 | A |
| 80 | A |
| 81 | A |
| 82 | A |
| 83 | A |
| 84 | B |
| 85 | A |
| 86 | A |
| 87 | A |
| 88 | A |
| 89 | A |
| 90 | C |
| 91 | B |
| 92 | C |
| 94 | A |
| 95 | A |
| 96 | A |
| 97 | B |
| 98 | B |
| 99 | B |
| 100 | C |
| 102 | C |
| 103 | D |
| 105 | B |
| 106 | B |
| 107 | B |
| 108 | B |
| 110 | D |
| 111 | D |
| 112 | B |
| 113 | D |
| 114 | B |
| 115 | D |
| 116 | B |
| 117 | B |
| 118 | D |
| 120 | D |
| 124 | C |
| 125 | B |
| 126 | B |
| 127 | A |
| 128 | B |
| 129 | B |
| 130 | C |
| 131 | B |
| 132 | A |
| 133 | A |
| 134 | A |
| 135 | A |
| 136 | A |

TABLE 10-continued

Assay results of inhibitory activities of the compounds disclosed herein on the proliferation of mouse spleen cells

| No. Example | IC$_{50}$ on Spleen Cell (nM) |
|---|---|
| 137 | A |
| 138 | A |
| 139 | A |
| 140 | A |
| 141 | B |
| 142 | A |
| 143 | B |
| 144 | A |
| 145 | B |
| 146 | B |
| 147 | A |
| 148 | A |
| 149 | B |
| 150 | A |
| 151 | A |
| 152 | A |
| 153 | A |
| 154 | A |
| 155 | B |
| 156 | B |
| 157 | A |
| 158 | B |
| 159 | A |
| 160 | B |
| 161 | B |
| 162 | B |
| 163 | A |
| 164 | B |
| 166 | A |
| 167 | C |
| 168 | B |
| 169 | B |
| 170 | A |
| 171 | A |
| 172 | B |
| 173 | B |
| 174 | B |
| 175 | B |
| 176 | B |
| 177 | B |
| 178 | A |
| 179 | B |
| 180 | B |
| 181 | A |
| 188 | A |
| 189 | A |
| 190 | A |
| 191 | A |
| 193 | A |
| 194 | B |
| 195 | A |
| 196 | B |
| 197 | A |
| 198 | A |
| 199 | A |
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | B |
| 212 | A |
| 213 | A |
| 214 | A |
| 215 | A |
| 217 | A |
| 218 | B |
| 219 | A |
| 221 | B |
| 223 | B |
| 224 | D |
| 225 | A |
| 227 | B |

TABLE 11

Assay results of inhibitory activities of a part of compounds disclosed herein on the proliferation of mouse spleen cells

| Example No. | IC$_{50}$ on Spleen Cell (nM) |
|---|---|
| 230 | <200 |
| 231 | <200 |
| 232 | <200 |
| 233 | <200 |
| 234 | <200 |
| 235 | <200 |

Use, Formulation, and Administration

Medical Uses and Indications

The biological data provided by the present disclosure show that the compounds disclosed herein are useful for the treatment or prevention of diseases caused by abnormalities of tyrosine kinases (JAK1, JAK2, JAK3, or TYK2). More than one fifth of the compounds disclosed herein have been proven to be able to strongly inhibit the activity of the JAK tyrosine kinase, and the JAK kinase family is closely related to the occurrence and metastasis of autoimmune diseases and cancers. Therefore, the compounds disclosed herein are useful for the treatment of autoimmune diseases, including but not limited to: psoriasis, vitiligo, dermatitis, alopecia areata, rheumatoid arthritis, colitis, multiple sclerosis, systemic lupus erythematosus, and Crohn's disease. The compounds disclosed herein are also useful in the treatment of cancer, including primary and metastatic cancers, including solid tumors. Such cancers include, but are not limited to: non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myelocytic leukemia, non-Hodgkin's lymphoma, nasopharyngeal cancer, esophageal cancer, brain tumor, B-cell and T-cell lymphoma, lymphoma, multiple myeloma, biliary sarcoma, and bile duct cancer. The compounds disclosed herein can also treat cancers that are resistant to one or more other treatments. In addition to autoimmune diseases and cancers, the compounds disclosed herein may also be used in other diseases related to JAK1 kinase and/or JAK2 kinase and/or JAK3 kinase, including but not limited to fundus oculi disease, pulmonary fibrosis, liver fibrosis, etc. The compounds disclosed herein can be used as monotherapy or combination therapy, and can be used in combination with multiple compounds disclosed herein or in combination with drugs other than the compounds disclosed herein.

Administration Methods

The administration method disclosed herein includes determining the therapeutically effective amount for a subject in need of a compound disclosed herein. The "therapeutically effective amount" varies depending on the stage, progression or severity of the disease. The daily dose of the compounds and compositions disclosed herein will depend on a variety of factors of patients, including the condition being treated, the severity of the condition, the efficacy of the specific compound used, the particular composition, age, weight, general health, gender and diet, route and timing of administration, metabolism and/or excretion rate of the compound, duration of treatment, etc. In addition, the required dose of the compound disclosed herein can be administered to humans and other animals after being formulated with a pharmaceutically acceptable carrier. Modes of administration include oral, rectal, parenteral, intracranial, intravaginal, intraperitoneal, topical (such as through transdermal patches, powders, ointments, or drops), sublingual, transbuccal, nasal spray, or the like. The effective dose of the compound disclosed herein is usually measured in terms of the amount administered per kg of the patient's body weight, preferably 0.1 to 125 mg/kg body weight, and generally 0.01 to 500 mg/kg body weight. The administration can be one or more times, daily, weekly, every other day or every multiple days, or an intermittent schedule. For example, the compound can be administered daily, weekly (e.g., every Monday), indefinitely, or for several weeks (e.g. 4-10 weeks). The effective dose of the compound disclosed herein will vary depending on the compound used, the mode of administration, the severity of the disease, the condition being treated, and various physical factors of the patient. In most cases, a satisfactory therapeutic effect can be achieved when the daily dose of the preferred compound disclosed herein is about 0.01 to 500 mg/kg. A preferred dose is 0.1 to 125 mg/kg, and a more preferred dose is 1 to 25 mg/kg. The parenteral dose is usually at about 10% to 20% of an oral dose level. When the compound disclosed herein is used as part of a combination therapy regimen, each component of a composition will be administered during a desired treatment period. Either as separate dosage units or as a single dosage form containing two components, the components in the composition may be administered simultaneously during a treatment period, or at different times during a treatment period, or one component can be applied as a pre-treatment of another component.

About Compounds

The compounds disclosed herein may be used for the treatment in free form or, where appropriate, in the form of a pharmaceutically acceptable salt or other derivative. As used herein, the term "pharmaceutically acceptable salt" means organic and inorganic salts of compounds disclosed herein, which are suitable for humans and lower animals, without excessive toxicity, irritation, allergic reactions, etc., and have a reasonable benefit/risk ratio. Amine salts, carboxylates, phosphonates, and other types of pharmaceutically acceptable salts of compounds are well known in the art. Such salts can be formed by reacting the compounds isolated and purified in the present disclosure with a suitable free base or acid.

Salts formed from pharmaceutically non-toxic acids include, but are not limited to, amino salts formed with inorganic acids such as hydrochloric acid, hydrobromic acid, phosphoric acid, sulfuric acid, or perchloric acid, or organic acids such as acetic acid, oxalic acid, maleic acid, tartaric acid, citric acid, succinic acid, or malonic acid, or the salts obtained by using methods well known in the art, such as ion exchange methods. Other pharmaceutically acceptable salts include adipate, alginate, ascorbate, aspartate, benzenesulfonate, benzoate, bisulfate, borate, butyrate, camphorate, camphorsulfonate, citrate, cyclopentane, digluconate, dodecylsulfate, ethanesulfonate, formate, fumarate, glucoheptonate, glycerophosphate, gluconate, hemisulfate, heptanoate, hexanoate, hydriodate, 2-isethionate, lactobionate, lactate, laurate, laurylsulfate, malate, maleate, malonate, methanesulfonate, 2-naphthalenesulfonate, nicotinate, nitrate, oleate, oxalate, palmitate, pamoate, pectinate, persulfate, 3-phenylperpropionate, phosphate, picrate, pivalate, propionate, stearate, succinate, sulfate, tartrate, thiocyanate, p-toluenesulfonate, undecanoate, valerate, etc. Representative alkali or alkaline earth metal salts include sodium, lithium, potassium, calcium, magnesium, etc. Other pharmaceutically acceptable salts include appropriate non-toxic ammonium, quaternary ammonium, and amine cations formed using ions such as halide, hydroxide, carboxylate, sulfate, phosphate, nitrate, lower alkyl sulfonate, and aryl sulfonate.

In addition, the term "prodrug" as used herein means a compound that can be converted into a compound represented by formula (I) disclosed herein in vivo. This conversion is the conversion of a prodrug into a parent compound by hydrolysis in the blood or by enzyme action in the blood or tissue.

Combination

The composition disclosed herein is composed of any one of the compounds (or prodrugs, or pharmaceutically acceptable salts, or other pharmaceutically acceptable derivatives thereof) described herein, and one or more pharmaceutically acceptable carriers or excipients. These compositions may optionally further comprise one or more additional therapeutic agents. The compounds disclosed herein can be co-administered to a desired patient with one or more other treatment regimens (e.g., Tofacitinib or other kinase inhibitors, interferons, bone marrow transplants, farnesyl transferase inhibitors, bisphosphonates, thalidomide administration combinations, cancer vaccines, hormone therapies, antibodies, radiation, etc.). The pharmaceutical composition of the compound may be another one or more anti-inflammatory or anti-cancer agents.

As described herein, the composition disclosed herein comprises a compound disclosed herein and a pharmaceutically acceptable carrier, including any and all solvents, diluents or other carriers, dispersion or suspension aids, surfactants, isotonic agents, thickeners or emulsifiers, preservatives, solid binders, lubricants, etc. to suit a particular dosage form required. Examples of some pharmaceutically acceptable carrier materials include, but are not limited to, sugars such as lactose, glucose and sucrose; starches such as corn starch and potato starch; cellulose and its derivatives such as sodium carboxymethyl cellulose, ethyl cellulose and cellulose acetate; tragacanth powder; malt; gelatin; talc powder; excipients such as cocoa butter and suppository wax; oils such as peanut oil, cottonseed oil, safflower oil, sesame oil, olive oil, corn oil and soybean oil; ethylene glycols, such as propylene glycol; esters such as ethyl oleate and ethyl laurate, agar; buffers such as magnesium hydroxide and aluminum hydroxide; alginic acid; pyrogen-free water; isotonic saline; Ringer's solution; ethanol, and phosphate buffered solutions, and other non-toxic compatible lubricants such as sodium lauryl sulfate and magnesium stearate, as well as colorants, release agents, coating agents, sweetening, flavoring and perfuming agents, preservatives and antioxidants can also be present in the composition.

Formulation

The present disclosure also encompasses a class of compositions in which the active compound disclosed herein is used in combination with one or more pharmaceutically acceptable carriers and/or diluents and/or adjuvants (collectively referred to herein as "carrier" materials), and, if necessary, other active ingredients. The active compounds disclosed herein may be administered by any suitable route, preferably in the form of a pharmaceutical composition suitable for such route of administration, in an effective dose required for the intended treatment. The compounds and compositions disclosed herein can be administered in the form of oral, mucosal, topical, rectal, transpulmonary such as by inhalation spray, or parenterally, including intravascular, intravenous, intraperitoneal, subcutaneous, intramuscular, intrasternal and infusion techniques. Its administration is in the form of dosage unit formulations and contains pharmaceutically acceptable carriers, adjuvants, and excipients. For oral administration, the pharmaceutical composition can be in the following forms, for example, tablets, capsules, suspensions or liquids. Examples of such dosage units are tablets or capsules. For example, they may contain an active ingredient in an amount of 1 to 2000 mg, preferably 1 to 500 mg, more commonly 5 to 200 mg. The appropriate daily dose for a person or other mammal may vary depending on the patient and other factors, but can be determined again using conventional methods. As mentioned previously, the amount of compound in the administration and dosage regimen of the compounds and/or compositions disclosed herein depends on a variety of factors, including the subject's age, weight, gender and medical conditions, the type of disease, the severity of the disease, the route and frequency of administration, and the specific compound used. Therefore, the dosage regimen can vary widely, but can be determined using standard methods. Atypical daily dose is 0.01 to 500 mg/kg body weight, preferably 0.1 to 125 mg/kg body weight, and more preferably 1 to 25 mg/kg body weight.

The active compound disclosed herein usually forms an administration route with one or more adjuvants, excipients or carriers. If administered orally, the compound can be combined with lactose, sucrose, starch powder, cellulose alkanoate, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and then compressed into tablets or made into capsules for convenient administration. Such capsules or tablets may contain a controlled release preparation, which can be provided by dispersing the active compound in hydroxypropyl methylcellulose. Formulations suitable for topical administration include liquid or semi-liquid formulations (e.g., tinctures, lotions, ointments, creams, or pastes) suitable for penetration through the skin, and drops suitable for administration to the eyes, ears, or nose. A suitable topical dose of the compound disclosed herein is 0.1 to 150 mg, one to four times a day, preferably once to twice a day. For topical administration, when using an ointment, an active ingredient can be used with any paraffin or water-miscible ointment as a base. Alternatively, an active ingredient can be formulated as a cream in a water-in-oil emulsion base. If desired, the aqueous phase of the cream base can include, for example, at least 30% by weight of a polyol such as propylene glycol, butan-1,3-diol, mannitol, sorbitol, glycerol, polyethylene glycol, and their mixtures. Topical formulations may include compounds that enhance absorption or penetration of the active ingredient through the skin or other affected areas. Examples of such dermal penetration enhancers include dimethyl sulfoxide and related analogs. The compound can also be administered via a transdermal device. Preferably, a transdermal administration will be accomplished using a patch containing a reservoir and a porous membrane or a solid matrix. The oily phase of the emulsions disclosed herein may be composed of known ingredients in a known manner, comprising a mixture of at least one emulsifier with a fat or oil or a mixture of both fats and oils. Preferably, a hydrophilic emulsifier can be used simultaneously in combination with a lipophilic emulsifier as a stabilizer, and it is also preferred that it can also be used in combination with oils and fats. Emulsifiers and emulsion stabilizers suitable for use in the formulations disclosed herein include Tween 60, Span 80, cetylstearyl alcohol, myristyl alcohol, glyceryl monostearate, sodium lauryl sulfate, single glyceryl distearate or its mixture with emulsifying wax, or other materials known in the art. Creams should preferably be non-greasy, non-staining and washable products, and have a suitable consistency to avoid leakage from tubes or other containers. Linear or branched, mono- or di-alkyl esters such as diisoadipate, isohexadecyl stearate, propylene glycol diesters of coconut fatty acids, isopropyl myristate, decyl oleate, isopropyl palmitate, butyl stearate, 2-ethylhexyl palmitate or mixed branched esters can also be used. Alternatively, high melting point lipids such as white soft paraffin and/or liquid paraffin or other mineral oils can be used. Formulations suitable for topical administration to eyes also include eye drops in which an active ingredient is dissolved or suspended in a suitable carrier, especially an aqueous solvent for the active ingredient. The weight ratio of an active ingredient in these preparations is preferably 0.5% to 20%, more preferably 0.5 to 10%, and the most preferably about 1.5%. Formulations for parenteral administration can be in the form of aqueous or non-aqueous isotonic sterile injection solutions or suspensions. These solutions and suspensions can be prepared from one or more sterile powders or granules by using the formulations mentioned herein for oral administration or carriers or diluents using other suitable dispersing or wetting agents and suspending agents. The compounds can be dissolved in water, polyethylene glycol, propylene glycol, ethanol, corn oil, cottonseed oil, peanut oil, sesame oil, benzyl alcohol, sodium chloride, tragacanth, and/or various buffers. Other adjuvants and modes of administration are well known in the pharmaceutical arts.

The active ingredient may also be administered by injection, a composition with a suitable carrier including saline, glucose, or water, or solubilized with cyclodextrin (Captisol), a co-solvent (i.e., propylene glycol), or a micelle (i.e., Tween 80). The formulation can also be a sterile injectable solution or suspension in a non-toxic parenterally acceptable diluent or solvent, such as 1,3-butanediol. The solvents that can be used are water, Ringer's solution and isotonic sodium chloride solution. In addition, a sterile, non-volatile oil is often used as a solvent or a suspension media. For this purpose, any mild fixed oil can be used, including synthetic mono- or di-glycerides.

For pulmonary administration, the pharmaceutical composition can be administered in the form of an aerosol or with an inhaler, including dry powder aerosol. Suppositories for rectal administration of the drug can be prepared by mixing the drug with a suitable nonirritating excipient such as cocoa butter and polyethylene glycols that are solid at room temperatures but liquid at the rectal temperature and will therefore melt in the rectum and release the drug. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings.

Such compositions may also comprise adjuvants, such as wetting, sweetening, flavoring, and perfuming agents.

The pharmaceutical composition disclosed herein comprises a compound of formula (I) described herein or a pharmaceutically acceptable salt thereof, a kinase inhibitor (small molecule, polypeptide, antibody, etc.), an immunosuppressive agent, an anticancer drug, an antiviral agent, an anti-inflammatory agent, an antifungal, an antibiotic, or an additional active agent of an anti-hyperplasia compound; and any pharmaceutically acceptable carrier, adjuvant, or excipient. Alternatively, the composition disclosed herein comprises a compound of formula (I) described herein or a pharmaceutically acceptable salt thereof, and a pharmaceutically acceptable carrier, adjuvant or excipient. Such composition may optionally include one or more additional therapeutic agents, including, for example, kinase inhibitors (small molecules, peptides, antibodies, etc.), immunosuppressants, anticancer agents, antivirals, anti-inflammatory agents, antifungals, antibiotics or anti-hyperplasia compounds.

The term "pharmaceutically-acceptable carrier or adjuvant" refers to a carrier or adjuvant that may be administered to a patient, together with a compound disclosed herein, and does not destroy the pharmacological activity thereof and is nontoxic when administered in doses sufficient to deliver a therapeutic amount of the compound. Pharmaceutically acceptable carriers, adjuvants and excipients that may be used in the pharmaceutical compositions disclosed herein include, but are not limited to, ion exchangers, alumina, aluminum stearate, lecithin, self-emulsifying drug delivery systems (SEDDS) such as d-atocopHerol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkyl, including 2 and 3-hydroxypropyl-cyclodextrin, or other dissolved derivatives can also be advantageously used to enhance delivery of compounds of the formulae described herein. The pharmaceutical composition can be orally administered in any acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase with emulsifying and/or suspending agents. If desired, certain sweetening and/or flavoring and/or coloring agents may be added. The pharmaceutical composition can include the use of liposomes or microencapsulation techniques, different examples of which can be found in literatures. The pharmaceutical composition can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents, examples of which are also well known in the prior art.

Drug Combination

The compounds disclosed herein can be used alone or in combination with one or more other compounds disclosed herein or in combination with one or more other agents. When administered in combination, the therapeutic agents can be formulated for simultaneous administration or sequential administration at different times, or the therapeutic agents can be administered as a single composition. The so-called "combination therapy" refers to the use of a compound disclosed herein together with another agent. The mode of administration is simultaneous co-administration of each agent or sequential administration of each agent. In either case, the purpose is to achieve the best effect of the drug. Co-administration includes simultaneous delivery of dosage forms and separate delivery of a single dosage form of each compound. Therefore, the administration of the compounds disclosed herein can be used concurrently with other known therapies in the art, for example, the use of radiation therapy or additional therapies such as cytostatic agents, cytotoxic agents, or other anticancer agents in cancer treatment to improve symptoms of cancers. The present disclosure is not limited to the order of administration; the compounds disclosed herein may be administered before, concurrently with, or after other anticancer or cytotoxic agents.

The above are the preferred embodiments disclosed herein. It should be noted that for those of ordinary skill in the art, without departing from the principles described in the present disclosure, several improvements and modifications may also be made to the embodiments disclosed herein. These improvements and modifications should also be regarded as the protection scope disclosed herein.

What is claimed is:

1. A compound, or a stereoisomer, a tautomer, a solvate or a pharmaceutically acceptable salt thereof, wherein the compound has a structural formula (I):

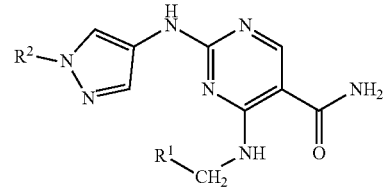

Formula (I)

wherein, $R^1$ is

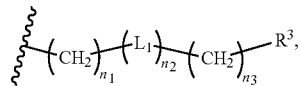

$n_1$ is 0 to 2, $n_2$ is 0 to 1, and $n_3$ is 0 to 5, $L_1$ is

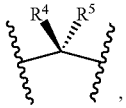, $R^4$ and/or $R^5$ are H, or linear $C_1$-$C_3$ alkyl;

$R^2$ is

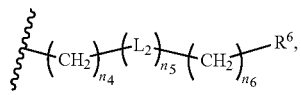, $n_4$ is 0 to 3, $n_5$ is 0 to 1, and $n_6$ is 0 to 5, $L_2$ is

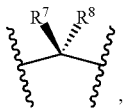, $R^7$ and/or $R^8$ are H, or linear $C_1$-$C_3$ alkyl;

$R^3$ is:
a) H, hydroxyl, or cyano,
b) linear or branched $C_1$-$C_5$ alkyl,
c) $C_3$-$C_7$ cycloalkyl,
d) linear or branched $C_1$-$C_5$ alkoxy,
e) linear or branched $C_1$-$C_5$ alkylthio,
f) a 5- to 7-membered heterocyclic ring,
g) substituted or unsubstituted 5-membered heteroaryl,
h) substituted or unsubstituted 6-membered aryl or heteroaryl,
i) a ring containing 0 to 3 heteroatoms formed by a 6-membered aryl or heteroaryl ring fused with a 5- or 6-membered ring, or a ring containing 1 to 3 heteroatoms formed by a 5-membered heteroaryl ring fused with a 5- or 6-membered ring;

$R^6$ is:
a) H, or hydroxyl,
b) —NR'R", wherein R' and R" are H or $C_1$-$C_3$ alkyl,
c) linear or branched $C_1$-$C_5$ alkyl,
d) $C_3$-$C_8$ cycloalkyl,
e) linear or branched $C_1$-$C_5$ alkoxy,
f) linear or branched $C_1$-$C_5$ alkylthio, or
g) heterocyclyl.

2. The compound, or the stereoisomer, the tautomer, the solvate or the pharmaceutically acceptable salt thereof according to claim 1, wherein the 5- to 7-membered heterocyclic ring contains 1 to 2 heteroatoms selected from O and/or N and/or S, wherein when the heteroatom is N, N is connected to H, $C_1$-$C_4$ alkyl, or $C_1$-$C_3$ acyl; and when the heteroatom is S, S is connected to 0 to 2 oxygen atoms.

3. The compound, or the stereoisomer, the tautomer, the solvate or the pharmaceutically acceptable salt thereof according to claim 1, wherein the substituted 5-membered heteroaryl group has a structural formula of

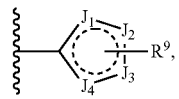, wherein:
$J_1$ and/or $J_2$ and/or $J_3$ and/or $J_4$ are C, N, S, or O,
$R^9$ is linear or branched $C_1$-$C_3$ alkyl.

4. The compound, or the stereoisomer, the tautomer, the solvate or the pharmaceutically acceptable salt thereof according to claim 1, wherein the substituted or unsubstituted 5-membered heteroaryl has a structural formula of

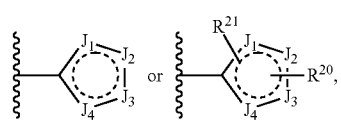, wherein:
$J_1$, $J_2$, $J_3$, and $J_4$ are each independently C, N, S, or O,
$R^{20}$ and $R^{21}$ are each independently linear or branched $C_1$-$C_3$ alkyl.

5. The compound, or the stereoisomer, the tautomer, the solvate or the pharmaceutically acceptable salt thereof according to claim 1, wherein the substituted or unsubstituted 6-membered aryl or heteroaryl has a structural formula of

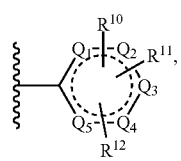, wherein:
$Q_1$, $Q_2$, $Q_3$, $Q_4$, and $Q_5$ are N or C;
$R^{10}$ and/or $R^{11}$ and/or $R^{12}$ are:
a) —F, —Cl, —Br, —$CF_3$, —$OCF_3$, or cyano,
b) —NR'R", wherein R' and R" are H or $C_1$-$C_3$ alkyl,
c) $C_1$-$C_3$ alkyl, $C_2$-$C_5$ alkynyl, or $C_3$-$C_5$ cycloalkyl,
d) $SO_2R^{13}$, wherein $R^{13}$ is H, or $C_1$-$C_3$ alkyl,
e)

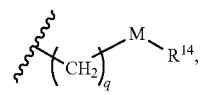, wherein q is 0 to 2, M is O or S, $R^{14}$ is H, or linear or branched $C_1$-$C_5$ alkyl,
f)

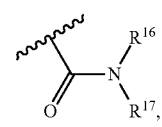, wherein $R^{15}$ and $R^{16}$ are linear alkyl.

6. The compound, or the stereoisomer, the tautomer, the solvate or the pharmaceutically acceptable salt thereof according to claim 1, wherein the substituted or unsubstituted 6-membered aryl or heteroaryl has a formula of

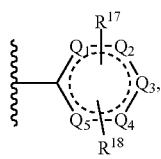

wherein:

$Q_1$, $Q_2$, $Q_3$, $Q_4$, and $Q_5$ are N or C;

$R^{17}$ and $R^{18}$ are each independently:

a) —H, b) —F, —Cl, —Br, —CF$_3$, —OCF$_3$, or cyano, c) —NR'R", wherein R' and R" are H, or $C_1$-$C_3$ alkyl, d) $C_1$-$C_3$ alkyl, $C_2$-$C_5$ alkynyl, $C_2$-$C_5$ alkenyl, or $C_3$-$C_5$ cycloalkyl, e) SO$_2$R$^{13}$, wherein R$^{13}$ is H, or $C_1$-$C_3$ alkyl, f)

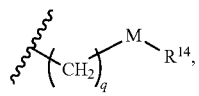

wherein q is 0 to 2, M is O or S, $R^{14}$ is H, or linear or branched $C_1$-$C_5$ alkyl, g)

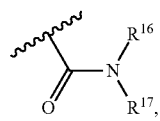

wherein $R^{15}$ and $R^{16}$ are linear $C_1$-$C_3$ alkyl, h) —(CH$_2$)$_t$—R$^{19}$, wherein t is 1 to 2, and R$^{19}$ is $C_3$-$C_5$ cycloalkyl.

7. The compound, or the stereoisomer, the tautomer, the solvate or the pharmaceutically acceptable salt thereof according to claim 1, wherein the heterocyclyl is a 5- or 6-membered heterocyclyl containing oxygen and/or nitrogen.

8. A compound, or a stereoisomer, a tautomer, a solvate or a pharmaceutically acceptable salt thereof, wherein the compound has a structural formula (I):

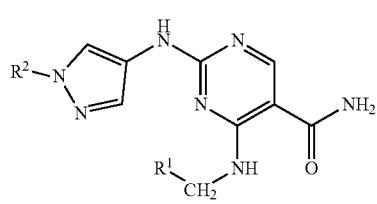

Formula (I)

wherein, $R^1$ is

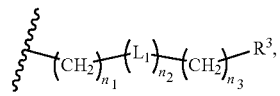

$n_1$ is 0 to 2, $n_2$ is 0 to 1, and $n_3$ is 0 to 5, $L_1$ is

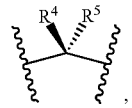

$R^4$ and/or $R^5$ are H, or linear $C_1$-$C_3$ alkyl;

$R^2$ is

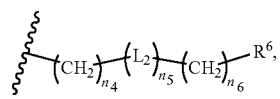

$n_4$ is 0 to 3, $n_5$ is 0 to 1, and $n_6$ is 0 to 5, $L_2$ is

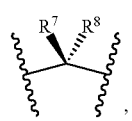

$R^7$ and/or $R^8$ are H, or linear $C_1$-$C_3$ alkyl;

$R^3$ is $C_1$-$C_3$ alkoxy substituted by $R^{22}$ or $C_1$-$C_3$ alkylthio substituted by $R^{22}$; wherein $R^{22}$ is hydroxyl, $C_1$-$C_3$ alkoxy, $C_1$-$C_3$ alkylthio, —NR'R", $C_1$-$C_3$ alkoxy substituted by hydroxyl, $C_1$-$C_3$ alkoxy substituted by amino, $C_1$-$C_3$ alkylthio substituted by hydroxyl, or $C_1$-$C_3$ alkylthio substituted by amino, wherein R' and R" is H or $C_1$-$C_3$ alkyl;

$R^6$ is:

a) H, or hydroxyl, b) —NR'R", wherein R' and R" are H or $C_1$-$C_3$ alkyl, c) linear or branched $C_1$-$C_5$ alkyl, d) $C_3$-$C_8$ cycloalkyl, e) linear or branched $C_1$-$C_5$ alkoxy, f) linear or branched $C_1$-$C_5$ alkylthio, or g)

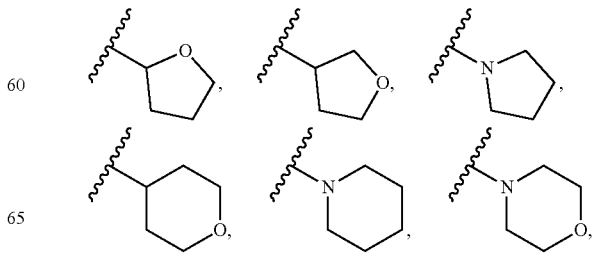

-continued

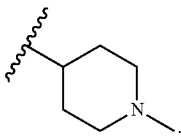

9. The compound, or the stereoisomer, the tautomer, the solvate or the pharmaceutically acceptable salt thereof according to claim 1, wherein said compound is selected from:
- 4-benzylamino-2-((1-methyl-1H-pyrazol-4-yl)amino)pyrimidin-5-carboxamide;
- 4-((2-methoxybenzyl)amino)-2-((1-methyl-1H-pyrazol-4-yl)amino)pyrimidin-5-carboxamide;
- 4-((2-fluoro-6-methoxybenzyl)amino)-2-((1-methyl-1H-pyrazol-4-yl)amino)pyrimidin-5-carboxamide;
- 4-((2,6-dimethylbenzyl)amino)-2-((1-methyl-1H-pyrazol-4-yl)amino)pyrimidin-5-carboxamide;
- 4-((2,6-dichlorobenzyl)amino)-2-((1-methyl-1H-pyrazol-4-yl)amino)pyrimidin-5-carboxamide;
- 4-((2,6-difluorobenzyl)amino)-2-((1-(2-methoxyethyl)-1H-pyrazol-4-yl)amino)pyrimidin-5-carboxamide;
- 4-((2-fluoro-6-methoxybenzyl)amino)-2-((1-(2-methoxyethyl)-1H-pyrazol-4-yl)amino)pyrimidin-5-carboxamide;
- 4-((4-amino-2-fluorobenzyl)amino)-2-((1-methyl-1H-pyrazol-4-yl)amino)pyrimidin-5-carboxamide;
- 4-n-butylamino-2-((1-methyl-1H-pyrazol-4-yl)amino)pyrimidin-5-carboxamide;
- 2-((1-methyl-1H-pyrazol-4-yl)amino)-4-(n-pentylamino)pyrimidin-5-carboxamide;
- 4-isobutylamino-2-((1-methyl-1H-pyrazol-4-yl)amino)pyrimidin-5-carboxamide;
- 2-((1-methyl-1H-pyrazol-4-yl)amino)-4-neopentylaminopyrimidin-5-carboxamide;
- 4-(isopentylamino)-2-((1-methyl-1H-pyrazol-4-yl)amino)pyrimidin-5-carboxamide;
- 4-((3,3-dimethylbutyl)amino)-2-((1-methyl-1H-pyrazol-4-yl)amino)pyrimidin-5-carboxamide;
- 2-((1-methyl-1H-pyrazol-4-yl)amino)-4-((4-methylpentyl)amino)pyrimidin-5-carboxamide;
- 4-((cyclopropylmethyl)amino)-2-((1-methyl-1H-pyrazol-4-yl)amino)pyrimidin-5-carboxamide;
- 4-((cyclobutylmethyl)amino)-2-((1-methyl-1H-pyrazol-4-yl)amino)pyrimidin-5-carboxamide;
- 4-((cyclopentylmethyl)amino)-2-((1-methyl-1H-pyrazol-4-yl)amino)pyrimidin-5-carboxamide;
- 4-((cyclohexylmethyl)amino)-2-((1-methyl-1H-pyrazol-4-yl)amino)pyrimidin-5-carboxamide;
- 4-((2-cyclopropylethyl)amino)-2-((1-methyl-1H-pyrazol-4-yl)amino)pyrimidin-5-carboxamide;
- 4-((2-cyclopentylethyl)amino)-2-((1-methyl-1H-pyrazol-4-yl)amino)pyrimidin-5-carboxamide;
- 4-((4-fluorobenzyl)amino)-2-((1-methyl-1H-pyrazol-4-yl)amino)pyrimidin-5-carboxamide;
- 4-((4-chlorobenzyl)amino)-2-((1-methyl-1H-pyrazol-4-yl)amino)pyrimidin-5-carboxamide;
- 4-((3-fluorobenzyl)amino)-2-((1-methyl-1H-pyrazol-4-yl)amino)pyrimidin-5-carboxamide;
- 4-((3-chlorobenzyl)amino)-2-((1-methyl-1H-pyrazol-4-yl)amino)pyrimidin-5-carboxamide;
- 4-((3-methylbenzyl)amino)-2-((1-methyl-1H-pyrazol-4-yl)amino)pyrimidin-5-carboxamide;
- 4-((2-fluorobenzyl)amino)-2-((1-methyl-1H-pyrazol-4-yl)amino)pyrimidin-5-carboxamide;
- 2-((1-methyl-1H-pyrazol-4-yl)amino)-4-((2-methylbenzyl)amino)pyrimidin-5-carboxamide;
- 2-((1-methyl-1H-pyrazol-4-yl)amino)-4-((2-ethylbenzyl)amino)pyrimidin-5-carboxamide;
- 4-((2-cyclopropylbenzyl)amino)-2-((1-methyl-1H-pyrazol-4-yl)amino)pyrimidin-5-carboxamide;
- 4-((2-chlorobenzyl)amino)-2-((1-methyl-1H-pyrazol-4-yl)amino)pyrimidin-5-carboxamide;
- 2-((1-methyl-1H-pyrazol-4-yl)amino)-4-((2-trifluoromethylbenzyl)amino)pyrimidin-5-carboxamide;
- 4-((2-cyanobenzyl)amino)-2-((1-methyl-1H-pyrazol-4-yl)amino)pyrimidin-5-carboxamide;
- 4-((2-ethoxybenzyl)amino)-2-((1-methyl-1H-pyrazol-4-yl)amino)pyrimidin-5-carboxamide;
- 4-((2-isopropoxybenzyl)amino)-2-((1-methyl-1H-pyrazol-4-yl)amino)pyrimidin-5-carboxamide;
- 2-((1-methyl-1H-pyrazol-4-yl)amino)-4-((2-trifluoromethoxybenzyl)amino)pyrimidin-5-carboxamide;
- 4-((2-(methoxymethyl)benzyl)amino)-2-((1-methyl-1H-pyrazol-4-yl)amino)pyrimidin-5-carboxamide;
- 4-((2,3-difluorobenzyl)amino)-2-((1-methyl-1H-pyrazol-4-yl)amino)pyrimidin-5-carboxamide;
- 4-((2-fluoro-3-chlorobenzyl)amino)-2-((1-methyl-1H-pyrazol-4-yl)amino)pyrimidin-5-carboxamide;
- 4-((2,3-dichlorobenzyl)amino)-2-((1-methyl-1H-pyrazol-4-yl)amino)pyrimidin-5-carboxamide;
- 4-((2-chloro-3-fluorobenzyl)amino)-2-((1-methyl-1H-pyrazol-4-yl)amino)pyrimidin-5-carboxamide;
- 4-((2-methyl-3-chlorobenzyl)amino)-2-((1-methyl-1H-pyrazol-4-yl)amino)pyrimidin-5-carboxamide;
- 4-((2,3-dimethylbenzyl)amino)-2-((1-methyl-1H-pyrazol-4-yl)amino)pyrimidin-5-carboxamide;
- 4-((2,4-difluorobenzyl)amino)-2-((1-methyl-1H-pyrazol-4-yl)amino)pyrimidin-5-carboxamide;
- 4-((2-fluoro-4-chlorobenzyl)amino)-2-((1-methyl-1H-pyrazol-4-yl)amino)pyrimidin-5-carboxamide;
- 4-((2-chloro-4-fluorobenzyl)amino)-2-((1-methyl-1H-pyrazol-4-yl)amino)pyrimidin-5-carboxamide;
- 4-((2-methyl-4-fluorobenzyl)amino)-2-((1-methyl-1H-pyrazol-4-yl)amino)pyrimidin-5-carboxamide;
- 4-((2-methyl-4-chlorobenzyl)amino)-2-((1-methyl-1H-pyrazol-4-yl)amino)pyrimidin-5-carboxamide;
- 4-((2-methoxy-4-fluorobenzyl)amino)-2-((1-methyl-1H-pyrazol-4-yl)amino)pyrimidin-5-carboxamide;
- 4-((2,5-difluorobenzyl)amino)-2-((1-methyl-1H-pyrazol-4-yl)amino)pyrimidin-5-carboxamide;
- 4-((2-fluoro-5-chlorobenzyl)amino)-2-((1-methyl-1H-pyrazol-4-yl)amino)pyrimidin-5-carboxamide;
- 4-((2-chloro-5-fluorobenzyl)amino)-2-((1-methyl-1H-pyrazol-4-yl)amino)pyrimidin-5-carboxamide;
- 4-((2-methyl-5-fluorobenzyl)amino)-2-((1-methyl-1H-pyrazol-4-yl)amino)pyrimidin-5-carboxamide;
- 4-((2-methyl-5-chlorobenzyl)amino)-2-((1-methyl-1H-pyrazol-4-yl)amino)pyrimidin-5-carboxamide;
- 4-((2-(trifluoromethyl)-5-fluorobenzyl)amino)-2-((1-methyl-1H-pyrazol-4-yl)amino)pyrimidin-5-carboxamide;
- 4-((2-methoxy-5-chlorobenzyl)amino)-2-((1-methyl-1H-pyrazol-4-yl)amino)pyrimidin-5-carboxamide;
- 4-((2,5-dimethoxybenzyl)amino)-2-((1-methyl-1H-pyrazol-4-yl)amino)pyrimidin-5-carboxamide;
- 4-((2,6-difluorobenzyl)amino)-2-((1-methyl-1H-pyrazol-4-yl)amino)pyrimidin-5-carboxamide;
- 4-((2-fluoro-6-chlorobenzyl)amino)-2-((1-methyl-1H-pyrazol-4-yl)amino)pyrimidin-5-carboxamide;

4-((2-fluoro-6-(trifluoromethyl)benzyl)amino)-2-((1-methyl-1H-pyrazol-4-yl)amino)pyrimidin-5-carboxamide;
4-((2-methyl-6-chlorobenzyl)amino)-2-((1-methyl-1H-pyrazol-4-yl)amino)pyrimidin-5-carboxamide;
4-((2,6-dimethoxybenzyl)amino)-2-((1-methyl-1H-pyrazol-4-yl)amino)pyrimidin-5-carboxamide;
4-((3,5-difluorobenzyl)amino)-2-((1-methyl-1H-pyrazol-4-yl)amino)pyrimidin-5-carboxamide;
4-((3,5-dimethoxybenzyl)amino)-2-((1-methyl-1H-pyrazol-4-yl)amino)pyrimidin-5-carboxamide;
4-((2,3,6-trifluorobenzyl)amino)-2-((1-methyl-1H-pyrazol-4-yl)amino)pyrimidin-5-carboxamide;
4-((2,3,5-trifluorobenzyl)amino)-2-((1-methyl-1H-pyrazol-4-yl)amino)pyrimidin-5-carboxamide;
4-((2,6-difluoro-3-methylbenzyl)amino)-2-((1-methyl-1H-pyrazol-4-yl)amino)pyrimidin-5-carboxamide;
4-((2-chloro-3,6-difluorobenzyl)amino)-2-((1-methyl-1H-pyrazol-4-yl)amino)pyrimidin-5-carboxamide;
4-((2,4,6-trifluorobenzyl)amino)-2-((1-methyl-1H-pyrazol-4-yl)amino)pyrimidin-5-carboxamide;
2-((1-methyl-1H-pyrazol-4-yl)amino)-4-(phenylethylamino)pyrimidin-5-carboxamide;
2-((1-methyl-1H-pyrazol-4-yl)amino)-4-((3-methylphenylethyl)amino)pyrimidin-5-carboxamide;
2-((1-methyl-1H-pyrazol-4-yl)amino)-4-((3-methoxyphenylethyl)amino)pyrimidin-5-carboxamide;
4-((2-fluorophenylethyl)amino)-2-((1-methyl-1H-pyrazol-4-yl)amino)pyrimidin-5-carboxamide;
4-((2-methylphenylethyl)amino)-2-((1-methyl-1H-pyrazol-4-yl)amino)pyrimidin-5-carboxamide;
4-((2-methoxyphenylethyl)amino)-2-((1-methyl-1H-pyrazol-4-yl)amino)pyrimidin-5-carboxamide;
4-((2-fluoro-6-chlorophenylethyl)amino)-2-((1-methyl-1H-pyrazol-4-yl)amino)pyrimidin-5-carboxamide;
2-((1-methyl-1H-pyrazol-4-yl)amino)-4-((pyridin-4-ylmethyl)amino)pyrimidin-5-carboxamide;
4-(((2-fluoropyridin-3-yl)methyl)amino)-2-((1-methyl-1H-pyrazol-4-yl)amino)pyrimidin-5-carboxamide;
4-(((2-methoxypyridin-3-yl)methyl)amino)-2-((1-methyl-1H-pyrazol-4-yl)amino)pyrimidin-5-carboxamide;
4-(((2-ethoxypyridin-3-yl)methyl)amino)-2-((1-methyl-1H-pyrazol-4-yl)amino)pyrimidin-5-carboxamide;
4-(((2-tert-butoxypyridin-3-yl)methyl)amino)-2-((1-methyl-1H-pyrazol-4-yl)amino)pyrimidin-5-carboxamide;
2-((1-methyl-1H-pyrazol-4-yl)amino)-4-((2-(pyridin-3-yl)ethyl)amino)pyrimidin-5-carboxamide;
2-((1-methyl-1H-pyrazol-4-yl)amino)-4-(((2,3-dihydrobenzo(b)(1,4)dioxan-5-yl)methyl)amino)pyrimidin-5-carboxamide;
2-((1-methyl-1H-pyrazol-4-yl)amino)-4-(((1H-indol-3-yl)methyl)amino)pyrimidin-5-carboxamide;
(S)-2-((1-methyl-1H-pyrazol-4-yl)amino)-4-((2-phenylpropyl)amino)pyrimidin-5-carboxamide;
(R)-2-((1-methyl-1H-pyrazol-4-yl)amino)-4-((2-phenylpropyl)amino)pyrimidin-5-carboxamide;
4-benzylamino-2-((1-(2-methoxyethyl)-1H-pyrazol-4-yl)amino)pyrimidin-5-carboxamide;
2-((1H-pyrazol-4-yl)amino)-4-((2,6-difluorobenzyl)amino)pyrimidin-5-carboxamide;
4-((2,6-difluorobenzyl)amino)-2-((1-ethyl-1H-pyrazol-4-yl)amino)pyrimidin-5-carboxamide;
4-((2,6-difluorobenzyl)amino)-2-((1-isopropyl-1H-pyrazol-4-yl)amino)pyrimidin-5-carboxamide;
4-((2,6-difluorobenzyl)amino)-2-((1-cyclopropyl-1H-pyrazol-4-yl)amino)pyrimidin-5-carboxamide;
4-((2,6-difluorobenzyl)amino)-2-((1-cyclobutyl-1H-pyrazol-4-yl)amino)pyrimidin-5-carboxamide;
4-((2,6-difluorobenzyl)amino)-2-((1-(tetrahydrofuran-3-yl)-1H-pyrazol-4-yl)amino)pyrimidin-5-carboxamide;
4-((2,6-difluorobenzyl)amino)-2-((1-(tetrahydro-2H-pyran-4-yl)-1H-pyrazol-4-yl)amino)pyrimidin-5-carboxamide;
4-((2,6-difluorobenzyl)amino)-2-((1-((tetrahydrofuran-2-yl)methyl)-1H-pyrazol-4-yl)amino)pyrimidin-5-carboxamide;
4-((2,6-difluorobenzyl)amino)-2-((1-((tetrahydrofuran-3-yl)methyl)-1H-pyrazol-4-yl)amino)pyrimidin-5-carboxamide;
4-((2,6-difluorobenzyl)amino)-2-((1-((tetrahydro-2H-pyran-4-yl)methyl)-1H-pyrazol-4-yl)amino)pyrimidin-5-carboxamide;
4-((2,6-difluorobenzyl)amino)-2-((1-(2-hydroxyethyl)-1H-pyrazol-4-yl)amino)pyrimidin-5-carboxamide;
4-((2,6-difluorobenzyl)amino)-2-((1-(2-methylthioethyl)-1H-pyrazol-4-yl)amino)pyrimidin-5-carboxamide;
4-((2,6-difluorobenzyl)amino)-2-((1-(2-(dimethylamino)ethyl)-1H-pyrazol-4-yl)amino)pyrimidin-5-carboxamide;
4-((2,6-difluorobenzyl)amino)-2-((1-(2-(morpholin-1-yl)ethyl)-1H-pyrazol-4-yl)amino)pyrimidin-5-carboxamide;
4-((2,6-difluorobenzyl)amino)-2-((1-(2-hydroxy-2-methylpropyl)-1H-pyrazol-4-yl)amino)pyrimidin-5-carboxamide;
4-((2-fluoro-6-chlorobenzyl)amino)-2-((1-(2-hydroxyethyl)-1H-pyrazol-4-yl)amino)pyrimidin-5-carboxamide;
4-((2-fluoro-6-chlorobenzyl)amino)-2-((1-(2-methoxyethyl)-1H-pyrazol-4-yl)amino)pyrimidin-5-carboxamide;
4-((2-fluoro-6-chlorobenzyl)amino)-2-((1-(2-(dimethylamino)ethyl)-1H-pyrazol-4-yl)amino)pyrimidin-5-carboxamide;
2-((1H-pyrazol-4-yl)amino)-4-((2-fluoro-6-methoxybenzyl)amino)pyrimidin-5-carboxamide;
4-((2-fluoro-6-methoxybenzyl)amino)-2-((1-ethyl-1H-pyrazol-4-yl)amino)pyrimidin-5-carboxamide;
4-((2-fluoro-6-methoxybenzyl)amino)-2-((1-isopropyl-1H-pyrazol-4-yl)amino)pyrimidin-5-carboxamide;
4-((2-fluoro-6-methoxybenzyl)amino)-2-((1-cyclopropyl-1H-pyrazol-4-yl)amino)pyrimidin-5-carboxamide;
4-((2-fluoro-6-methoxybenzyl)amino)-2-((1-cyclobutyl-1H-pyrazol-4-yl)amino)pyrimidin-5-carboxamide;
4-((2-fluoro-6-methoxybenzyl)amino)-2-((1-cyclopentyl-1H-pyrazol-4-yl)amino)pyrimidin-5-carboxamide;
4-((2-fluoro-6-methoxybenzyl)amino)-2-((1-cyclohexyl-1H-pyrazol-4-yl)amino)pyrimidin-5-carboxamide;
4-((2-fluoro-6-methoxybenzyl)amino)-2-((1-cycloheptyl-1H-pyrazol-4-yl)amino)pyrimidin-5-carboxamide;
4-((2-fluoro-6-methoxybenzyl)amino)-2-((1-(tetrahydro-2H-pyran-4-yl)-1H-pyrazol-4-yl)amino)pyrimidin-5-carboxamide;
4-((2-fluoro-6-methoxybenzyl)amino)-2-((1-(2-hydroxyethyl)-1H-pyrazol-4-yl)amino)pyrimidin-5-carboxamide;
4-((2-fluoro-6-methoxybenzyl)amino)-2-((1-(2-methylthioethyl)-1H-pyrazol-4-yl)amino)pyrimidin-5-carboxamide;

4-((2-fluoro-6-methoxybenzyl)amino)-2-((1-(2-(dimethylamino)ethyl)-1H-pyrazol-4-yl)amino)pyrimidin-5-carboxamide;
4-((2-fluoro-6-methoxybenzyl)amino)-2-((1-(1-methylpiperidin-4-yl)-1H-pyrazol-4-yl)amino)pyrimidin-5-carboxamide;
4-((2-fluoro-6-methoxybenzyl)amino)-2-((1-(2-(pyrrolidin-1-yl)ethyl)-1H-pyrazol-4-yl)amino)pyrimidin-5-carboxamide;
4-((2-fluoro-6-methoxybenzyl)amino)-2-((1-(2-(piperidin-1-yl)ethyl)-1H-pyrazol-4-yl)amino)pyrimidin-5-carboxamide;
4-((2-fluoro-6-methoxybenzyl)amino)-2-((1-(2-(morpholin-1-yl)ethyl)-1H-pyrazol-4-yl)amino)pyrimidin-5-carboxamide;
4-((2-fluoro-6-methoxybenzyl)amino)-2-((1-(6-methoxyhexyl)-1H-pyrazol-4-yl)amino)pyrimidin-5-carboxamide;
4-((2-fluoro-6-methoxybenzyl)amino)-2-((1-(2-hydroxy-2-methylpropyl)-1H-pyrazol-4-yl)amino)pyrimidin-5-carboxamide;
4-((2-fluoro-6-(trifluoromethyl)benzyl)amino)-2-((1-(2-hydroxyethyl)-1H-pyrazol-4-yl)amino)pyrimidin-5-carboxamide;
4-((2-fluoro-6-(trifluoromethyl)benzyl)amino)-2-((1-(2-methoxyethyl)-1H-pyrazol-4-yl)amino)pyrimidin-5-carboxamide;
4-((2-fluoro-6-(trifluoromethyl)benzyl)amino)-2-((1-(2-(dimethylamino)ethyl)-1H-pyrazol-4-yl)amino)pyrimidin-5-carboxamide;
4-((2-methoxybenzyl)amino)-2-((1-(2-hydroxyethyl)-1H-pyrazol-4-yl)amino)pyrimidin-5-carboxamide;
4-((2-methoxy-5-chlorobenzyl)amino)-2-((1-(2-hydroxyethyl)-1H-pyrazol-4-yl)amino)pyrimidin-5-carboxamide;
4-((2,6-dimethylbenzyl)amino)-2-((1-(2-hydroxyethyl)-1H-pyrazol-4-yl)amino)pyrimidin-5-carboxamide;
4-((2-chloro-6-methylbenzyl)amino)-2-((1-(2-hydroxyethyl)-1H-pyrazol-4-yl)amino)pyrimidin-5-carboxamide;
4-((2,6-dichlorobenzyl)amino)-2-((1-(2-hydroxyethyl)-1H-pyrazol-4-yl)amino)pyrimidin-5-carboxamide;
4-((2,3,6-trifluorobenzyl)amino)-2-((1-(2-hydroxyethyl)-1H-pyrazol-4-yl)amino)pyrimidin-5-carboxamide;
4-((2,6-difluoro-3-methylbenzyl)amino)-2-((1-(2-hydroxyethyl)-1H-pyrazol-4-yl)amino)pyrimidin-5-carboxamide;
4-((2-chloro-3,6-difluorobenzyl)amino)-2-((1-(2-hydroxyethyl)-1H-pyrazol-4-yl)amino)pyrimidin-5-carboxamide; and
4-((2-fluoro-3-methoxybenzyl)amino)-2-((1-(2-methoxyethyl)-1H-pyrazol-4-yl)amino)pyrimidin-5-carboxamide.

10. The compound, or the stereoisomer, the tautomer, the solvate or the pharmaceutically acceptable salt thereof according to claim 1, wherein said compound is selected from:
2-((1-tert-butyl-1H-pyrazol-4-yl)amino)-4-(isopentylamino)pyrimidin-5-carboxamide;
4-(isopentylamino)-2-((1-(tetrahydro-2H-pyran-4-yl)-1H-pyrazol-4-yl)amino)pyrimidin-5-carboxamide;
2-((1-tert-butyl-1H-pyrazol-4-yl)amino)-4-((2-(2-hydroxyethoxy)ethyl)amino)pyrimidin-5-carboxamide;
4-((2-(2-hydroxyethoxy)ethyl)amino)-2-((1-(tetrahydro-2H-pyran-4-yl)-1H-pyrazol-4-yl)amino)pyrimidin-5-carboxamide;
2-((1-ethyl-1H-pyrazol-4-yl)amino)-4-((2-ethylbenzyl)amino)pyrimidin-5-carboxamide;
4-((2-ethylbenzyl)amino)-2-((1-propyl-1H-pyrazol-4-yl)amino)pyrimidin-5-carboxamide;
4-((2-ethylbenzyl)amino)-2-((1-isopropyl-1H-pyrazol-4-yl)amino)pyrimidin-5-carboxamide;
2-((1-cyclopropyl-1H-pyrazol-4-yl)amino)-4-((2-ethylbenzyl)amino)pyrimidin-5-carboxamide;
2-((1-tert-butyl-1H-pyrazol-4-yl)amino)-4-((2-ethylbenzyl)amino)pyrimidin-5-carboxamide;
4-((2-ethylbenzyl)amino)-2-((1-(tetrahydro-2H-pyran-4-yl)amino)pyrimidin-5-carboxamide;
2-((1-methyl-1H-pyrazol-4-yl)amino)-4-((2-propylbenzyl)amino)pyrimidin-5-carboxamide;
4-((2-isopropylbenzyl)amino)-2-((1-methyl-1H-pyrazol-4-yl)amino)pyrimidin-5-carboxamide;
4-((2-(cyclopropylmethyl)benzyl)amino)-2-((1-methyl-1H-pyrazol-4-yl)amino)pyrimidin-5-carboxamide;
2-((1-tert-butyl-1H-pyrazol-4-yl)amino)-4-((2-methoxybenzyl)amino)pyrimidin-5-carboxamide;
2-((1-tert-butyl-1H-pyrazol-4-yl)amino)-4-((2,6-difluorobenzyl)amino)pyrimidin-5-carboxamide;
4-((2-chloro-6-fluorobenzyl)amino)-2-((1-ethyl-1H-pyrazol-4-yl)amino)pyrimidin-5-carboxamide;
4-((2-chloro-6-fluorobenzyl)amino)-2-((1-propyl-1H-pyrazol-4-yl)amino)pyrimidin-5-carboxamide;
4-((2-chloro-6-fluorobenzyl)amino)-2-((1-isopropyl-1H-pyrazol-4-yl)amino)pyrimidin-5-carboxamide;
4-((2-chloro-6-fluorobenzyl)amino)-2-((1-cyclopropyl-1H-pyrazol-4-yl)amino)pyrimidin-5-carboxamide;
2-((1-tert-butyl-1H-pyrazol-4-yl)amino)-4-((2-chloro-6-fluorobenzyl)amino)pyrimidin-5-carboxamide;
4-((2-chloro-6-fluorobenzyl)amino)-2-((1-cyclobutyl-1H-pyrazol-4-yl)amino)pyrimidin-5-carboxamide;
4-((2-chloro-6-fluorobenzyl)amino)-2-((1-cyclopentyl-1H-pyrazol-4-yl)amino)pyrimidin-5-carboxamide;
4-((2-chloro-6-fluorobenzyl)amino)-2-((1-cyclohexyl-1H-pyrazol-4-yl)amino)pyrimidin-5-carboxamide;
4-((2-chloro-6-fluorobenzyl)amino)-2-((1-(tetrahydro-2H-pyran-4-yl)-1H-pyrazol-4-yl)amino)pyrimidin-5-carboxamide;
4-((2-bromo-6-fluorobenzyl)amino)-2-((1-methyl-1H-pyrazol-4-yl)amino)pyrimidin-5-carboxamide;
4-((2-bromo-6-fluorobenzyl)amino)-2-((1-ethyl-1H-pyrazol-4-yl)amino)pyrimidin-5-carboxamide;
4-((2-fluoro-6-methylbenzyl)amino)-2-((1-methyl-1H-pyrazol-4-yl)amino)pyrimidin-5-carboxamide;
4-((2-fluoro-6-methylbenzyl)amino)-2-((1-ethyl-1H-pyrazol-4-yl)amino)pyrimidin-5-carboxamide;
2-((1-ethyl-1H-pyrazol-4-yl)amino)-4-((2-fluoro-6-(trifluoromethyl)benzyl)amino)pyrimidin-5-carboxamide;
2-((1-tert-butyl-1H-pyrazol-4-yl)amino)-4-((2-fluoro-6-(trifluoromethyl)benzyl)amino)pyrimidin-5-carboxamide;
4-((2-ethyl-6-fluorobenzyl)amino)-2-((1-methyl-1H-pyrazol-4-yl)amino)pyrimidin-5-carboxamide;
2-((1-ethyl-1H-pyrazol-4-yl)amino)-4-((2-ethyl-6-fluorobenzyl)amino)pyrimidin-5-carboxamide;
2-((1-tert-butyl-1H-pyrazol-4-yl)amino)-4-((2-ethyl-6-fluorobenzyl)amino)pyrimidin-5-carboxamide;
2-((1-tert-butyl-1H-pyrazol-4-yl)amino)-4-((2-fluoro-6-methoxybenzyl)amino)pyrimidin-5-carboxamide;
4-((2,6-dimethylbenzyl)amino)-2-((1-ethyl-1H-pyrazol-4-yl)amino)pyrimidin-5-carboxamide;
4-((2,6-dimethylbenzyl)amino)-2-((1-isopropyl-1H-pyrazol-4-yl)amino)pyrimidin-5-carboxamide;

2-((1-tert-butyl-1H-pyrazol-4-yl)amino)-4-((2,6-dimethylbenzyl)amino)pyrimidin-5-carboxamide;

4-((2,6-dimethylbenzyl)amino)-2-((1-(tetrahydro-2H-pyran-4-yl)-1H-pyrazol-4-yl)amino)pyrimidin-5-carboxamide;

4-((2-ethynylbenzyl)amino)-2-((1-methyl-1H-pyrazol-4-yl)amino)pyrimidin-5-carboxamide;

2-((1-methyl-1H-pyrazol-4-yl)amino)-4-((2-vinylbenzyl)amino)pyrimidin-5-carboxamide;

2-((1-methyl-1H-pyrazol-4-yl)amino)-4-((2-(prop-1-en-1-yl)benzyl)amino)pyrimidin-5-carboxamide; and 4-((2-allylbenzyl)amino)-2-((1-methyl-1H-pyrazol-4-yl)amino)pyrimidin-5-carboxamide.

11. A compound of formula (I), or a stereoisomer, a tautomer, a hydrate, a solvate, or a pharmaceutically acceptable salt thereof:

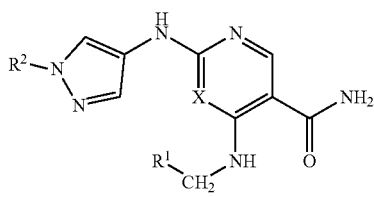

Formula (I)

wherein,
X is N;
$R^1$ is

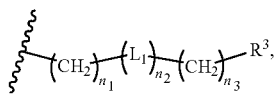

$n_1$ is an integer of 0 to 8, $n_2$ is an integer of 0 to 1, $n_3$ is an integer of 0 to 8, and the sum of $n_1$, $n_2$, and $n_3$ is 10 or less;

$L_1$ is

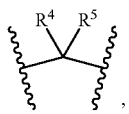

$R^4$ and $R^5$ are each independently H, or $C_1$-$C_3$ alkyl, and $R^4$ and $R^5$ are the same or different, $R^3$ is $C_2$-$C_8$ alkenyl which is unsubstituted or substituted with $C_1$-$C_3$ alkyl, or $C_4$-$C_8$ cycloalkenyl which is unsubstituted or substituted with $C_1$-$C_3$ alkyl;

$R^2$ is

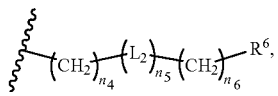

$n_4$ is an integer of 0 to 8, $n_5$ is an integer of 0 to 1, $n_6$ is an integer of 0 to 8, and the sum of $n_4$, $n_5$, and $n_6$ is 10 or less;

$L_2$ is

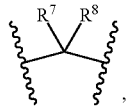

$R^7$ and $R^8$ are each independently H, or $C_1$-$C_3$ alkyl, and $R^7$ and $R^8$ are the same or different, $R^6$ is —H, hydroxyalkyl, $C_1$-$C_5$ alkyl, $C_3$-$C_8$ cycloalkyl, $C_1$-$C_5$ alkoxyalkyl, $C_1$-$C_5$ alkylthioalkyl, 5- to 6-membered heterocyclyl, or —NR'R'', wherein R' and R'' are each independently H, or $C_1$-$C_3$ alkyl.

12. The compound, or the stereoisomer, the tautomer, the hydrate, the solvate, or the pharmaceutically acceptable salt thereof according to claim 11,
wherein $R^3$ is

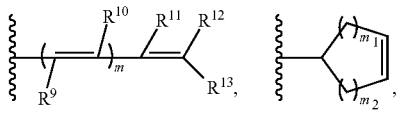

$R^9$, $R^{10}$, $R^{11}$, $R^{12}$, and $R^{13}$ are each independently H, or $C_1$-$C_3$ alkyl, and m is an integer of 0 to 2, $m_1$ is an integer of 0 to 5, $m_2$ is an integer of 0 to 5, and the sum of $m_1$ and $m_2$ is less than or equal to 5.

13. The compound, or the stereoisomer, the tautomer, the hydrate, the solvate, or the pharmaceutically acceptable salt thereof according to claim 11,
wherein, $R^3$ is

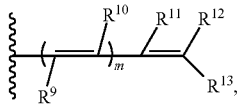

$R^9$ and $R^{10}$ are each independently H, or $C_1$-$C_3$ alkyl, and any one of $R^{11}$, $R^{12}$, and $R^{13}$ is $C_4$-$C_6$ alkyl, and the rest are each independently H, or $C_1$-$C_3$ alkyl, and m is an integer of 0 to 2.

14. The compound, or the stereoisomer, the tautomer, the hydrate, the solvate, or the pharmaceutically acceptable salt thereof according to claim 12, wherein $n_1$ is an integer of 0 to 2, $n_2$ is an integer of 0 to 1, $n_3$ is an integer of 0 to 3, $R^4$ and $R^5$ are each independently H, or methyl, and $R^4$ and $R^5$ are the same or different;

$R^9$, $R^{10}$, $R^{11}$, $R^{12}$, and $R^{13}$ are each independently H, methyl or ethyl, and m is 0 or 1.

15. The compound, or the stereoisomer, the tautomer, the hydrate, the solvate, or the pharmaceutically acceptable salt thereof according to claim 14, wherein $R^3$ is

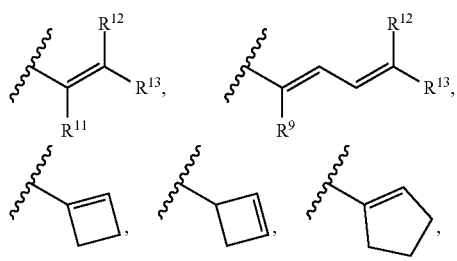

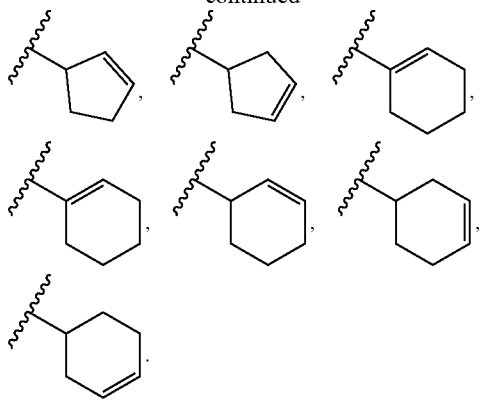

$R^9$, $R^{11}$, $R^{12}$, and $R^{13}$ are each independently H, methyl, or ethyl.

16. The compound, or the stereoisomer, the tautomer, the hydrate, the solvate, or the pharmaceutically acceptable salt thereof according to claim 11, wherein $n_4$ is an integer of 0 to 3, $n_5$ is an integer of 0 to 1, $n_6$ is an integer of 0 to 5, $R^7$ and $R^8$ are each independently H, or methyl, and $R^7$ and $R^8$ are the same or different;

$R^6$ is —H, hydroxyethyl, hydroxypropyl, $C_1$-$C_5$ alkyl, $C_3$-$C_8$ cycloalkyl, $C_1$-$C_5$ alkoxyethyl, $C_1$-$C_5$ alkoxypropyl, $C_1$-$C_5$ alkylthioethyl, 5- to 6-membered heterocyclyl, or —NR'R", wherein R' and R" are each independently H, or $C_1$-$C_3$ alkyl.

17. The compound, or the stereoisomer, the tautomer, the hydrate, the solvate, or the pharmaceutically acceptable salt thereof according to claim 16, wherein $R^6$ is H, hydroxyethyl, hydroxypropyl, methyl, ethyl, propyl, isopropyl, tert-butyl, cyclopropyl, cyclobutyl, cyclopentyl, cyclohexyl, methoxyethyl, ethoxyethyl, propoxyethyl, isopropoxyethyl, methoxypropyl, ethoxypropyl, propoxypropyl, isopropoxypropyl, methylthioethyl, ethylthioethyl, propylthioethyl, isopropylthioethyl, 5- to 6-membered heterocyclyl, or —NR'R", wherein R' and R" are each independently H, methyl, or ethyl;

wherein the 5- to 6-membered heterocyclyl is a heterocyclyl containing 1 to 2 heteroatoms selected from N, O, and S, which is unsubstituted or substituted with 1 to 2 substituents selected from hydroxy, $C_1$-$C_3$ alkyl, and $C_1$-$C_3$ acyl.

18. The compound, or the stereoisomer, the tautomer, the hydrate, the solvate, or the pharmaceutically acceptable salt thereof according to claim 17, wherein the heterocyclyl containing 1 to 2 heteroatoms selected from N, O, and S is selected from any one of the following groups:

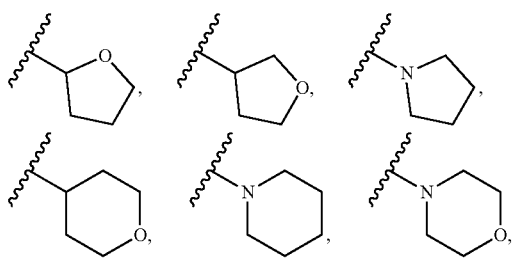

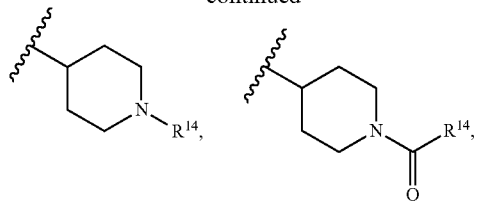

wherein $R^{14}$ is H, methyl, ethyl, propyl, or isopropyl.

19. The compound, or the stereoisomer, the tautomer, the hydrate, the solvate, or the pharmaceutically acceptable salt thereof according to claim 11, wherein said compound of formula (I) is selected from:
    4-(but-3-en-1-ylamino)-2-((1-(tert-butyl)-1H-pyrazol-4-yl)amino)pyrimidin-5-carboxamide;
    2-((1-tert-butyl-1H-pyrazol-4-yl)amino)-4-((2-methylallyl)amino)pyrimidin-5-carboxamide;
    2-((1-(tert-butyl)-1H-pyrazol-4-yl)amino)-4-((3-methylbut-2-en-1-yl)amino)pyrimidin-5-carboxamide;
    2-((1-(tert-butyl)-1H-pyrazol-4-yl)amino)-4-(pent-4-en-1-ylamino)pyrimidin-5-carboxamide;
    4-((2-methylallyl)amino)-2-((1-(tetrahydro-2H-pyran-4-yl)-1H-pyrazol-4-yl)amino)pyrimidin-5-carboxamide;
    4-((3-methylbut-2-en-1-yl)amino)-2-((1-(tetrahydro-2H-pyran-4-yl)-1H-pyrazol-4-yl)amino)pyrimidin-5-carboxamide;
    4-(but-3-en-1-ylamino)-2-((1-(tetrahydro-2H-pyran-4-yl)-1H-pyrazol-4-yl)amino)pyrimidin-5-carboxamide; and
    2-((1-(tetrahydro-2H-pyran-4-yl)-1H-pyrazol-4-yl)amino)-4-(pent-4-en-1-ylamino)pyrimidin-5-carboxamide.

20. The compound, or the stereoisomer, the tautomer, the hydrate, the solvate, or the pharmaceutically acceptable salt thereof according to claim 11, wherein said compound of formula (I) is selected from:
    2-((1-(tert-butyl)-1H-pyrazol-4-yl)amino)-4-((cyclopent-3-en-1-ylmethyl)amino)pyrimidin-5-carboxamide;
    4-((cyclopent-3-en-1-ylmethyl)amino)-2-((1-(tetrahydro-2H-pyran-4-yl)-1H-pyrazol-4-yl)amino)pyrimidin-5-carboxamide;
    4-(allylamino)-2-((1-(tert-butyl)-1H-pyrazol-4-yl)amino)pyrimidin-5-carboxamide;
    (Z)-2-((1-tert-butyl-1H-pyrazol-4-yl)amino)-4-((pent-2-en-1-yl)amino)pyrimidin-5-carboxamide;
    (E)-2-((1-tert-butyl-1H-pyrazol-4-yl)amino)-4-((4-methylpent-2-en-1-yl)amino)pyrimidin-5-carboxamide;
    (E)-2-((1-tert-butyl-1H-pyrazol-4-yl)amino)-4-((pent-3-en-1-yl)amino)pyrimidin-5-carboxamide;
    2-((1-tert-butyl-1H-pyrazol-4-yl)amino)-4-((3-methylbut-3-en-1-yl)amino)pyrimidin-5-carboxamide;
    2-((1-tert-butyl-1H-pyrazol-4-yl)amino)-4-((4-methylpent-3-en-1-yl)amino)pyrimidin-5-carboxamide;
    2-((1-tert-butyl-1H-pyrazol-4-yl)amino)-4-((4-methylpent-4-en-1-yl)amino)pyrimidin-5-carboxamide;
    2-((1-tert-butyl-1H-pyrazol-4-yl)amino)-4-((5-methylhex-4-en-1-yl)amino)pyrimidin-5-carboxamide;
    (E)-2-((1-tert-butyl-1H-pyrazol-4-yl)amino)-4-((5-methylhex-2-en-1-yl)amino)pyrimidin-5-carboxamide;
    2-((1-tert-butyl-1H-pyrazol-4-yl)amino)-4-(((2E,4E)-hex-2,4-dien-1-yl)amino)pyrimidin-5-carboxamide; and
    2-((1-tert-butyl-1H-pyrazol-4-yl)amino)-4-(((2E,4E)-hept-2,4-dien-1-yl)amino)pyrimidin-5-carboxamide.

21. The compound, or the stereoisomer, the tautomer, the hydrate, the solvate, or the pharmaceutically acceptable salt thereof according to claim 1, wherein the pharmaceutically acceptable salt of the compound is selected from one or more salts of the compound as follows: hydrochloride, hydrobromide, hydriodate, perchlorate, sulfate, nitrate, phosphate, formate, acetate, propionate, glycolate, lactate, succinate, maleate, tartrate, malate, citrate, fumarate, gluconate, benzoate, mandelate, mesylate, isethionate, benzenesulfonate, oxalate, palmitate, 2-naphthalenesulfonate, p-toluenesulfonate, cyclohexylaminosulfonate, salicylate, hexonate, trifluoroacetate, aluminum, calcium, chloroprocaine, choline, diethanolamine, ethylenediamine, lithium, magnesium, potassium, sodium, and zinc.

22. A pharmaceutical composition comprising the compound, or the stereoisomer, the tautomer, the hydrate, the solvate, or the pharmaceutically acceptable salt thereof according to claim 1, and one or more pharmaceutically acceptable carriers or excipients.

23. The pharmaceutical composition according to claim 22, wherein the pharmaceutical composition further comprises one or more other therapeutic agents.

24. The compound, or the stereoisomer, the tautomer, the solvate or the pharmaceutically acceptable salt thereof according to claim 1, wherein the ring mentioned in item i) a ring containing 0 to 3 heteroatoms formed by a 6-membered aryl or heteroaryl ring fused with a 5- or 6-membered ring, or a ring containing 1 to 3 heteroatoms formed by a 5-membered heteroaryl ring fused with a 5- or 6-membered ring is selected from the group consisting of:

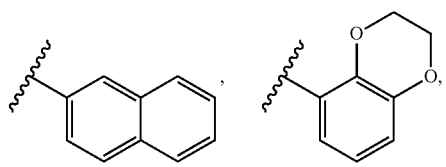

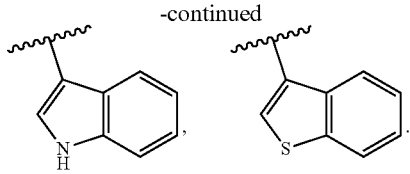

25. The compound, or the stereoisomer, the tautomer, the solvate or the pharmaceutically acceptable salt thereof according to claim 7, wherein the 5- or 6-membered heterocyclyl containing oxygen and/or nitrogen is selected from the group consisting of:

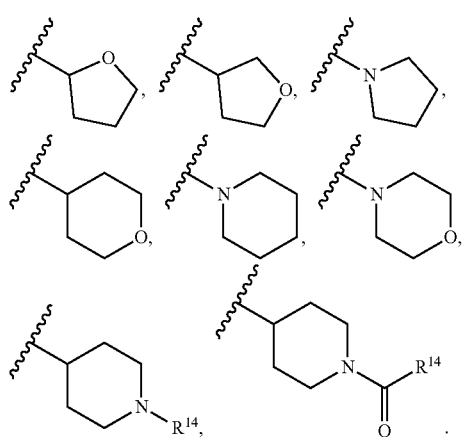

26. The compound, or the stereoisomer, the tautomer, the solvate or the pharmaceutically acceptable salt thereof according to claim 2, wherein the 5- to 7-membered heterocyclic ring contains 1 to 2 heteroatoms selected from O and/or N and/or S, wherein when the heteroatom is N, N is connected to H, $C_1$-$C_4$ alkyl, acetyl, trifluoroacetyl, propionyl, or N,N-diformyl.

* * * * *

UNITED STATES PATENT AND TRADEMARK OFFICE
CERTIFICATE OF CORRECTION

PATENT NO. : 11,344,549 B2
APPLICATION NO. : 16/642552
DATED : May 31, 2022
INVENTOR(S) : Qiang Zhang et al.

Page 1 of 2

It is certified that error appears in the above-identified patent and that said Letters Patent is hereby corrected as shown below:

On the Title Page

Insert the following:
--(73) Assignee: BEIJING SCITECH-MQ PHARMACEUTICALS LIMITED, Beijing (CN)--

In the Claims

At Column 136, Lines 60-65, Claim 5, please replace the formula in f):

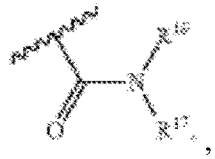
,

With the formula:

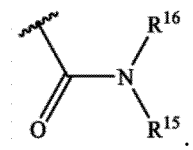
.

At Column 137, Lines 35-40, Claim 6, please replace the formula in g):

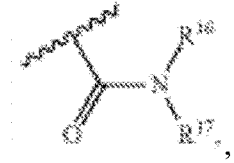
,

Signed and Sealed this
Seventeenth Day of January, 2023

Katherine Kelly Vidal
*Director of the United States Patent and Trademark Office*

CERTIFICATE OF CORRECTION (continued)
U.S. Pat. No. 11,344,549 B2

With the formula:

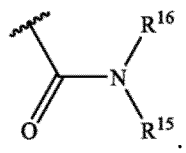

At Column 150, Lines 25-30, Claim 25, please delete the last two formulas:

" 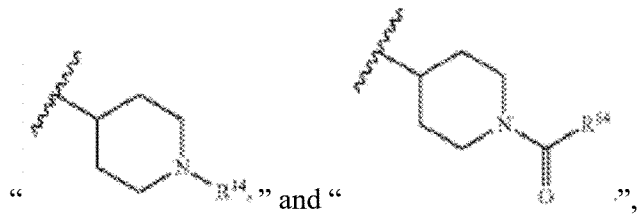 " and " ",

And insert the formula:

-- 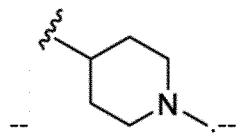 --